United States Patent
Lee et al.

(10) Patent No.: US 12,383,539 B2
(45) Date of Patent: Aug. 12, 2025

(54) TREATING ESSENTIAL TREMOR USING (R)-2-(4-ISOPROPYLPHENYL)-N-(1-(5-(2,2,2-TRIFLUOROETHOXY)PYRIDIN-2-YL)ETHYL)ACETAMIDE

(71) Applicant: Cavion, Inc., Charlottesville, VA (US)

(72) Inventors: Margaret Scott Lee, Middleton, MA (US); Spyridon Papapetropoulos, Wellesley, MA (US); Michelle S. Higgin, Holly Springs, NC (US); Muralikrishna Duvvuri, Chapel Hill, NC (US); Bruce N. Rehlaender, Cary, NC (US); Evan Newbold, Charlottesville, VA (US)

(73) Assignee: Cavion, Inc., Palo Alto, CA (US)

( * ) Notice: Subject to any disclaimer, the term of this patent is extended or adjusted under 35 U.S.C. 154(b) by 1046 days.

(21) Appl. No.: 17/282,730

(22) PCT Filed: Oct. 3, 2019

(86) PCT No.: PCT/US2019/054498
§ 371 (c)(1),
(2) Date: Apr. 2, 2021

(87) PCT Pub. No.: WO2020/072773
PCT Pub. Date: Apr. 9, 2020

(65) Prior Publication Data
US 2022/0016095 A1    Jan. 20, 2022

Related U.S. Application Data

(60) Provisional application No. 62/780,049, filed on Dec. 14, 2018, provisional application No. 62/740,755, filed on Oct. 3, 2018.

(51) Int. Cl.
| | | |
|---|---|---|
| A61K 31/44 | (2006.01) | |
| A61K 9/00 | (2006.01) | |
| A61K 31/4412 | (2006.01) | |
| A61P 25/08 | (2006.01) | |
| A61P 25/14 | (2006.01) | |
| A61P 25/16 | (2006.01) | |

(52) U.S. Cl.
CPC ........ *A61K 31/4412* (2013.01); *A61K 9/0053* (2013.01); *A61K 31/44* (2013.01); *A61P 25/08* (2018.01); *A61P 25/14* (2018.01); *A61P 25/16* (2018.01)

(58) Field of Classification Search
CPC ................................ A61K 31/44; A61P 25/14
USPC ....................................................... 514/351
See application file for complete search history.

(56) References Cited

U.S. PATENT DOCUMENTS

| | | |
|---|---|---|
| 4,808,605 A | 2/1989 | Branca et al. |
| 6,451,991 B1 | 9/2002 | Martin et al. |
| 7,112,319 B2 | 9/2006 | Broderick et al. |
| 7,319,098 B2 | 1/2008 | Cho et al. |
| 7,875,636 B2 | 1/2011 | Barrow |
| 8,133,998 B2 | 3/2012 | Pajouhesh et al. |
| 8,263,627 B2 | 9/2012 | Barrow |
| 8,586,619 B2 | 11/2013 | Wu et al. |
| 8,637,513 B2 | 1/2014 | Barrow |
| 8,916,743 B2 | 12/2014 | Ohmori et al. |
| 10,292,989 B2 | 5/2019 | Jevtovic-todorovic et al. |
| 11,311,522 B1 | 4/2022 | Lee et al. |
| 2001/0049447 A1 | 12/2001 | Li et al. |
| 2003/0158143 A1 | 8/2003 | Gleave et al. |
| 2004/0198822 A1 | 10/2004 | Fraser |
| 2005/0245535 A1 | 11/2005 | Hangeland et al. |
| 2006/0003985 A1 | 1/2006 | Renger et al. |
| 2008/0293786 A1 | 11/2008 | Hahn et al. |
| 2009/0270413 A1 | 10/2009 | Galemmo, Jr. et al. |
| 2009/0325979 A1 | 12/2009 | Choi et al. |
| 2010/0004286 A1 | 1/2010 | Cho et al. |
| 2010/0056545 A1 | 3/2010 | Shin et al. |
| 2010/0094006 A1 | 4/2010 | Nam et al. |
| 2010/0137403 A1 | 6/2010 | Malstrom et al. |
| 2010/0151022 A9 | 6/2010 | Lenaerts |
| 2010/0216841 A1 | 8/2010 | Barrow et al. |
| 2014/0004186 A1 | 1/2014 | Hustvedt |
| 2014/0155444 A1 | 6/2014 | Tung et al. |
| 2017/0189342 A1 | 7/2017 | Nguyen et al. |
| 2018/0280357 A1 | 10/2018 | Maricich |

(Continued)

FOREIGN PATENT DOCUMENTS

| | | |
|---|---|---|
| CN | 102695506 A | 9/2012 |
| EP | 1757590 B1 | 12/2009 |
| EP | 1568695 B1 | 3/2016 |

(Continued)

OTHER PUBLICATIONS

Ashford, S. et al. (2006), "Goal Attainment For Spasticity Management Using Botulinum Toxin," Physiotherapy Research International 11(1):24-34.
Bailus, B.J. et al. (Jun. 2014). "The Prospect Of Molecular Therapy For Angelman Syndrome And Other Monogenic Neurologic Disorders," BMC Neurosci. 15(1):76, 7 pages.
Bain, P.G. et al. (1993). "Assessing Tremor Severity," Journal of Neurology, Neurosurgery & Psychiatry 56 (8):868-873.

(Continued)

*Primary Examiner* — Raymond J Henley, III
(74) *Attorney, Agent, or Firm* — Choate, Hall & Stewart LLP; Kristen C. Buteau; Alisha A. Contractor

(57) ABSTRACT

This invention relates to methods and materials for treating mammals having, or at risk of developing, one or more movement disorders (e.g., essential tremor, epilepsy, and/or Parkinson's disease). For example, compositions including one or more T-type calcium channel antagonists (e.g., one or more Cav3 antagonists such as CX-8998) are provided, as well as methods for administering such compositions to a mammal having, or at risk of developing, one or more movement disorders (e.g., essential tremor, epilepsy, and/or Parkinson's disease) to treat the mammal.

32 Claims, 83 Drawing Sheets

(56) References Cited

U.S. PATENT DOCUMENTS

| | | |
|---|---|---|
| 2020/0163943 A1 | 5/2020 | Maricich et al. |
| 2020/0197377 A1 | 6/2020 | Maricich |

FOREIGN PATENT DOCUMENTS

| | | |
|---|---|---|
| KR | 20090044924 A | 5/2009 |
| KR | 101679262 B1 | 11/2016 |
| WO | 1993004047 A1 | 3/1993 |
| WO | 2004003500 A1 | 1/2004 |
| WO | 2005007124 A2 | 1/2005 |
| WO | 2005009392 A2 | 2/2005 |
| WO | 2005007124 A3 | 12/2005 |
| WO | 2006023881 A2 | 3/2006 |
| WO | 2006023883 A2 | 3/2006 |
| WO | 2005009392 A3 | 4/2006 |
| WO | 2006023883 A3 | 7/2006 |
| WO | 2006098969 A2 | 9/2006 |
| WO | 2007002361 A2 | 1/2007 |
| WO | 2007002884 A2 | 1/2007 |
| WO | 2007007852 A1 | 1/2007 |
| WO | 2006098969 A3 | 3/2007 |
| WO | 2007002361 A3 | 4/2007 |
| WO | 2007002884 A3 | 4/2007 |
| WO | 2007073497 A2 | 6/2007 |
| WO | 2007120729 A3 | 1/2008 |
| WO | 2008007835 A1 | 1/2008 |
| WO | 2008018655 A1 | 2/2008 |
| WO | 2008033447 A1 | 3/2008 |
| WO | 2008033456 A1 | 3/2008 |
| WO | 2008033460 A2 | 3/2008 |
| WO | 2008033465 A1 | 3/2008 |
| WO | 2008033464 A3 | 5/2008 |
| WO | 2008050200 A1 | 5/2008 |
| WO | 2008110008 A1 | 9/2008 |
| WO | 2008117148 A1 | 10/2008 |
| WO | 2009009015 A1 | 1/2009 |
| WO | 2006023881 A3 | 4/2009 |
| WO | 2009054982 A1 | 4/2009 |
| WO | 2009054983 A1 | 4/2009 |
| WO | 2009054984 A1 | 4/2009 |
| WO | 2009035307 A3 | 5/2009 |
| WO | 2009056934 A1 | 5/2009 |
| WO | WO-2009/133128 A1 | 11/2009 |
| WO | 2009146540 A1 | 12/2009 |
| WO | 2009146539 A8 | 3/2010 |
| WO | 2010083264 A1 | 7/2010 |
| WO | 2010141842 A2 | 12/2010 |
| WO | WO-2011/093393 A1 | 8/2011 |
| WO | 2011019262 A3 | 9/2011 |
| WO | 2012094615 A2 | 7/2012 |
| WO | 2013169857 A1 | 11/2013 |
| WO | 2014110409 A2 | 7/2014 |
| WO | 2016203239 A1 | 12/2016 |
| WO | WO-2016/187718 A1 | 12/2016 |
| WO | WO-2017/044578 A1 | 3/2017 |
| WO | 2017070680 A1 | 4/2017 |
| WO | WO-2017/058353 A1 | 4/2017 |
| WO | WO-2017/117569 A1 | 7/2017 |
| WO | 2018200844 A1 | 11/2018 |
| WO | 2018200850 A1 | 11/2018 |
| WO | 2019175395 A1 | 9/2019 |
| WO | 2020072773 A9 | 7/2020 |
| WO | 2021067697 A1 | 4/2021 |

OTHER PUBLICATIONS

Bermejo-Pareja, F. (2011, e-pub Apr. 12, 2011). "Essential Tremor—A Neurodegenerative Disorder Associated With Cognitive Defects?" Nature Reviews Neurology 7(5):273-282.

Bermejo-Pareja, F. et al. (Sep. 14, 2012). "Cognitive Features Of Essential Tremor: A Review Of The Clinical Aspects And Possible Mechanistic Underpinnings," Tremor And Other Hyperkinetic Movements 2:13 pages.

Bezençon, O et al. (2017). "Milestones To The Discovery Of T-Type Calcium Channel Blockers For The Treatment Of Generalized Epilepsies," CHIMIA International Journal for Chemistry 71(10):722-729.

Blom, K.F. et al. (Nov. 8, 2004). "Preparative LC-MS Purification: Improved Compound Specific Method Optimization," J Comb. Chem. 6(6):874-883.

Bourinet, E. et al. (Jan. 26, 2005). "Silencing Of The Cav3.2 T-Type Calcium Channel Gene In Sensory Neurons Demonstrates Its Major Role In Nociception," EMBO J. 24(2):315-324.

Carter, P. et al. (May 1992). "Humanization of an Anti-p185HER2 Antibody for Human Cancer Therapy," Proc. Natl. Acad. Sci. USA 89:4285-4289.

Casillas-Espinosa, P.M. et al. (Aug. 14, 2015). "Z944, A Novel Selective T-Type Calcium Channel Antagonist Delays The Progression Of Seizures In The Amygdala Kindling Model," PLOS One 10(8):e0130012, 1-12.

Cech, T.R. (Nov. 25, 1988). "Ribozymes And Their Medical Implications," JAMA 260(20):3030-3034.

Chandran, V. et al. (2012). "Non-Motor Features In Essential Tremor," Acta Neurologica Scandinavica 125 (5):332-337.

clinicaltrials.gov (Apr. 5, 2017). "A Phase 2 RCT Study of CX-8998 for Essential Tremor," clinicaltrials.gov No. NCT03101241, 8 pages, retrieved from https://clinicaltrials.gov/ct2/show/NCT03101241.

Cribbs, L.L. et al. (Jul. 13, 1998). "Cloning And Characterization Of Alpha1h From Human Heart, A Member Of The T-Type Ca2+ Channel Gene Family," Circulation Research 83(1):103-109.

Elbe, R. et al. (2013, e-pub Sep. 3, 2013). "Task Force Report: Scales For Screening And Evaluating Tremor: Critique And Recommendations," Movement Disorders 28(13):1793-1800.

Elble, R. et al. (Jun. 26, 2008). "1094 The Essential Tremor Rating Assessment Scale (TETRAS)," Mov Disord. 23 (Suppl 1):S357.

Elble, R. et al. (Oct. 2012). "Reliability Of A New Scale For Essential Tremor," Movement Disorders 27 (12):1567-1569, 10 pages.

Elble, R.J. et al. (Jan. 1996). "Quantification Of Essential Tremor In Writing And Drawing," Movement Disorders: Official Journal Of The Movement Disorder Society 11(1):70-78.

Ertel, E.A et al. (Mar. 2000). "Nomenclature Of Voltage-Gated Calcium Channels," Neuron 25(3):533-535.

Fahn, S. et al. (1987). Recent Developments in Parkinson's Disease 2:153-163 and 293-304, 8 pages, as retrieved on May 21, 2021 from https://www.parkinsons.va.gov/resources/UPDRS.asp.

Fahn, S. et al. (1988). "Clinical Rating Scale For Tremor," Parkinson's Disease And Movement Disorders 2:225-234.

Flatters, S.J.L. (Jun. 1, 2005). "T-Type Calcium Channels: A Potential Target For The Treatment Of Chronic Pain," Drugs Future 30(6):573-580.

Gadde, K.M. et al. (Aug. 15, 2007). "Combination Therapy Of Zonisamide And Bupropion For Weight Reduction In Obese Women: A Preliminary, Randomized, Open-Label Study," Journal of Clinical Psychiatry 68(8):1226-1229.

George, M.S. et al. (Dec. 1994). "Social Phobia Secondary To Physical Disability: A Review Of Benign Essential Tremor (BET) And Stuttering," Psychosomatics 35(6):520-523, 7 pages.

Giordanetto, F. et al. (Jan. 1, 2011). "T-Type Calcium Channels Inhibitors: A Patent Review," Expert Opin. Ther. Pat. 21(1):85-101.

Handforth, A. et al. (2005). "Pharmacologic Evidence for Abnormal Thalamocortical Functioning in GABAA Receptor β3 Subunit-Deficient Mice, a Model of Angelman Syndrome," Epilepsia 46(12):1860-1870.

Hanyu, H. (2007). "Nilvadipine Prevents Cognitive Decline In Patients With Mild Cognitive Impairment," Intl J Geriatr Psychiatry 22:1264-1266.

Haseloff, J. et al. (Aug. 1988). "Simple RNA Enzymes With New And Highly Specific Endoribonuclease Activities," Nature 334(6183):585-591.

Haubenberger, D. et al. (Sep. 2016). "Transducer-Based Evaluation Of Tremor," Movement Disorders 31 (9):1327-1336, 21 pages.

Hoffman, J.D. et al. (Aug. 30, 2011-Sep. 3, 2011). "Objective Measure Of Upper Extremity Motor Impairment In Parkinson's Disease With Inertial Sensors," Conf Proc IEEE Eng Med Biol Soc., 4378-4381.

(56) References Cited

OTHER PUBLICATIONS

Huang, H.-S. et al. (Jan. 2012). "Topoisomerase Inhibitors Unsilenced The Dormant Allele Ofube3a In Neurons", Nature 481(7380):185-189, 14 pages.
Huguenard, J.R. et al. (Sep. 1, 1994). "Intrathalamic Rhythmicity Studied In Vitro: Nominal T-Current Modulation Causes Robust Antioscillatory Effects," J Neuroscience 14(9):5485-5502.
Iannetti, P. et al. (Jul. 1, 2009, e-pub. Mar. 2009). Addition Of Verapamil In The Treatment Of Severe Myoclonic Epilepsy In Infancy, Epilepsy Research 85(1):89-95.
Iftinca, M.C. et al. (2009, e-pub. Nov. 29, 2008). "Regulation Of Neuronal T-Type Calcium Channels," Trends In Pharmacological Sciences 30(1):32-40.
Iinuma, K et al. (Dec. 1, 2004). "Clinical Efficacy Of Zonisamide In Childhood Epilepsy After Long-Term Treatment: A Postmarketing, Multi-Institutional Survey," Seizure GB, 13:534-539.
International Preliminary Report on Patentability issue date of Oct. 29, 2019, for Patent Application No. PCT/US2018/029610, filed Apr. 26, 2018, 5 pages.
International Preliminary Report on Patentability issue date of Apr. 24, 2018 for Patent Application No. PCT/US2016/058487, filed Oct. 24, 2016, 6 pages.
International Preliminary Report on Patentability issue date of Oct. 29, 2019, for Patent Application No. PCT/US2018/029616, filed Apr. 26, 2018, 5 pages.
International Search Report and Written Opinion of the Searching Authority mailed Jul. 11, 2018, for Patent Application No. PCT/US2018/029616, filed Apr. 26, 2018, 7 pages.
International Search Report and Written Opinion of the Searching Authority mailed May 8, 2018, for Patent Application No. PCT/US2018/18356, filed Feb. 15, 2018, 9 pages.
International Search Report and Written Opinion of the Searching Authority mailed on Dec. 10, 2019, for Patent Application No. PCT/US2019/054498, 13 pages.
International Search Report and Written Opinion of the Searching Authority mailed on Jan. 3, 2017, for Patent Application No. PCT/US2016/058487, filed Oct. 24, 2016, 8 pages.
International Search Report and Written Opinion of the Searching Authority mailed on Jan. 13, 2021, for Patent Application No. PCT/US2020/053944, 8 pages.
International Search Report and Written Opinion of the Searching Authority mailed on Jul. 19, 2018, for Patent Application No. PCT/US2018/029610, filed Apr. 26, 2018, 7 pages.
Jefferies, A.C. et al. (Feb. 1989). "A Catalytic 13-Mer Ribozyme," Nucleic Acids Res. 17(4):1371-1377.
Jiang, Y.-H., et al. (Oct. 1998). "Mutation Of The Angelman Ubiquitin Ligase In Mice Causes Increased Cytoplasmic P53 And Deficits Of Contextual Learning And Long-Term Potentiation," Neuron 21(4):799-811.
Jinnah, H. et al. (2020). "Efficacy and Safety of CX-8998 in T-CALM, a Randomized, Double-Blind, Placebo-Controlled, Phase 2a Trial in Participants With Essential Tremor: Subgroup Analysis by Baseline Tremor Severity," International Parkinson and Movement Disorder Society, Virtual Congress 2020, Sep. 12-14, 2020, 1 page.
Jinnah, H.A. et al. (2020). "Efficacy And Safety Of CX-8998 In T-Calm, A Randomized, Double-Blind, Placebo-Controlled, Phase 2a Trial In Participants With Essential Tremor: Subgroup Analysis By Baseline Tremor Severity," Virtual presentation presented at American Academy of Neurology, May 18, 2020, 12 pages.
Jinnah, H.A. et al. (Apr. 14, 2020). "Efficacy And Safety Of CX-8998 In T-CALM, A Randomized, Double-Blind, Placebo-Controlled, Phase 2a Trial In Participants With Essential Tremor: Subgroup Analysis By Baseline Tremor Severity (1842)," Neurology 94 (Suppl 15), 7 pages, Abstract Only.
Jinnah, H.A. et al. (Sep. 2020). "Efficacy And Safety Of CX-8998 In T-CALM, A Randomized, Double-Blind, Placebo-Controlled, Phase 2a Trial In Participants With Essential Tremor: Subgroup Analysis By Baseline Tremor Severity. [MDS 2020 Abstract 1474]," Mov Disord. 35 (Suppl 1):S687, 3 pages.

Jones, P. et al. (May 29, 1986). "Replacing The Complementarity-Determining Regions In A Human Antibody With Those From A Mouse," Nature 321:522-525.
Kamper, S.J. et al. (2009). "Global Rating Of Change Scales: A Review Of Strengths And Weaknesses And Considerations For Design," Journal of Manual & Manipulative Therapy 17(3):163-170.
Keened, L. et al. (1989). "Flunarizine As A Supplementary Medication In Refractory Childhood Epilepsy A Double-Blind Crossover Study", Canadian Journal Of Neurological Sciences 16(2):191-193.
Khan, F. et al. (Apr. 2008). "Use Of Goal Attainment Scaling In Inpatient Rehabilitation For Persons With Multiple Sclerosis," Archives Of Physical Medicine And Rehabilitation 89(4):652-659.
Kim, S.-H. et al. (Dec. 1987). "Three-Dimensional Model Of The Active Site Of The Self-Splicing Rrna Precursor Of Tetrahymena," Proc. Natl. Acad. Sci. USA 84(24):8788-8792.
Kiresuk, T.J. et al. (1968). "Goal Attainment Scaling: A General Method For Evaluating Comprehensive Community Mental Health Programs," Community Mental Health Journal 4(6):443-453.
Lee, J,-H. et al. (Mar. 15, 1999). "Cloning And Expression Of A Novel Member Of The Low Voltage-Activated T-Type Calcium Channel Family," Journal of Neuroscience 19(6):1912-1921.
Lee, M. (2019). "The Biology Of Pathological Oscillations In The Brain: Potential Novel Targets For Tremor Disorders," International Congress of Parkinson's Disease and Movement Disorders, Nice, France, Sep. 22-26, 2019, 21 pages.
Lee, M. et al. (Apr. 9, 2018). Reversal Of Allodynia And Neurophysiological Outcomes By CX-8998, A Potent, 1-3 Selective T-Type Calcium Channel Modulator, In A Model Of Bortezomib Induced Peripheral Neurotoxicity (S7.004), Neurology 90:6 pages (Abstract Only).
Lee, M.S. et al. (2018). "Therapeutic Exposures of CX-8998, A Potent, Selective and State Dependent T-type Calcium Channel (Cav3) Antagonist with Dose Dependent Efficacy in Cav3 Driven Neurological Models," Mov Disord. 33(suppl 2):S10, Poster presented at International Congress of the Parkinson and Movement Disorder Society, Oct. 5-9, 2018, Hong Kong.
Lee, M.S. et al. (2018). "Therapeutic Exposures of CX-8998, A Potent, Selective Cav3 Channel Antagonist With Dose Dependent Efficacy in Cav3 Driven Neurological Models," Neurotherapeutics 15:830, Poster #31 presented at American Society for Experimental Neurotherapeutics, Mar. 7-10, 2018, Rockville, MD.
Llinás, R.R. (2003). "Thalamo-Cortical Dysrhythmia Syndrome: Neuropsychiatric Features," An R Acad Nac Med (Madr). 120(2):267-290, 52 pages, English Translation.
Llinás, R.R. et al. (2007). "γ-Band Deficiency And Abnormal Thalamocortical Activity In P/Q-Type Channel Mutant Mice," Proceedings of the National Academy of Sciences 104(45):17819-17824.
Long, M.A. et al. (Dec. 15, 2002). "Rhythmicity Without Synchrony In The Electrically Uncoupled Inferior Olive," Journal of Neuroscience 22(24):10898-10905.
Lopez, S.J. et al. (Jan. 4, 2019). "UBE3A: An E3 Ubiquitin Ligase With Genome-Wide Impact In Neurodevelopmental Disease," Frontiers In Molecular Neuroscience, 11(476):1-8.
Lorenz, D. et al. (2006). "Quality Of Life And Personality In Essential Tremor Patients," Movement Disorders: Official Journal Of The Movement Disorder Society 21(8):1114-1118.
Louis, E.D. (Oct. 2000). "Essential Tremor," Arch Neurol. 57(10):1522-1524, 5 pages.
Louis, E.D. et al. (1998). "How Common Is The Most Common Adult Movement Disorder? Estimates Of The Prevalence Of Essential Tremor Throughout The World," Movement Disorders: Official Journal Of The Movement Disorder Society 13(1):5-10.
Louis, E.D. et al. (2010). "How Common Is The Most Common Adult Movement Disorder? Update On The Worldwide Prevalence Of Essential Tremor," Movement Disorders 25(5):534-541.
Louis, E.D. et al. (Jul. 2015). "Tremor-Related Quality Of Life: A Comparison Of Essential Tremor Vs. Parkinson's Disease Patients." Parkinsonism & Related Disorders 21(7):729-735, 20 pages.
Maricich, Y. et al. (2017). "TETRAS Applicability and Study Design in Randomized, Placebo Controlled Clinical Evaluation of Cav3 modulation for patients with essential tremor," Mov Disord.

(56) References Cited

OTHER PUBLICATIONS

32(suppl 2):S296, Poster presented at International Congress of the Parkinson and Movement Disorder Society, Jun. 4-8, 2017, Vancouver, BC, Canada.

McGivern, J.G. (Mar. 2006). "Targeting N-Ty1)E And T-Ty1)E Calcium Channels For The Treatment Of Pain," Drug Discovery Today 11(5-6):245-253.

Miller, A.R. et al. (Feb. 2014). "Mapping Genetic Modifiers Of Survival In A Mouse Model of Dravet Syndrome," Genes Brain Behav. 13(2):163-172.

Mitsi, G. et al. (Jun. 13, 2017). "Biometric Digital Health Technology For Measuring Motor Function In Parkinson's Disease: Results From A Feasibility And Patient Satisfaction Study," Frontiers In Neurology 8:273, 5 pages.

Molineux, M.L. et al. (Apr. 4, 2006). "Specific T-Type Calcium Channel Isoforms Are Associated With Distinct Burst Phenotypes In Deep Cerebellar Nuclear Neurons," Proc Natl Acad Sci USA 103(14):5555-5560.

Mostile, G. et al. (2010). "Correlation Between Kinesia System Assessments And Clinical Tremor Scores In Patients With Essential Tremor," Movement Disorders 25(12):1938-1943.

Nicoll, R.A. (Jan. 18, 2017). "A Brief History Of Long-Term Potentiation," Neuron 93(2):281-290.

Nolt, D.H. et al. (Dec. 15, 2003). "Assessment Of Anticonvulsant Effectiveness And Safety In Patients With Angelman's Syndrome Using An Internet Questionnaire," American Journal Of Health-System Pharmacy 60(24):2583-2587.

Odgerel, Z. et al. (2019, e-pub. Jan. 16, 2018). "Whole Genome Sequencing And Rare Variant Analysis In Essential Tremor Families," PloS One 14(8):e0220512.

Ondo, W. et al. (2020). "Efficacy and Safety of the T-Type Calcium Channel Modulator CX-8998 in T-CALM, a Randomized, Double-Blind, Placebo-Controlled, Phase 2a Trial in Participants with Essential Tremor," Annals of Neurology. vol. 88. 111 River St, Hoboken 07030-5774, NJ USA: 3 pages.

Ondo, W. et al. (2020). "Efficacy and Safety of the T-Type Calcium Channel Modulator CX-8998 in T-CALM, a Randomized, Double-Blind, Placebo-Controlled, Phase 2a Trial in Participants With Essential Tremor," Annual Meeting of the American Neurological Association, Virtual Meeting, Oct. 4-9, 2020, 1 page.

Papapetropoulos, S. et al. (2008). "A Questionnaire-Based (UM-PDHQ) Study Of Hallucinations In Parkinson's Disease," BMC Neurology 8(1):1-8.

Papapetropoulos, S. et al. (2018). "A Novel, State-dependent Cav3 Channel Antagonist in Phase 2 Development for Tremor and Epilepsy," Neurotherapeutics 15:832, Poster presented at American Society for Experimental Neurotherapeutics, Mar. 7-10, 2018, Rockville, MD, 819-835.

Papapetropoulos, S. et al. (2018). "A Phase 2 Efficacy Study of an Oral, Potent and Selective T-Type Calcium (Cav3) Modulator in Essential Tremor Patients (T-CALM): Design and Dose Selection Rationale," Neurology. 2018;90 (suppl 15):P6.060, Poster presented at American Academy of Neurology, Apr. 21-27, 2018, Los Angeles, CA, 1 page.

Papapetropoulos, S. et al. (2018). "A Proof-of-Principle Quantitative EEG Study of an Oral, Potent and Selective T-Type Calcium Modulator in Healthy Volunteers," 90(suppl 15):P4.261, Poster presented at American Academy of Neurology, Apr. 21-27, 2018, Los Angeles, CA, 6 pages.

Papapetropoulos, S. et al. (2018). "Proof-of-Principle Quantitative EEG Study of CX-8998, an Oral, Potent and Selective T-Type Calcium Antagonist in Development for Symptomatic Treatment of Essential Tremor and Parkinson's Disease Tremor," Mov Disord. 33(suppl 2):S22, Poster presented at International Congress of the Parkinson and Movement Disorder Society, Oct. 5-9, 2018, Hong Kong.

Papapetropoulos, S. et al. (2019). "Efficacy Results From A Phase 2, Double-Blind, Placebo-Controlled Study Of CX-8998 A State-Dependent T-Type Calcium (Cav3) Channel Modulator In Essential Tremor Patients (T-CALM)," American Academy of Neurology, Philadelphia, PA, May 4-10, 2019, 16 pages.

Papapetropoulos, S. et al. (Jun. 11, 2019). "A Phase 2, Randomized, Double-Blind, Placebo-Controlled Trial Of CX-8998, A Selective Modulator Of The T-Type Calcium Channel In Inadequately Treated Moderate To Severe Essential Tremor: T-CALM Study Design And Methodology For Efficacy Endpoint And Digital Biomarker Selection," Frontiers in Neurology 10:597, 11 pages.

Papapetropoulos, S. et al. (Mar. 25, 2021). "A Phase 2 Proof-of-Concept, Randomized, Placebo-Controlled Trial of CX-8998 in Essential Tremor," Mov Disord., 8 pages.

Park, Y-G. et al. (2010). "Cav3.1 Is A Tremor Rhythm Pacemaker In The Inferior Olive," Proceedings Of The National Academy of Sciences 107(23):10731-10736.

Park, Y-G. et al. (2013). "The Potential Roles Of T-Type Ca2+ Channels In Motor Coordination," Frontiers In Neural Circuits 7:172, 11 pages.

Pasek, J.G. et al. (Sep. 2015, e-pub Sep. 1, 2016). "Differential Camkii Regulation By Voltage-Gated Calcium Channels In The Striatum," Mol. Cell. Neurosci. 68:234-243, 26 pages.

Perez-Reyes, E. (1998). "Molecular Characterization Of A Novel Family Of Low Voltage-Activated, T-Type, Calcium Channels," Journal Of Bioenergetics And Biomembranes 30(4):313-318.

Peturssion, S. et al. (Nov. 1997). "Protecting Groups in Carbohydrate Chemistry," J Chem. Educ. 74(11):1297-1303.

Powell, K.L. et al. (May 2014, e-pub Jul. 9, 2013). "Low Threshold T-Type Calcium Channels As Targets For Novel Epilepsy Treatments, " British Journal of Clinical Pharmacology 77(5):729-739.

Pubchem (Jun. 14, 2012). "[(IS,2S)-6-Fluoro-2-[2-[methyl-[5-(1-methylbenzimidazol-2-yl)pentyl]-1-propan-2-yl-3,4-dihydro-1H-naphthalen-2-yl] N-butylcarbamate," CID 57173592, 10 pages, as retrieved on http://pubchem.ncbi.nim.nih.gov/compound/57173592.

Pulliam, C.L. et al. (2014). "Continuous In-Home Monitoring Of Essential Tremor," Parkinsonism & Related Disorders 20(1):37-40.

Radin, M.J. et al. (Nov. 1993). "Treatment of Obese Female and Male SHHF/Mcc-facp Rats with Antihypertensive Drugs, Nifedipine and Enalapril: Effects on Body Weight, Fat Distribution, Insulin Resistance and Systolic Pressure," Obesity Research 1(6):433-442.

Reger, T.S. et al. (2011, e-pub Jan. 26, 2011) "Pyridyl Amides As Potent Inhibitors Of T-Type Calcium Channels." Bioorganic & Medicinal Chemistry Letters 21(6):1692-1696.

Riechmann, L. et al. (Mar. 24, 1988). "Reshaping Human Antibodies for Therapy," Nature 33(6162):323-327.

Siegrist, R. et al. (2016). "Structure-Activity Relationship, Drug Metabolism And Pharmacokinetics Properties Optimization, And In Vivo Studies Of New Brain Penetrant Triple T-Type Calcium Channel Blockers." Journal Of Medicinal Chemistry 59(23):10661-10675.

Silva-Santos, S. et al. (May 2015). "Ube3a Reinstatement Identifies Distinct Developmental Windows In A Murine Angelman Syndrome Model," J. Clin. Invest. 125(5):2069-2076.

Sims, M.J. et al. (Aug. 15, 1993). "A Humanized CD18 Antibody Can Block Function Without Cell Destruction," J. Immunol. 151(4):2296-2308.

So-Hee, E. et al. (Apr. 1, 2011). "Comparative Trial Of Low- And High-Dose Zonisamide As Monotherapy For Childhood Epilepsy", Seizure 20(7):558-563.

Still, W.C. et al. (Jul. 1978). "Rapid Chromatographic Technique For Preparative Separations With Moderate Resolution," The Journal of Organic Chemistry 43(14):2923-2925.

Tröster, A.I. et al. (2005). "Quality Of Life In Essential Tremor Questionnaire (QUEST): Development And Initial Validation." Parkinsonism & Related Disorders 11(6):367-373.

U.S. Appl. No. 17/282,730, Lee et al., filed Apr. 2, 2021.(Not submitted herewith pursuant to the waiver of 37 C.F.R. § 1.98(a)(2)(iii) issued by the Office on Sep. 21, 2004).

Verhoeyen, M. et al. (Mar. 25, 1988). "Reshaping Human Antibodies: Grafting An Antilysozyme Activity," Science 239(4857):1534-1536.

Voller, B. et al. (Apr. 2014). "Alcohol Challenge And Sensitivity To Change Of The Essential Tremor Rating Assessment Scale," Movement Disorders 29(4): 555-558, 10 pages.

(56) References Cited

OTHER PUBLICATIONS

Xiang, Z. et al. (Dec. 21, 2011, e-pub Oct. 17, 2011). "The Discovery and Characterization of ML218: A Novel, Centrally Active T-Type Calcium Channel Inhibitor with Robust Effect in STN Neurons and in a Rodent Model of Parkinson's Disease," ACS Chemical Neuroscience 2(12):730-742.

Yamauchi, T. et al. (May 2005). "Neuronal Ca2+/Calmodulin-Dependent Protein Kinase II-Discovery, Progress In A Quarter Of A Century, And Perspective: Implication For Learning And Memory," Biological and Pharmaceutical Bulletin 28(8):1342-1354.

Yağmur, I, et al. (May 28, 2016). "Benign Prostatic Hyperplasia: Case Report Of A 17-Year-Old," Journal of Pediatric Urology 12(4):267-e1, 8 pages. (Abstract Only).

Zamponi, G.W. et al. (Oct. 2015). "The Physiology, Pathology, And Pharmacology Of Voltage-Gated Calcium Channels And Their Future Therapeutic Potential," Pharmacological Reviews 67(4):821-870.

Zesiewicz, T.A. et al. (Nov. 8, 2011). "Evidence-Based Guideline Update: Treatment Of Essential Tremor: Report Of The Quality Standards Subcommittee Of The American Academy Of Neurology," Neurology 77(19):1752-1755.

Didsbury, J. et al., Abstracts of 20th Annual ASENT Meeting, Neurotherapeutics, 15:819-835 (2018).

Egan, M.F. et al., Randomized controlled study of the T-type calcium channel antagonist MK-8998 for the treatment of acute psychosis in patients with schizophrenia, Hum. Psychopharmacol., 28(2):124-133 (2013).

Matsunaga, S. et al., Memantine monotherapy for Alzheimer's disease: a systematic review and meta-analysis, PLoS One, 10(4):e0123289 (2015).

Miwa, H. and Kondo, T., T-type calcium channel as a new therapeutic target for tremor, Cerebellum, 10(3):563-569 (2011).

Nicita, F. et al., Efficacy of verapamil as an adjunctive treatment in children with drug-resistant epilepsy: a pilot study, Seizure, 23(1):36-40 (2014).

Plosker, G.L., Stiripentol : in severe myoclonic epilepsy of infancy (dravet syndrome), CNS Drugs, 26(11):993-1001 (2012).

Porter, V.R. et al., Frequency and characteristics of anxiety among patients with Alzheimer's disease and related dementias, J. Neuropsychiatry Clin. Neurosci., 15(2):180-186 (2003).

Zadionchenko, V.S., Use of Calcium Channel Blockers in Patients With Cardiovascular Pathology: Focus on Diltiazem, Consilium Medicum 17(5):54-63, Russian Language only, (2015).

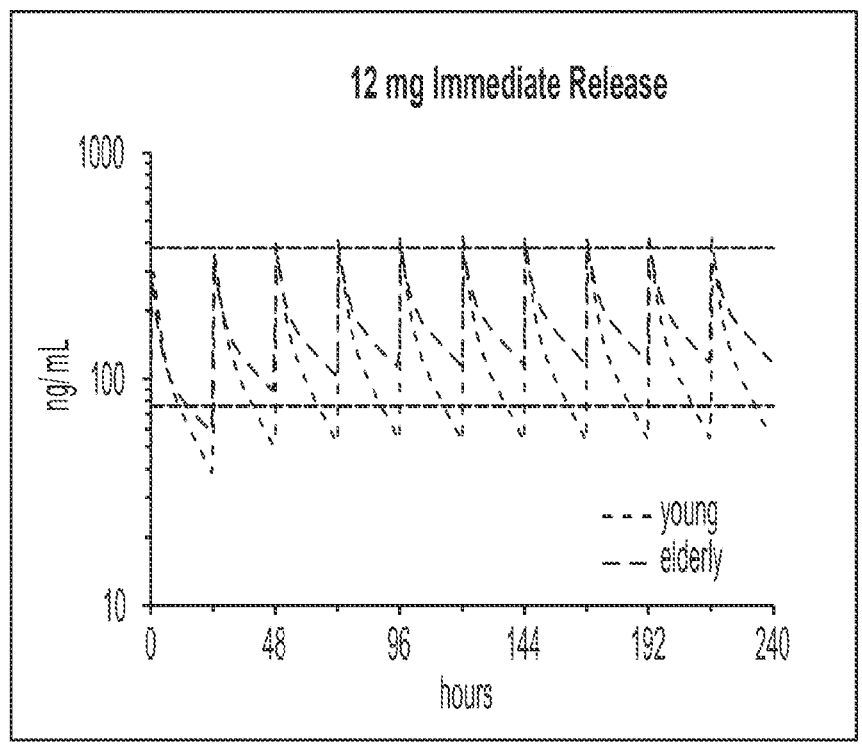
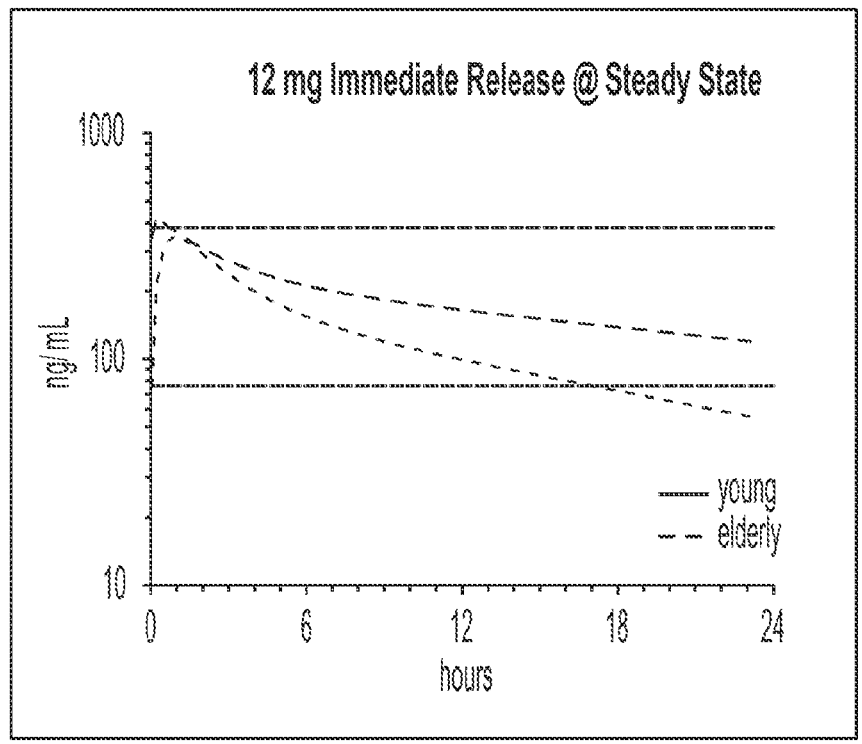
FIG. 28

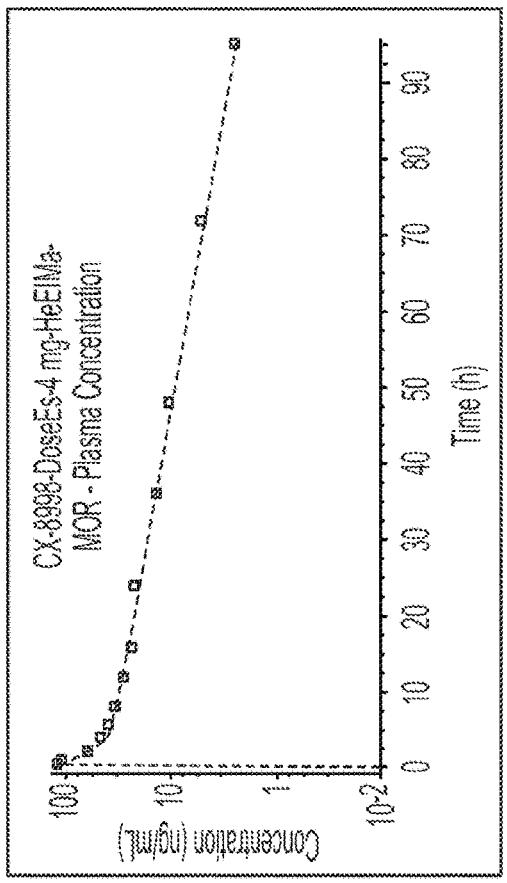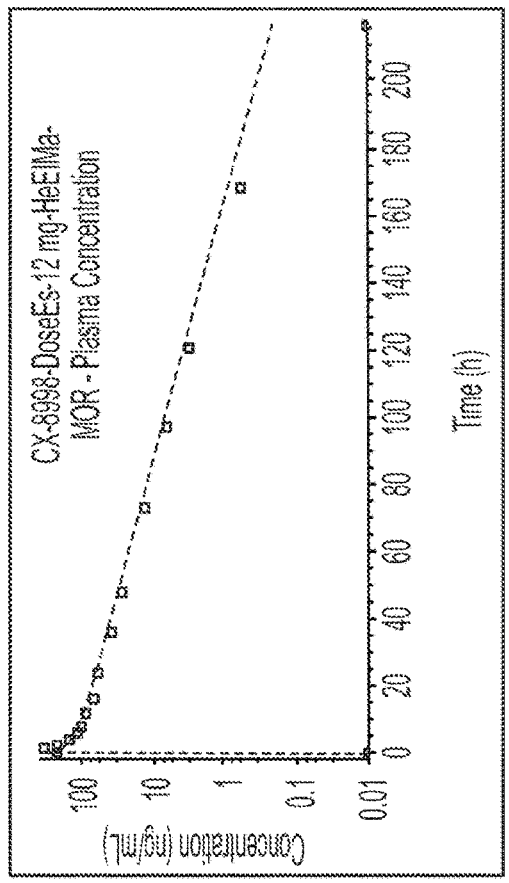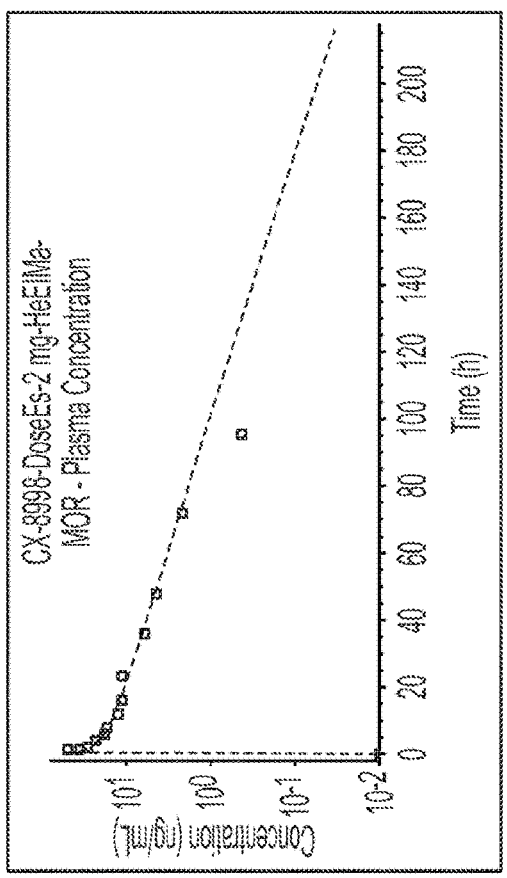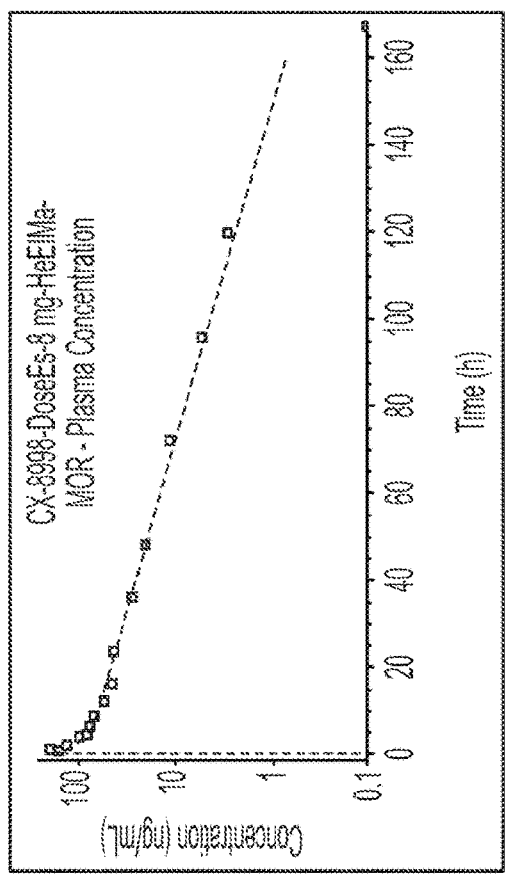
FIG. 31

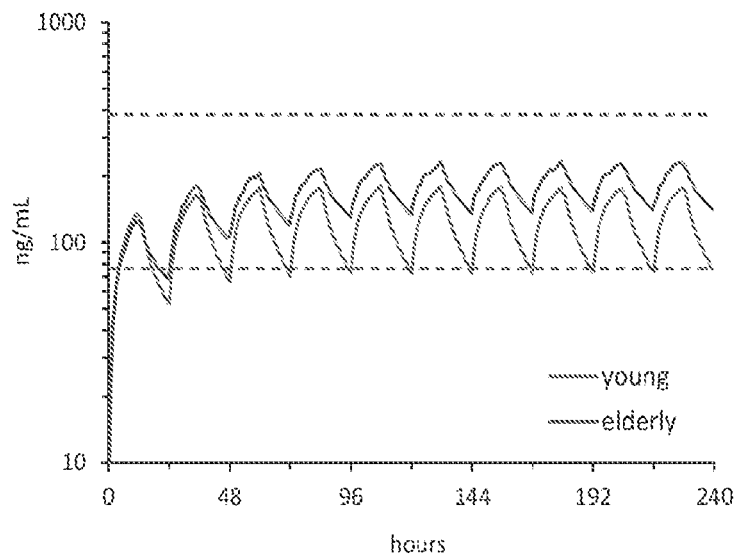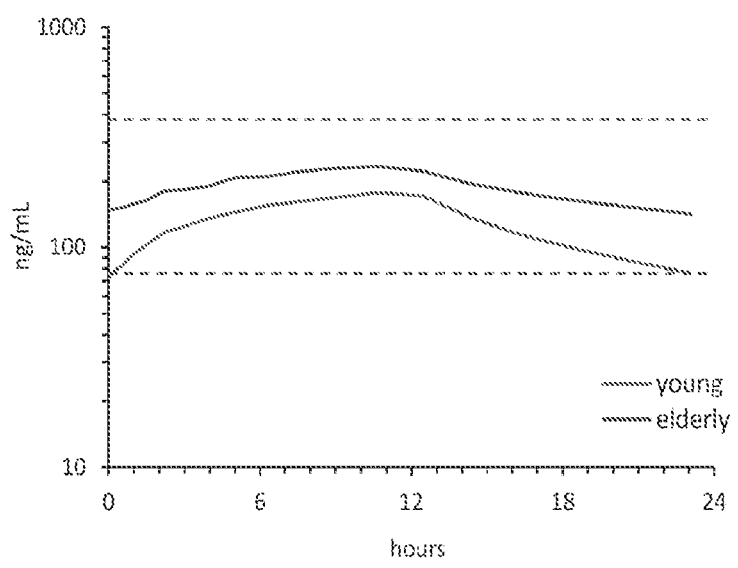
FIG. 38

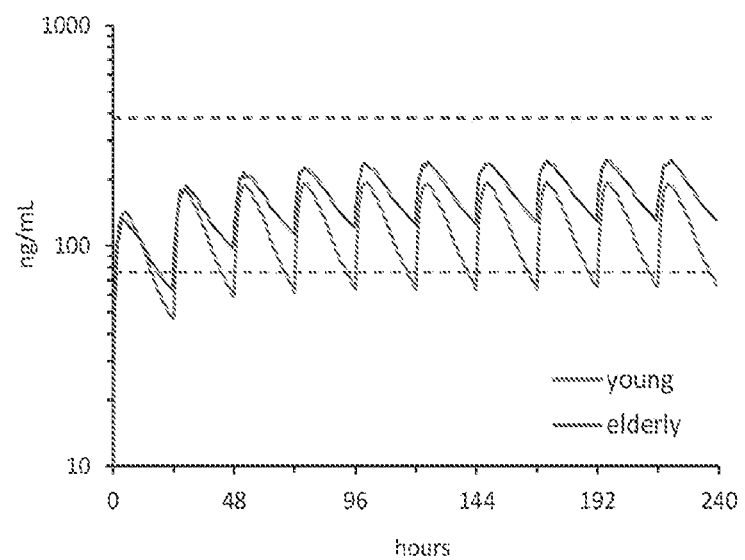
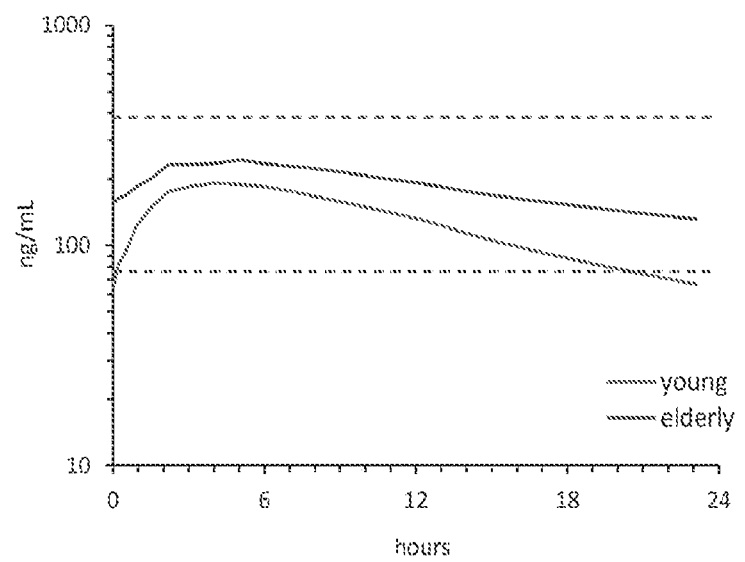
FIG. 39

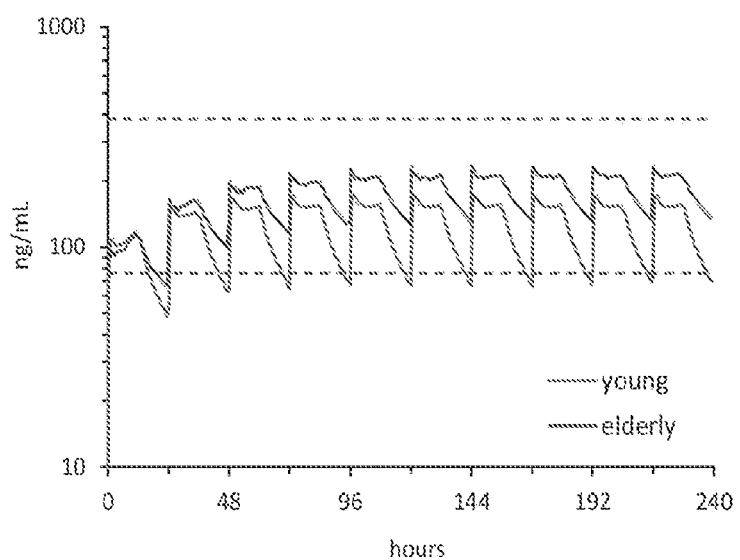
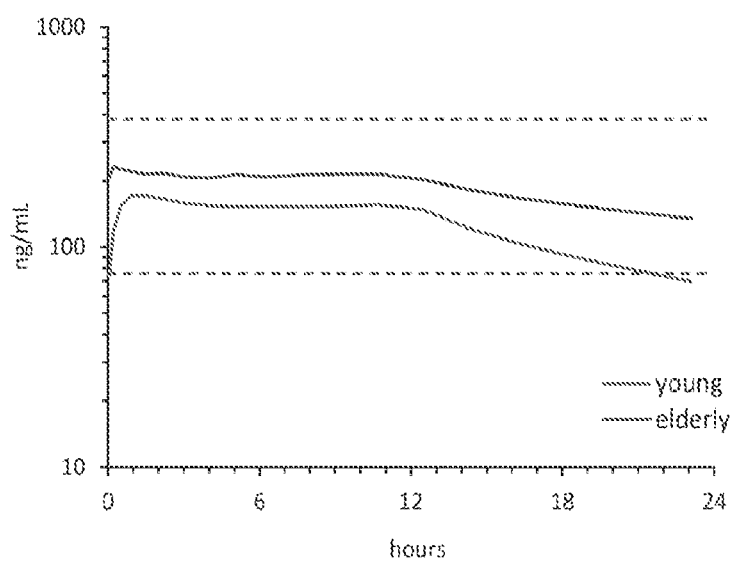
FIG. 40

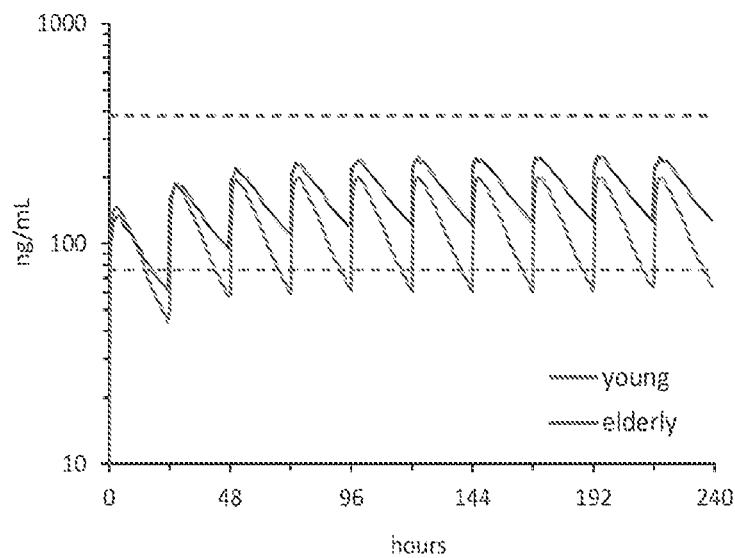
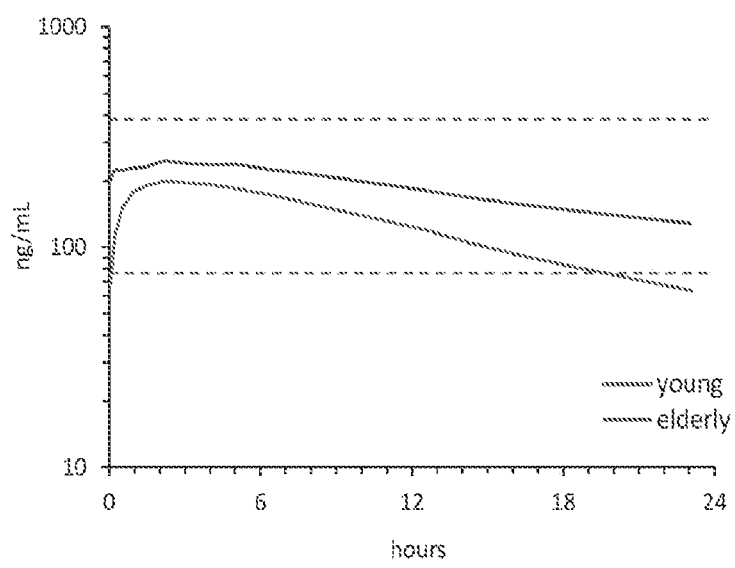
FIG. 41

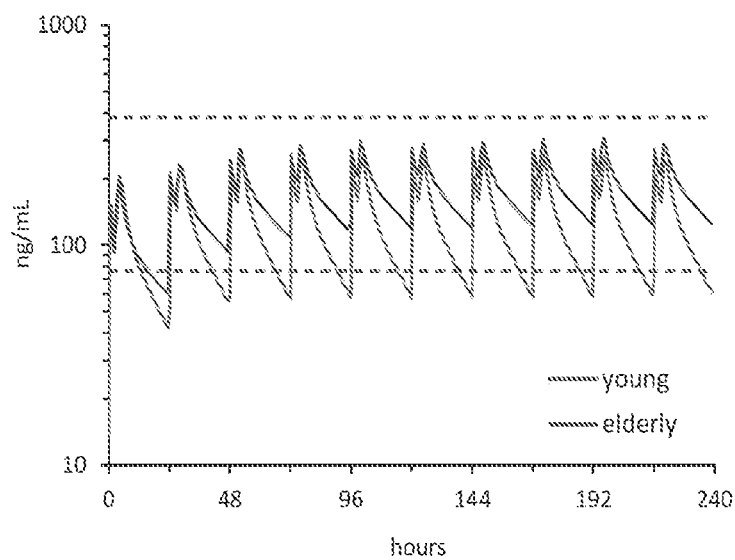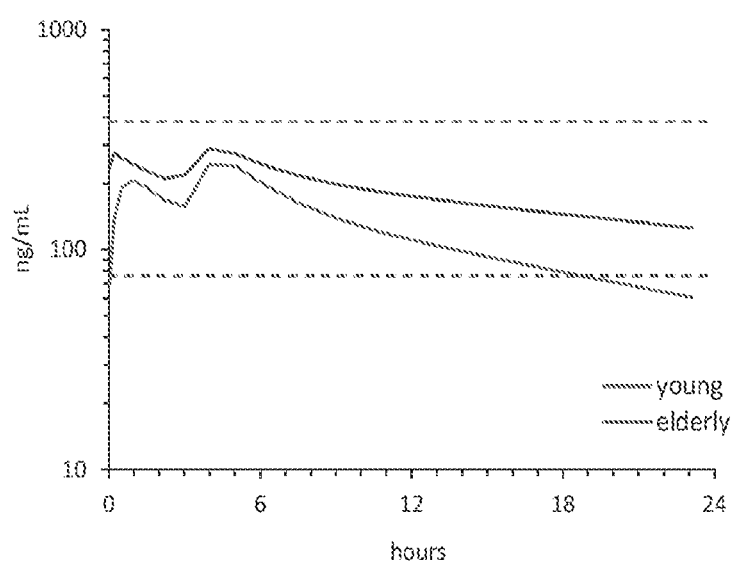
FIG. 42

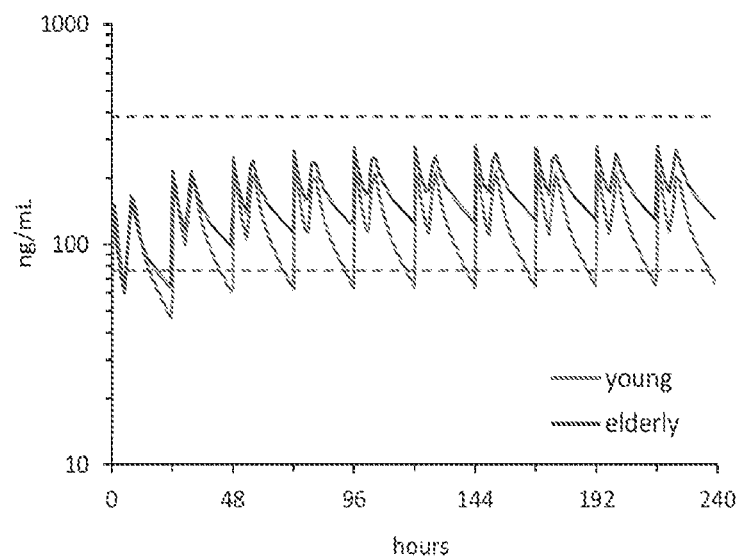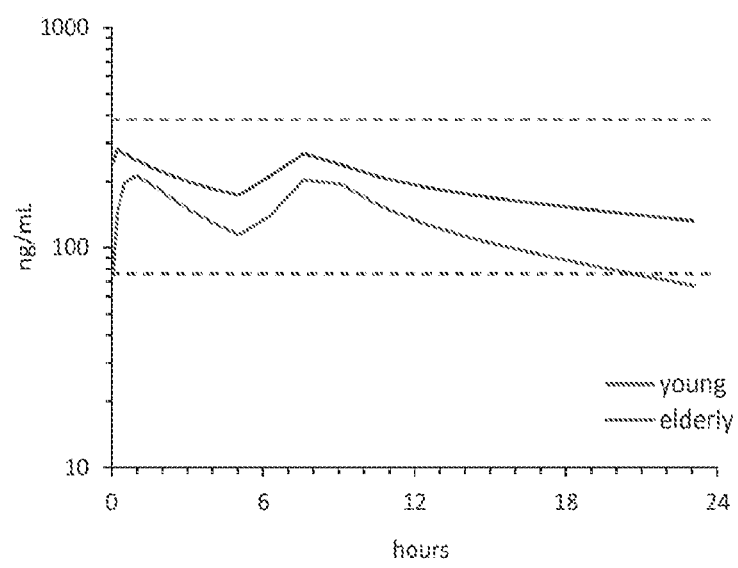
FIG. 43

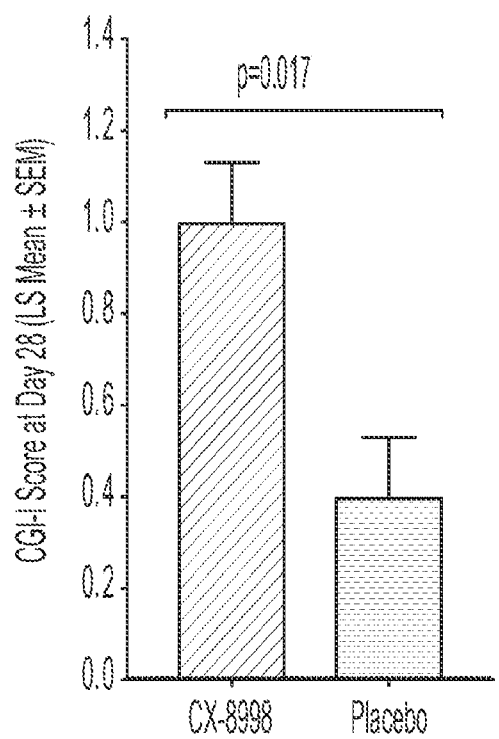 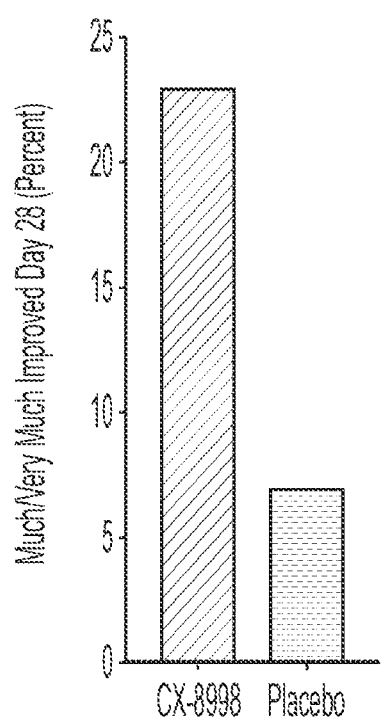
FIG. 50A                    FIG. 50B

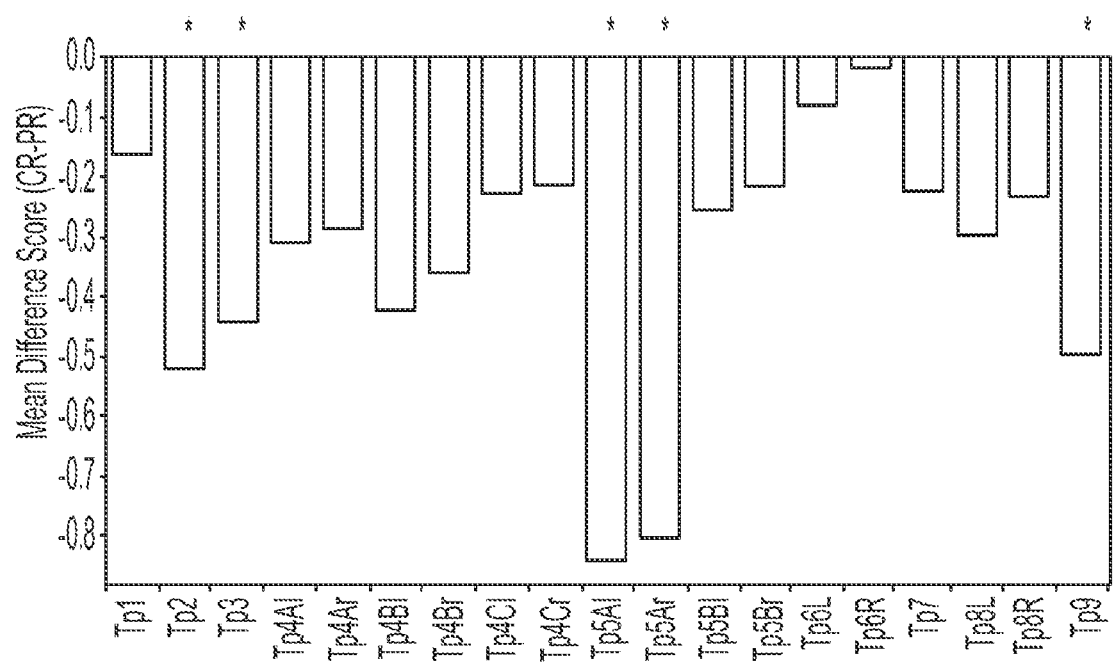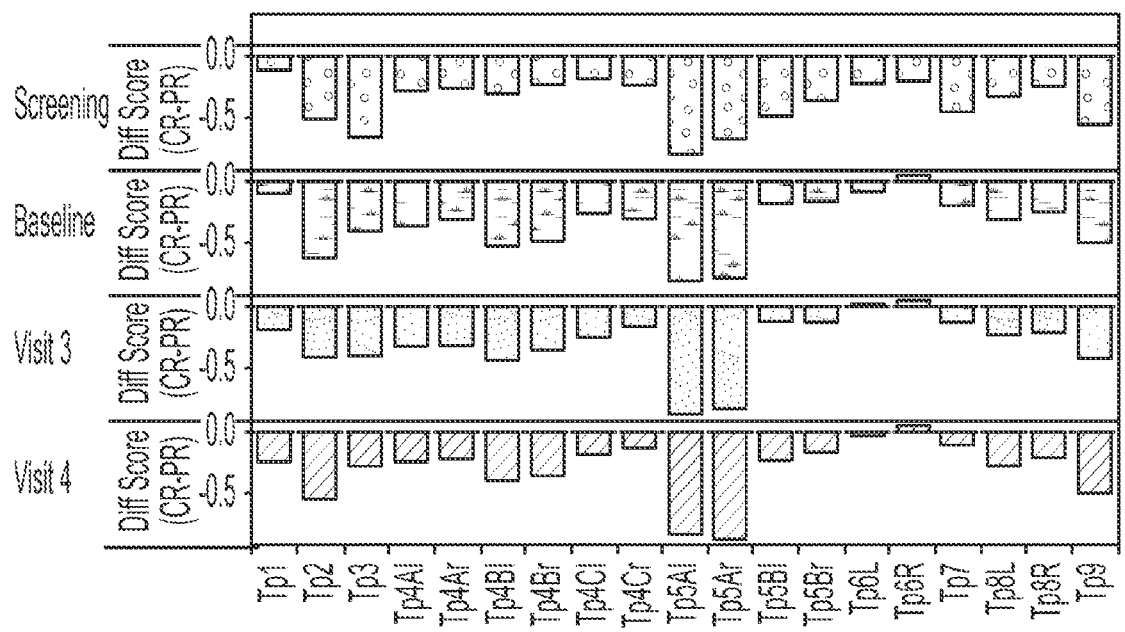
FIG. 51

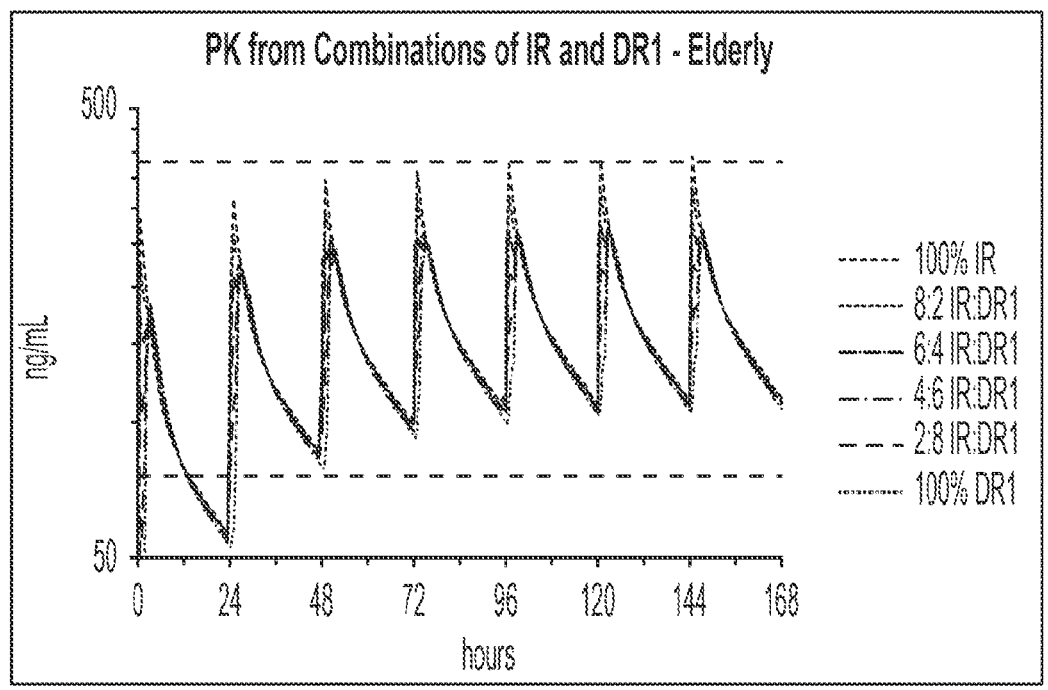
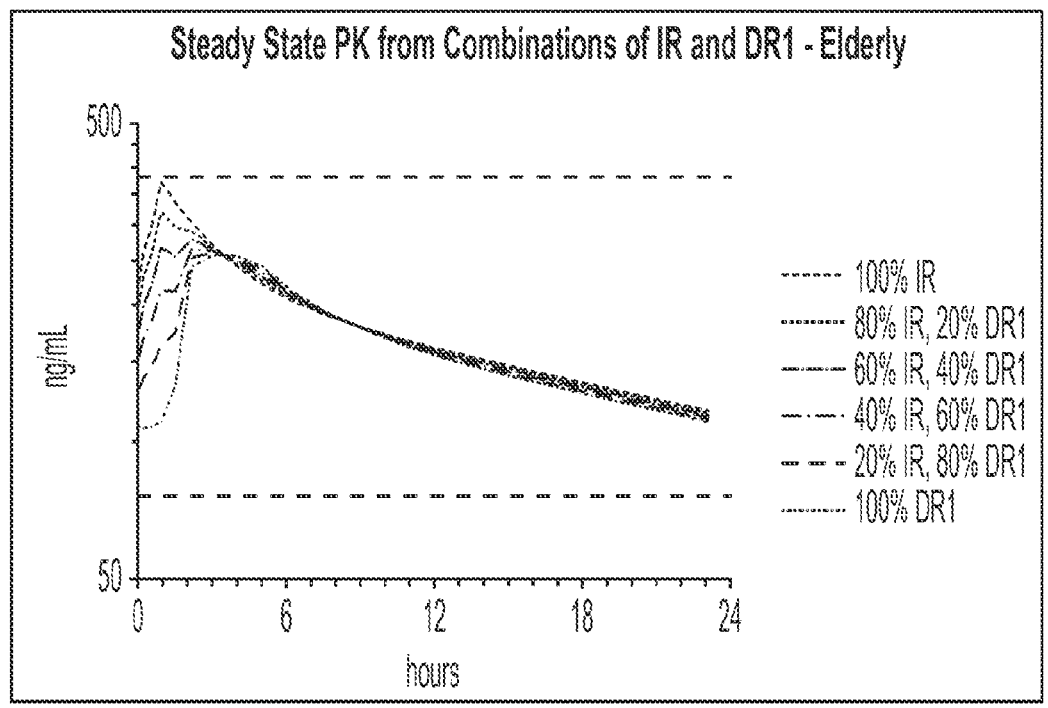
FIG. 58

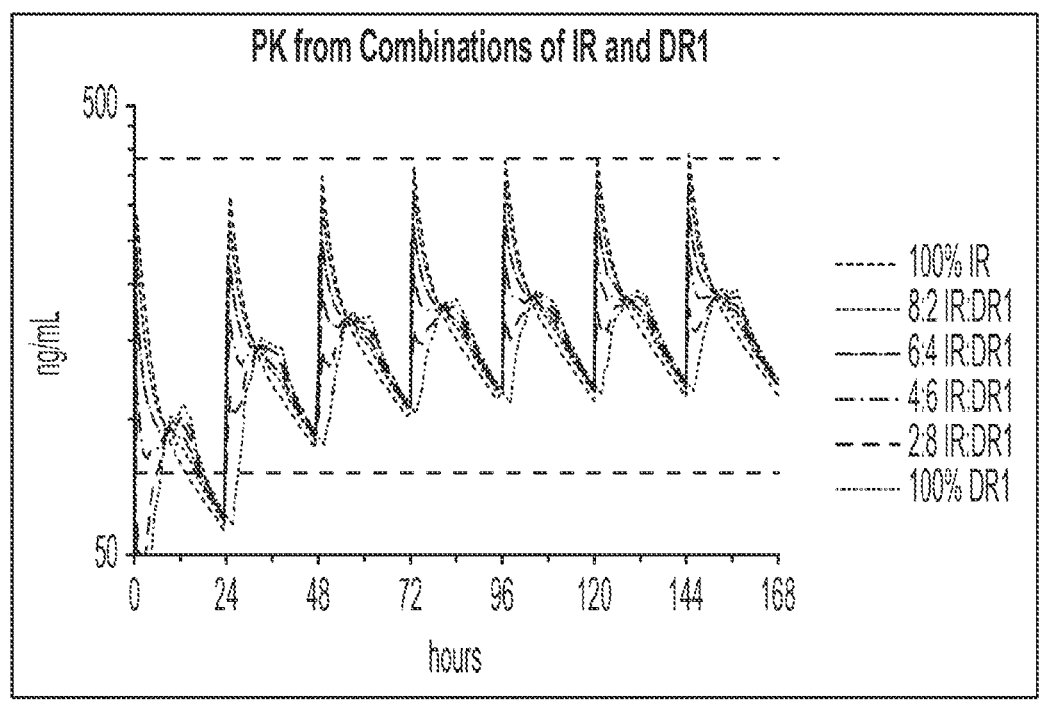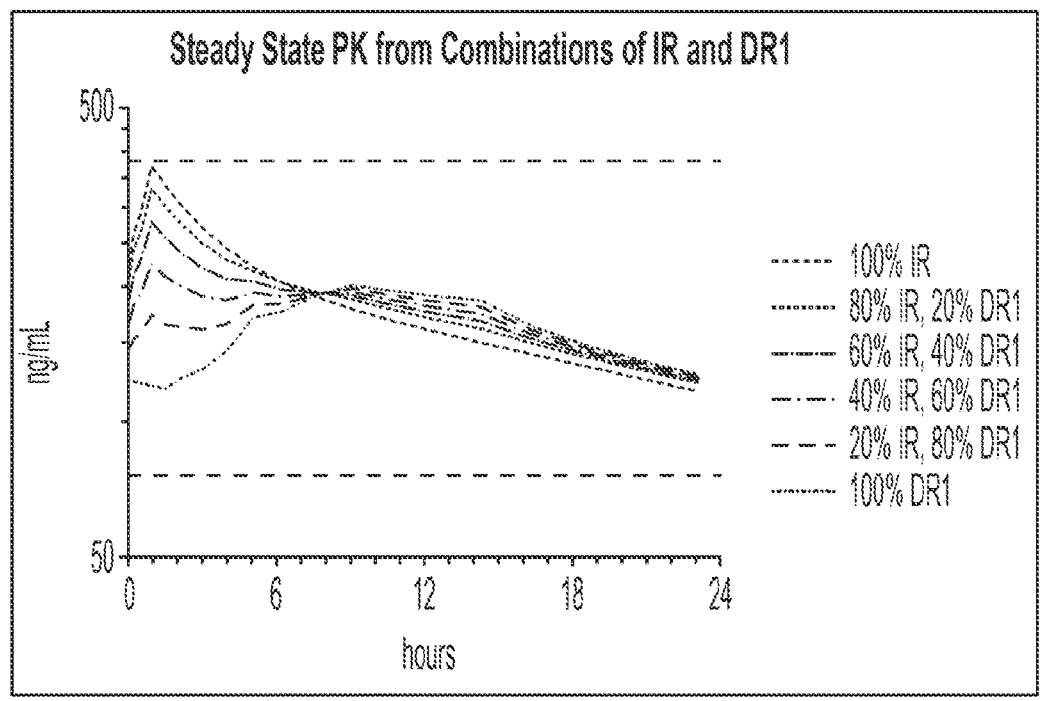
FIG. 59

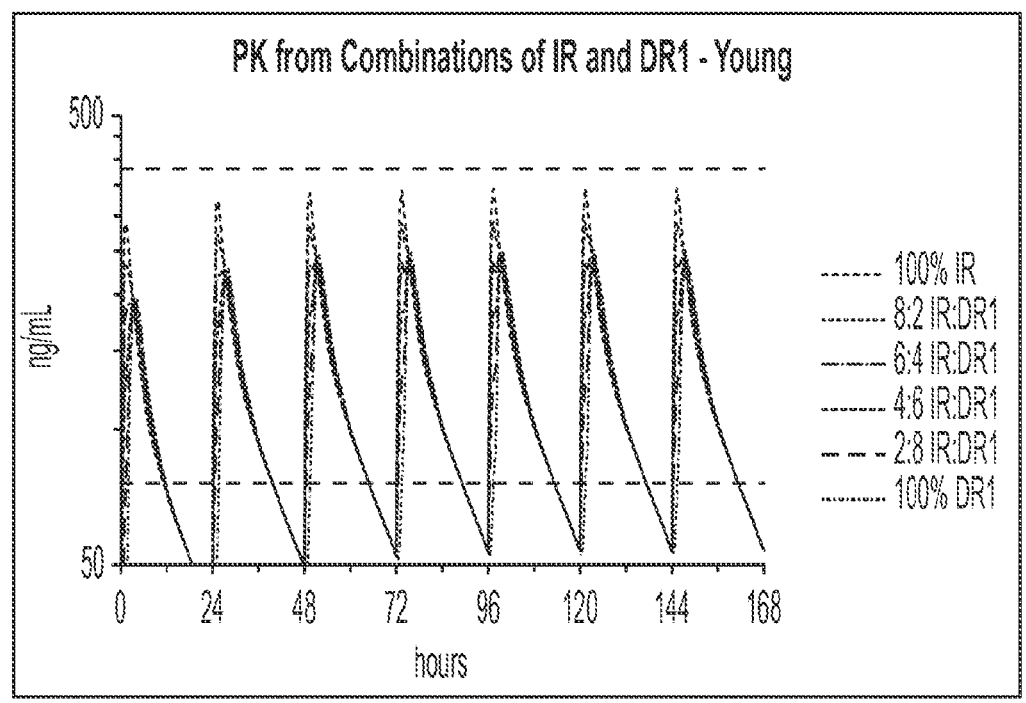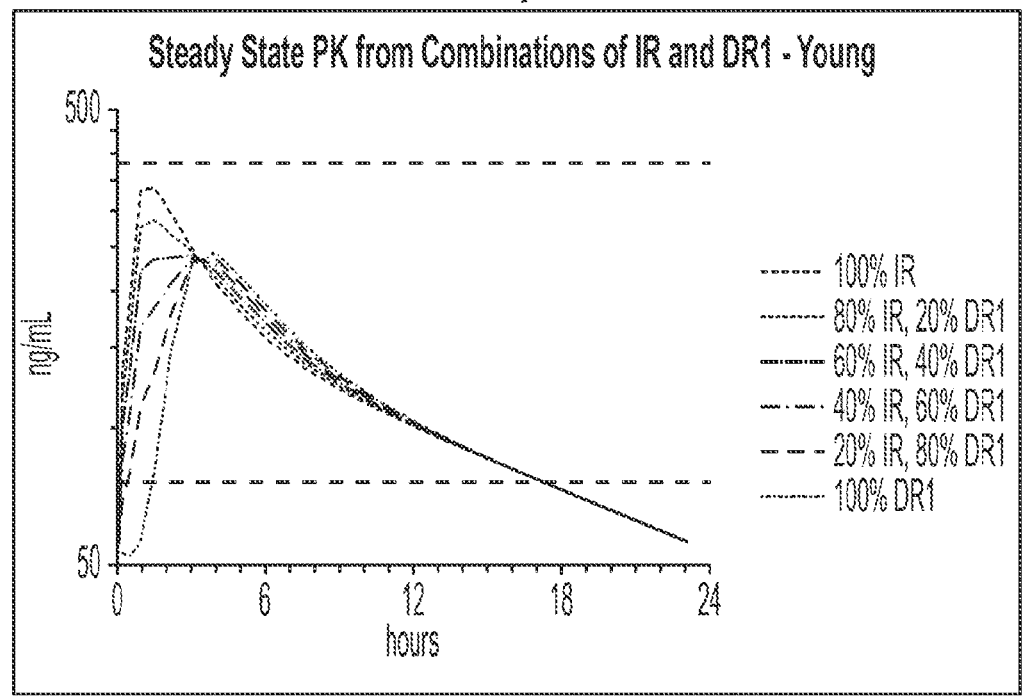
FIG. 60

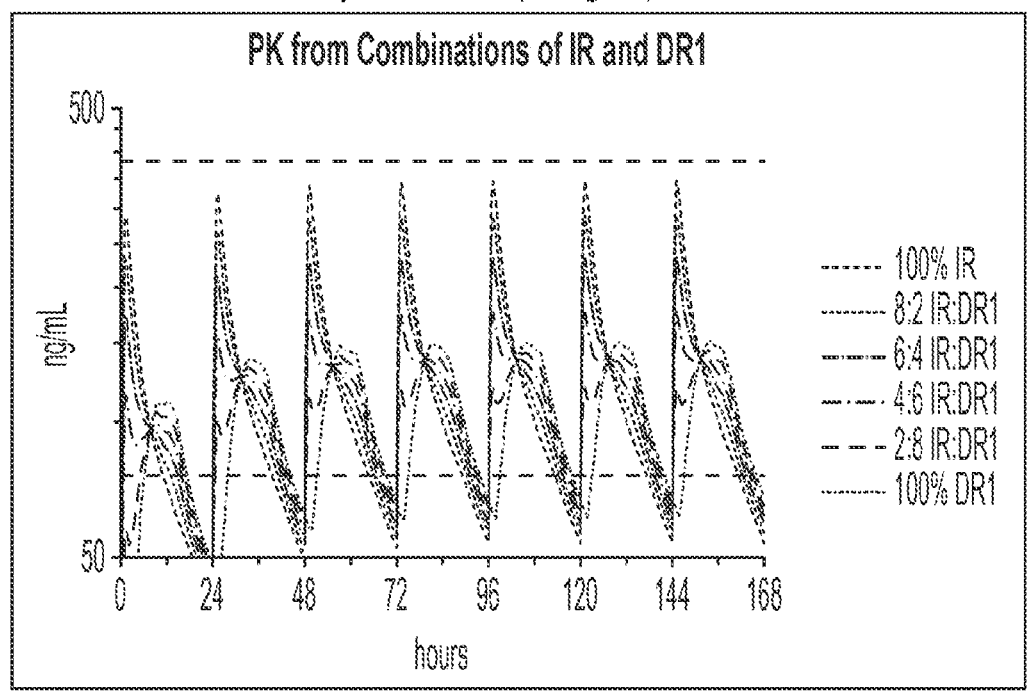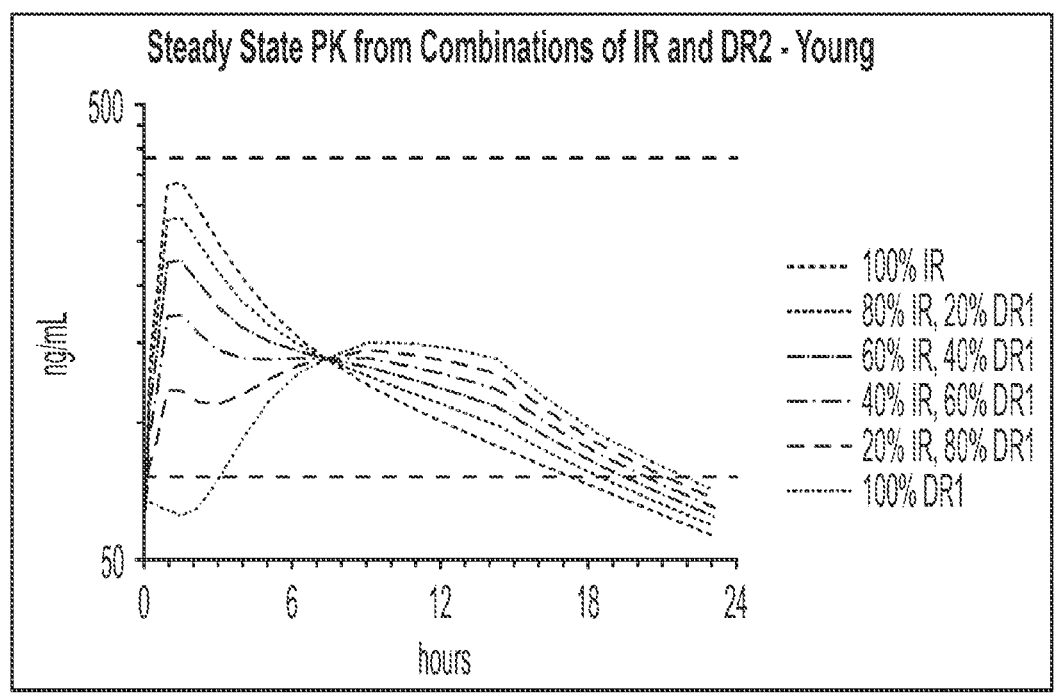
FIG. 61

TREATING ESSENTIAL TREMOR USING (R)-2-(4-ISOPROPYLPHENYL)-N-(1-(5-(2,2,2-TRIFLUOROETHOXY)PYRIDIN-2-YL)ETHYL) ACETAMIDE

CROSS REFERENCE TO RELATED APPLICATIONS

This application is a United States national phase application under 35 U.S.C. § 371 of International Application No. PCT/US2019/054498, filed on Oct. 3, 2019, which claims the benefit of U.S. Patent Application Ser. No. 62/740,755, filed on Oct. 3, 2018, and claims the benefit of U.S. Patent Application Ser. No. 62/780,049, filed on Dec. 14, 2018. The disclosure of the prior applications are considered part of (and is incorporated by reference in) the disclosure of this application.

TECHNICAL FIELD

This invention relates to methods and materials for treating mammals having, or at risk of developing, one or more movement disorders (e.g., essential tremor, epilepsy, and/or Parkinson's disease). In particular, this document relates to compositions including one or more T-type calcium channel antagonists (e.g., one or more Cav3 antagonists such as CX-8998), and administering such compositions to a mammal having, or at risk of developing, one or more movement disorders (e.g., essential tremor, epilepsy, and/or Parkinson's disease) to treat the mammal.

BACKGROUND

Essential Tremor is among the most prevalent of all movement disorders in adults. In a 2010 meta-analysis, Louis et al. (1998 *Movement Disorders.* 13(1):5-10) estimated the pooled prevalence (all ages) to be 0.9%, with statistically significant heterogeneity across studies (I2=99%, p<0.001). The prevalence in adults ≥65 years old was estimated to be 4.6% (Louis and Ferreira, 2010 *Mov Disord.* 25(5):534-541). While ET does not shorten life expectancy, its impact on the patient's ability to perform activities of daily living (ADLs, such as writing and eating) at home and in the work place negatively affects quality of life, social interactions, and mental status (Lorenz et al., 2006 *Mov Disord.* 21(8):1114-1118; Louis et al., 2015 *Parkinsonism Relat Disord.* 21(7):729-735; George et al., 1994 *Psychosomatics.* 35(6):520-523; and Zesiewicz et al., 2011 *Neurology.* 77(19):1752-1755). It is increasingly recognized that ET is not a monosymptomatic disorder (Bermejo-Pareja, 2011 *Nature Reviews Neurology.* 7(5):273-282). Effects on cognitive functions are heterogeneous and include impairments in attention, executive function, verbal fluency, visuospatial functioning, memory, and working memory (Bermejo-Pareja et al., 2012 "V. Cognitive Features of Essential Tremor: A Review of the Clinical Aspects and Possible Mechanistic Underpinnings," pages 2:02-74-541-1 in *Tremor and Other Hyperkinetic Movements* (Louis, ed.) 2012).

Sleep disturbances and fatigue are also more common in patients with ET than in their age-matched controls (Chandran et al., 2012 *Acta Neurol Scand.* 125:332-7). Essential tremor typically worsens over time and can be severe in some people. It is a significant disability that affects many activities of daily living and can be a source of social embarrassment, phobia, depression & anxiety.

T-type calcium channels are members of a family of voltage-activated calcium channels (Cav), each of which is defined by a unique pore-forming alpha subunit with distinct physiological properties that can be further modulated by association with various accessory subunits (Zamponi et al., 2015 *Pharmacol Rev.* 67:821-70). A unique and discriminating property of T-type calcium channels is their ability to activate upon small depolarizations of the membrane, at relatively low voltages, allowing a surge of calcium entry into excitable cells that leads to further membrane depolarization, activation of additional ion channel subtypes, and initiation of an action potential. Another important feature of this class of channels is their relatively rapid inactivation (the "T" in "T-type" is for transient) and relatively slow functional recovery from this inactivated state. Together these properties enable Cav3 channels to transiently respond to small changes in sensory input and then quickly reset, giving them a key role in setting of the resting membrane potential and, thus, in the overall excitability and oscillatory activity of the cell (Iftinca et al., 2009 *Trends Pharmacol Sci.* 30:32-40).

The T-type calcium channel, Cav3, its isoforms (Cav3.1, Cav3.2, and Cav3.3), and their genes CACNA1G, CACNA1H, and CACNA1I were discovered and cloned in the early 1990s and their function as low-threshold, voltage-gated calcium channels was elucidated (Perez-Reyes, 1998 *Bioenerg Biomembr.* 30:313-8; Cribbs et al., 1998 *Circ Res.* 83:103-9; Lee et al., 1999 *J Neurosci.* 19(6):1912-21). Isoforms of Cav3 are expressed throughout the central nervous system (CNS) and the peripheral nervous system, including the thalamocortical pathway, where Cav3.1 is the most common isoform (Ertel et al., 2000 *Neuron.* 25:533-5). Deep cerebellar nuclei, substantia nigra, globus pallidus externa, globus pallidus interna, subthalamic nucleus (STN), have been noted to have oscillations in healthy hosts and excessive rhythmicity in animals and humans with pathologic conditions of the nervous system. It has been discovered that Cav3 is a mediator of subthreshold oscillations and excessive rhythmicity in pathophysiologic states found in tremor, neuropathic pain, epilepsy, and Parkinson's disease (Llinás, 2003 *An R Acad Nac Med (Madr).* 120:267-90; Handforth et al., 2005 *Epilepsia.* 46:1860-70; Llinás et al., 2007 *Proc Natl Acad Sci.* 104:17819-24; Park et al., 2013 *Front Neural Circuits.* 7:172).

The inferior olive (IO) appears to function as a tremor generator, and animal models suggest the IO functions as an intrinsic pacemaker (Long et al., 2002 *J Neurosci.* 22:10898-905). Essential tremor (ET) may result from excessive rhythmic synchronous firing of populations of neurons in the IO, which affects the function of the cerebellum (Elbe et al., 1996 *Mov Disord.* 11:70-78). Cav3 is highly expressed in the IO and the cerebellum. Cav3.1 is the predominate Cav3 isoform that is expressed in the IO. Within the cerebellar system, it is also found on Purkinje cell bodies, deep cerebellar nuclei, stellate, basket, dendrites and Golgi cells (Molineux et al., 2006 *Proc Natl Acad Sci USA.* 103:5555-60). In these locations, Cav3 functions as a tremor generator and ongoing rhythm pacemaker (Park et al., 2010 *Proc Natl Acad Sci USA.* 107:10731-6).

SUMMARY

This document provides methods and materials for treating mammals having, or at risk of developing, a movement disorder (e.g., essential tremor, epilepsy, and/or Parkinson's disease). For example, a composition including one or more T-type calcium channel antagonists (e.g., one or more Cav3 antagonists such as CX-8998) can be administered to a mammal in need thereof (e.g., a mammal having, or at risk of developing, a movement disorder) to treat the mammal. CX-8998 is a highly selective voltage-activated Cav antagonist. As demonstrated herein, an oral dosage form of a composition including CX-8998 can be formulated to include a first component designed for delayed and/or sustained CX-8998 release and a second component designed for immediate CX-8998 release, such that the dosage form, when orally administered to a mammal (e.g., a mammal having movement disorder) can provide the mammal with plasma levels of CX-8998 within a therapeutically beneficial range for about 12 hours (e.g., for twice daily dosing) or for about 24 hours (e.g., for once daily dosing).

Currently, propranolol is the only medication approved for the treatment of essential tremor in the United States. The lack of any new positive recommendations by the 2011 Academy of Neurology evidence-based guideline update on the treatment of essential tremor (as compared to the 2005 guidelines) attests to the poor yield of present approaches to drug discovery (Zesiewicz et al., 2011 *Neurology.* 77(19): 1752-1755). Thus, the ability to deliver one or more T-type calcium channel antagonists (e.g., one or more Cav3 antagonists such as CX-8998) in therapeutic amounts provides a unique and unrealized opportunity to treat humans having essential tremor. Further, delivering one or more T-type calcium channel antagonists (e.g., one or more Cav3 antagonists such as CX-8998) in a non-invasive manner while maintaining the therapeutic amounts for a sustained period of time can maximize daytime efficacy, limit $C_{max}$ related adverse events, and limit nighttime sleep disturbances (and potentially hormonal effects), while reducing the frequency of dosing required for therapeutic benefit.

In general, one aspect of this document features an oral dosage form comprising a Cav3 antagonist or a pharmaceutically acceptable salt thereof, where the dosage form includes a controlled release component including the Cav3 antagonist, and where the dosage form optionally contains an immediate release component including the Cav3 antagonist; where the oral dosage form, when administered a human of about 35 years of age or older, can be effective to provide: a) a $C_{max}$ of the Cav3 antagonist at steady state of no greater than twice the mean plasma concentration over 24 hours; and b) a plasma concentration of the Cav3 antagonist at steady state of from about 400 nM to about 1000 nM for at least 18 hours. The oral dosage form, when administered to the human, can be effective to maintain the $C_m$ax of the Cav3 antagonist at steady state of from 1 to 2 times the mean plasma concentration over 24 hours. The oral dosage form can be administered to the human once daily. The Cav3 antagonist can have a structure of:

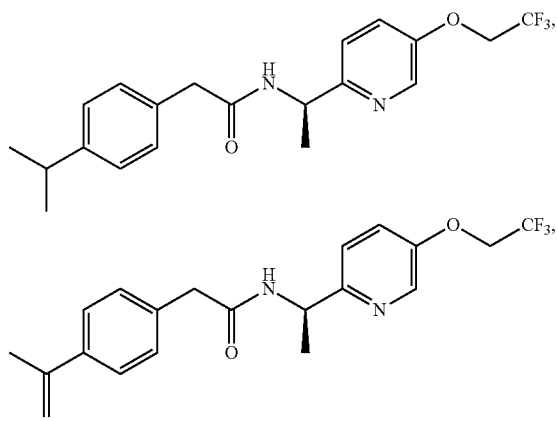

-continued

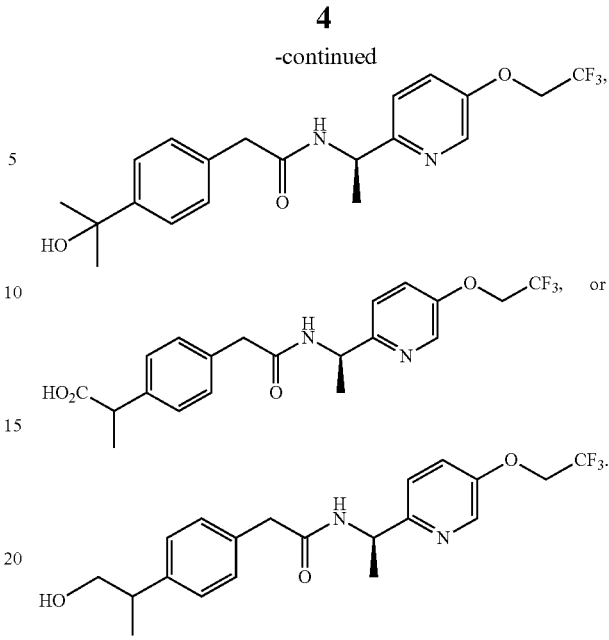

The Cav3 antagonist can include a hydrochloride salt. The oral dosage form can be a capsule, a pill, a tablet, or a suspension. The controlled release component can include particles, a tablet, a mini-tablet, a solution, a suspension, a capsule, or a mixture thereof. The particles can be granules, pellets, beads, microparticles, or nanoparticles, or a mixture thereof. The oral dosage form can include a capsule. The capsule can be a gelatin capsule or a hydroxypropyl methylcellulose capsule. The at least one particle in a plurality of particles comprising the Cav3 antagonist in the controlled release component can include a coating comprising a pH-sensitive enteric polymer. In some cases, at least a portion of the pH-sensitive enteric polymer coating can dissolve at a pH of about 6. The pH-sensitive enteric polymer coating can dissolve at a pH of about 6, the pH-sensitive enteric polymer can include, by weight, about 6.25% methacrylic acid copolymer L, about 6.25% methacrylic acid copolymer S, about 1.25% triethyl citrate, and about 6.25% talc. In some cases, at least a portion of the pH-sensitive enteric polymer coating can dissolve at a pH of about 7. The pH-sensitive enteric polymer coating can dissolve at a pH of about 7, the pH-sensitive enteric polymer can include, by weight, about 17.4% EUDRAGIT® FS 30 D, and about 2.6% PlasACRYL® T20. The controlled release component can include, by weight, about 5.0% of the Cav3 antagonist, about 57.7% lactose monohydrate, about 25.0% crospovidone, about 8.0% citric acid anhydrous, about 2.0% sodium lauryl sulfate (SLS), about 2.0% hydroxypropyl cellulose (HPC), about 0.3% butylated hydroxyanisole (BHA), and about 0.1% butylated hydroxytoluene (BHT). The oral dosage form also can include the immediate release component, where the immediate release component includes a plurality of particles comprising the Cav3 antagonist. One or more of the particles in the immediate release component can include, by weight, about 5.0% of the Cav3 antagonist, about 57.7% lactose monohydrate, about 25.0% crospovidone, about 8.0% citric acid anhydrous, about 2.0% SLS, about 2.0% HPC, about 0.3% BHA, and about 0.1% BHT. One or more of the particles in the immediate release component, when the oral dosage form is administered to a human, can release at least 80% of the Cav3 antagonist present in the immediate release component within 45 minutes of administration. The oral dosage form can include about 30% of the Cav3 antagonist in the immediate release component and about 70% of the Cav3 antagonist in the controlled release component. The oral dosage form, when administered to a human, can be effective to reach at least 25% of the $C_{max}$ of the Cav3 antagonist within 30 minutes. The Cav3 antagonist can reduce the activity of a T-type calcium channel.

In another aspect, this document features an oral dosage form comprising a Cav3 antagonist or a pharmaceutically acceptable salt thereof, where the dosage form includes a controlled release component including the Cav3 antagonist, and where the dosage form optionally contains an immediate release component including the Cav3 antagonist; where the oral dosage form, when administered a human less than about 35 years of age, can be effective to provide: a) a $C_{max}$ of the Cav3 antagonist at steady state of no greater than 2.5 times the mean plasma concentration over 24 hours; and b) a plasma concentration of the Cav3 antagonist at steady state of from about 400 nM to about 1000 nM for at least 15 hours. The oral dosage form, when administered to the human, can be effective to maintain the Cmax of the Cav3 antagonist at steady state of from 1 to 2.5 times the mean plasma concentration over 24 hours. The oral dosage form can be administered to the human once daily. The Cav3 antagonist can have a structure of:

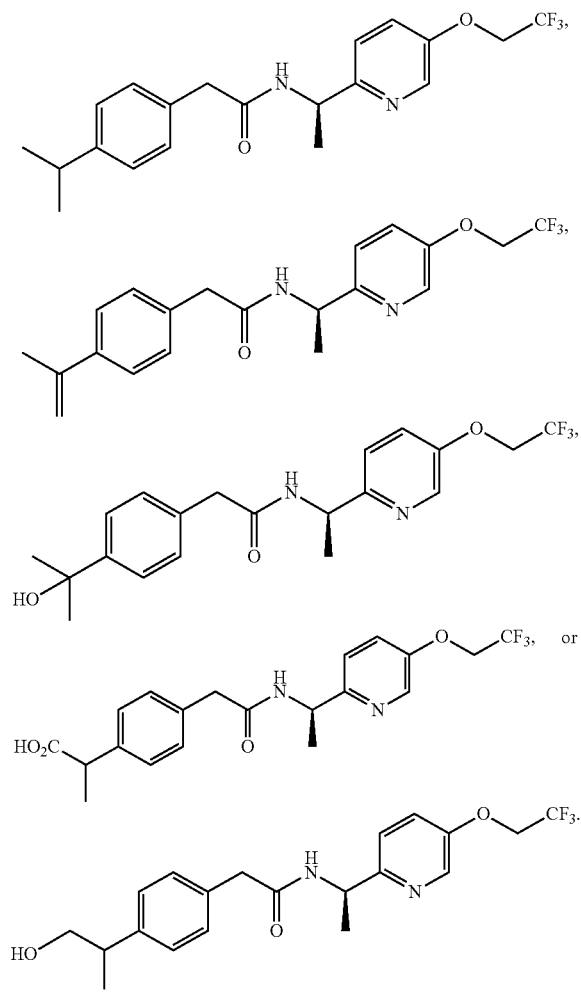

The Cav3 antagonist can include a hydrochloride salt. The oral dosage form can be a capsule, a pill, a tablet, or a suspension. The controlled release component can include particles, a tablet, a mini-tablet, a solution, a suspension, a capsule, or a mixture thereof. The particles can be granules, pellets, beads, microparticles, or nanoparticles, or a mixture thereof. The oral dosage form can include a capsule. The capsule can be a gelatin capsule or a hydroxypropyl methylcellulose capsule. The at least one particle in a plurality of particles comprising the Cav3 antagonist in the controlled release component can include a coating comprising a pH-sensitive enteric polymer. In some cases, at least a portion of the pH-sensitive enteric polymer coating can dissolve at a pH of about 6. The pH-sensitive enteric polymer coating can dissolve at a pH of about 6, the pH-sensitive enteric polymer can include, by weight, about 6.25% methacrylic acid copolymer L, about 6.25% methacrylic acid copolymer S, about 1.25% triethyl citrate, and about 6.25% talc. In some cases, at least a portion of the pH-sensitive enteric polymer coating can dissolve at a pH of about 7. The pH-sensitive enteric polymer coating can dissolve at a pH of about 7, the pH-sensitive enteric polymer can include, by weight, about 17.4% EUDRAGIT® FS 30 D, and about 2.6% PlasACRYL® T20. The controlled release component can include, by weight, about 5.0% of the Cav3 antagonist, about 57.7% lactose monohydrate, about 25.0% crospovidone, about 8.0% citric acid anhydrous, about 2.0% SLS, about 2.0% HPC, about 0.3% BHA, and about 0.1% BHT. The oral dosage form also can include the immediate release component, where the immediate release component includes a plurality of particles comprising the Cav3 antagonist. One or more of the particles in the immediate release component can include, by weight, about 5.0% of the Cav3 antagonist, about 57.7% lactose monohydrate, about 25.0% crospovidone, about 8.0% citric acid anhydrous, about 2.0% SLS, about 2.0% HPC, about 0.3% BHA, and about 0.1% BHT. One or more of the particles in the immediate release component, when the oral dosage form is administered to a human, can release at least 80% of the Cav3 antagonist present in the immediate release component within 45 minutes of administration. The oral dosage form can include about 30% of the Cav3 antagonist in the immediate release component and about 70% of the Cav3 antagonist in the controlled release component. The oral dosage form, when administered to a human, can be effective to reach at least 25% of the $C_{max}$ of the Cav3 antagonist within 30 minutes. The Cav3 antagonist can reduce the activity of a T-type calcium channel.

In another aspect, this document features an oral dosage form including a Cav3 antagonist or a pharmaceutically acceptable salt thereof, where the dosage form can include a capsule including: a) an immediate release component including one or more granules including the Cav3 antagonist, and b) a controlled release component including one or more granules including the Cav3 antagonist; where the oral dosage form, when administered to a human, can be effective to maintain a mean plasma concentration of the Cav3 antagonist of from about 400 nM to about 1000 nM for at least 12 hours. The oral dosage form, when administered to a human, can be effective to maintain the mean plasma concentration of the Cav3 antagonist of from about 400 nM to about 1000 nM for at least 18 hours. The oral dosage form, when administered to a human, can be effective to maintain the mean plasma concentration of the Cav3 antagonist of from about 400 nM to about 1000 nM for from about 12 hours to about 24 hours. The Cav3 antagonist can have a structure of:

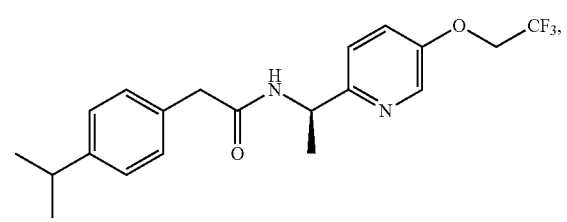

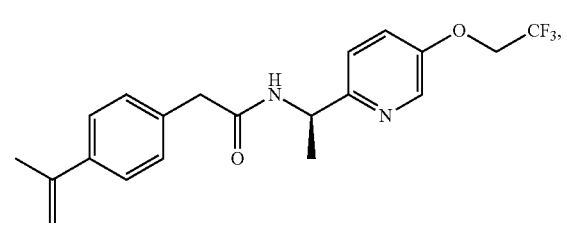

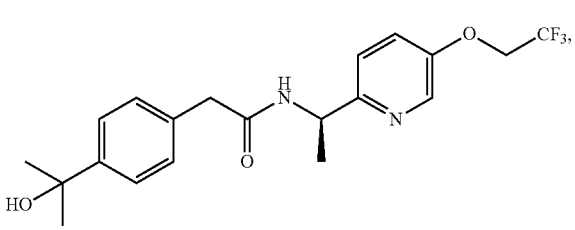

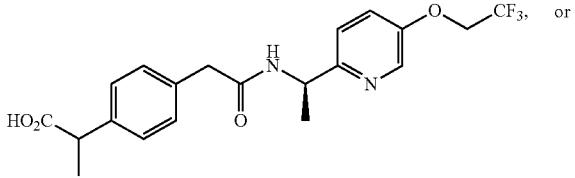

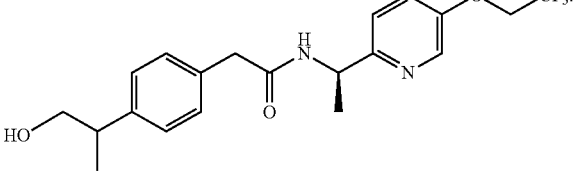

The Cav3 antagonist can include a hydrochloride salt. The Cav3 antagonist can reduce activity of a T-type calcium channel.

In another aspect, this document features an oral dosage form including a Cav3 antagonist or a pharmaceutically acceptable salt thereof, where the dosage form can include a tablet including: a) an immediate release component including one or more granules including the Cav3 antagonist, and b) a controlled release component including one or more granules including the Cav3 antagonist; where the oral dosage form, when administered to a human, can be effective to maintain a mean plasma concentration of the Cav3 antagonist of from about 400 nM to about 1000 nM for at least 12 hours. The oral dosage form, when administered to a human, can be effective to maintain the mean plasma concentration of the Cav3 antagonist of from about 400 nM to about 1000 nM for at least 18 hours. The oral dosage form, when administered to a human, can be effective to maintain the mean plasma concentration of the Cav3 antagonist of from about 400 nM to about 1000 nM for from about 12 hours to about 24 hours. The Cav3 antagonist can have a structure of:

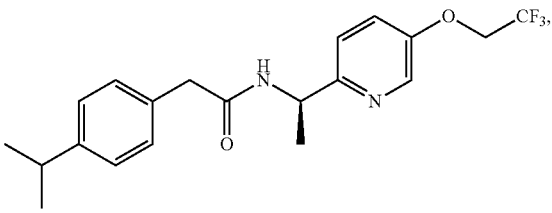

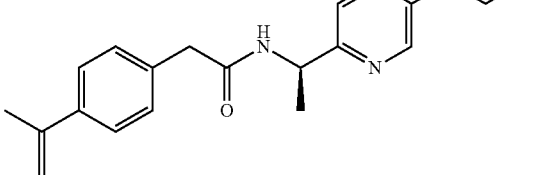

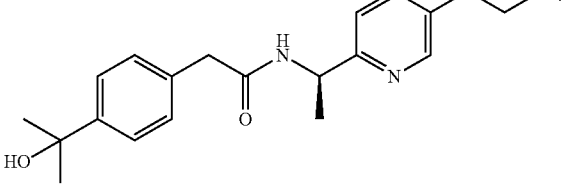

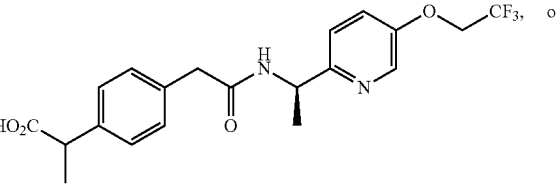

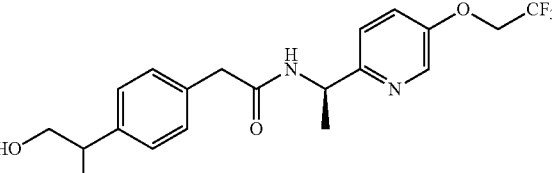

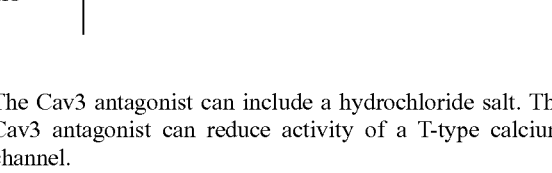

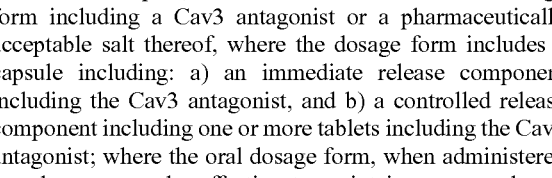

The Cav3 antagonist can include a hydrochloride salt. The Cav3 antagonist can reduce activity of a T-type calcium channel.

In another aspect, this document features an oral dosage form including a Cav3 antagonist or a pharmaceutically acceptable salt thereof, where the dosage form includes a capsule including: a) an immediate release component including the Cav3 antagonist, and b) a controlled release component including one or more tablets including the Cav3 antagonist; where the oral dosage form, when administered to a human, can be effective to maintain a mean plasma concentration of the Cav3 antagonist of from about 400 nM to about 1000 nM for at least 12 hours. The immediate release component can include a plurality of granules. The immediate release component can include a plurality of beads and/or pellets. The one or more tablets can include one or more mini-tablets. The oral dosage form, when administered to a human, can be effective to maintain the mean plasma concentration of the Cav3 antagonist of from about 400 nM to about 1000 nM for at least 18 hours. The oral dosage form, when administered to a human, can be effective to maintain the mean plasma concentration of the Cav3 antagonist of from about 400 nM to about 1000 nM for from about 12 hours to about 24 hours. The Cav3 antagonist can have a structure of:

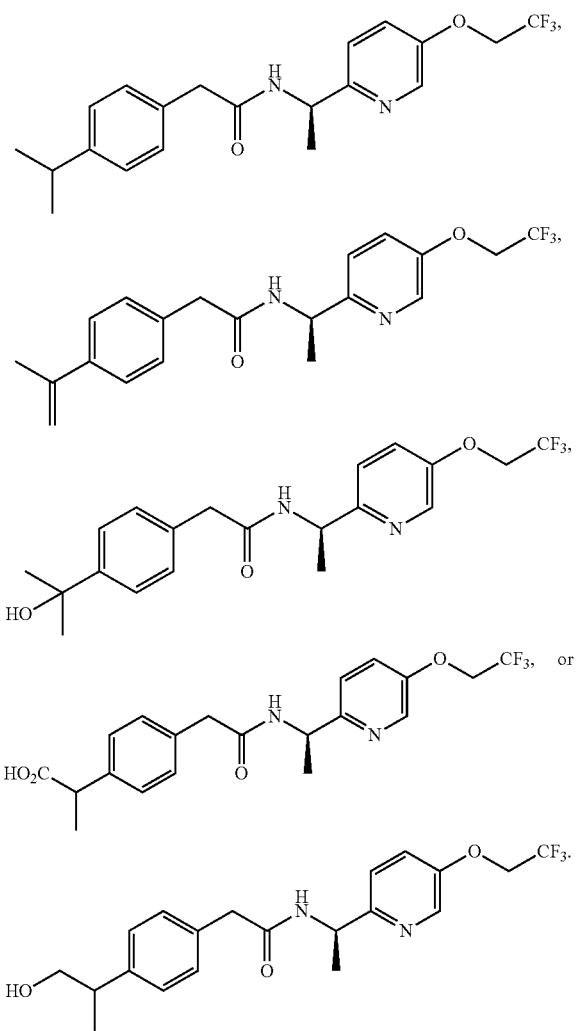

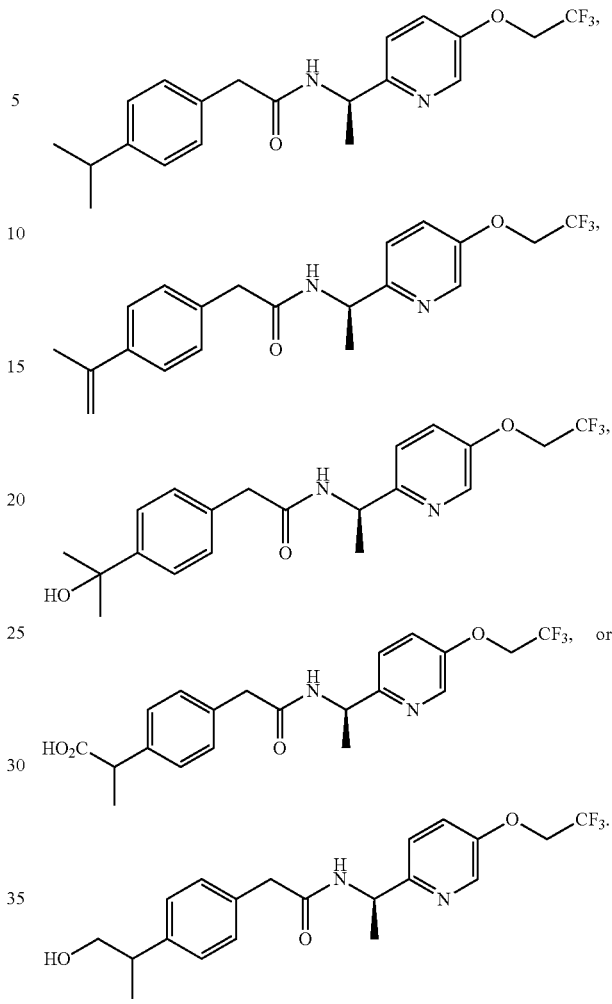

The Cav3 antagonist can include a hydrochloride salt. The Cav3 antagonist can reduce activity of a T-type calcium channel.

In another aspect, this document features an oral dosage form including a Cav3 antagonist or a pharmaceutically acceptable salt thereof, where the dosage form can include a capsule including: a) an immediate release component including the Cav3 antagonist, where the immediate release component can be a liquid, and b) a controlled release component including the Cav3 antagonist, where the controlled release component includes one or more solid components that can be granules, beads, pellets, and/or mini-tablets; where the oral dosage form, when administered to a human, can be effective to maintain a mean plasma concentration of the Cav3 antagonist of from about 400 nM to about 1000 nM for at least 12 hours. The oral dosage form, when administered to a human, can be effective to maintain the mean plasma concentration of the Cav3 antagonist of from about 400 nM to about 1000 nM for at least 18 hours. The oral dosage form, when administered to a human, can be effective to maintain the mean plasma concentration of the Cav3 antagonist of from about 400 nM to about 1000 nM for from about 12 hours to about 24 hours. The Cav3 antagonist can have a structure of:

The Cav3 antagonist can include a hydrochloride salt. The Cav3 antagonist can reduce activity of a T-type calcium channel.

In another aspect, this document features an oral dosage form including a Cav3 antagonist or a pharmaceutically acceptable salt thereof, where the dosage form includes a capsule containing an interior capsule, where the interior capsule fits within the oral dosage capsule such that a space is present between an outer surface of the interior capsule and an inner surface of the oral dosage capsule; where the space present between the outer surface of the interior capsule and the inner surface of the oral dosage capsule can contain an immediate release component including the Cav3 antagonist, where the immediate release component can be a liquid; where the interior capsule contains a controlled release component including the Cav3 antagonist; and where the oral dosage form, when administered to a human, can be effective to maintain a mean plasma concentration of the Cav3 antagonist of from about 400 nM to about 1000 nM for at least 12 hours. The oral dosage form, when administered to a human, can be effective to maintain the mean plasma concentration of the Cav3 antagonist of from about 400 nM to about 1000 nM for at least 18 hours. The oral dosage form, when administered to a human, can be effective to maintain the mean plasma concentration of the Cav3 antagonist of from about 400 nM to about 1000 nM for from about 12 hours to about 24 hours. The Cav3 antagonist can have a structure of:

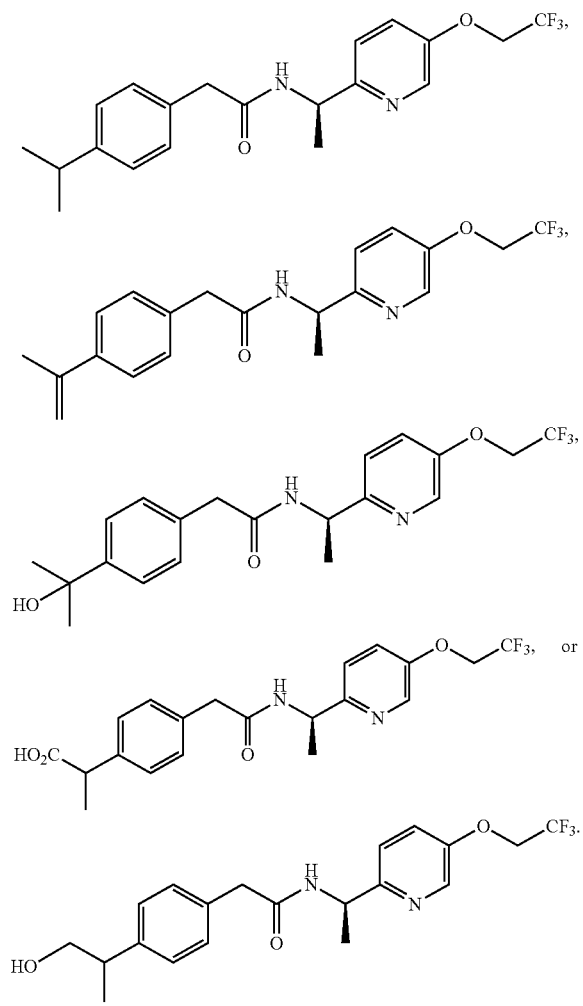

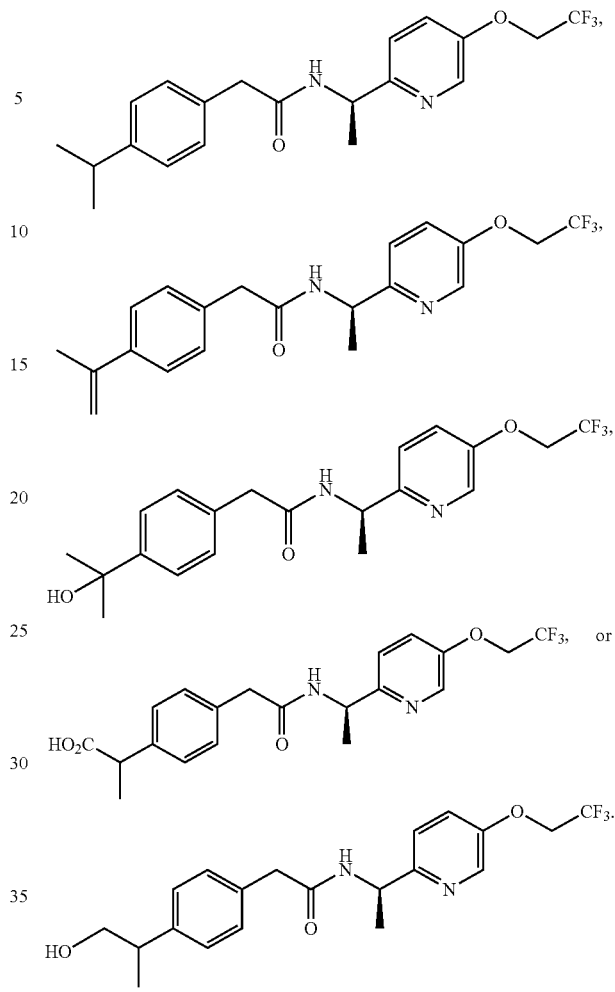

The Cav3 antagonist can include a hydrochloride salt. The Cav3 antagonist can reduce activity of a T-type calcium channel.

In another aspect, this document features an oral dosage form including a Cav3 antagonist or a pharmaceutically acceptable salt thereof, where the dosage form includes a suspension including: a) an immediate release component including the Cav3 antagonist, where the immediate release component is a liquid, and b) a controlled release component including the Cav3 antagonist, where the controlled release component includes one or more solid components that can be granules, beads, pellets, and/or mini-tablets; where the one or more solid components are suspended within the liquid; and where the oral dosage form, when administered to a human, is effective to maintain a mean plasma concentration of the Cav3 antagonist of from about 400 nM to about 1000 nM for at least 12 hours. The oral dosage form, when administered to a human, can be effective to maintain the mean plasma concentration of the Cav3 antagonist of from about 400 nM to about 1000 nM for at least 18 hours. The oral dosage form, when administered to a human, can be effective to maintain the mean plasma concentration of the Cav3 antagonist of from about 400 nM to about 1000 nM for from about 12 hours to about 24 hours. The Cav3 antagonist can have a structure of:

The Cav3 antagonist can include a hydrochloride salt. The Cav3 antagonist can reduce activity of a T-type calcium channel.

In another aspect, this document features an oral dosage form including a Cav3 antagonist or a pharmaceutically acceptable salt thereof, where the dosage form includes a suspension including: a) a liquid phase, b) an immediate release component including the Cav3 antagonist, where the immediate release component includes one or more solid components that can be granules, beads, pellets, and/or mini-tablets; where the one or more solid components are suspended within the liquid, and c) a controlled release component including the Cav3 antagonist, where the controlled release component includes one or more solid components that can be granules, beads, pellets, and/or mini-tablets; where the one or more solid components are suspended within the liquid; and where the oral dosage form, when administered to a human, can be effective to maintain a mean plasma concentration of the Cav3 antagonist of from about 400 nM to about 1000 nM for at least 12 hours. The oral dosage form, when administered to a human, can be effective to maintain the mean plasma concentration of the Cav3 antagonist of from about 400 nM to about 1000 nM for at least 18 hours. The oral dosage form, when administered to a human, can be effective to maintain the mean plasma concentration of the Cav3 antagonist of from about 400 nM to about 1000 nM for from about 12 hours to about 24 hours. The Cav3 antagonist can have a structure of:

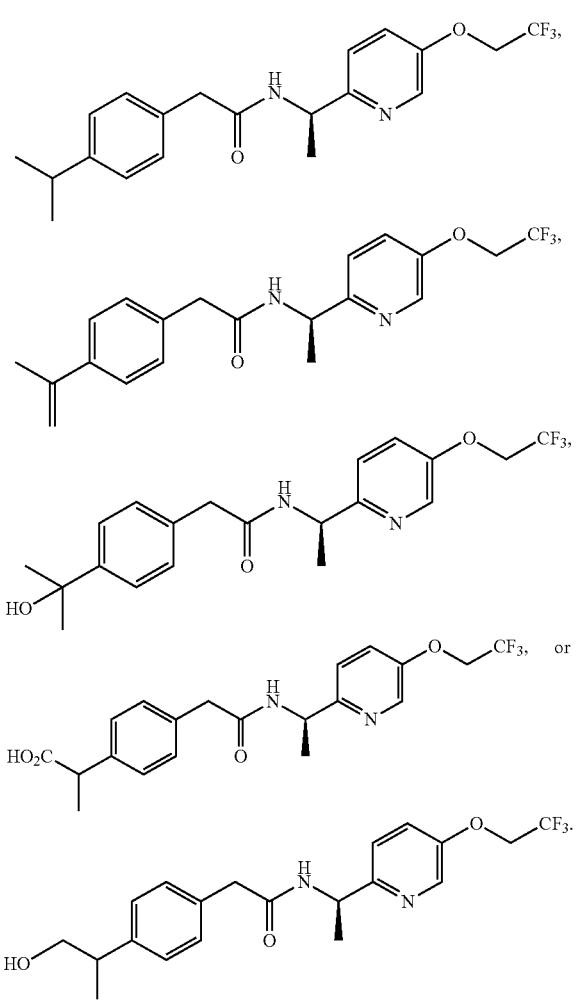

The Cav3 antagonist can include a hydrochloride salt. The Cav3 antagonist can reduce activity of a T-type calcium channel.

In another aspect, this document features methods for treating a patient having a movement disorder. The methods can include, or consist essentially of, administering to the patient in need thereof (e.g., a patient having a movement disorder) an oral dosage form provided herein. The patient can be a human adult 35 years of age or older. The patient can be human adult is less than about 35 years of age. The movement disorder can be essential tremor, idiopathic generalized epilepsy with absence seizures, or tremor associated with Parkinson's disease. The oral dosage form can be administered (e.g., can be administered once daily) to the patient between 6 am and noon. The oral dosage form can be administered (e.g., can be administered once daily) to the patient within 4 hours of waking. The controlled release component can include a plurality of particles including the Cav3 antagonist, where at least one particle in the plurality of particles including the Cav3 antagonist in the controlled release component includes a coating including a pH-sensitive enteric polymer, and where at least a portion of the pH-sensitive enteric polymer coating dissolves at an intestinal pH. The patient can have fasted for at least 4 hours prior to being administered the oral dosage form. The Cav3 antagonist can be effective to reduce or eliminate tremors associated with the movement disorder. The patient can experience reduced adverse events as compared to a human that is administered only an immediate release component of the Cav3 antagonist. The adverse event can be dizziness, headache, euphoria, disturbance in attention, paresthesia, hallucination, insomnia, dry mouth, dysguesia, hypoesthesia, somnolence, lethargy, sleep disturbance, nausea, vomiting, akathisia, decreased level of consciousness, syncope, memory impairment, anxiety, restlessness, fatigue, irritability, constipation, tinnitus, anorexia, emotional disturbances, sexual impotency, diplopia, nystagmus, drowsiness, morbilliform skin eruptions, granulocytopenia, agranulocytosis, red-cell hypoplasia, aplasia, or any combinations thereof.

Unless otherwise defined, all technical and scientific terms used herein have the same meaning as commonly understood by one of ordinary skill in the art to which this invention pertains. For example, the terms "e.g." and "such as," and grammatical equivalents thereof, the phrase "and without limitation" is understood to follow unless explicitly stated otherwise. For example, the singular forms "a," "an," and "the" include plural referents unless the context clearly dictates otherwise. For example, the term "about" means "approximately" (e.g., plus or minus approximately 10% of the indicated value). Although methods and materials similar or equivalent to those described herein can be used to practice the invention, suitable methods and materials are described below. It is appreciated that certain features of the invention, which are, for clarity, described in the context of separate embodiments, can also be provided in combination in a single embodiment. Conversely, various features of the invention which are, for brevity, described in the context of a single embodiment, can also be provided separately or in any suitable subcombination. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 11A shows CX-8998 metabolite MOL. FIG. 11B shows CX-8998 metabolite M02. FIG. 11C shows CX-8998 metabolite M03. FIG. 11D shows CX-8998 metabolite M04.

FIG. 28 contains graphs showing a release profile of CX-8998 of a single dose in elderly males and of 7 daily doses young males.

FIG. 38 contains graphs showing zero order release from an osmotic pump tablet.

FIG. 39 contains graphs showing first order release from a matrix tablet having coated beads in a capsule.

FIG. 40 contains graphs showing a burst and zero order release from an osmotic pump tablet with an IR release coating.

FIG. 41 contains graphs showing a burst and first order release from a mixture of IR beads and slow release beads in a matric tablet with an IR coating.

FIG. 42 contains graphs showing a double burst with a 3 hour delay from a mixture of IR beads and pH 6 enteric-coated beads from an IR tablet with enteric coating and an IR coating.

FIG. 43 contains graphs showing a double burst with a 6 hour delay from a mixture of IR beads and pH 7 enteric-coated beads from an IR tablet with enteric coating and an IR coating.

FIG. 47A contains a schematic of an exemplary T-CALM Design. FIG. 47B contains a flow chart of an exemplary T-CALM Design.

FIG. 51 contains graphs showing differences in TETRAS performance subscores. The upper panel shows the difference scores by item, where negative scores indicate lower scoring by the independent video rater (CR) than the investigator (PR). The upper panel shows difference scores across all visits.

FIG. 58 contains graphs showing simulated dissolution rates of various ratios of IR and MR1 beads in the elderly.

FIG. 59 contains graphs showing simulated dissolution rates of various ratios of IR and MR2 beads in the elderly.

FIG. 60 contains graphs showing simulated dissolution rates of various ratios of IR and MR1 beads in the non-elderly.

FIG. 61 contains graphs showing simulated dissolution rates of various ratios of IR and MR2 beads in the non-elderly.

Like reference symbols in the various drawings indicate like elements.

DETAILED DESCRIPTION

Figure 1:
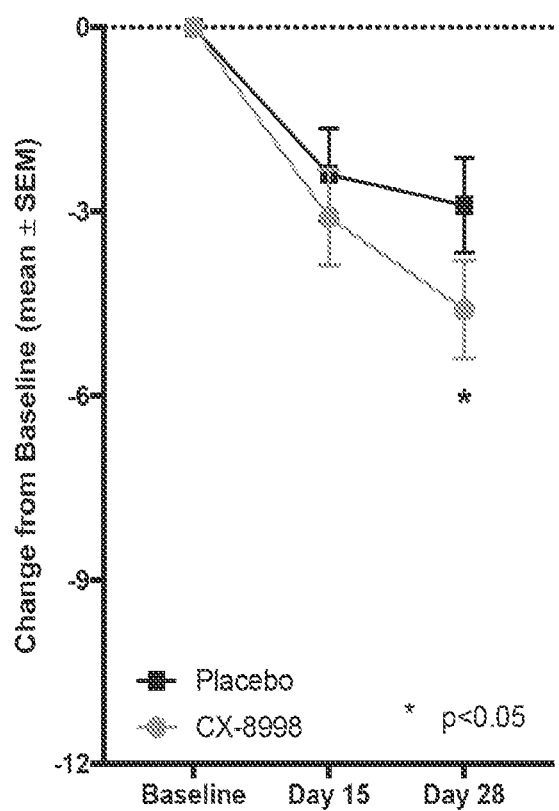
FIG. 1 is a graph showing the change from baseline to day 28 in the Tremor Research Group (TRG) Essential Tremor Rating Assessment Scale (TETRAS)-performance subscale (PS) as rated by investigator.

This document provides methods and materials for treating mammals (e.g., a human patient) having, or at risk of developing, a movement disorder (e.g., essential tremor, epilepsy, and/or Parkinson's disease). In some cases, this document provides compositions including one or more T-type calcium channel antagonists (e.g., one or more Cav3 antagonists such as CX-8998) as well as the use of such compositions in the manufacture of a medicament for treating a movement disorder (e.g., essential tremor, epilepsy, and/or Parkinson's disease).

In some cases, a composition including one or more T-type calcium channel antagonists (e.g., one or more Cav3 antagonists such as CX-8998) can be a controlled release composition that includes one or more components of compositions, where each component can be formulated to modify the release rate of the one or more T-type calcium channel antagonists from the composition (e.g., to achieve specific target pharmacokinetic outcomes) when administered to a human patient. For example, a composition including CX-8998 can be an oral dosage form having a first component designed for delayed and/or sustained CX-8998 release and, optionally, a second component designed for immediate CX-8998 release, such that the dosage form, when orally administered to a mammal (e.g., a human patient having movement disorder) can provide the mammal with therapeutically effective plasma levels of CX-8998 for about 12 hours or about 24 hours.

In some cases, a composition including one or more T-type calcium channel antagonists (e.g., one or more Cav3 antagonists such as CX-8998) can be designed to provide specific target pharmacokinetic outcomes when administered to a human patient. For example, because T-type calcium channel antagonists can cause undesirable symptoms (e.g., adverse effects or side effects) when plasma concentrations in a human patient are too high, and because T-type calcium channel antagonists can have little or no effect (e.g., little or no therapeutic effect) when plasma concentrations are too low, it is desirable that a dosage form, after administration to a human patient, can provide a plasma concentration of a T-type calcium channel antagonist that is above an effective minimum concentration while minimally exceeding a maximum concentration above which certain undesirable symptoms become more common, and can do so for an extended period of time. For example, a composition including one or more T-type calcium channel antagonists, when administered as a single oral dose, may yield a maximal plasma concentration in a human patient of, on average, not more than 1200 nM while maintaining plasma concentrations, on average, of above 400 nM, and can maintain such a plasma concentration for at least 12 hours, at least 15 hours, or at least 18 hours.

In some cases, this document provides methods of using compositions including one or more T-type calcium channel antagonists (e.g., one or more Cav3 antagonists such as CX-8998). For example, a composition including one or more T-type calcium channel antagonists (e.g., an oral dosage form having a first component designed for delayed and/or sustained CX-8998 release and, optionally, a second component designed for immediate CX-8998 release, such that the dosage form, when orally administered to a patient having movement disorder can provide the patient with therapeutically effective plasma levels of CX-8998 for about 12 hours) can be administered to a patient having, or at risk of developing, a movement disorder to treat the patient. The methods and materials provided herein can be used to provide a patient in need thereof with sustained CX-8998 action over a long period of time (e.g., about 24 hours). For example, when an oral dosage form of a composition including CX-8998 includes a first component designed for delayed and/or sustained CX-8998 release and a second component designed for immediate CX-8998 release, the immediate release component can be effective to quickly achieve therapeutically effective plasma levels of CX-8998 within a patient, and the delayed and/or sustained release component can be effective to sustain the therapeutically effective plasma levels of CX-8998 within the patient.

Compositions

This document provides compositions (e.g., pharmaceutically acceptable compositions) including one or more T-type calcium channel antagonists (e.g., one or more Cav3 antagonists such as CX-8998). In some cases, a T-type calcium channel antagonist can inhibit (e.g., can reduce or eliminate) activity of a T-type calcium channel. In some cases, this document provides compositions including CX-8998. CX-8998 (also referred to as MK-8998) is a highly selective voltage-activated calcium channel (Cav) antagonist that can inhibit Cav3 (e.g., can inhibit Cav3 with nanomolar (nM) potency), and is highly selective for Cav3 (e.g., having >100-fold selectivity against other ion channel targets). CX-8998 can be used for dose-dependent tremor reduction, reduction and/or elimination of seizures, and/or reduction and/or elimination of pain. As used herein, the term "CX-8998" can also refer to CX-8998 structural analogs provided that the CX-8998 structural analog maintains the pharmaceutical function of CX-8998 as described herein (e.g., dose-dependent tremor reduction, reduction and/or elimination of seizures, and/or reduction and/or elimination of pain). Chemical names for CX-8998 include, without limitation, (R)-2-(4-Isopropylphenyl)-N-(1-(5-(2,2,2-Trifluoroethoxy)pyridin-2-yl)ethyl)acetamide and 2-(4-Isopropylphenyl)-N-{1R)-1-(5-(2,2,2-trifluoroethoxy)pyridine-2-yl)ethyl}acetamide hydrochloride. The chemical structure of CX-8998 is as shown below.

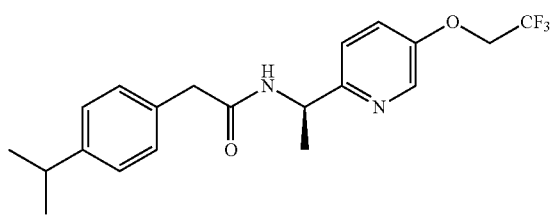 [SMILES: CC(C)c1ccc(CC(=O)N[C@H](C)c2ccc(OCC(F)(F)F)cn2)cc1]

CX-8998 can be in any appropriate form of CX-8998. In some cases, CX-8998 can be in the form of a base (e.g., a free base form of the compound). In some cases, CX-8998 can be in the form of a salt (e.g., a salt form of the compound). In cases where CX-8998 is a salt, the CX-8998 salt can be any appropriate salt. A CX-8998 salt can include a salt formed with any appropriate acid (e.g., hydrochloric acids, citric acids, hydrobromic acids, maleic acids, phosphoric acids, sulfuric acids, fumaric acids, and tartaric acids). For example, CX-8998 can be a CX-8998 hydrochloride salt (e.g., CX-8998-HCl). In some cases, CX-8998 can be deuterated. In some cases, CX-8998 can be in the form of a CX-8998 polymorph. In some cases, CX-8998 can be the form of a structural isomer of CX-8998 (e.g., a CX-8998 tautomer).

In some cases, one or more components of compositions (e.g., pharmaceutically acceptable compositions) provided herein (e.g., compositions including one or more T-type calcium channel antagonists such as CX-8998) can cross the blood brain barrier. For example, when a composition includes CX-8998, the CX-8998 can cross the blood brain barrier. For example, when a composition including CX-8998 also includes one or more additional components, the CX-8998 can be released from the composition and can cross the blood brain barrier. For example, when a composition including CX-8998 also includes one or more additional components, the CX-8998 can be released from the composition and can cross the blood brain barrier while the one or more additional components do not cross the blood brain barrier.

In some cases, one or more components of compositions (e.g., pharmaceutically acceptable compositions) provided herein (e.g., compositions including one or more T-type calcium channel antagonists such as CX-8998) do not cross the blood brain barrier. For example, when a composition including CX-8998 also includes one or more additional components, the CX-8998 can be released from the composition and can cross the blood brain barrier while the one or more additional components do not cross the blood brain barrier.

A composition (e.g., a pharmaceutically acceptable composition) including one or more T-type calcium channel antagonists (e.g., one or more Cav3 antagonists such as CX-8998) can include, in addition to or in place of a T-type calcium channel antagonist, a metabolite of a T-type calcium channel antagonist. In some implementations, a T-type calcium channel antagonist present in a compositions described herein can be metabolized into (e.g., metabolized by a mammal following administration of the composition to the mammal) one or more metabolites of a T-type calcium channel antagonist. In some cases, a metabolite of a T-type calcium channel antagonist such as a metabolite of CX-8998 can be a T-type calcium channel antagonist (e.g., a Cav3 antagonist). For example, when a composition includes CX-8998, the composition can include one or more CX-8998 metabolites and/or the CX-8998 can be metabolized into one or more CX-8998 metabolites. A CX-8998 metabolite can be any appropriate metabolite. In some cases, a metabolite can be bound to a protein (e.g., a plasma protein). In some cases, a metabolite can be free (e.g., not bound to any protein). In some cases, a metabolite can cross the blood brain barrier (e.g., can be present in the cerebrospinal fluid (CSF) and/or the CNS). Examples of CX-8998 metabolites include, without limitation metabolite 01 (M01), M02, M03, and M04. In some cases, a composition described herein can include and/or be metabolized into M01 and M02. The chemical structures of exemplary CX-8998 metabolites are as shown below.

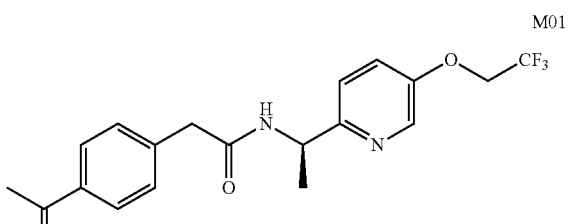

M01

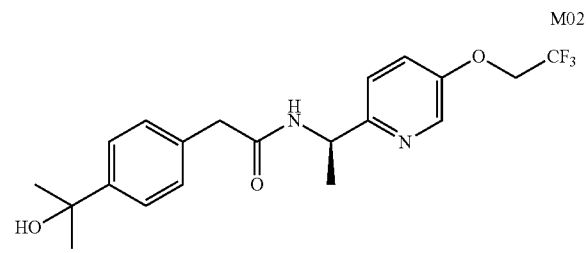

M02

-continued

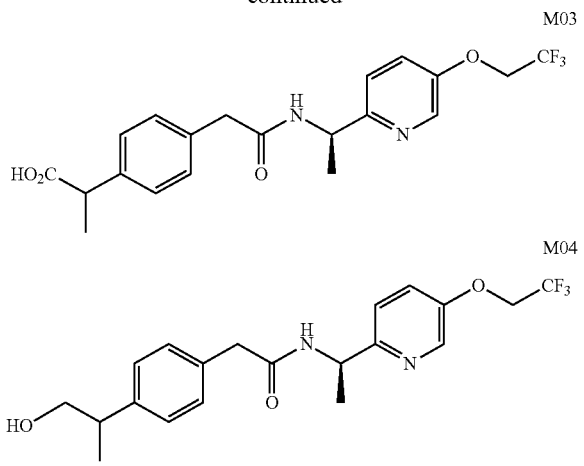

M03

M04

In some cases, a T-type calcium channel antagonist in a composition (e.g., pharmaceutically acceptable composition) including one or more T-type calcium channel antagonists (e.g., one or more Cav3 antagonists such as CX-8998) can be selective for (e.g., can selectively bind to) all 3 Cav3 isoforms. "Selective" in this context means that the Cav3 antagonist is more potent at antagonizing Cav3 channels compared with other voltage activated calcium channels (e.g., high voltage activated channels such as an L-type cardiac channel (Cavl)) and/or compared with other types of ion channels (e.g., chloride channels, potassium channels, and sodium channels). Selectivity can be determined using any appropriate method. For example, selectivity can be determined by comparing the $IC_{50}$ of a Cav3 antagonist in inhibiting a first type of ion channel (e.g., a Cav3 channel) with its $IC_{50}$ in inhibiting a second type of ion channel (e.g., a sodium channel). If the $IC_{50}$ for inhibiting the first type of channel is lower than the $IC_{50}$ for inhibiting the second type of channel, then the Cav3 antagonist can be considered selective for the first type of channel. An $IC_{50}$ ratio of 0.1 (or lower) denotes 10-fold (or greater) selectivity. An $IC_{50}$ ratio of 0.01 (or lower) denotes 100-fold (or greater) selectivity. An $IC_{50}$ ratio of 0.001 (or lower) denotes 1000-fold (or greater) selectivity. In some cases, a T-type calcium channel antagonist in a composition described herein can have selectivity for Cav3 that is 10-fold or greater, 100-fold or greater, or 1000-fold or greater compared with other types of ion channels. For example, when a T-type calcium channel antagonist in a composition described herein is CX-8998, the composition can have greater than 100-fold selectivity against other ion channels. In some cases, a T-type calcium channel antagonist in a composition described herein can selectively target one or more Cav3 isoforms (e.g., Cav3.1, Cav3.2, and/or Cav3.3). In some cases, a composition described herein can selectively target all three Cav3 isoforms (e.g., Cav3.1, Cav3.2, and Cav3.3).

In some cases, a T-type calcium channel antagonist in a composition described herein (e.g., a composition containing one or more T-type calcium channel antagonists such as CX-8998) can have selectivity for Cav3 in a state-dependent manner. In some cases, a T-type calcium channel antagonist in a composition described herein can have from about 29-fold to about 45-fold greater selectivity for Cav3 under hyperpolarizing conditions as compared to depolarizing conditions. For example, when a T-type calcium channel antagonist in a composition described herein is CX-8998, the CX-8998 can have selectivity for Cav3 (e.g., Cav3.3) can have an $IC_{50}$ of about 3.6 nM under depolarizing conditions, and can have an $IC_{50}$ of about 161 nM under hyperpolarizing conditions. For example, when a T-type calcium channel antagonist in a composition described herein is CX-8998, the CX-8998 can have an $IC_{50}$ for antagonizing Cav3.3 of about 84 nM under depolarizing conditions, and can having an $IC_{50}$ for antagonizing Cav3.3 of about 2.4 M under hyperpolarizing conditions. For example, when a T-type calcium channel antagonist in a composition described herein is CX-8998, the CX-8998 can have selectivity for Cav3.1 can have an $IC_{50}$ of about 69 nM under depolarizing conditions, and can have an $IC_{50}$ of about 2.4 M under hyperpolarizing conditions.

In some cases, a T-type calcium channel antagonist in a composition (e.g., pharmaceutically acceptable composition) including one or more T-type calcium channel antagonists (e.g., one or more Cav3 antagonists such as CX-8998) can be a potent Cav3 antagonist. For example, when a T-type calcium channel antagonist in a composition described herein is CX-8998, the CX-8998 can be more potent at antagonizing Cav3 than other ion channels. For example, CX-8998 can have nM potency (e.g., nM levels of CX-8998 are sufficient to antagonize Cav3). In some cases, a T-type calcium channel antagonist in a composition described herein can potently inhibit one or more Cav3 isoforms (e.g., Cav3.1, Cav3.2, and/or Cav3.3). In some cases, a T-type calcium channel antagonist in a composition described herein can potently inhibit all three Cav3 isoforms (e.g., Cav3.1, Cav3.2, and Cav3.3).

A composition (e.g., a pharmaceutically acceptable composition) including one or more T-type calcium channel antagonists (e.g., one or more Cav3 antagonists such as CX-8998) can include the one or more Cav3 antagonists as the sole active ingredient(s).

A composition (e.g., a pharmaceutically acceptable composition) including one or more T-type calcium channel antagonists (e.g., one or more Cav3 antagonists such as CX-8998) can include the one or more T-type calcium channel antagonists together with one or more additional active ingredients. For example, a composition can include one or more T-type calcium channel antagonists together with one or more additional agents used to treat one or more movement disorders (e.g., essential tremor, epilepsy, and/or Parkinson's disease). Examples of agents used to treat one or more movement disorders include, without limitation, beta blockers (e.g., propranolol), anti-seizure medications (e.g., primidone, gabapentin, topiramate, zonisamide, ethosuximide, pregabalin, valproate, phenytoin, and mibefradil), tranquilizers (e.g., alprazolam and clonazepam), administering one or more dopamine agonists (e.g., carbidopa-levodopa, pramipexole, ropinirole, rotigotine, and apomorphine), monoamine oxidase B (MAO B) inhibitors (e.g., selegiline, rasagiline, and safinamide), catechol O-methyl-transferase (COMT) inhibitors (e.g., entacapon, and tolcapone), and anticholinergics (e.g., benztropine and trihexyphenidyl).

A composition (e.g., a pharmaceutically acceptable composition) described herein (e.g., a composition containing one or more T-type calcium channel antagonists such as CX-8998) can include one or more additional components (e.g., one or more inactive ingredients). For example, a therapeutically effective amount of CX-8998 can be formulated into a composition including one or more additional components and administered to a mammal having, or at risk of developing, one or more movement disorders (e.g., essential tremor, epilepsy, and/or Parkinson's disease) to treat the mammal. Any additional components (e.g., pharmaceutically acceptable carriers) used to formulate a composition (e.g., a pharmaceutically acceptable composition) described herein (e.g., containing one or more T-type calcium channel antagonists) can be of high purity and can be substantially free of potentially harmful contaminants (e.g., at least National Formulary (NF) grade and/or United States Pharmacopeia (USP) grade). For example, when intended for administration to a human, a composition described herein can be manufactured or formulated under Good Manufacturing Practice standards as defined in the applicable regulations of the U.S. Food and Drug Administration and/or by similar regulatory bodies in other countries. For example, compositions described herein can be sterile and/or substantially isotonic and/or in full compliance with all (e.g., current) Good Manufacturing Practice regulations of the U.S. Food and Drug Administration.

A composition described herein (e.g., a composition containing one or more T-type calcium channel antagonists such as CX-8998) can be formulated into a pharmaceutically acceptable composition. For example, a therapeutically effective amount of CX-8998 can be formulated into a pharmaceutically acceptable composition and administered to a mammal having, or at risk of developing, one or more movement disorders (e.g., essential tremor, epilepsy, and/or Parkinson's disease) to treat the mammal. As used herein, the term "pharmaceutically acceptable" refers to compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio. For example, a therapeutically effective amount of CX-8998 can be formulated together with one or more pharmaceutically acceptable carriers (e.g., additives, diluents, and/or excipients). In some cases, pharmaceutically acceptable carrier can be an active component of a composition described herein. When a pharmaceutically acceptable carrier is an active component of a composition described herein, the pharmaceutically acceptable carrier can have any one or more functions in the composition. For example, a pharmaceutically acceptable carrier can be a filler, a diluent, a bulking agent, a binder, a disintegrant, a wicking agent, a matrix-forming polymer, a coating agent, a pH-sensitive polymer, a pore-former, a glidant, a lubricant, an osmotic agent, a humectant, an antioxidant, an antimicrobial, a solubility enhancer, a penetration enhancer, a crystallization inhibiter, and/or a solvent in a composition described herein. In some cases, a pharmaceutically acceptable carrier can be an inactive component of a composition described herein. A pharmaceutically acceptable carrier can be a solid, semi-solid, or liquid material. A pharmaceutically acceptable carrier can be any pharmaceutically acceptable compound which acts as a vehicle, carrier, or medium for one or more T-type calcium channel antagonists. Examples of pharmaceutically acceptable carriers that may be used in a pharmaceutically acceptable composition described herein include, without limitation, lactose monohydrate, crospovidone, citric acid, sodium lauryl sulfate, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose, cellulose-based substances, sodium carboxymethylcellulose, polyacrylates, waxes, polyethylene-polyoxypropylene-block polymers, polyethylene glycol (PEG; PEG-containing molecules such as vitamin E PEG succinate and PEG-200), Tween such as Tween-80, cyclodextrin, dimethylsulfoxide (DMSO), wool fat, lactose, dextrose, sucrose, sorbitol, mannitol, starches, gum acacia, calcium phosphate, alginates, tragacanth, gelatin, calcium silicate, microcrystalline cellulose, polyvinylpyrrolidone, syrup, and methyl cellulose. A composition described herein also can include, for example, fillers (e.g., lactose, sucrose, mannitol, modified or unmodified starches, cellulose derivatives such as microcrystalline cellulose, hydroxypropyl cellulose, and croscarmellose sodium, and mineral salts such as calcium phosphate), disintegrants (e.g., croscarmellose, sodium starch glycolate, and crospovidone), binders (e.g., hydrophilic polymers such as cellulose derivatives (e.g., hydroxypropyl melthylcellulose), carbopol, povidone, and modified starches), surfactants (e.g., acyl sulfates, polysorbates such as polysorbate-80, fatty acids and their derivatives, poloxamers, tergitol, and other amphiphilic molecules), lubricating agents (e.g., talc, magnesium stearate, and mineral oil) wetting agents, emulsifying and suspending agents, preserving agents (e.g., methyl- and propylhydroxy-benzoates), sweetening agents, and/or flavoring agents. In some cases, a pharmaceutically acceptable composition including one or more T-type calcium channel antagonists described herein can include lactose monohydrate, crospovidone, citric acid, and sodium lauryl sulfate. For example, when a composition described herein includes CX-8998, the composition can include, by weight, about 5% CX-8998, about 60% lactose monohydrate, about 25% crospovidone, about 8% citric acid, and about 2% sodium lauryl sulfate. It will be understood that use of certain additional components (e.g., pharmaceutically acceptable carriers) can result in the formation of pharmaceutical salts from one or more T-type calcium channel antagonists (e.g., a pharmaceutically acceptable salt of CX-8998 such as a CX-8998-HCl salt).

A composition (e.g., a pharmaceutically acceptable composition) described herein (e.g., a composition containing one or more T-type calcium channel antagonists such as CX-8998) can be formulated in a unit dosage form. The term "unit dosage forms" refers to physically discrete units suitable as unitary dosages for human subjects and other mammals, each unit containing a predetermined quantity of active ingredient calculated to produce the desired therapeutic effect, in association with a suitable pharmaceutical excipient. In some cases, a unit dosage can be administered once a day (e.g., a once daily dose). In some cases, a unit dosage can be administered more than once a day (e.g., BID or three times a day (TID)). For example, a unit dosage can contain from about 0.5 mg to about 1,000 mg (1 g) of one or more T-type calcium channel antagonists per day (e.g., from about 0.5 mg to about 900 mg, from about 0.5 mg to about 800 mg, from about 0.5 mg to about 700 mg, from about 0.5 mg to about 600 mg, from about 0.5 mg to about 500 mg, from about 0.5 mg to about 400 mg, from about 0.5 mg to about 300 mg, from about 0.5 mg to about 200 mg, from about 0.5 mg to about 100 mg, from about 0.5 mg to about 50 mg, from about 0.5 mg to about 30 mg, from about 0.5 mg to about 20 mg, from about 5 mg to about 1,000 mg, from about 10 mg to about 1,000 mg, from about 25 mg to about 1,000 mg, from about 100 mg to about 1,000 mg, from about 200 mg to about 1,000 mg, from about 300 mg to about 1,000 mg, from about 400 mg to about 1,000 mg, from about 500 mg to about 1,000 mg, from about 600 mg to about 1,000 mg, from about 750 mg to about 1,000 mg, from about 5 mg to about 750 mg, from about 10 mg to about 500 mg, from about 15 mg to about 400 mg, from about 20 mg to about 300 mg, from about 25 mg to about 250 mg, from about 30 mg to about 200 mg, from about 3 mg to about 30 mg, from about 5 mg to about 25 mg, from about 8 mg to about 16 mg, from about 40 mg to about 150 mg, or from about 50 mg to about 100 mg of CX-8998 per day). In some cases, each dosage contains about 8 mg of CX-8998. In some cases, each dosage contains about 10 mg of CX-8998. In some cases, each dosage contains about 16 mg of CX-8998. In some cases, each dosage contains about 20 mg of CX-8998. In some cases, each dosage contains about 24 mg of CX-8998.

A composition (e.g., a pharmaceutically acceptable composition) described herein (e.g., a composition containing one or more T-type calcium channel antagonists such as CX-8998) can include any appropriate amount of one or more T-type calcium channel antagonists (e.g., CX-8998). The amount (e.g., proportion or concentration) of one or more T-type calcium channel antagonists in a composition described herein can vary depending upon a number of factors including dosage, chemical characteristics (e.g., hydrophobicity), and the route of administration. For example, when a composition includes CX-8998, the composition can include, by weight, from about 0.5% to about 60% CX-8998 (e.g., from about 1% to about 60%, from about 3% to about 60%, from about 5% to about 60%, from about 8% to about 60%, from about 10% to about 60%, from about 12% to about 60%, from about 15% to about 60%, from about 20% to about 60%, from about 25% to about 60%, from about 30% to about 60%, from about 40% to about 60%, from about 50% to about 60%, from about 0.5% to about 50%, from about 0.5% to about 40%, from about 0.5% to about 30%, from about 0.5% to about 20%, from about 0.5% to about 15%, from about 0.5% to about 10%, from about 0.5% to about 7%, from about 0.5% to about 5%, from about 0.5% to about 2%, from about 1% to about 50%, from about 5% to about 30%, from about 10% to about 20%, from about 1% to about 5%, from about 5% to about 10%, from about 10% to about 15%, from about 15% to about 20%, from about 20% to about 30%, from about 30% to about 40%, or from about 40% to about 50% CX-8998). In some cases, a composition can include, by weight, about 5% CX-8998.

A composition (e.g., a pharmaceutically acceptable composition) described herein. (e.g., a composition containing one or more T-type calcium channel antagonists such as CX-8998) can be formulated for administration in any appropriate form. A composition described herein can be in a solid form (e.g., a tablet or a capsule), a liquid form (e.g., a solution or a suspension), or a semi-solid form (e.g., a gel, a lotion, a cream, an ointment, a soft gel, or a gummy). Examples of forms in which a composition described herein can be formulated include, without limitation, solutions, suspensions, tablets, pellets, beads, pills, powders (e.g., lyophilized powders), granules, lozenges, sachets, cachets, elixirs, emulsions, syrups, aerosols (e.g., solid aerosols or liquid aerosols), lotions, creams, and ointments. In some cases, a dosage form of a composition described herein also can include one or more additional components (e.g., cosmetic and/or flavor components). When a composition is in a solid form, the solid composition can include one or more particles (e.g., one or more granules, one or more pellets, one or more beads, one or more microparticles, and/or one or more nanoparticles, or mixtures of granules, pellets, beads, microparticles, and nanoparticles, and subcombinations thereof). When a composition includes one or more particles, a particle can be any appropriate size. For example, a particle can have a longest dimension (e.g., a diameter) that is from about 0.2 mm to about 2.0 mm (e.g., from about 0.2 mm to about 1.8 mm, from about 0.2 mm to about 1.5 mm, from about 0.2 mm to about 1.2 mm, from about 0.2 mm to about 1.0 mm, from about 0.2 mm to about 0.8 mm, from about 0.2 mm to about 0.6 mm, from about 0.5 mm to about 2.0 mm, from about 0.7 mm to about 2.0 mm, from about 1.0 mm to about 2.0 mm, from about 1.2 mm to about 2.0 mm, from about 1.5 mm to about 2.0 mm, from about 1.8 mm to about 2.0 mm, from about 0.3 mm to about 1.8 mm, from about 0.5 mm to about 1.5 mm, from about 0.5 mm to about 1.0 mm, or from about 1.0 mm to about 1.5 mm). In some cases, a particle can have a longest dimension that is from about 0.5 mm to about 1 mm. When a composition includes one or more particles, a particle can be any appropriate shape. For example, a particle can be round (e.g., spherical). For example, a dosage form can include one or more non-functional coatings (e.g., one or more coatings that do not include one or more T-type calcium channel antagonists and do not alter the release of the one or more T-type calcium channel antagonists in a composition described herein). In some cases, one or more forms of a composition described herein (e.g., oral dosage forms) can be contained within a capsule (e.g., a soft gelatin capsule, a hard gelatin capsule, or a hard hydroxypropyl methylcellulose capsule). For example, a composition described herein can be contained within a hard gelatin capsule or a hard hydroxypropyl methylcellulose capsule. A capsule can be any shape (e.g., oval-shaped). When a composition described herein is contained within a capsule, the capsule can be any appropriate size (e.g., a size 4, size 3, size 2, size 1, size 0, size 00, size 000, size 0EL, or size 00 EL capsule). In some cases, a pharmaceutically acceptable composition containing one or more T-type calcium channel antagonists can be a sterile composition. For example, a pharmaceutically acceptable composition containing one or more T-type calcium channel antagonists can include aqueous and non-aqueous sterile injection solutions that can contain antioxidants (e.g., butylated hydroxyanisole (BHA) and/or butylated hydroxytoluene (BHT)), stabilizers, buffers, bacteriostats, and solutes which render the composition isotonic with the blood of the intended recipient; and aqueous and non-aqueous sterile suspensions which may include suspending agents and thickening agents. In some cases, a pharmaceutically acceptable composition including one or more T-type calcium channel antagonists described herein can include a capsule containing a plurality of Cav3 antagonist-containing pellets and/or Cav3 antagonist-containing beads. For example, when a composition described herein includes CX-8998, the composition can include a capsule containing a plurality of CX-8998-containing pellets and/or CX-8998-containing beads.

A composition (e.g., a pharmaceutically acceptable composition) described herein (e.g., a composition containing one or more T-type calcium channel antagonists such as CX-8998) can be formulated for administration in any appropriate timing. In some cases, a pharmaceutically acceptable composition containing CX-8998 can be an immediate release composition. The term "immediate release" as used herein refers to a composition that is formulated to release all (e.g., 100%) or substantially all (e.g., at least 70%, at least 75%, at least 80%, at least 85%, at least 90%, at least 95%, at least 97%, at least 98%, or at least 99%) of the active ingredient (e.g., one or more T-type calcium channel antagonists such as CX-8998) within about 30 minutes (e.g., about 35 minutes, about 40 minutes, about 45 minutes, about 50 minutes, or about 60 minutes) following administration of the composition. For example, an immediate release composition including CX-8998 can be formulated to release at least 75% of the CX-8998 within about 45 minutes. In some cases, in an immediate release composition no deliberate effort is made to modify the release rate of the active ingredient. In some cases, a pharmaceutically acceptable composition containing CX-8998 can be a controlled release composition (e.g., a modified release composition) such as a delayed release composition, a sustained release composition, or an extended release composition. The term "controlled release" as used herein refers to a compositions that is formulated to release the active ingredient (e.g., one or more T-type calcium channel antagonists such as CX-8998) in a manner that can optimize a plasma concentration profile of the active ingredient and/or is more convenient for the patient (e.g., allows for less frequent administration). In some cases a controlled release composition can contain a single component. In some cases, a controlled release composition can include a plurality (e.g., two, three, or more) of components each of which is formulated to release the active ingredient in a specific manner. For example, a controlled release composition can include one or more components formulated for immediate release and one or more components formulated for delayed and/or sustained release. The term "delayed release" as used herein refers to a composition that is formulated to delay release of the active ingredient (e.g., one or more T-type calcium channel antagonists such as CX-8998). For example, when the composition is an oral dosage form, a delayed release composition can be formulated to delay release of the active ingredient until the composition has passed through the stomach (e.g., to prevent the drug from being destroyed or inactivated by, for example, gastric juices or where it may irritate the gastric mucosa). In some cases, a delayed release composition can be formulated to delay release until the dosage form or one or more components of the dosage form has passed further down the intestinal tract. For example, a composition including CX-8998 can be coated with a delayed release coating to obtain a delayed release composition. In some cases, delayed release coatings can be formed from one or more slowly eroding polymers. In some cases, delayed release coatings can be formed from one or more pH independent polymers. In some cases, delayed release coatings can be formed from one or more pH-sensitive polymers. For example, pH-sensitive enteric polymers are insoluble at low pH but soluble at higher pH, such that an enteric polymer can form an impermeable layer in the low pH of the stomach (e.g., at a pH of about 1 to about 3) but can swell and then erode once exposed to the more neutral pH of the intestines (e.g., at a pH of about 5 to about 8), such as a pH of greater than about 6 as in the small intestine or a pH of greater than about 7 as in the colon. For example, pH-sensitive carbomers are substantially insoluble at low pH (e.g., at a pH of about 1 to about 5) but swell to form thick gels at neutral and alkaline pH values (e.g., at a pH of greater than about 6). In some cases, a pharmaceutically acceptable composition containing CX-8998 can be a sustained release composition. When a composition (e.g., a solid composition including one or more particles such as one or more granules, one or more pellets, one or more beads, one or more microparticles, and/or one or more nanoparticles) contains a coating, the coating can be any appropriate thickness. For example, a coating can have a thickness that is from about 50 μm to about 100 μm (e.g., from about 50 μm to about 90 μm, from about 50 μm to about 80 μm, from about 50 μm to about 70 μm, from about 50 μm to about 60 μm, from about 60 μm to about 100 μm, from about 70 μm to about 100 μm, from about 80 μm to about 100 μm, from about 90 μm to about 100 μm, from about 60 μm to about 90 μm, from about 70 m to about 80 μm, from about 60 μm to about 70 μm, from about 70 μm to about 80 μm, or from about 80 μm to about 90 μm). For example, a coating can have a thickness that is effective to increase the weight the coated particle (e.g., as compared to a particle that is not coated) by about 20%. The term "sustained release" (SR) as used herein refers to a composition that is formulated to release the active ingredient (e.g., one or more T-type calcium channel antagonists such as CX-8998) at a rate that can maintain a substantially constant drug concentration (e.g., a minimum effective concentration) for a prolonged period of time. In some cases, sustained release compositions can maintain a substantially constant drug concentration (e.g., a minimum effective concentration) for a specific period of time. For example, sustained release compositions can include one or more hydrophilic polymers that can swell upon contact with water and can impede the release of the active agent. For example, sustained release compositions can include one or more coatings comprising an insoluble polymer such as ethyl cellulose and a soluble pore-forming agent. For example, when a sustained release composition is formulated as a bead or a pellet, the sustained release composition can include one or more polymers (e.g., pH-insensitive polymers and/or pH-sensitive polymers) in the formulation. In some cases, a pharmaceutically acceptable composition containing CX-8998 can be a controlled release composition.

In some cases, a controlled released composition release at least a portion of the active ingredient (e.g., one or more T-type calcium channel antagonists such as CX-8998) rapidly in what is termed "burst release." In some cases, a burst release from a controlled release composition or from a component of a controlled release composition can be used as in addition to an immediate release component of a composition. In some cases, a burst release from a controlled release composition or from a component of a controlled release composition can be used as a substitute for an immediate release component of a composition.

In some cases, a pharmaceutically acceptable composition including one or more T-type calcium channel antagonists described herein can include at least one component (e.g., a first component) that includes a delayed release and/or sustained release composition, and, optionally, a component (e.g., a second component) that includes an immediate release composition. For example, when a composition described herein includes CX-8998, the composition can, in some embodiments include at least a first component that is formulated for delayed and/or sustained release of CX-8998 and, optionally, a second component that is formulated for immediate release of CX-8998. In some cases where a pharmaceutically acceptable composition includes one or more T-type calcium channel antagonists described herein includes at least a first component formulated for delayed and/or sustained release of CX-8998 and, optionally, a second component that is formulated for immediate release of CX-8998, the composition can include any appropriate ratio of the components. When a pharmaceutically acceptable composition including one or more T-type calcium channel antagonists described herein includes a first component formulated for delayed and/or sustained release of CX-8998 and a second component that is formulated for immediate release of CX-8998, the composition can include any appropriate amount (e.g., about 10%, about 15%, about 20%, about 25%, about 30%, about 35%, about 40%, about 45%, about 50%, about 55%, about 60%, about 65%, about 70%, about 75%, about 80%, about 85%, about 90%, or about 95%) of the first component and any appropriate amount (e.g., about 10%, about 15%, about 20%, about 25%, about 30%, about 35%, about 40%, about 45%, about 50%, about 55%, about 60%, about 65%, about 70%, about 75%, about 80%, about 85%, about 90%, or about 95%) of the second component. For example, the composition can include about 40% of a first component that is formulated for delayed and/or sustained release of CX-8998 and about 60% of a second component that is formulated for immediate release of CX-8998. For example, the composition can include about 25% of a first component that is formulated for delayed and/or sustained release of CX-8998 and about 35% of a second component that is formulated for delayed and/or sustained release of CX-8998 (e.g., a second component that is formulated for a delayed and/or sustained release of CX-8998 that is different (e.g., in its composition and/or in its release profile) of the first component), and about 40% of a third component that is formulated for immediate release of CX-8998. In some cases where a composition is designed to release the active ingredient (e.g., one or more T-type calcium channel antagonists such as CX-8998) at two or more different times, a first release (e.g., a delayed and/or sustained release) and a subsequent release (e.g., an immediate release) can overlap. In some cases where a composition is designed to release the active ingredient (e.g., one or more T-type calcium channel antagonists such as CX-8998) at two or more different times, a first release (e.g., a delayed and/or sustained release) and a subsequent release (e.g., an immediate release) can be serial (e.g., do not overlap).

The release rate of a composition (e.g., a pharmaceutically acceptable composition) described herein (e.g., a composition containing one or more T-type calcium channel antagonists such as CX-8998) can be determined using any appropriate method. For example, dissolution testing (e.g., single-stage or two-stage dissolution testing) with high-performance liquid chromatography (HPLC) and/or spectrophotometry can be used to determine the rate at which one or more T-type calcium channel antagonists (e.g., CX-8998) is/are released from a composition containing one or more T-type calcium channel antagonists. In some cases, the release rate of a composition can be determined as described elsewhere (see, e.g., United States Pharmacopeia (USP) chapter 117).

A T-type calcium channel antagonist in a composition (e.g., a pharmaceutically acceptable composition) described herein (e.g., a composition containing one or more T-type calcium channel antagonists such as CX-8998) can have any appropriate dissolution rate. In some cases, a T-type calcium channel antagonist in a composition described herein can have essentially the same rate of dissolution (e.g., a rate of dissolution that is about 90% to about 110% the same) as a substantially pure T-type calcium channel antagonist (e.g., a T-type calcium channel antagonist that is not present in a composition). For example, when a T-type calcium channel antagonist in a composition described herein is CX-8998, the CX-8998 in the composition can have essentially the same rate of dissolution as substantially pure CX-8998 (e.g., when surface area, stirring speed, pH, and/or ionic-strength of the dissolution medium are kept constant).

A composition (e.g., a pharmaceutically acceptable composition) described herein (e.g., a composition containing one or more T-type calcium channel antagonists such as CX-8998) can be designed for any appropriate type of administration (e.g., oral, topical, parenteral, or inhaled administration). In some cases, a composition can be designed for oral administration (e.g., as an oral dosage form). For example, when a composition includes CX-8998, the composition can be designed as an oral CX-8998 dosage form.

When being administered by oral administration, a pharmaceutical composition containing one or more T-type calcium channel antagonists (e.g., one or more Cav3 antagonists such as CX-8998) can be in the form of, for example, a pill, tablet, capsule, solution, or suspension. In some cases, a pharmaceutically acceptable composition including one or more T-type calcium channel antagonists described herein can include a capsule including a plurality of Cav3 antagonist-containing pellets and/or Cav3 antagonist-containing beads. In some cases, a capsule can include a component (e.g., a first component) that includes a delayed release and/or sustained release composition, and, optionally, a component (e.g., a second component) that includes an immediate release composition. For example, when a composition includes CX-8998, the composition can include a capsule containing a plurality of CX-8998-containing pellets and/or CX-8998-containing beads, a portion of which are formulated for immediate release and a portion of which are formulated for delayed and/or sustained release. In some cases, a pharmaceutically acceptable composition including one or more T-type calcium channel antagonists described herein can include a capsule including a plurality of Cav3 antagonist-containing granules. For example, when a composition includes CX-8998, the composition can include a capsule containing a plurality of CX-8998-containing granules, a portion of which are formulated for immediate release and a portion of which are formulated for delayed and/or sustained release. In some cases, a pharmaceutically acceptable composition including one or more T-type calcium channel antagonists described herein can include a tablet including two or more (e.g., two, three, four, or more) layers. In some cases, a tablet can include a component (e.g., a first layer) that includes a delayed release and/or sustained release composition, and, optionally, a component (e.g., a second layer) that includes an immediate release composition. For example, when a composition includes CX-8998, the composition can include a tablet containing a layer of CX-8998 formulated for immediate release and a layer of CX-8998 formulated for delayed and/or sustained release. In some cases, a pharmaceutically acceptable composition including one or more T-type calcium channel antagonists described herein can include a tablet including a core and one or more (e.g., one, two, three, or more) coatings. For example, in some cases where a tablet includes a core and a coating, a tablet core can contain CX-8998 formulated for delayed and/or sustained release, and the tablet core can be coated with a coating containing CX-8998 formulated for immediate release. For example, in some cases where a tablet includes a core and a coating, a tablet core containing CX-8998 can be coated with a coating that delays and/or sustains the release of CX-8998 from the core, and the tablet core can be further coated with CX-8998 formulated for immediate release. In some cases, where a tablet includes a core and a coating, the tablet can be an osmotic pump tablet (e.g., a tablet have an osmotic pressure-driven delivery system). For example, an osmotic pump tablet can include a core and a coating where the tablet core can include CX-8998 and an osmotic agent, and the tablet core can be coated with a coating containing a semipermeable membrane having one or more holes (e.g., at least one precisely drilled hole) such that water diffusing across the semipermeable membrane can generate an osmotic pressure that can force the CX-8998, as a solution and/or suspension, out of the tablet core through the hole(s). In some cases, an osmotic pump table can be coated one or more coatings containing CX-8998 (e.g., CX-8998 formulated for immediate release). In some cases, a capsule can include a component (e.g., one or more particles such as a tablet, beads, pellets, granules, and/or a powder, or mixtures thereof) that includes an immediate release composition, and a component (e.g., a tablet or a coating) that includes CX-8998 formulated for delayed release and/or sustained release. For example, when a composition includes CX-8998, the composition can include a first tablet containing CX-8998 formulated for delayed and/or sustained release and, optionally, a second tablet containing CX-8998 formulated for immediate release. For example, when a composition includes CX-8998, the composition can include a plurality of beads, pellets, granules, and/or a powder containing CX-8998 formulated for immediate release and a tablet containing CX-8998 formulated for delayed and/or sustained release. In some cases, the composition comprises one or more components for immediate release and one or more components for delayed and/or sustained release.

When being administered by topical administration, a pharmaceutical composition containing one or more T-type calcium channel antagonists (e.g., one or more Cav3 antagonists such as CX-8998) can be administered transdermally, epidermally, ophthalmically, and/or to mucous membranes (e.g., intranasally, vaginally, and rectally). When being administered by topical administration, a pharmaceutical composition containing one or more Cav3 antagonists can be in the form of, for example, transdermal patches, ointments, lotions, creams, gels, drops, suppositories, sprays, liquids and powders (e.g., lyophilized powders).

When being administered by parenteral administration, a pharmaceutical composition containing one or more T-type calcium channel antagonists (e.g., one or more Cav3 antagonists such as CX-8998) can be administered by intravenous, intraarterial, subcutaneous, intraperitoneal, intramuscular intracranial (e.g., intrathecal or intraventricular) injection or infusion. When being administered by parenteral administration, a pharmaceutical composition containing one or more T-type calcium channel antagonists can be in the form of, for example, liquids, gels, drops, suppositories, sprays, powders (e.g., lyophilized powders), emulsions, suspensions, microparticles, in-situ gels, and drug-containing implants. When being administered by parenteral administration, a pharmaceutical composition containing one or more T-type calcium channel antagonists can be administered in the form of a one or more bolus doses or may be administered by a continuous perfusion (e.g., by an infusion pump or by an implantable device that provides gradual release).

When being administered by inhaled administration (e.g., inhalation), a pharmaceutical composition containing one or more T-type calcium channel antagonists (e.g., one or more Cav3 antagonists such as CX-8998) can be pulmonary (e.g., can be administered to the nasal cavity, upper airways, or lower airways). For example, administration of a pharmaceutical composition containing one or more T-type calcium channel antagonists can include inhalation or insufflation of a liquid (e.g., an aerosol) and/or a solid (e.g., powder). When being administered by inhaled administration, a pharmaceutical composition containing one or more T-type calcium channel antagonists can be in the form of, for example, liquids (e.g., solutions and suspensions), gels, and powders (e.g., lyophilized powders). When being administered by inhaled administration, a pharmaceutical composition containing one or more T-type calcium channel antagonists can be administered by, for example, a nasal spray pump, a nebulizer, a metered dose inhaler, or a dry powder inhaler.

A composition (e.g., a pharmaceutically acceptable composition) described herein (e.g., a composition containing one or more T-type calcium channel antagonists such as CX-8998) can be administered locally or systemically. In some cases, a composition containing one or more T-type calcium channel antagonists can be administered systemically by an oral administration to a mammal (e.g., a human). For example, when a composition includes CX-8998, the composition can be formulated as an oral dosage form such as a capsule (e.g., a capsule containing a plurality of CX-8998-containing pellets and/or CX-8998-containing beads, a portion of which are formulated for immediate release and a portion of which are formulated for delayed and/or sustained release).

Any appropriate method can be used to formulate a composition (e.g., a pharmaceutically acceptable composition) described herein (e.g., a composition containing one or more T-type calcium channel antagonists such as CX-8998). Examples of methods that can be used to formulate solid compositions described herein include, without limitation, dry blending, wet granulation, spray-drying, hot-melt extrusion, roller compaction, compression, extrusion, spheronization, fluid bed drying, tray drying, fluid bed coating, pan coating, and encapsulation. Examples of methods that can be used to formulate liquid and semisolid compositions described herein include, without limitation, blade mixing, high-shear mixing, homogenization, microfluidizing, media milling, filtration, lyophilization, and autoclaving. In cases where a composition described herein includes pellets and/or beads, the pellets and/or beads can be generated by extrusion and spheronization of a wet mass containing the active ingredient (e.g., one or more T-type calcium channel antagonists such as CX-8998) and, optionally, additional components such as selected excipients (e.g., lactose monohydrate, crospovidone (e.g., polyplasdone XL-10), citric acid, sodium lauryl sulfate (SLS), hydroxypropylcellulose (HPC) such as HPC-SL, microcrystalline cellulose, croscarmellose sodium, magnesium stearate, hydroxypropyl methylcellulose, povidone, and talc). For example, extrusion and spheronization of a wet mass of CX-8998, lactose monohydrate, crospovidone, citric acid, and sodium lauryl sulfate can be used to generate pellets and/or beads (e.g., immediate release pellets and/or beads) containing, by weight, about 5% CX-8998, about 60% lactose monohydrate, about 25% crospovidone, about 8% citric acid, and about 2% SLS. For example, extrusion and spheronization of a wet mass of CX-8998, lactose monohydrate, crospovidone, citric acid, and sodium lauryl sulfate can be used to generate pellets and/or beads (e.g., immediate release pellets and/or beads) containing, by weight, about 5% CX-8998, about 60% lactose monohydrate, about 25% crospovidone, about 8% citric acid, and about 2% SLS. In some cases, the pellets and/or beads can be prepared by blending the dry ingredients, slowly adding water while stirring in a planetary mixer, extruding the resulting wet mass, spheronizing the extrudate, and then drying the resulting pellets and/or beads in a fluid bed dryer. These processes will be understood by those skilled in the art. In cases where a composition described herein includes granules, the granules can be generated by wet granulation of a wet mass containing the active ingredient (e.g., one or more T-type calcium channel antagonists such as CX-8998) and, optionally, additional components such as selected excipients (e.g., lactose monohydrate, crospovidone (e.g., polyplasdone XL-10), citric acid, SLS, HPC such as HPC-SL, microcrystalline cellulose, croscarmellose sodium, magnesium stearate, and TPGS). For example, wet granulation of a wet mass of CX-8998, lactose monohydrate, microcrystalline cellulose, croscarmellose sodium, HPC, magnesium stearate, and TPGS can be used to generate granules (e.g., immediate release granules) containing, by weight, about 2% CX-8998, about 20% lactose monohydrate, about 63% microcrystalline cellulose, about 3% croscarmellose sodium, about 3% HPC, about 0.5% magnesium stearate, and about 10% TPGS. In some cases, the granules can be prepared by blending dry powders in a V-blender or in the bowl of a planetary mixer or high-shear granulator, granulating with addition of water or binder solution in a planetary mixer or high-shear mixer, milling or screening, drying in a fluid bed dryer or tray dryer, optionally milling the dried granules, and then blending them with lubricant and/or glidant. These processes will be understood by those skilled in the art.

In cases where a composition (e.g., a pharmaceutically acceptable composition) described herein (e.g., a composition containing one or more T-type calcium channel antagonists such as CX-8998) includes delayed release pellets and/or beads and/or sustained release pellets and/or beads, the delayed release pellets and/or beads and/or sustained release pellets and/or beads can be generated by coating pellets and/or beads with a sustained release coating and/or a delayed release coating. For example, pellets and/or beads (e.g., immediate release pellets and/or beads) can be coated with a sustained release coating and/or a delayed release coating using a fluid bed coater with Wurster inserts. For example, inert, edible spheres such as sugar spheres (nonpareils) or microcrystalline cellulose spheres (suglets) (e.g., edible spheres containing (e.g., coated with) one or more T-type calcium channel antagonists) can be coated with a sustained release coating and/or a delayed release coating using a fluid bed coater with Wurster inserts. In some cases, a coating can be applied (e.g., to a sphere, pellet, and/or bead) using a film coating method such as using a fluidized bed spray coating process. Other processes for coating spheres, pellets, and/or beads are understood by those skilled in the art. In some cases, a sustained release bead/pellet and/or a delayed release pellet/bead can be generated by coating an immediate release pellet/bead. For example, a delayed release pellet/bead and/or a sustained release bead/pellet can be generated by coating an immediate release pellet/bead with a sustained release coating and/or a delayed release coating. In some cases, a delayed release pellet/bead and/or a sustained release bead/pellet can be generated independently of any immediate release pellet/bead. For example, a delayed release pellet/bead and/or a sustained release bead/pellet can be generated by formulating a pellet/bead (e.g., an uncoated pellet/bead) to provide gradual release of the active ingredient (e.g., CX-8998).

A composition (e.g., a pharmaceutically acceptable composition) described herein (e.g., a composition containing one or more T-type calcium channel antagonists such as CX-8998) can be sterilized using any appropriate method. In some cases, a composition described herein can be sterilized by conventional sterilization techniques. In some cases, a composition described herein can be filtration sterilized.

A composition (e.g., a pharmaceutically acceptable composition) described herein (e.g., a composition containing one or more T-type calcium channel antagonists such as CX-8998) can have any appropriate pH. For example, the pH of a pharmaceutically acceptable composition containing one or more T-type calcium channel antagonists can be from about 3 to about 11. In some cases, the pH of a pharmaceutically acceptable composition containing one or more T-type calcium channel antagonists can be from 5 to about 9. In some cases, the pH of a pharmaceutically acceptable composition containing one or more T-type calcium channel antagonists can be from about 7 to about 8. It will be understood that use of certain additional components (e.g., pharmaceutically acceptable carriers) can alter (e.g., can be used to alter) the pH of a composition described herein.

In some cases, a composition (e.g., a pharmaceutically acceptable composition) described herein (e.g., a composition containing one or more T-type calcium channel antagonists such as CX-8998) can include one or more detectable labels. In some cases, a detectable label can be suitable for in vivo use within a mammal (e.g., a human). Examples of detectable labels include, without limitation, radioisotopes (e.g., $^{14}C$), non radioactive isotopes (e.g., deuterium, and $^{13}C$), spin labels, fluorescent tags, and enzymes. For example, when a composition includes CX-8998, the CX-8998 can be $^{14}C$-labeled CX-8998. For example, a detectable label can be detected to allow imaging of the compositions following administration to a mammal. Imaging can enable a physician or another professional in the field to determine the spatial and/or temporal presence of an administered composition within a mammal.

In some cases, a composition (e.g., a pharmaceutically acceptable composition) described herein (e.g., a composition containing one or more T-type calcium channel antagonists such as CX-8998) can include one or more T-type calcium channel antagonists, methylcellulose, polyethylene glycol (PEG) 400, PEG-200, Tween-80, and/or cyclodextrin. For example, when a composition includes CX-8998, the composition can include CX-8998 and about 0.5 to about 1% methylcellulose. For example, when a composition includes CX-8998, the composition can include CX-8998 and about 90% PEG 400. For example, when a composition includes CX-8998, the composition can include CX-8998 and about 80% PEG-200. For example, when a composition includes CX-8998, the composition can include CX-8998 and about 10% Tween-80. For example, when a composition includes CX-8998, the composition can include CX-8998 and about 30% cyclodextrin.

In some cases, a composition (e.g., a pharmaceutically acceptable composition) described herein (e.g., a composition containing one or more T-type calcium channel antagonists such as CX-8998) can include one or more T-type calcium channel antagonists, methylcellulose, and/or polysorbate-80. For example, when a composition includes CX-8998, the composition can include CX-8998, about 0.5% methylcellulose, and about 10% polysorbate-80. For example, when a composition includes CX-8998, the composition can include CX-8998, about 0.5% methylcellulose, and about 0.1% polysorbate-80.

In some cases, a composition (e.g., a pharmaceutically acceptable composition) described herein (e.g., a composition containing one or more T-type calcium channel antagonists such as CX-8998) can include about 2 milligrams of one or more T-type calcium channel antagonists as a blend of components that are wet granulated together and magnesium stearate. For example, when a composition includes CX-8998, the composition can include about 2 milligrams of CX-8998 (e.g., a free base equivalent of CX-8998) as a blend with microcrystalline cellulose, lactose, croscarmellose sodium, vitamin E PEG succinate, and hydroxypropyl cellulose that are wet granulated together, and magnesium stearate.

In some cases, a composition (e.g., a pharmaceutically acceptable composition) described herein (e.g., a composition containing one or more T-type calcium channel antagonists such as CX-8998) can include about 10 mg of one or more T-type calcium channel antagonists in an immediate release component and about 10 mg of one or more T-type calcium channel antagonists in a delayed release component. For example, when a composition includes CX-8998, the composition can include about 10 mg of CX-8998 (e.g., a free base equivalent of CX-8998) in an immediate release component and about 10 mg of CX-8998 (e.g., a free base equivalent of CX-8998) in a delayed release component. In some cases, the immediate release component can include immediate release beads formed by extrusion and spheronization, and the delayed release component can include beads formed by extrusion and spheronization and coated with one or more pH-sensitive enteric polymers having a dissolution pH or about pH 5.5 to about pH 7 (e.g., pH 6, pH 6.5, or pH 7).

In some cases, a composition (e.g., a pharmaceutically acceptable composition) described herein (e.g., a composition containing one or more T-type calcium channel antagonists such as CX-8998) can include about 7 milligrams of one or more T-type calcium channel antagonists in an immediate release component and about 13 milligrams of one or more T-type calcium channel antagonists in a delayed release component. For example, when a composition includes CX-8998, the composition can include about 7 milligrams of CX-8998 (e.g., a free base equivalent of CX-8998) in an immediate release component and about 13 milligrams of CX-8998 (e.g., a free base equivalent of CX-8998) in a delayed release component. In some cases, the immediate release component can include immediate release beads formed by extrusion and spheronization, and the delayed release component can include beads formed by extrusion and spheronization and coated with one or more pH-sensitive enteric polymers having a dissolution pH of about pH 5.5 to about pH 7 (e.g., pH 6, pH 6.5, or pH 7).

In some cases, a composition (e.g., a pharmaceutically acceptable composition) described herein (e.g., a composition containing one or more T-type calcium channel antagonists such as CX-8998) can be a controlled release composition in a solid dosage form (e.g., a pill, a capsule, and a tablet) including a first component having granules containing CX-8998 which are formulated for delayed and/or sustained release of CX-8998 and a second component having granules containing CX-8998 which are formulated for immediate release of CX-8998. For example, a controlled release capsule can include a first component having granules containing CX-8998 and formulated for delayed and/or sustained release of CX-8998 and, optionally, also can include a second component having granules containing CX-8998 and formulated for immediate release of CX-8998. For example, a controlled release tablet can include a first component having granules containing CX-8998 and formulated for delayed and/or sustained release of CX-8998 and, optionally, also can include a second component having granules containing CX-8998 and formulated for immediate release of CX-8998. In some cases, a first component having granules containing CX-8998 and formulated for delayed and/or sustained release of CX-8998 and, optionally, a second component having granules containing CX-8998 and formulated for immediate release of CX-8998 can be compressed into tablets (e.g., monolithic tablets and tablets having two or more layers).

In some cases, a composition (e.g., a pharmaceutically acceptable composition) described herein (e.g., a composition containing one or more T-type calcium channel antagonists such as CX-8998) can be a controlled release composition including two or more (e.g., two, three, four, or more) solid dosage forms (e.g., pills, capsules, and tablets) where at least one solid dosage form contains CX-8998 which is formulated for immediate release of CX-8998 and at least one solid dosage form contains CX-8998 which is formulated for delayed and/or sustained release of CX-8998. For example, a controlled release composition includes two or more solid dosage forms where at least one solid dosage form contains CX-8998 which is formulated for immediate release of CX-8998 and at least one solid dosage form contains CX-8998 which is formulated for delayed and/or sustained release of CX-8998, the two or more solid dosage forms can be make up single dose.

In some cases, a composition (e.g., a pharmaceutically acceptable composition) described herein (e.g., a composition containing one or more T-type calcium channel antagonists such as CX-8998) can be a controlled release composition having a capsule containing a first component having one or more (e.g., one, two, three, four, or more tablets containing CX-8998 which are formulated for delayed and/or sustained release of CX-8998 and/or one or more (e.g., one, two, three, four, or more) mini-tablets containing CX-8998 which are formulated for delayed and/or sustained release of CX-8998and, optionally, a second component containing CX-8998 which is formulated for immediate release of CX-8998. For example, a controlled release capsule can include a first component having one or more tablets and/or one or more mini-tablets containing CX-8998 and formulated for delayed and/or sustained release of CX-8998 and, optionally, also can include a second component containing CX-8998 and formulated for immediate release of CX-8998. In some cases, a first component having one or more tablets and/or one or more mini-tablets containing CX-8998 and formulated for delayed and/or sustained release of CX-8998 and, optionally, a second component having one or more tablets and/or one or more mini-tablets containing CX-8998 and formulated for immediate release of CX-8998 can be within a capsule. In some cases, a first component having one or more tablets and/or one or more mini-tablets containing CX-8998 and formulated for delayed and/or sustained release of CX-8998 and, optionally, a second component having a powder containing CX-8998 formulated for immediate release of CX-8998 can be within a capsule. In some cases, a first component having one or more tablets and/or one or more mini-tablets containing CX-8998 and formulated for delayed and/or sustained release of CX-8998 and, optionally, a second component having granules containing CX-8998 formulated for immediate release of CX-8998 can be within a capsule. In some cases, a first component having one or more tablets and/or one or more mini-tablets containing CX-8998 and formulated for delayed and/or sustained release of CX-8998 and, optionally, a second component having beads and/or pellets containing CX-8998 formulated for immediate release of CX-8998 can be within a capsule.

In some cases, a composition (e.g., a pharmaceutically acceptable composition) described herein (e.g., a composition containing one or more T-type calcium channel antagonists such as CX-8998) can be a controlled release composition having a capsule containing a first solid component (e.g., granules, beads, pellets, and tablets) containing CX-8998 which is formulated for delayed and/or sustained release of CX-8998 and, optionally, a second liquid component (e.g., a solution or a suspension) containing CX-8998 which is formulated for immediate release of CX-8998. For example, a controlled release capsule can include a first solid component having granules containing CX-8998 and formulated for delayed and/or sustained release of CX-8998 and can include a second liquid component containing CX-8998 formulated for immediate release of CX-8998. In some cases, a first component having granules containing CX-8998 and formulated for delayed and/or sustained release of CX-8998 and, optionally, a second liquid component containing CX-8998 formulated for immediate release of CX-8998 can be within a capsule. In some cases, a first component having beads and/or pellets containing CX-8998 and formulated for delayed and/or sustained release of CX-8998 and, optionally, a second liquid component containing CX-8998 formulated for immediate release of CX-8998 can be within a capsule. In some cases, a first component having one or more (e.g., one, two, three, four, or more) tablets containing CX-8998 and formulated for delayed and/or sustained release of CX-8998 and, optionally, a second liquid component containing CX-8998 formulated for immediate release of CX-8998 can be within a capsule and/or one or more (e.g., one, two, three, four, or more) mini-tablets containing CX-8998 which are formulated for delayed and/or sustained release of CX-8998.

In some cases, a composition (e.g., a pharmaceutically acceptable composition) described herein (e.g., a composition containing one or more T-type calcium channel antagonists such as CX-8998) can be a controlled release composition having a first (e.g., exterior) capsule and a second (e.g., interior) capsule (e.g., a second capsule sized to fit within the first capsule such that a space is present between the outer surface of the second capsule and the inner surface of the first capsule) and containing a first component containing CX-8998 which is formulated for delayed and/or sustained release of CX-8998 and, optionally, a second component containing CX-8998 which is formulated for immediate release. For example, a controlled release capsule that includes an interior capsule that fits within the controlled release capsule, can include a first component containing CX-8998 and formulated for delayed and/or sustained release of CX-8998, and, optionally, can include a second component having granules containing CX-8998 and formulated for immediate release of CX-8998 contained within the interior capsule and/or in the space present between the interior capsule and the exterior capsule. In some cases, an exterior capsule can contain an interior capsule containing a first component that is a solid component (e.g., granules, beads, pellets, and tablets such as mini-tablets) containing CX-8998 and formulated for delayed and/or sustained release of CX-8998 and, optionally, a second component that is a liquid component (e.g., a solution or a suspension) containing CX-8998 formulated for immediate release of CX-8998, where the liquid component containing CX-8998 and formulated for immediate release of CX-8998, when present, is present in a space between the outer surface of the interior capsule and the inner surface of the exterior capsule. In some cases, an exterior capsule can contain an interior capsule having a first component containing CX-8998 formulated for immediate release of CX-8998, and the interior capsule can include a coating that can delay the release of the first component containing CX-8998 formulated for immediate release of CX-8998.

In some cases, a composition (e.g., a pharmaceutically acceptable composition) described herein (e.g., a composition containing one or more T-type calcium channel antagonists such as CX-8998) can be a controlled release composition that is a suspension including a liquid phase (e.g., a solution) and a plurality of solid components (e.g., granules, beads, pellets, and tablets such as mini-tablets) suspended in the liquid phase. For example, a controlled release suspension including a liquid phase and a plurality of solid components can include one or more T-type calcium channel antagonists such as CX-8998 in a liquid phase, can include one or more T-type calcium channel antagonists in solid components suspended in the liquid phase, or can include one or more T-type calcium channel antagonists in both a liquid phase and in solid components suspended in the liquid phase. In some cases, a plurality of solid components containing CX-8998 and formulated for immediate release of CX-8998 and a second plurality of solid components containing CX-8998 and formulated for delayed and/or sustained release of CX-8998 can be suspended in a liquid phase of a controlled release suspension. In some cases, a controlled release suspension can include a liquid phase containing CX-8998 and formulated for immediate release of CX-8998 and can include a plurality of solid components containing CX-8998 and formulated for delayed and/or sustained release of CX-8998 suspended in the liquid phase.

Treatment Methods

This document also provides methods for treating a mammal (e.g., a human) having, or risk or developing, one or more movement disorders. For example, a mammal having, or at risk of developing, one or more movement disorders can be administered a composition described herein (e.g., a composition containing one or more T-type calcium channel antagonists such as CX-8998) to treat the mammal. The term "treating" or "treatment" refers to one or more of (1) preventing a movement disorder; e.g., preventing a movement disorder in an individual who may be predisposed to the movement disorder but does not yet experience or display the pathology or symptomatology of the movement disorder; (2) inhibiting a movement disorder; e.g., inhibiting a movement disorder in an individual who is experiencing or displaying the pathology or symptomatology of the movement disorder (i.e., arresting further development of the pathology and/or symptomatology); and (3) ameliorating a movement disorder; for example, ameliorating a movement disorder in an individual who is experiencing or displaying the pathology or symptomatology of the movement disorder (i.e., reversing the pathology and/or symptomatology) such as decreasing the severity of movement disorder or reducing or alleviating one or more symptoms of the movement disorder. For example, when a mammal having, or at risk of developing, a movement disorder is administered a composition including CX-8998, the composition including CX-8998 can be effective to reduce or eliminate one or more symptoms of the movement disorder. Examples of symptoms of movement disorders include, without limitation, tremors (e.g., rhythmic tremors), unsteady gait (e.g., ataxia), dystonic movements, freezing (bradykinesia), tics, spasms, other dyskinetic movements, seizures, pain, sensory problems, psychiatric symptoms, cognitive impairment, hearing impairment, and mood changes. When a symptom is a tremor, the tremor can be any appropriate type of tremor (e.g., a familial tremor, an action tremor, a postural tremor, a kinetic tremor, and/or a resting tremor). In some cases, a mammal having, or at risk of developing, a movement disorder can be administered a composition including CX-8998, to reduce or eliminate tremors in the mammal. When a symptom is a tremor, the tremor can affect any appropriate part of a mammal (e.g., hands, head, voice, arms, fingers, legs, chin, and other parts of a mammal's body). In some cases, a mammal having, or at risk of developing, a movement disorder can be administered a composition including CX-8998, to reduce or eliminate tremors in the mammal's hand(s). For example, one or more T-type calcium channel antagonists can be administered to a mammal in need thereof (e.g., a mammal having, or at risk of developing, a movement disorder) as described herein to reduce the severity of one or more symptoms of a movement disorder in the mammal by, for example, 10, 20, 30, 40, 50, 60, 70, 80, 90, 95, or more percent. Any appropriate method can be used to evaluate the severity of a movement disorder and/or a symptom of a movement disorder.

In some cases, the severity of a movement disorder and/or a symptom of a movement disorder can include evaluating one or more global functional measures. In some cases, the severity of a movement disorder and/or a symptom of a movement disorder can include evaluating one or more specific functional measures. Examples of methods that can be used to evaluate the severity of a movement disorder and/or a symptom of a movement disorder include, without limitation, measurements of activities of daily living (e.g., as measured using TETRAS), clinician global impression of improvement (e.g., as measured using CGI-I), patient global impression of change (e.g., as measured using PGIC), tremor specific goal attainment (e.g., as measured using GAS), quality of life (e.g., as measured using QUEST tremor medication satisfaction sub-item), and archimedes spiral (e.g., as measured using pen and paper as in the TETRAS-PS sub-item and/or measured digitally using a tablet and stylus such as in iMotor). In some cases, methods for measuring the severity of a movement disorder and/or a symptom of a movement disorder can be as described in the Examples section. For example, when using TETRAS to measure activities of daily living, the higher the score the worse the tremor such that a decrease in score is an improvement in tremor. In some cases, methods that can be used to evaluate the severity of a movement disorder and/or a symptom of a movement disorder can be as described elsewhere (see, e.g., Elble et al, 2013 *Movement Disorders,* 28 1793; Fahn et al. "Clinical rating Scale for Tremor," p. 225-34 In: Jankovik J and Tolosa E. *Parkinson's Disease and Movement Disorders.* 1988 Baltimore-Milnich: Urban & Schwarzenberg; and Haubenberger et al, 2016 *Movement Disorders,* 31, No. 9; Fahn et al., "Members of the UPDRS Development Committee," pp 153-163 and 293-304 In: Fahn et al. (eds.) *Recent Developments in Parkinson's Disease*, Vol 2. 1987 Florham Park, NJ. Macmillan Health Care Information; Treatment guidelines for essential tremor by the American academy of neurology such as those available at the website aan.com/Guidelines/home/GuidelineDetail/492; and Treatment guidelines for Parkinson's disease by the American academy of neurology such as those available at the website movementdisorders.org/MDS-Files1/Resources/PDFs/TreatmentsforMotorSymptomsofPD-2018.pdf.

In some cases, compositions (e.g., pharmaceutically acceptable compositions) including one or more T-type calcium channel antagonists (e.g., one or more Cav3 antagonists such as CX-8998) can be administered to a mammal (e.g., a mammal having, or at risk of developing, one or more movement disorders) when the mammal is in a fasting state. For example, a mammal can have fasted (or have been instructed to fast) for at least 4 hours (e.g., about 4 hours, about 5 hours, about 6 hours, about 7 hours, about 8 hours, about 9 hours, about 10 hours, about 11 hours, or about 12 hours) prior to administering a composition including one or more T-type calcium channel antagonists.

In some cases, compositions (e.g., pharmaceutically acceptable compositions) including one or more T-type calcium channel antagonists (e.g., one or more Cav3 antagonists such as CX-8998) can be administered to a mammal (e.g., a mammal having, or at risk of developing, one or more movement disorders) when the mammal is in a fed (e.g., non-fasting) state.

Any appropriate mammal having, or at risk of developing, a movement disorder (e.g., essential tremor, epilepsy, and/or Parkinson's disease) can be treated as described herein. Examples of mammals that can be treated as described herein (e.g., by administering a composition containing one or more T-type calcium channel antagonists such as CX-8998) include, without limitation, humans, non-human primates (e.g., monkeys), dogs, cats, horses, cows, pigs, sheep, mice, and rats. In some cases, a human having, or at risk of developing, a movement disorder can be treated with a composition containing one or more T-type calcium channel antagonists such as CX-8998 to reduce or eliminate one or more symptoms of the movement disorder.

When treating a mammal having one or more movement disorders as described herein (e.g., by administering a composition containing one or more T-type calcium channel antagonists such as CX-8998), the mammal can be any appropriate age. In some cases, appropriate humans for treatment are adults (e.g., young adults, middle-aged adults, and elderly adults). For example, an adult human can be 18 years of age or older (e.g., 20 years of age or older, 30 years of age or older, 40 years of age or older, 50 years of age or older, 60 years of age or older, 65 years of age or older, 70 years of age or older, or 75 years of age or older). In some cases, an adult can be from about 18 years of age to about 100 years of age (e.g., from about 18 years to about 90 years, from about 18 years to about 80 years, from about 18 years to about 75 years, from about 18 years to about 70 years, from about 18 years to about 65 years, from about 18 years to about 60 years, from about 18 years to about 55 years, from about 18 years to about 50 years, from about 18 years to about 45 years, from about 18 years to about 40 years, from about 20 years to about 100 years, from about 30 years to about 100 years, from about 40 years to about 100 years, from about 50 years to about 100 years, from about 60 years to about 100 years, from about 65 years to about 100 years, from about 70 years to about 100 years, from about 75 years to about 100 years, from about 80 years to about 100 years, from about 20 years to about 55 years, from about 20 years to about 40 years, from about 22 years to about 39 years, from about 40 years to about 80 years, from about 40 years to about 66 years, from about 40 years to about 60 years, from about 50 years to about 80 years, from about 55 years to about 75 years, from about 57 years to about 75 years, or from about 57 years to about 70 years of age). In some cases, appropriate humans for treatment are adolescents (e.g., a human no more than 18 years old. For example, a human adolescents can be from about 1 year of age to about 18 years of age (e.g., from about 1 to about 17 years of age, from about 1 to about 16 years of age, from about 1 to about 15 years of age, from about 1 to about 14 years of age, from about 1 to about 13 years of age, from about 1 to about 12 years of age, from about 1 to about 11 years of age, from about 1 to about 10 years of age, from about 1 to about 8 years of age, from about 1 to about 5 years of age, from about 1 to about 3 years of age, from about 5 to about 18 years of age, from about 10 to about 18 years of age, from about 12 to about 18 years of age, from about 15 to about 18 years of age, from about 16 to about 18 years of age, from about 2 to about 16 years of age, from about 5 to about 15 years of age, from about 8 to about 12 years of age, from about 2 to about 8 years of age, or from about 5 to about 15 years of age). For examples, an adolescent can be about 16 years of age.

When treating a mammal having one or more movement disorders as described herein (e.g., by administering a composition containing one or more T-type calcium channel antagonists such as CX-8998), the mammal can be a female or a male.

When treating a mammal having one or more movement disorders as described herein (e.g., by administering a composition containing one or more T-type calcium channel antagonists such as CX-8998), a composition containing one or more T-type calcium channel antagonists such as CX-8998 can be administered at any appropriate time. In some cases, a composition containing one or more T-type calcium channel antagonists such as CX-8998 can be administered to a mammal in the morning. For example, a composition containing one or more T-type calcium channel antagonists such as CX-8998 can be administered to a mammal between from about 6 am to about noon (e.g., from about 6 am to about 11 am, from about 6 am to about 10 am, from about 6 am to about 9 am, from about 6 am to about 8 am, from about 6 am to about 7 am, from about 7 am to about noon, from about 8 am to about noon, from about 9 am to about noon, from about 10 am to about noon, from about 11 am to about noon, from about 7 am to about 11 am, from about 8 am to about 10 am, from about 7 am to about 9 am, from about 8 am to about 10 am, or from about 9 am to about 11 am). For example, a composition containing one or more T-type calcium channel antagonists such as CX-8998 can be administered to a mammal within about 4 hours (e.g., about 4 hours after waking, about 3 hours after waking, about 2 hours after waking, about 1 hour after waking, about 30 minutes after waking, or immediately after waking).

When treating a mammal having one or more movement disorders as described herein (e.g., by administering a composition containing one or more T-type calcium channel antagonists such as CX-8998), the mammal can have any appropriate movement disorder(s). In some cases, a movement disorder can include tremors. For example, the methods and materials provided herein can be used to treat a mammal having, or at risk of developing, tremors. Examples of movement disorders that can be treated by administering a composition containing one or more T-type calcium channel antagonists such as CX-8998 include, without limitation, essential tremor, Parkinson's disease (e.g., tremor associated with Parkinson's disease), ataxias (e.g., spinocerebellar ataxia and Friedreich's ataxia), epilepsies (e.g., idiopathic generalized epilepsy with absence seizures and pediatric epilepsies), dystonias (e.g., generalized dystonia, focal dystonia, pantothenate kinase-associated neurodegeneration (PKAN), and Hallervorden-Spatz disease), hemiballismus, cerebellar disorders, athetosis, spasticity, bradykinesia, tardive dyskinesia, Huntington's disease, myoclonus, Tourette's syndrome, chorea, tics, progressive supranuclear palsy, multiple system atrophy, corticobasoganlionic degeneration, plasticity, restless legs/arms syndrome, orthostatic tremor, stiff person syndrome, hyperkinetic movement disorders, Rett syndrome, and Wilson's disease. In some cases, a mammal having, or at risk of developing, essential tremor can be treated by administering a composition containing one or more T-type calcium channel antagonists such as CX-8998. In some cases, a mammal having, or at risk of developing, Parkinson's disease can be treated by administering a composition containing one or more T-type calcium channel antagonists such as CX-8998.

In some cases, compositions (e.g., pharmaceutically acceptable compositions) including one or more T-type calcium channel antagonists (e.g., one or more Cav3 antagonists such as CX-8998) can be administered to a mammal having, or at risk of developing other conditions and/or disorders such as, but not limited to, neuropathic pain, psychiatric disorders, autism spectrum disorders, and obsessive compulsive disorder.

When treating a mammal having one or more movement disorders as described herein (e.g., by administering a composition containing one or more T-type calcium channel antagonists such as CX-8998), the mammal can be administered any appropriate amount of a composition (e.g., a pharmaceutically acceptable composition) described herein (e.g., a composition containing one or more T-type calcium channel antagonists such as CX-8998). In some cases, a mammal having, or at risk of developing, one or more movement disorders can be administered a therapeutically effective amount a composition containing one or more T-type calcium channel antagonists such as CX-8998. The term "therapeutically effective amount" refers to the amount of active compound (e.g., one or more T-type calcium channel antagonists such as CX-8998) that elicits the biological or medicinal response that is being sought in a tissue, system, animal, individual or human by a researcher, veterinarian, medical doctor or other clinician. An effective amount of one or more T-type calcium channel antagonists described herein can vary depending on the severity of the movement disorder and/or one or more symptoms/complications associated with the movement disorder, the route of administration, the age and general health condition of the mammal, excipient usage, the possibility of co-usage with other therapeutic treatments such as use of other agents, and the judgment of the treating physician. For example, a composition (e.g., a composition for use in a veterinary and/or research animal such as a dog or rat) can include a dose of one or more T-type calcium channel antagonists can be from about 1 mg/kg to about 1000 mg/kg of body weight per day (e.g., from about 5 mg/kg to about 1000 mg/kg, from about 10 mg/kg to about 1000 mg/kg, from about 20 mg/kg to about 1000 mg/kg, from about 25 mg/kg to about 1000 mg/kg, from about 30 mg/kg to about 1000 mg/kg, from about 50 mg/kg to about 1000 mg/kg, from about 75 mg/kg to about 1000 mg/kg, from about 100 mg/kg to about 1000 mg/kg, from about 250 mg/kg to about 1000 mg/kg, from about 500 mg/kg to about 1000 mg/kg, from about 750 mg/kg to about 1000 mg/kg, from about 1 mg/kg to about 750 mg/kg, from about 1 mg/kg to about 500 mg/kg, from about 1 mg/kg to about 300 mg/kg, from about 1 mg/kg to about 250 mg/kg, from about 1 mg/kg to about 200 mg/kg, from about 1 mg/kg to about 150 mg/kg, from about 1 mg/kg to about 125 mg/kg, from about 1 mg/kg to about 100 mg/kg, from about 1 mg/kg to about 75 mg/kg, from about 1 mg/kg to about 50 mg/kg, from about 1 mg/kg to about 30 mg/kg, from about 5 mg/kg to about 500 mg/kg, from about 10 mg/kg to about 300 mg/kg, from about 15 mg/kg to about 200 mg/kg, from about 20 mg/kg to about 100 mg/kg, from about 25 mg/kg to about 75 mg/kg, from about 10 mg/kg to about 30 mg/kg, from about 20 mg/kg to about 50 mg/kg, from about 30 mg/kg to about 60 mg/kg, or from about 50 mg/kg to about 75 mg/kg of body weight per day). For example, when a composition includes CX-8998, the dose of CX-8998 can be about 10 mg/kg of body weight per day. For example, when a composition includes CX-8998, the dose of CX-8998 can be about 30 mg/kg of body weight per day. For example, when a composition includes CX-8998, the dose of CX-8998 can be about 60 mg/kg of body weight per day. For example, a composition (e.g., a composition for use in a human) can include a dose of one or more T-type calcium channel antagonists can be from about 10 µg/kg to about 1000 µg/kg of body weight per day (e.g., from about 10

μg/kg to about 900 μg/kg, from about 10 μg/kg to about 800 μg/kg, from about 10 μg/kg to about 700 μg/kg, from about 10 μg/kg to about 600 μg/kg, from about 10 μg/kg to about 500 μg/kg, from about 10 μg/kg to about 400 μg/kg, from about 10 μg/kg to about 300 μg/kg, from about 10 μg/kg to about 200 μg/kg, from about 10 μg/kg to about 100 μg/kg, from about 10 μg/kg to about 50 μg/kg, from about 50 μg/kg to about 1000 μg/kg, from about 100 μg/kg to about 1000 μg/kg, from about 200 μg/kg to about 1000 μg/kg, from about 300 μg/kg to about 1000 μg/kg, from about 400 μg/kg to about 1000 μg/kg, from about 500 μg/kg to about 1000 μg/kg, from about 600 μg/kg to about 1000 μg/kg, from about 700 μg/kg to about 1000 μg/kg, from about 800 μg/kg to about 1000 μg/kg, from about 900 μg/kg to about 1000 μg/kg, from about 50 μg/kg to about 900 μg/kg, from about 100 μg/kg to about 800 μg/kg, from about 200 μg/kg to about 700 μg/kg, from about 300 μg/kg to about 600 μg/kg, from about 400 μg/kg to about 500 μg/kg, from about 100 μg/kg to about 200 μg/kg, from about 200 μg/kg to about 300 μg/kg, from about 300 μg/kg to about 400 μg/kg, from about 400 μg/kg to about 500 μg/kg, from about 500 μg/kg to about 600 μg/kg, from about 600 μg/kg to about 700 μg/kg, from about 700 μg/kg to about 800 μg/kg, or from about 800 μg/kg to about 900 μg/kg of body weight per day). For example, when a composition includes CX-8998, the dose of CX-8998 can be about 100 μg/kg of body weight per day. For example, when a composition includes CX-8998, the dose of CX-8998 can be about 300 μg/kg of body weight per day. For example, when a composition includes CX-8998, the dose of CX-8998 can be about 600 μg/kg of body weight per day. In some cases, the dose can depend on such variables as the type and extent of progression of the disease or disorder, the overall health status of the particular patient, the relative biological efficacy of the compound selected, formulation of the excipient, and its route of administration. In some cases, the dose can be increased over time. For example, a dose can be titrated up to a final dose over a period of time (e.g., 1 week, 2 weeks, 3 weeks, or 4 weeks). In some cases, the dose can be decreased over time. For example, a dose can be decreased to a maintenance dose after one or more symptoms have been reduced or eliminated. The dose can be administered, e.g., once a day, twice a day, three times a day, or four times a day. In some cases, the dose can be administered once daily. In some cases, the dose can be administered twice daily.

In some cases, an effective amount of one or more T-type calcium channel antagonists in a composition (e.g., pharmaceutically acceptable compositions) described herein (e.g., a composition containing one or more T-type calcium channel antagonists such as CX-8998) can be extrapolated from dose-response curves derived from in vitro or in vivo model test systems. The effective amount (e.g., a therapeutically effective amount) can remain constant or can be adjusted as a sliding scale or variable dose depending on the mammal's response to treatment. Various factors can influence the actual effective amount used for a particular application. For example, a food effect (e.g., whether the mammal being administered the composition is in a fed state or a fasting state), the frequency of administration, duration of treatment, use of multiple treatment agents, route of administration, and severity of the movement disorder (e.g., essential tremor, epilepsy, and/or Parkinson's disease) may require an increase or decrease in the actual effective amount administered.

The frequency of administration can be any frequency that reduces the severity of movement disorder (e.g., essential tremor, epilepsy, and/or Parkinson's disease) without producing significant toxicity to the mammal. For example, the frequency of administration can be from about once a week to about three times a day, from about twice a month to about six times a day, or from about twice a week to about once a day. The frequency of administration can remain constant or can be variable during the duration of treatment. A course of treatment with a composition (e.g., pharmaceutically acceptable compositions) described herein (e.g., a composition containing one or more T-type calcium channel antagonists such as CX-8998) can include rest periods. For example, a pharmaceutically acceptable composition containing a therapeutically effective amount of one or more T-type calcium channel antagonists can be administered daily over a two-week period followed by a two-week rest period, and such a regimen can be repeated multiple times. As with the effective amount, various factors can influence the actual frequency of administration used for a particular application. For example, the effective amount, duration of treatment, use of multiple treatment agents, route of administration, and severity of the movement disorder (e.g., essential tremor, epilepsy, and/or Parkinson's disease) may require an increase or decrease in administration frequency.

An effective duration for administering a composition (e.g., pharmaceutically acceptable compositions) described herein (e.g., a composition containing one or more T-type calcium channel antagonists such as CX-8998) can be any duration that that reduces the severity of movement disorder (e.g., essential tremor, epilepsy, and/or Parkinson's disease) without producing significant toxicity to the mammal. For example, the effective duration can vary from several days to several weeks, months, or years. In some cases, the effective duration for the treatment of movement disorder (e.g., essential tremor, epilepsy, and/or Parkinson's disease) can range in duration from about one month to about 10 years. In some cases, the effective duration for the treatment of movement disorder (e.g., essential tremor, epilepsy, and/or Parkinson's disease) can be indefinite (e.g., the lifespan of the mammal being treated). For example, a composition including one or more T-type calcium channel antagonists can be administered to a mammal (e.g., a mammal having, or at risk of developing, one or more movement disorders) for from about 1 week to about 9 weeks (e.g., from about 1 week to about 8 weeks, from about 1 week to about 7 weeks, from about 1 week to about 6 weeks, from about 1 week to about 5 weeks, from about 1 week to about 4 weeks, from about 1 week to about 3 weeks, from about 1 week to about 2 weeks, from about 2 weeks to about 9 weeks, from about 3 weeks to about 9 weeks, from about 4 weeks to about 9 weeks, from about 5 weeks to about 9 weeks, from about 6 weeks to about 9 weeks, from about 7 weeks to about 9 weeks, from about 8 weeks to about 9 weeks, from about 2 weeks to about 8 weeks, from about 3 weeks to about 7 weeks, from about 4 weeks to about 6 weeks, from about 2 weeks to about 4 weeks, from about 3 weeks to about 5 weeks, from about 4 weeks to about 6 weeks, from about 5 weeks to about 7 weeks, or from about 6 weeks to about 8 weeks). In some cases, a composition including CX-8998 can be administered to a mammal (e.g., a mammal having, or at risk of developing, one or more movement disorders) for about 2 weeks (e.g., about 15 days). In some cases, a composition including CX-8998 can be administered to a mammal (e.g., a mammal having, or at risk of developing, one or more movement disorders) for about 4 weeks (e.g., about 28 days). For example, a composition including one or more T-type calcium channel antagonists can be administered to a mammal (e.g., a mammal having, or at risk of developing, one or more movement disorders) for about 8 weeks or longer. For example, a composition including one or more T-type calcium channel antagonists can be administered to a mammal (e.g., a mammal having, or at risk of developing, one or more movement disorders) for about 12 weeks or longer. For example, a composition including one or more T-type calcium channel antagonists can be administered to a mammal (e.g., a mammal having, or at risk of developing, one or more movement disorders) for about 2 months or longer. For example, a composition including one or more T-type calcium channel antagonists can be administered to a mammal (e.g., a mammal having, or at risk of developing, one or more movement disorders) for about 4 months or longer. For example, a composition including one or more T-type calcium channel antagonists can be administered to a mammal (e.g., a mammal having, or at risk of developing, one or more movement disorders) for about 6 months or longer. For example, a composition including one or more T-type calcium channel antagonists can be administered to a mammal (e.g., a mammal having, or at risk of developing, one or more movement disorders) for about 12 months or longer. For example, a composition including one or more T-type calcium channel antagonists can be administered to a mammal (e.g., a mammal having, or at risk of developing, one or more movement disorders) for about 24 months or longer. Multiple factors can influence the actual effective duration used for a particular treatment. For example, an effective duration can vary with the frequency of administration, effective amount, use of multiple treatment agents, route of administration, and severity of the condition being treated.

In some cases, when a mammal having, or at risk of developing, one or more movement disorders is administered a composition including CX-8998, the composition can be effective to achieve a minimum effective concentration (MEC) of CX-8998 (e.g., the minimum concentration of CX-8998 in a mammal's plasma required to produce a therapeutic effect described herein). For example, a MEC of CX-8998 can be from about 100 nM to about 1800 nM (e.g., from about 200 nM to about 1800 nM, from about 300 nM to about 1800 nM, from about 400 nM to about 1800 nM, from about 500 nM to about 1800 nM, from about 700 nM to about 1800 nM, from about 1000 nM to about 1800 nM, from about 1200 nM to about 1800 nM, from about 1500 nM to about 1800 nM, from about 100 nM to about 1500 nM, from about 100 nM to about 1200 nM, from about 100 nM to about 1000 nM, from about 100 nM to about 800 nM, from about 100 nM to about 700 nM, from about 100 nM to about 600 nM, from about 100 nM to about 500 nM, from about 100 nM to about 400 nM, from about 100 nM to about 300 nM, from about 200 nM to about 1500 nM, from about 300 nM to about 1200 nM, from about 500 nM to about 1000 nM, from about 600 nM to about 800 nM, from about 200 nM to about 400 nM, from about 400 nM to about 600 nM, or from about 300 nM to about 500 nM).

In some cases, a composition including CX-8998 can be administered to a mammal (e.g., a mammal having, or at risk of developing, one or more movement disorders) to achieve a MEC of CX-8998 of about 200 nM. In some cases, a composition including CX-8998 can be administered to a mammal (e.g., a mammal having, or at risk of developing, one or more movement disorders) to achieve a MEC of CX-8998 of about 209 nM. In some cases, a composition including CX-8998 can be administered to a mammal (e.g., a mammal having, or at risk of developing, one or more movement disorders) to achieve a MEC of CX-8998 of about 215 nM.

In some cases, when a mammal having, or at risk of developing, one or more movement disorders is administered a composition including one or more Cav3 antagonists such as CX-8998, the composition can be effective to maintain a MEC of the Cav3 antagonist(s) (e.g., in the mammal's blood and/or in a blood sample obtained from the mammal such as a plasma sample) for any appropriate amount of time. For example, a MEC of CX-8998 can be maintained in the mammal for at least about 12 hours (e.g., about 12 hours, about 13 hours, about 14 hours, about 15 hours, about 16 hours, about 17 hours, about 18 hours, about 19 hours, about 20 hours, about 21 hours, about 22 hours, about 23 hours, about 24 hours, about 25 hours, or about 26 hours). For example, a MEC of CX-8998 can be maintained for from about 10 hours to about 15 hours (e.g., for from about 10 hours to about 14 hours, for from about 10 hours to about 13 hours, for from about 10 hours to about 12 hours, for from about 10 hours to about 11 hours, for from about 11 hours to about 15 hours, for from about 12 hours to about 15 hours, for from about 13 hours to about 15 hours, for from about 14 hours to about 15 hours, for from about 11 hours to about 14 hours, for from about 12 hours to about 13 hours, for from about 11 hours to about 12 hours, or for from about 13 hours to about 14 hours). In some cases, a composition including CX-8998 can be administered to a mammal (e.g., a mammal having, or at risk of developing, one or more movement disorders) to maintain a MEC of CX-8998 for about 12 hours. For example, a MEC of CX-8998 can be maintained for from about 22 hours to about 26 hours (e.g., for from about 22 hours to about 25 hours, for from about 22 hours to about 24 hours, for from about 22 hours to about 23 hours, for from about 23 hours to about 26 hours, for from about 24 hours to about 26 hours, for from about 25 hours to about 26 hours, for from about 23 hours to about 25 hours, or for from about 23 hours to about 24 hours). In some cases, a composition including CX-8998 can be administered to a mammal (e.g., a mammal having, or at risk of developing, one or more movement disorders) to maintain a MEC of CX-8998 for about 24 hours.

In some cases, when a mammal having, or at risk of developing, one or more movement disorders is administered a composition including CX-8998, the composition can be effective to achieve a maximum safe concentration (e.g., the maximum concentration of CX-8998 that is well tolerated (e.g., result in minimal, reduced, or no side effects and/or adverse events such as dizziness, headache, euphoria, disturbance in attention, paresthesia, hallucination, insomnia, dry mouth, dysguesia, hypoesthesia, somnolence, lethargy, sleep disturbance, nausea, vomiting, akathisia, decreased level of consciousness, syncope, memory impairment, anxiety, restlessness, fatigue, irritability, constipation, tinnitus, anorexia, emotional disturbances, sexual impotency, diplopia, nystagmus, drowsiness, morbilliform skin eruptions, granulocytopenia, agranulocytosis, red-cell hypoplasia, and aplasia) in a mammal's plasma) of CX-8998. For example, a maximum safe concentration of CX-8998 can be from about 1000 nM to about 1800 nM (e.g., from about 1100 nM to about 1800 nM, from about 1200 nM to about 1800 nM, from about 1300 nM to about 1800 nM, from about 1400 nM to about 1800 nM, from about 1500 nM to about 1800 nM, from about 1600 nM to about 1800 nM, from about 1700 nM to about 1800 nM, from about 1000 nM to about 1700 nM, from about 1000 nM to about 1600 nM, from about 1000 nM to about 1500 nM, from about 1000 nM to about 1400 nM, from about 1000 nM to about 1300 nM, from about 1000 nM to about 1200 nM, from about 1000 nM to about 1100 nM, from about 1100 nM to about 1700 nM, from about 1200 nM to about 1600 nM, from about 1300 nM to about 1500 nM, from about 1100 nM to about 1300 nM, from about 1200 nM to about 1400 nM, from about 1300 nM to about 1500 nM, from about 1400 nM to about 1600 nM, or from about 1500 nM to about 1700 nM).

In some cases, when a mammal having, or at risk of developing, one or more movement disorders is administered a composition including one or more Cav3 antagonists such as CX-8998, the composition can be effective to maintain a $C_{max}$ (e.g., the maximum concentration achieved in a mammal's plasma) below the tolerability threshold of Cav3 antagonist(s). For example, a $C_{max}$ of CX-8998 can be less about 1800 nM (e.g., about 1700 nM, about 1600 nM, about 1500 nM, about 1400 nM, about 1300 nM, about 1200 nM, about 1100 nM, about 1000 nM, about 990 nM, about 980 nM, about 970 nM, about 960 nM, about 950 nM, about 940 nM, about 930 nM, about 920 nM, about 910 nM, or about 900 nM). For example, a $C_{max}$ of CX-8998 can be from about 900 nM to about 1800 nM (e.g., from about 1000 nM to about 1800 nM, from about 1200 nM to about 1800 nM, from about 1400 nM to about 1800 nM, from about 1500 nM to about 1800 nM, from about 1600 nM to about 1800 nM, from about 900 nM to about 1700 nM, from about 900 nM to about 1500 nM, from about 900 nM to about 1400 nM, from about 900 nM to about 1300 nM, from about 900 nM to about 1200 nM, from about 900 nM to about 1100 nM, from about 1000 nM to about 1500 nM, or from about 1200 nM to about 1400 nM). In some cases, a composition including CX-8998 can be administered to a mammal (e.g., a mammal having, or at risk of developing, one or more movement disorders) to achieve a $C_{max}$ of CX-8998 of about 900 nM. In some cases, a composition including CX-8998 can be administered to a mammal (e.g., a mammal having, or at risk of developing, one or more movement disorders) to achieve a $C_{max}$ of CX-8998 of about 1000 nM.

In some cases, when a mammal having, or at risk of developing, one or more movement disorders is administered a composition including one or more Cav3 antagonists such as CX-8998, the composition can be effective to maintain an area under the curve (AUC) of the Cav3 antagonist(s) from about 3,000 nM*hour to about 10,000 nM*hour. For example, an AUC of CX-8998 can be from about from about 3,000 nM*hour to about 9,000 nM*hour, from about 3,000 nM*hour to about 8,000 nM*hour, from about 3,000 nM*hour to about 7,000 nM*hour, from about 3,000 nM*hour to about 6,000 nM*hour, from about 3,000 nM*hour to about 5,000 nM*hour, from about 3,000 nM*hour to about 4,000 nM*hour, from about 4,000 nM*hour to about 10,000 nM*hour, from about 5,000 nM*hour to about 10,000 nM*hour, from about 6,000 nM*hour to about 10,000 nM*hour, from about 7,000 nM*hour to about 10,000 nM*hour, from about 8,000 nM*hour to about 10,000 nM*hour, from about 9,000 nM*hour to about 10,000 nM*hour, from about 4,000 nM*hour to about 9,000 nM*hour, from about 5,000 nM*hour to about 8,000 nM*hour, from about 6,000 nM*hour to about 7,000 nM*hour, from about 4,000 nM*hour to about 6,000 nM*hour, from about 5,000 nM*hour to about 7,000 nM*hour, from about 6,000 nM*hour to about 8,000 nM*hour, or from about 7,000 nM*hour to about 9,000 nM*hour. An AUC can be measured at any appropriate time (e.g., any appropriate time after administration of a composition including CX-8998 to a mammal having, or at risk of developing, one or more movement disorders). An AUC can be measured for any appropriate time interval (e.g., any appropriate duration of time after administration of a composition including CX-8998 to a mammal having, or at risk of developing, one or more movement disorders). For example, an AUC can be measured for from about 12 hours ($AUC_{0-24}$ or $AUC_{24}$) to about 36 hours ($AUC_{0-36}$ or $AUC_{36}$; e.g., from about 12 hours to about 32 hours, from about 12 hours to about 28 hours, from about 12 hours to about 24 hours, from about 12 hours to about 20 hours, from about 12 hours to about 18 hours, from about 18 hours to about 36 hours, from about 22 hours to about 36 hours, from about 24 hours to about 36 hours, from about 15 hours to about 32 hours, from about 18 hours to about 24 hours, from about 12 hours to about 15 hours, from about 15 hours to about 18 hours, from about 18 hours to about 22 hours, from about 22 hours to about 26 hours, from about 26 hours to about 30 hours, or from about 30 hours to about 32 hours). In some cases, an AUC can be measured for about 24 hours (e.g., $AUC_{0-24}$ or $AUC_{24}$).

Figure 74:
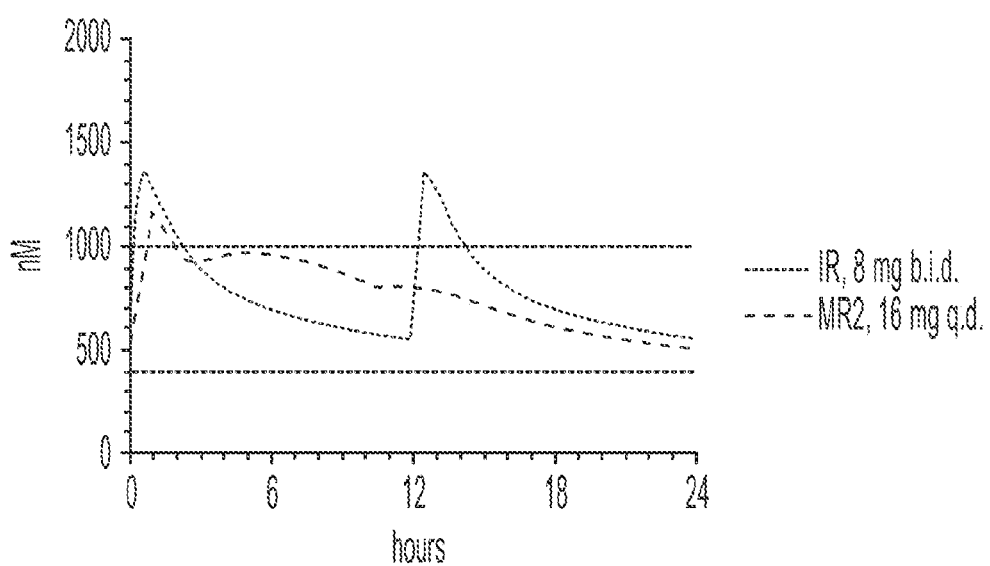
FIG. 74 contains a graph showing an exemplary once daily dosing of MR2 CX-8998 and twice daily dosing of an IR CX-8998.

In some cases, when a mammal having, or at risk of developing, one or more movement disorders is administered a composition including one or more Cav3 antagonists such as CX-8998, the composition can be effective to maintain a plasma concentration (e.g., a mean plasma concentration) of the Cav3 antagonist(s) in the mammal that is between a MEC of CX-8998 (e.g., about 400 nM CX-8998) and a $C_{max}$ of CX-8998 (e.g., about 1000 nM). For example, when a composition including CX-8998 is administered to a mammal, the composition can be effective to maintain a mean plasma concentration of CX-8998 in the mammal that is from about 400 nM CX-8998 to about 1000 nM CX-8998. For example, when a composition including CX-8998 is administered to a mammal, the composition can be effective to maintain a mean plasma concentration of CX-8998 in the mammal as shown in FIG. 74. In cases where a composition including CX-8998 includes a first component formulated for delayed and/or sustained release of CX-8998 and, optionally, a second component formulated for immediate release of CX-8998, the first component formulated for delayed and/or sustained release of CX-8998 can be effective to maintain a plasma concentration (e.g., a mean plasma concentration) of CX-8998 that is between a MEC of CX-8998 (e.g., about 400 nM CX-8998) and a $C_{max}$ of CX-8998 (e.g., about 1000 nM) such that the composition can be effective to maintain a concentration of CX-8998 that is between a MEC of CX-8998 and a $C_{max}$ of CX-8998, and the second component formulated for immediate release of CX-8998, when present, can be effective to rapidly (e.g., in less than about 60 minutes) achieve a plasma concentration (e.g., a mean plasma concentration) that is at least a MEC of CX-8998 (e.g., at least about 400 nM CX-8998). For example, when a composition including CX-8998 that includes a first component formulated for delayed and/or sustained release of CX-8998 and, optionally, a second component formulated for immediate release of CX-8998 is administered to a mammal, the composition can be effective to achieve a mean plasma concentration of CX-8998 in less than about 60 minutes, and can be effective to maintain a mean plasma concentration of CX-8998 in the mammal that is from about 400 nM CX-8998 to about 1000 nM CX-8998. A mean plasma concentration of including CX-8998 achieved by a composition described herein including CX-8998 can be maintained for any appropriate amount of time (e.g., for any appropriate duration of time after administration of a composition including CX-8998 to a mammal having, or at risk of developing, one or more movement disorders). For example, a mean plasma concentration of CX-8998 that is from about 400 nM to about 1000 nM can be maintained for at least about 12 hours (e.g., about 12 hours, about 13 hours, about 14 hours, about 15 hours, about 16 hours, about 17 hours, about 18 hours, about 19 hours, about 20 hours, about 21 hours, about 22 hours, about 23 hours, about 24 hours, about 25 hours, or about 26 hours). In some cases, a mean plasma concentration of from about 400 nM CX-8998 to about 1000 nM CX-8998 can be maintained for from about 12 hours to about 36 hours (e.g., from about 12 hours to about 32 hours, from about 12 hours to about 28 hours, from about 12 hours to about 24 hours, from about 12 hours to about 20 hours, from about 12 hours to about 18 hours, from about 18 hours to about 36 hours, from about 22 hours to about 36 hours, from about 24 hours to about 36 hours, from about 15 hours to about 32 hours, from about 18 hours to about 24 hours, from about 12 hours to about 15 hours, from about 15 hours to about 18 hours, from about 18 hours to about 22 hours, from about 22 hours to about 26 hours, from about 26 hours to about 30 hours, or from about 30 hours to about 32 hours). For example, a mean plasma concentration of from about 400 nM CX-8998 to about 1000 nM CX-8998 can be maintained for about 18 hours. For example, a mean plasma concentration of from about 400 nM CX-8998 to about 1000 nM CX-8998 can be maintained for about 24 hours. For example, when a composition including CX-8998 is administered to a mammal, the composition can be effective to maintain a mean plasma concentration of CX-8998 in the mammal that is from about 400 nM CX-8998 to about 1000 nM CX-8998 for about 24 hours (e.g., can have an AUC of about 400 nM*hour and about 1000 nM*hour for about 24 hours).

In some cases, when a mammal having, or at risk of developing, one or more movement disorders is administered a composition including one or more Cav3 antagonists such as CX-8998, the composition can be effective to maintain a maximum concentration ($C_{max}$) of the Cav3 antagonist(s) divided by a mean plasma concentration of the Cav3 antagonist(s) at 24 hours after administration (e.g., plasma concentration at 24 hours $$\left( e.g., \frac{C_{max}}{\text{plasma concentration at 24 hours}} \right)$$

that is less than 5.0 (e.g., about 5, about 4.5, about 4, about 3.5, about 3, about 2.5, about 2, about 1.5, or about 1.0). For example, when a composition including CX-8998 is administered to a mammal, the composition can be effective to maintain a $$\frac{C_{max}}{\text{plasma concentration at 24 hours}}$$

of CX-8998 in the mammal that is from about 1.0 to about 5.0 (e.g., from about 1.0 to about 4.5, from about 1.0 to about 4.0, from about 1.0 to about 3.5, from about 1.0 to about 3.0, from about 1.0 to about 2.5, from about 1.0 to about 2.0, from about 1.5 to about 5.0, from about 2.0 to about 5.0, from about 2.5 to about 5.0, from about 3.0 to about 5.0, from about 3.5 to about 5.0, from about 4.0 to about 5.0, from about 1.5 to about 4.5, from about 2.0 to about 4.0, from about 1.5 to about 2.5, from about 2.5 to about 3.5, or from about 3.5 to about 4.5).

In some cases, when a mammal having, or at risk of developing, one or more movement disorders is administered a composition including one or more Cav3 antagonists such as CX-8998, the composition can be effective to achieve a $C_{max}$ that is lower than a $C_{max}$ achieved from an immediate release composition including one or more Cav3 antagonists such as CX-8998 (e.g., an immediate release composition including one or more Cav3 antagonists of the same dose). For example, when a composition including CX-8998 is administered to a mammal, the composition can be effective to maintain a $C_{max}$ of CX-8998 that is from about 30% to about 70% (e.g., from about 30% to about 60%, from about 30% to about 50%, from about 30% to about 40%, from about 40% to about 70%, from about 50% to about 70%, from about 60% to about 70%, or from about 40% to about 60%) lower than a $C_{max}$ achieved from an immediate release composition including CX-8998.

In some cases, methods of treating a mammal having, or at risk of developing, one or more movement disorders as described herein (e.g., by administering a composition containing one or more T-type calcium channel antagonists such as CX-8998), also can include identifying the mammal as having, or as being at risk of developing, one or more movement disorders. Any appropriate method can be used to identify a mammal as having a movement disorder. Methods of identifying a mammal as having, or at risk of developing a movement disorder can include, without limitation, reviewing the mammal's medical history, reviewing the mammal's family history, conducting a physical examination (e.g., neurological examinations including checking tendon reflexes, muscle strength and tone, ability to feel certain sensations, posture and coordination, and/or gait), laboratory tests (e.g., laboratory tests including checking the mammal's blood and/or urine for thyroid disease, metabolic problems, drug side effects, alcohol levels, and/or levels of chemicals that may cause tremor), imaging (e.g., functional imaging), performance tests (e.g., performance tests to evaluate the tremor itself including drinking from a glass, holding arms outstretched, writing, and/or drawing a spiral), and/or a dopamine transporter scan. In some cases, identifying a mammal as having, or at risk of developing a movement disorder can include genetic testing. For example, testing for the presence or absence of one or more genetic variants that associated with movement disorders, can be used for identifying a mammal as having, or at risk of developing a movement disorder (e.g., essential tremor). For example, genetic variants associate with a movement disorder (e.g., essential tremor) can be as described elsewhere (see, e.g., Odgerel et al, 2018 bioRxiv doi: http://dx.doi.org/10.1101/248443).

In some cases, when treating a mammal having, or at risk of developing, one or more movement disorders (e.g., essential tremor, epilepsy, and/or Parkinson's disease) as described herein (e.g., by administering a composition containing one or more T-type calcium channel antagonists such as CX-8998), the treatment also can include one or more additional therapies. A therapy can be any appropriate therapy (e.g., a therapy used to treat one or more movement disorders and/or one or more symptoms associated with a movement disorder) such as administering one or more pharmaceuticals, administering one or more nutraceuticals, physical therapies, occupational therapies, surgeries, ultrasound thalamotomy, neurostimulation techniques, digital therapeutics, and alternative medicines. Examples of therapies that can be used to treat a mammal having, or at risk of developing, essential tremor and/or one or more symptoms associated with essential tremor include, without limitation, administering one or more beta blockers (e.g., propranolol), administering one or more anti-seizure medications (e.g., primidone, gabapentin, topiramate, pregabalin, zonisamide, and ethosuximide), administering one or more tranquilizers (e.g., alprazolam and clonazepam), injections of onabotulinumtoxinA (botox), physical therapy, occupational therapy, surgery (e.g., deep brain stimulation), ultrasound thalamotomy (e.g., focused/guided ultrasound thalamotomy), neurostimulation (e.g., transcranial magnetic stimulation), and digital therapeutics (e.g., devices such as tremor canceling wearables and utensils such as tremor spoons). In some cases, a therapy that can be used to treat a mammal having, or at risk of developing, essential tremor and/or one or more symptoms associated with essential tremor can be as described elsewhere (see, e.g., Treatment guidelines for essential tremor by the American academy of neurology such as those available at aan.com/Guidelines/home/GuidelineDetail/492). Examples of therapies that can be used to treat a mammal having, or at risk of developing, Parkinson's disease and/or one or more symptoms associated with Parkinson's disease include, without limitation, administering one or more dopamine agonists (e.g., carbidopa-levodopa, pramipexole, ropinirole, rotigotine, and apomorphine), administering one or more monoamine oxidase B (MAO B) inhibitors (e.g., selegiline, rasagiline, and safinamide), administering one or more catechol O-methyltransferase (COMT) inhibitors (e.g., entacapon, and tolcapone), administering one or more anticholinergics (e.g., benztropine and trihexyphenidyl), administering amantadine, physical therapy, occupational therapy, and surgery (e.g., deep brain stimulation). In some cases, a therapy that can be used to treat a mammal having, or at risk of developing, Parkinson's disease and/or one or more symptoms associated with Parkinson's disease can be as described elsewhere (see, e.g., Treatment guidelines for Parkinson's disease by the American academy of neurology such as those available at the website movementdisorders.org/MDS-Files1/Resources/PDFs/TreatmentsforMotorSymptomsofPD-2018.pdf). In cases where a mammal having, or at risk of developing, one or more movement disorders is treated with a composition containing one or more T-type calcium channel antagonists (e.g., one or more Cav3 antagonists such as CX-8998) and is treated with one or more additional therapies, the one or more additional therapies can be administered at the same time or independently. For example, a composition containing one or more T-type calcium channel antagonists (e.g., CX-8998) can be administered first, and the one or more additional therapies administered second, or vice versa.

This document also provides methods for identifying the presence, absence, or amount of total active moiety (TAM) in a composition (e.g., a pharmaceutically acceptable composition) described herein (e.g., a composition containing one or more T-type calcium channel antagonists such as CX-8998). The term "TAM" as used herein refers to the sum of the active components present in a composition. For example, when a composition includes CX-8998, the TAM can include one or more of CX 8998, M01, M02, M03, and/or M04. For example, when a composition includes CX-8998, the methods can include identifying the presence, absence, or amount of CX 8998 and metabolites M01, M02, M03, and M04. In some cases, mass spectrometry (MS) methods can be used for the quantitation (e.g., simultaneous quantitation) of CX-8998, M01, M02, M03, and/or M04. Any appropriate MS method can be used. In some cases, a liquid chromatography-tandem MS (LC/MS/MS) bioanalytical method can be used for the simultaneous quantitation of CX-8998 and metabolites M01, M02, M03, and M04. For example, LC/MS/MS can be used to quantifying the TAM associated with CX-8998. In some cases, identifying the presence, absence, or amount of TAM (e.g., of CX 8998, M01, M02, M03, and/or M04) in a composition can be effective to determine acceptance criteria for system performance suitability, quantitation range, calibration linearity, assay accuracy and precision, and/or assay recovery. For example, when a composition includes CX-8998, identifying the presence, absence, or amount of CX 8998, M01, M02, M03, and/or M04 can be effective to determine acceptance criteria for system performance suitability, quantitation range, calibration linearity, assay accuracy and precision, and assay recovery.

This document also provides kits containing one or more materials described herein. For example, materials provided in kits described herein can be used for treating mammals (e.g., humans) having, or at risk of developing, one or more movement disorders (e.g., essential tremor, epilepsy, and/or Parkinson's disease) as described herein. In some cases, a composition (e.g., a pharmaceutically acceptable composition) including one or more T-type calcium channel antagonists (e.g., one or more Cav3 antagonists such as CX-8998) can be combined with packaging material and sold as a kit. For example, a kit can include a composition including one or more T-type calcium channel antagonists described herein presented in unit-dose or multi-dose containers. A container can be any appropriate size (e.g., a 60 cc container). A container can be any appropriate material (e.g., high-density polyethylene (HDPE) such as a white HDPE). A container can include a closure (e.g., a child-resistant closure). A close can be any appropriate material (e.g., polypropylene such as a white, 33-mm polypropylene). In some cases, no desiccant is included in the bottles. In some cases, no cotton is included in the bottles. In some cases, a kit can include a pharmaceutically acceptable composition including CX-8998 described herein in the form of tablets or capsules (e.g., tablets or capsules for oral administration) having a component (e.g., a first component) that is a sustained release composition, and, optionally, a component (e.g., a second component) that is an immediate release composition. In some cases, the packaging material included in such a kit typically contains instructions or a label describing how the composition can be used, for example, to treat mammal (e.g., a human) having, or at risk of developing, one or more movement disorders (e.g., essential tremor, epilepsy, and/or Parkinson's disease) as described herein. For example, a kit can include instructions or a label instructing a mammal to not eat for at least about 4 hours (e.g., about 4 hours, about 5 hours, about 6 hours, about 7 hours, about 8 hours, about 9 hours, about 10 hours, about 11 hours, or about 12 hours) prior to taking the composition. For example, a kit can include instructions or a label instructing a mammal to take the composition with food. For example, a kit can include instructions or a label instructing a mammal to take the composition within about 4 hours (e.g., about 4 hours after waking, about 3 hours after waking, about 2 hours after waking, about 1 hour after waking, about 30 minutes after waking, or immediately after waking) of waking. In some cases, the packaging material included in such a kit typically contains instructions or a label describing how the composition can be stored (e.g., to be stored between from about 15° C. to about 30° C., or from about 20° C. to about 25° C.).

The invention will be further described in the following examples, which do not limit the scope of the invention described in the claims.

EXAMPLES

The Essential Tremor Rating Assessment Scale (TETRAS) The Tremor Research Group first published the TRG Essential Tremor Rating Assessment Scale (TETRAS) in 2008 (Elble et al., 2008 MovDisord. 23(Suppl 1):S1-6). TETRAS consists of a 9-item performance subscale and a 12-item activities of daily living (ADL) subscale. TETRAS was developed as a rapid clinical assessment of ET that requires no equipment other than pen and paper. Administration of the performance subscale takes less than 10 minutes. The scale employs objective metrics to reduce experiential rater bias.

To evaluate the inter-rater reliability of TETRAS, Elble et al. (2012 *Mov Disord.* 27(12):1567-1569) videotaped 50 TETRAS exams, including assessments of 44 patients with ET and 6 controls. The severity of ET ranged from mild to severe. Ten specialists rated the patients in the videos 2 times with an interval of 1 to 2 months separating the ratings. Of the 10 raters, 6 had been involved in the development of TETRAS, and 4 had never used the scale.

Inter-rater reliability of the scale was calculated using a two-way random effects intraclass correlation (ICC) with an absolute agreement definition. The inter- and intra-rater ICC for head and upper limb tremor ranged from 0.86 to 0.96, and the ICC for the total score were 0.94 and 0.96. The ICC for voice, face, trunk and leg were less robust (Elble et al. 2012 *Mov Disord.* 27(12):1567-1569).

The TETRAS Performance subscale is widely used in clinical practice and has high content validity and strong inter-rater reliability. The TETRAS ADL and performance scores are highly correlated, and the TETRAS ratings of upper extremity function correlate strongly with transducer measures (accelerometry) of upper limb tremor (Mostile et al., 2010 *Mov Disord.* 25(12):1938-1943). TETRAS is also shown to be sensitive to change in tremor over time (Voller et al., 2014 *Mov Disord.* 29(4):555-558).

The higher the score the worse the tremor—a decrease in score is an improvement in tremor.

Example 1. Significant Change from Baseline to Day 28 in the TETRAS-PS as Rated by Investigator TETRAS Performance Subscale The Performance subscale quantifies tremor in the head, face, voice, limbs and trunk. Each item is rated on a 0 to 4 rating scale, with scoring of upper limb tremor allowing for 0.5-point increments. Specific amplitude ranges (measured in centimeters) define the tremor rating. Raters first estimate the maximum amplitude of tremor and then assign the corresponding rating. The sum of the individual rating scores provides the overall Performance score, ranging from 0 to 64. The complete TETRAS Performance Subscale is as shown below.

Scoring is 0-4. For most items, the scores are defined only by whole numbers, but 0.5 increments may be used if you believe the rating is between two whole number ratings and cannot be reconciled to a whole number. Each 0.5 increment in rating is specifically defined for the assessment of upper limb postural and kinetic tremor and the dot approximation task (items 4 and 8). All items of the examination, except standing tremor, are performed with the patient seated comfortably. For each item, score the highest amplitude seen at any point during the exam. Instruct patients not to attempt to suppress the tremor, but to let it come out.

1. Head tremor: The head is rotated fully left and right and then observed for 10 s in mid position. Patient then is instructed to gaze fully to the left and then to the right with the head in mid position. The nose should be used as the landmark to assess and rate the largest amplitude excursions during the examination.

0=no tremor
   1=slight tremor (<0.5 cm)
   2=mild tremor (0.5-<2.5 cm)
   3=moderate tremor (2.5-5 cm)
   4=severe or disfiguring tremor (>5 cm)

2. Face (including jaw) tremor Smile, close eyes, open mouth, purse lips. The highest amplitude of the most involved facial anatomy is scored, regardless of whether it occurs during rest or activation. Repetitive blinking or eye fluttering should not be considered as part of facial tremor.

0=no tremor
   1=slight; barely perceptible tremor
   2=mild: noticeable tremor
   3=moderate: obvious tremor, present in most voluntary facial contractions
   4=severe: gross disfiguring tremor 3. Voice tremor: First ask subject to produce an extended "aaah" sound and eee" sound for 5 seconds each. Then assess speech during normal conversation by asking patients "How do you spend your average day?"

0=no tremor
   1=slight: tremor during aaah, and eee and no tremor during speech
   2=mild: tremor in "aaah" and "eee" and minimal tremor in speech
   3=moderate: obvious tremor in speech that is fully intelligible
   4=severe: some words difficult to understand 4. Upper limb tremor: Tremor is assessed during three maneuvers: forward horizontal reach posture, lateral "wing beating" posture and finger-nose-finger testing. Each upper limb is assessed and scored individually. The forward horizontal reach posture is held for 5 seconds. The lateral wing beating posture is held for 20 seconds. The finger-nose-finger movement is executed three times. Amplitude assessment should be estimated using the maximally displaced point of the hand at the point of greatest displacement along any single plane. For example, the amplitude of a pure supination-pronation tremor, pivoting around the wrist would be assessed at either the thumb or fifth digit.

a) Forward outstretched postural tremor: Subjects should bring their anns forward, slightly lateral to midline and parallel to the ground. The wrist should also be straight and the fingers abducted so that they do not touch each other.
   b) Lateral "wing beating" postural tremor: Subjects will abduct their arms parallel to the ground and flex the elbows so that the two hands do not quite touch each other and are at the level of the nose. The fingers are abducted so that they do not touch each other. The posture should be held for 20 seconds.
   c) Kinetic tremor Subjects extend only their index finger. They then touch a set object or the examiners finger located to the full extent of their reach, which is located at the same height (parallel to the ground) and slightly lateral to the midline Subjects then touch their own nose (or chin if the tremor is severe) and repeat this back and forth three times. Only the position along the trajectory of greatest tremor amplitude is assessed. This will typically be either at the nose or at the point of full limb extension.

For all three hand tremor ratings 0=no tremor
   1=tremor is barely visible
   1.5=tremor is visible, but less than 1 cm 2=tremor is 1-<3 cm amplitude 2.5=tremor is 3-<5 cm amplitude
3=tremor is 5-<10 cm amplitude
3.5=tremor is 10-<20 cm amplitude
4=tremor is >20 cm amplitude
5. Lower limb tremor: Raise each lower limb horizontally parallel to the ground for 5 seconds each. Then perform a standard heel to shin maneuver with each leg, three times. The maximum tremor in either maneuver is scored, and only the limb with the largest tremor is scored. Tremor may exist in any part of the limb, including foot.
0=no tremor
1=slight: barely perceptible
2=mild, less than 1 cm at any point
3=moderate tremor, less than 5 cm at any point
4=severe tremor, greater than 5 cm
6. Archimedes spirals: Demonstrate how to draw Archimedes spiral that approximately fills 14 of an unlined page of standard (letter) paper. The lines of the spiral should be approximately 1.3 cm (0.5 inch) apart. Then ask the subject to copy the spiral. Test and score each hand separately. Use a ballpoint pen. The pen should be held such that no part of the limb touches the table. Secure the paper on the table in a location that is suitable for the patient's style of drawing. Score the tremor in the spiral, not the movement of the limb.
0=normal
1=slight: tremor barely visible.
2=mild: obvious tremor
3=moderate: portions of figure not recognizable.
4=severe: figure not recognizable
7. Handwriting: Have patient write the standard sentence "This is a sample of my best handwriting" using the dominant hand only. Patients must write cursively (i.e, no printing). They cannot hold or stabilize their hand with the other hand. Use a ballpoint pen. Secure the paper on the table in a location that is suitable for the patient's style of writing. Score the tremor in the writing, not the movement of the limb.
0=normal
1=slight: untidy due to tremor that is barely visible.
  2=mild: legible, but with considerable tremor.
3=moderate: some words illegible.
4=severe: completely illegible
8. Dot approximation task: The examiner makes a dot or X and instructs the subject to hold the tip of the pen "as close as possible to the dot (or center of an X) without touching it, (ideally approximately 1 mm) for 10 seconds". Each hand is score separately.
0=no tremor
1=tremor is barely visible
1.5=tremor is visible, but less than 1 cm 2=tremor is 1-<3 cm amplitude
2=tremor is 3-<5 cm amplitude
3=tremor is 5-<10 cm amplitude
3.5=tremor is 10-<20 cm amplitude
4=tremor is 20 cm amplitude
9. Standing tremor: Subjects are standing, unaided if possible. The knees are 10-20 cm apart and are flexed 10-20°. The arms are down at the subject's side. Tremor is assessed at any point on the legs or trunk
0=no tremor
1=barely perceptible tremor
2=obvious but mild tremor, does not cause instability
  3=moderate tremor, impairs stability of stance
4=severe tremor, unable to stand without assistance The principal investigator (or sub-principal investigator) scored the TETRAS performance subscale, the TETRAS Performance Subscale scores provided by the investigator were utilized in the statistical analyses of efficacy.

The efficacy analysis of the TETRAS performance subscale was conducted using an analysis of covariance (ANCOVA) model with fixed effects for treatment, concomitant anti-tremor medication use, site type, and Baseline value of the TETRAS performance subscale. The mean change from Baseline in TETRAS performance scale indicates that the CX-8998 arm is different from placebo (FIG. 1 and Table 1). All testing is performed using the least square (LS) means from the ANCOVA model and a two-sided test at the alpha=0.05 level of significance. If the data indicate a departure from the normal distribution, a corresponding rank test is performed.

TABLE 1

Change from Baseline to Day 15 and Day 28 in the TETRAS-PS as Rated by Physician.

| | CX-8998 | | | | Placebo | | |
|---|---|---|---|---|---|---|---|
| | LS mean | standard error of mean | N | p value vs placebo | LS mean | standard error of mean | N |
| Day 15 (8 mg BID) | -3.1 | 0.78 | 39 | 0.378 | -2.4 | 0.75 | 44 |
| Day 28 (10 mg BID) | -4.6 | 0.8 | 37 | 0.027 | -2.9 | 0.77 | 42 |

Example 2. Significant Change from Baseline to Day 15 and Day 28 in the TETRAS-ADL TETRAS Activities of Daily Living Subscale The ADL subscale includes many of the items assessed in the scales described elsewhere (see, e.g., Fahn et al., "Clinical rating scale for tremor," pages 225-234 in *Parkinson's Disease and Movement Disorders* (Jankovic et al., eds.), Baltimore: Williams & Wilkins, 1993; Louis, 2000 *Arch Neurol.* 57(10): 1522-1524; and Bain et al., 1993 *J Neurol Neurosurg Psychiatry* 56(8):868-873), including eating and drinking, dressing and personal hygiene, carrying items and finer motor skills. Each item is rated on a 0 to 4 scale, with 0 representing normal activity and 4 representing severe abnormality. The sum of the individual scores provides the overall score, ranging from 0 to 48. The complete TETRAS ADL Subscale is as follows.
Activities of Daily Living Subscale
Rate tremor's impact on activities of daily living (0-4 scoring).
1. Speaking
  0=Normal.
  1=Slight voice tremulousness, only when "nervous".
  2=Mild voice tremor. All words easily understood.
  3=Moderate voice tremor. Some words difficult to understand.
  4=Severe voice tremor. Most words difficult to understand.
2. Feeding with a Spoon
  0=Normal.
  1=Slightly abnormal. Tremor is present but does not interfere with feeding with a spoon.
  2=Mildly abnormal. Spills a little.
  3=Moderately abnormal. Spills a lot or changes strategy to complete task such as using two hands or leaning over.

4=Severely abnormal. Cannot feed with a spoon.
3. Drinking from a Glass
   0=Normal.
   1=Slightly abnormal. Tremor is present but does not interfere with drinking from a glass.
   2=Mildly abnormal. Spills a little.
   3=Moderately abnormal. Spills a lot or changes strategy to complete task such as using two, hands or leaning over.
   4=Severely abnormal. Cannot drink from a glass or uses straw or sippy cup.
4. Hygiene
   0=Normal.
   1=Slightly abnormal. Tremor is present but does not interfere with hygiene.
   2=Mildly abnormal. Some difficulty but can complete task.
   3=Moderately abnormal. Unable to do most fine tasks such as putting on lipstick or shaving unless changes strategy such as using two hands or using the less affected hand. 4=Severely abnormal. Cannot complete hygiene tasks independently.
5. Dressing
   0=Normal.
   1=Slightly abnormal. Tremor is present but does not interfere with dressing
   2=Mildly abnormal. Able to do everything but has difficulty due to tremor.
   3=Moderately abnormal. Unable to do most dressing unless changes strategy such as using Velcro, buttoning shirt before putting it on or avoiding shoes with laces.
   4=Severely abnormal. Cannot dress independently.
6. Pouring
   0=Normal.
   1=Slightly abnormal. Tremor is present but does not interfere with pouring
   2=Mildly abnormal. Must be very careful to avoid spilling but may spill occasionally.
   3=Moderately abnormal. Must use two hands or uses other strategies to avoid spilling.
   4=Severely abnormal. Cannot pour.
7. Carrying Food Trays, Plates or Similar Items
   0=Normal.
   1=Slightly abnormal. Tremor is present but does not interfere with carrying food trays, plates or similar items.
   2=Mildly abnormal. Must be very careful to avoid spilling items on food tray.
   3=Moderately abnormal. Uses strategies such as holding tightly against body to carry.
   4=Severely abnormal. Cannot carry food trays or similar items.
8. Using Keys
   0=Normal.
   1=Slightly abnormal. Tremor is present but can insert key with one hand without difficulty.
   2=Mildly abnormal. Commonly misses target but still routinely puts key in lock with one hand.
   3=Moderately abnormal. Needs to use two hands or other strategies to put key in lock.
   4=Severely abnormal. Cannot put key in lock.
9. Writing
   0=Normal.
   1=Slightly abnormal. Tremor is present but does not interfere with writing.
   2=Mildly abnormal. Difficulty writing due to tremor.
   3=Moderately abnormal. Cannot write without using strategies such as holding the writing hand with the other hand, holding pen differently or using large pen.
   4=Severely abnormal. Cannot write.
10. Working. If Patient is Retired, Ask as if they were Still Working. If the Patient is a Housewife, Ask the Question as it Relates to Housework:
   0=Normal.
   1=Slightly abnormal. Tremor is present but does not affect performance at work or at home.
   2=Mildly abnormal. Tremor interferes with work; able to do everything, but with errors.
   3=Moderately abnormal. Unable to continue working without using strategies such as changing jobs or using special equipment.
   4=Severely abnormal. Cannot perform any job or household work.
11. Overall Disability with the Most Affect Task (Name Task, e.g. Using Computer Mouse, Writing, Etc.)
   Task _____
   0=Normal.
   1=Slightly abnormal. Tremor is present but does not affect task.
   2=Mildly abnormal. Tremor interferes with task but still able to perform task.
   3=Moderately abnormal. Can do task but must use strategies.
   4=Severely abnormal. Cannot do the task.
12. Social Impact
   0=None.
   1=Aware of tremor, but it does not affect lifestyle or professional life.
   2=Feels embarrassed by tremor in some social situations or professional meetings.
   3=Avoids participating in some social situations or professional meetings because of tremor.
   4=Avoids participating in most social situations or professional meetings because of tremor.

Figure 2:
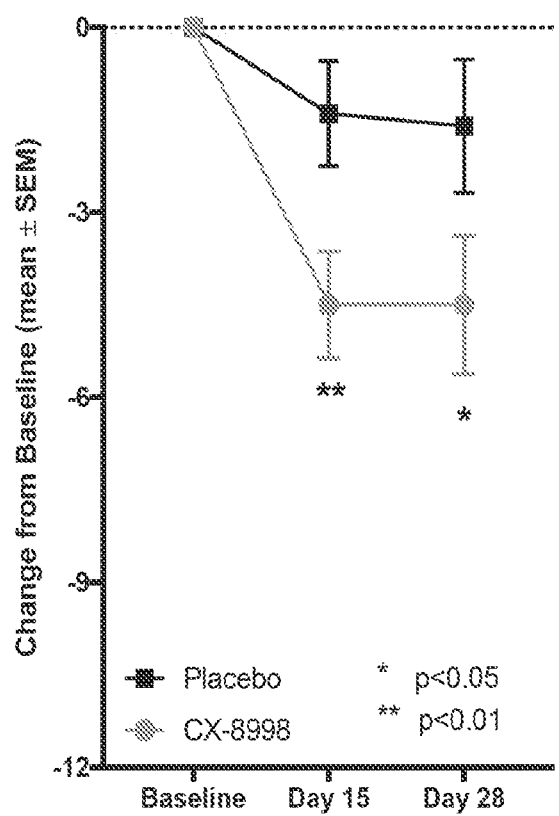
FIG. 2 is a graph showing the change from baseline to day 15 and day 28 in the TETRAS—activities of daily living (ADL).

Analyses of the TETRAS-ADL was conducted using the same type of ANCOVA model as described for the TETRAS-PS, using two-sided tests at the alpha=0.05 level of significance (FIG. 2 and Table 2).

TABLE 2

Change from Baseline to Day 15 and Day 28 in the TETRAS-ADL.

| | CX-8998 | | | | Placebo | | |
|---|---|---|---|---|---|---|---|
| | LS mean | standard error of mean | N | p value vs placebo | LS mean | standard error of mean | N |
| Day 15 (8 mg BID) | −4.5 | 0.87 | 39 | 0.005 | −1.4 | 0.85 | 43 |
| Day 28 (10 mg BID) | −4.5 | 1.12 | 37 | 0.049 | −1.6 | 1.08 | 42 |

Figure 3:
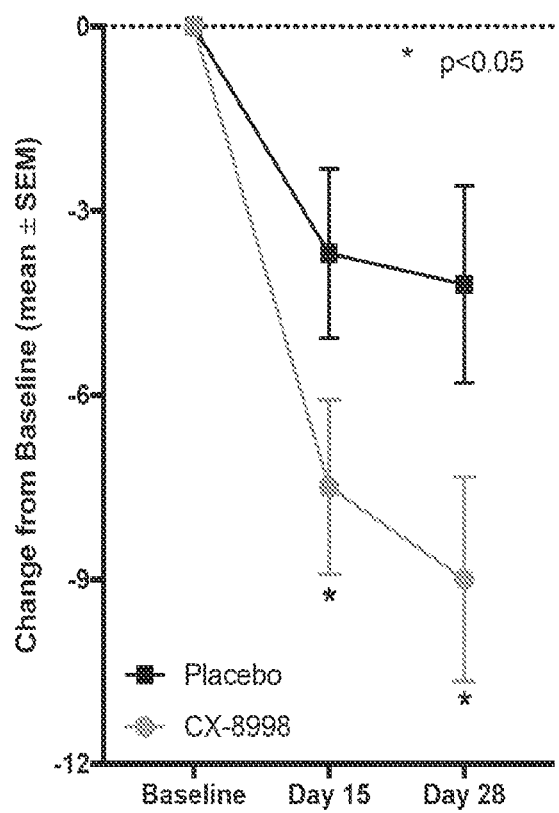
FIG. 3 is a graph showing the change from baseline to day 15 and day 28 in the TETRAS total score.

Example 3. Significant Change from Baseline to Day 15 and Day 28 in the TETRAS Total Score TETRAS Total Score The Total TETRAS score was defined as the sum of the TETRAS performance subscale total score and the TETRAS ADL subscale score. TETRAS TOTAL score combines both patient reported outcome and objective measurement of tremor amplitude in a single score. Analyses of the TETRAS-ADL was conducted using the same type of ANCOVA model as described for the TETRAS-PS, using two-sided tests at the alpha=0.05 level of significance (FIG. 3 and Table 3).

TABLE 3

Change from Baseline to Day 15 and Day 28 in the TETRAS-Total

| | CX-8998 | | | | Placebo | | |
|---|---|---|---|---|---|---|---|
| | LS mean | standard error of mean | N | p value vs placebo | LS mean | standard error of mean | N |
| Day 15 (8 mg BID) | −7.5 | 1.42 | 39 | 0.04 | −3.7 | 1.38 | 43 |
| Day 28 (10 mg BID) | −9 | 1.66 | 37 | 0.029 | −4.2 | 1.6 | 42 |

Example 4. Significant Change from Baseline to Day 28 in the TETRAS-PS Spiral Task (Item 6)

The Archimedes spiral item of the TETRAS-PS subscale (Item 6) incorporates a routine clinical assessment of functional tremor impact into the TETRAS scoring of tremor severity. The investigator demonstrates how to draw an Archimedes spiral that approximately fills V4 of an unlined page of standard (letter) paper using a ballpoint pen. The lines of the spiral should be approximately 1.3 cm (0.5 inch) apart. The investigator then asks the subject to copy the spiral. Each hand is tested and scored separately. The pen is held such that no part of the limb touches the table and the paper is secured on the table in a location that is suitable for the patient's style of drawing. The tremor in the spiral is scored, not the movement of the limb.

Figure 4:
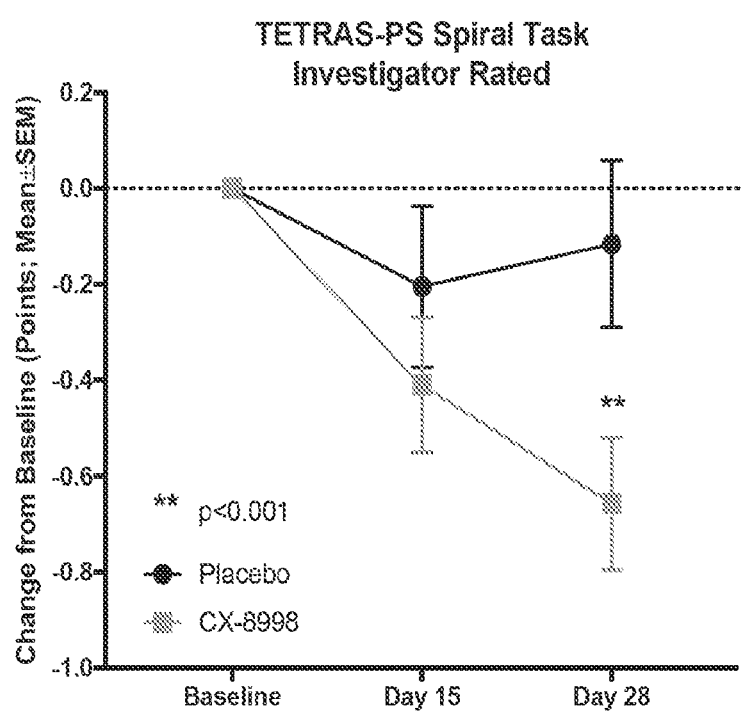
FIG. 4 is a graph showing the change from baseline to day 28 in the TETRAS-PS spiral task.

0=normal; 1=slight: tremor barely visible; 2=mild: obvious tremor; 3=moderate: portions of figure not recognizable; 4=severe: figure not recognizable Scores for TETRAS-PS subscale item 6 were summed for both hands and the mean change from baseline was calculated for Day 15 and Day 28 (FIG. 4 and Table 4). Statistical significance was calculated by Mann-Whitney non-parametric t-test (two tailed).

TABLE 4

Change from Baseline to Day 15 and Day 28 in the TETRAS-PS Spiral Item.

| | CX-8998 | | | | Placebo | | |
|---|---|---|---|---|---|---|---|
| | Mean | standard error of mean | N | p value vs placebo | Mean | standard error of mean | N |
| Day 15 (8 mg BID) | −0.41 | 0.141 | 39 | 0.19 | −0.205 | 0.168 | 44 |
| Day 28 (10 mg BID) | −0.658 | 0.137 | 39 | 0.0031 | −0.116 | 0.174 | 43 | p-value by Mann Whitney non-parametric t-test (two tailed)

Example 5. Significant Change from Baseline to Day 15 and Day 28 in Functional Tremor Frequency Measured by Digital Spirography (iMotor)

iMotor, developed by Apptomics, Inc., is an application specifically designed to objectively quantify motor function in patients with movement disorders (see, e.g., Mitsi et al., 2017 *Front. Neurol.* 8:273). The application requires the patient to complete a cycle of evaluations measuring motor function.

For the Archimedes spiral item of iMotor, subjects are asked to draw a spiral using a digital stylus on a tablet-based application. Prompts instruct the subject to trace a dotted grey mid-line that begins at the start of the spiral without lifting the stylus off the screen. The test is not timed. Subjects are asked to complete the task twice—one with the right and one with the left hand.

Figure 5:
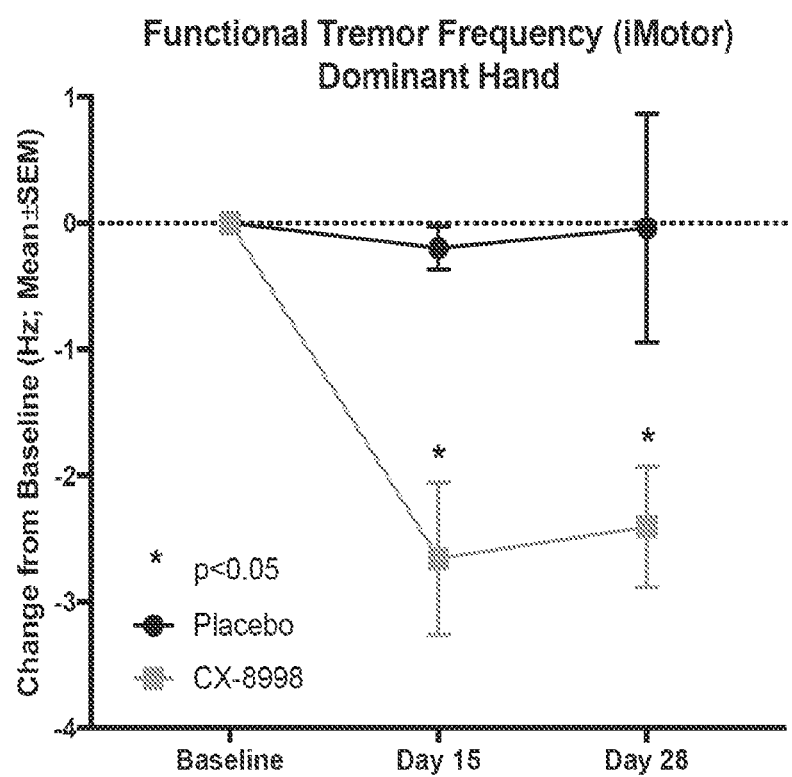
FIG. 5 is a graph showing the change from baseline to day 15 and day 28 in functional tremor frequency measured by digital spirography.

Functional tremor frequency (in Hz) is calculated by the iMotor algorithm based on the number and timing of stylus crosses of the mid-line. The mean change from baseline to Day 15 and Day 28 was calculated for the dominant hand. Statistical significance was calculated by Mann-Whitney non-parametric t-test (two tailed) (FIG. 5 and Table 5).

TABLE 5

Change from Baseline to Day 15 and Day 28 in Functional Tremor Frequency by iMotor.

| | CX-8998 | | | | Placebo | | |
|---|---|---|---|---|---|---|---|
| | Mean | standard error of mean | N | p value vs placebo | Mean | standard error of mean | N |
| Day 15 (8 mg BID) | −2.66 | 0.604 | 3 | 0.012 | −0.196 | 0.169 | 3 |
| Day 28 (10 mg BID) | −2.41 | 0.477 | 3 | 0.012 | −0.0384 | 0.906 | 3 | p-value by Mann Whitney non-parametric t-test (two tailed)

Example 6. Significant Difference from Placebo in Clinical Global Impression of Improvement (CGI-I) at Day 28

Clinical Global Impression Scale

The Clinical Global Impressions Scale (CGI) was developed for use in NIMH-sponsored clinical trials to provide a brief, stand-alone assessment of the clinician's view of a patient's global functioning before and after initiating a study medication (Guy (ed.), *ECDEU Assessment Manual for Psychopharmacology*. Rockville, MD: US Department of Health, Education, and Welfare Public Health Service Alcohol, Drug Abuse, and Mental Health Administration; 1976). The CGI is a summary measure that takes into account all available information, including knowledge of the patient's history, psychosocial circumstances, symptoms, behavior, and the impact of the symptoms on the patient's ability to function. The CGI has two forms—the CGI-Severity, which rates illness severity at baseline, and the CGI-Improvement, which rates change from baseline.

CGI-Improvement (CGI-I)

The CGI-I consists of a single 7-point rating of total improvement or change from baseline CGI-S, regardless of whether or not the change is due entirely to drug treatment. Raters select one response based on the following question, "Compared to your subject's condition at the beginning of treatment, how much has your subject changed?" Scores are: 1=Very much improved; 2=Much improved; 3=Minimally improved; 4=No change; 5=Minimally worse; 6=Much worse; 7=Very much worse.

Figure 6:
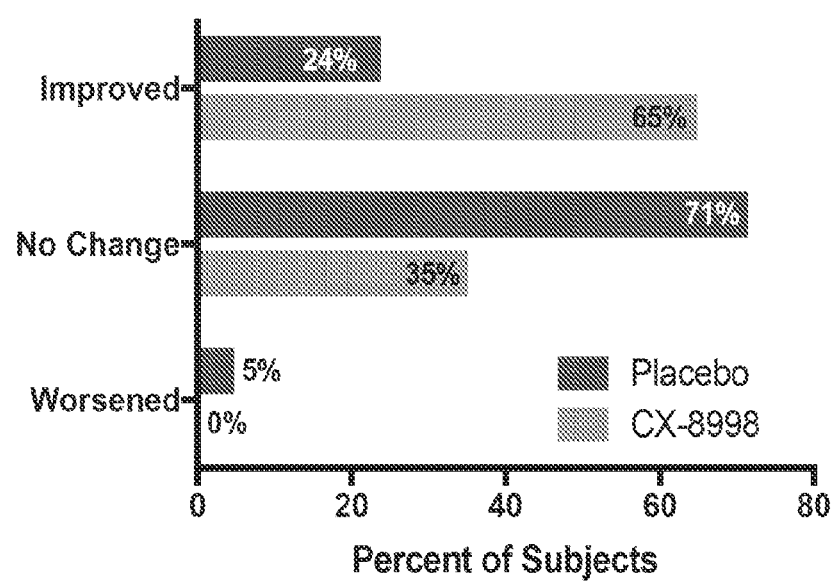
FIG. 6 is a graph showing the difference from placebo in clinical global impression of improvement (CGI-I) at day 28.

Treatment success as measured by CGI-I was summarized using descriptive statistics. Differences between treatment groups were assessed using an ANCOVA model with fixed effects for treatment, anti-tremor medication use, and site type (FIG. 6 and Table 6).

TABLE 6

Mean CGI-I Score at Day 28 by Treatment Group.

|  | CX-8998 | | Placebo | |
| --- | --- | --- | --- | --- |
|  | number | percentage | number | percentage |
| Worsened | 0 | 0 | 2 | 4.76 |
| No Change | 13 | 35.14 | 30 | 71.43 |
| Improved | 24 | 64.86 | 10 | 23.81 |
| Total | 37 | 100 | 42 | 100 |
| p value vs placebo | | 0.001 | | |

Example 7. Significant Difference from Placebo in Patient Global Impression of Change (PGIC) at Day 15 and Day 28

Global rating of change (GRC) scales were designed to quantify a patient's improvement or deterioration over time, usually either to determine the effect of an intervention or to chart the clinical course of a condition. GRC scales ask a patient to assess his or her current health status, recall that status at the beginning of treatment, and then calculate the difference between the two. The simplicity of GRC scales makes them easy to administer and applicable to a wide range of patients (see, e.g., Kamper et al., 2009 *The Journal of Manual & Manipulative Therapy* 17(3):163-170).

The Patient Global Impression of Change (PGIC) is a 7-point GRC consisting of one question: "With respect to your essential tremor, how would you describe yourself now, as compared to when you started taking the study drug?" Subjects will choose one of the following answers: "very much worse, much worse, minimally worse, no change, minimally improved, much improved, very much improved."

Figure 7:
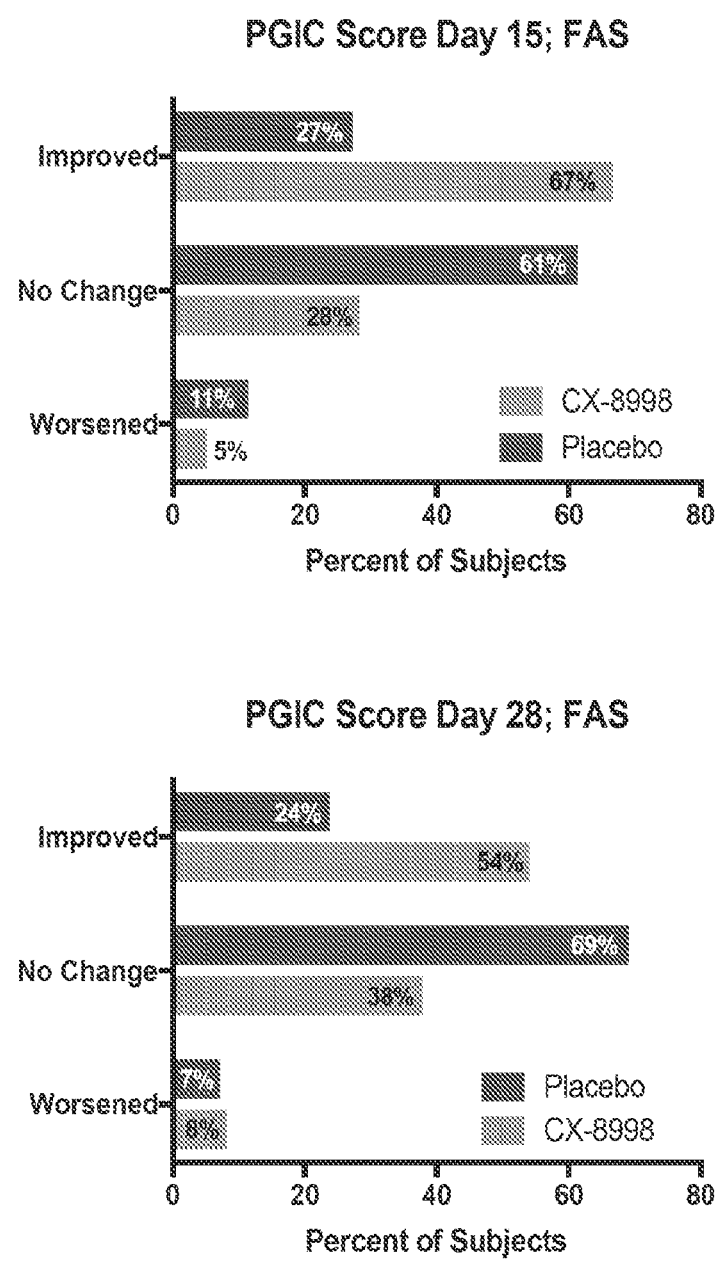
FIG. 7 contains graphs showing the difference from placebo in patient global impression of change (PGIC) at day 15 and day 28.

Treatment success as measured by PGIC was summarized using descriptive statistics. Differences between treatment groups were assessed using an ANCOVA model with fixed effects for treatment, anti-tremor medication use, and site type (FIG. 7 and Table 7).

Example 8. Significant Difference from Placebo in Goal Attainment Scale (GAS)

Goal Attainment Scaling (GAS) is a tool that involves the development of a written set of goals between a physician and patient and was used for monitoring patient progress. GAS was developed in 1968 (see, e.g., Kiresuk & Sherman, 1968 *Community Mental Health Journal* 4:443-453) and has been employed in patients with physical disorders including spasticity (see, e.g., Ashford et al., 2006 *Physiother Res Int.* 11(1):24-34) and multiple sclerosis (Khan et al., 2008 *Arch Phys Med Rehabil.* 89(4):652-9).

GAS frames the discussion in terms of individual patient-desired goals rather than universally applied health states. Goal-oriented care prompts patients to articulate which health goals are most important to them. Patients and clinicians can then monitor progress in reaching them.

Subjects identify 3 health goals at Baseline. Examples of goals are drinking from a cup, buttoning a shirt or ability to write. Goals may be either active or passive. All goals will be specifically tailored to the individual, with each subject required to rate each goal at baseline on the level of importance, based on a 3-point scale (1=fairly important; 2=very important; 3=extremely important). For the investigator, the feasibility of attaining each goal must be considered before the goals are set and adjusted accordingly if needed. Once each goal is set, the investigator is asked to rate the degree of difficulty in achieving each of the set goals, based on another 3-point scale (1=probable; 2=possible; 3=doubtful.)

Progress towards each goal is scored on a 5-point scale: −2=Worse than Baseline (unfavorable outcome); −1=No change from Baseline; 0=Achieved the defined goal (expected outcome); +1=Better than expected outcome; +2=Best anticipated outcome.

Figure 8:
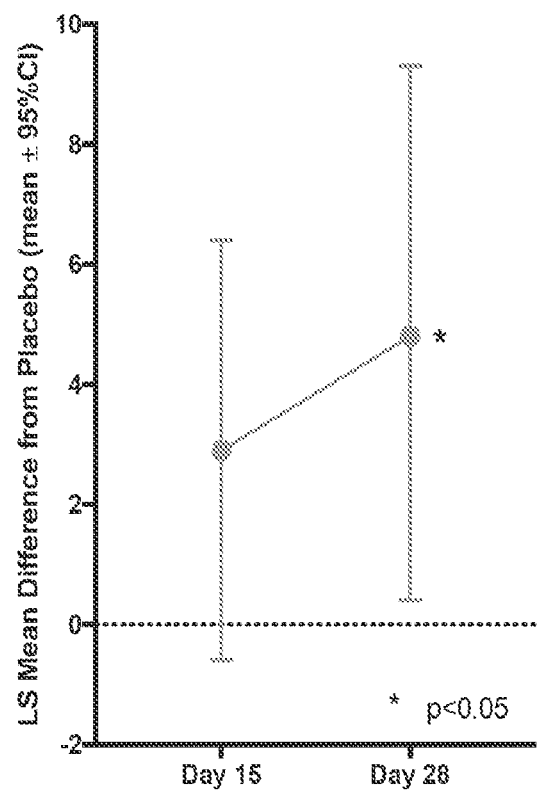
FIG. 8 is a graph showing the difference from placebo in goal attainment scale (GAS).

GAS is mapped to the values −2 to 2, from the worst outcome to the best outcome, respectively. Differences between treatment groups were assessed using an ANCOVA model with fixed effects for treatment, anti-tremor medication use, and site type (FIG. 8 and Table 8).

Overall GAS Score=50+(10*sum of weights)/square root(0.7*sum of weights**2)+[0.3*(sum of weights)**2].

TABLE 7

Mean PGIC Score at Day 15 and Day 28 by Treatment Group.

|  | Day 15 | | | | Day 28 | | | |
| --- | --- | --- | --- | --- | --- | --- | --- | --- |
|  | CX-8998 | | Placebo | | CX-8998 | | Placebo | |
|  | number | percent | number | percent | Number | percent | Number | percent |
| Worsened | 2 | 5.12 | 5 | 11.36 | 3 | 8.11 | 3 | 7.14 |
| No Change | 11 | 28.2 | 27 | 61.36 | 14 | 37.84 | 29 | 69.05 |
| Improved | 26 | 66.67 | 12 | 27.27 | 20 | 54.05 | 10 | 23.81 |
| Total | 39 | 100 | 44 | 100 | 37 | 100 | 42 | 100 |
| p value vs placebo | | 0.003 | | | | 0.089 | | |

TABLE 8

Mean Difference From Placebo in Goal Attainment Score.

| | LS Mean Difference from Placebo | Confidence Interval | p value | N |
|---|---|---|---|---|
| Day 15 (8 mg BID) | 2.9 | (−0.6, 6.4) | 0.103 | 39 |
| Day 28 (10 mg BID) | 4.8 | (0.4, 9.3) | 0.034 | 37 |

Example 9. Significant Increase Vs Placebo in Percentage of Subjects Satisfied with Anti-Tremor Medication at Day 15 and Day 28 (QUEST Sub-Item)

The QUEST is a 30-item questionnaire that contributes to 5 sub-scales (physical, psychosocial, communication, hobbies/leisure and work/finance) and a total score, plus 3 additional items relating to sexual function and satisfaction with tremor control and medication side effects within the last month of treatment. Initial reports provide preliminary support of its reliability and validity. The internal consistency was very good to excellent for 4 scales and the total score, and moderately high for the Work/Finance scale (see, e.g., Tröster et al., 2005 *Parkinsonism Relat Disord.* 11(6): 367-373). These reliability coefficients are also supportive of the QUEST's construct validity.

Figure 9:
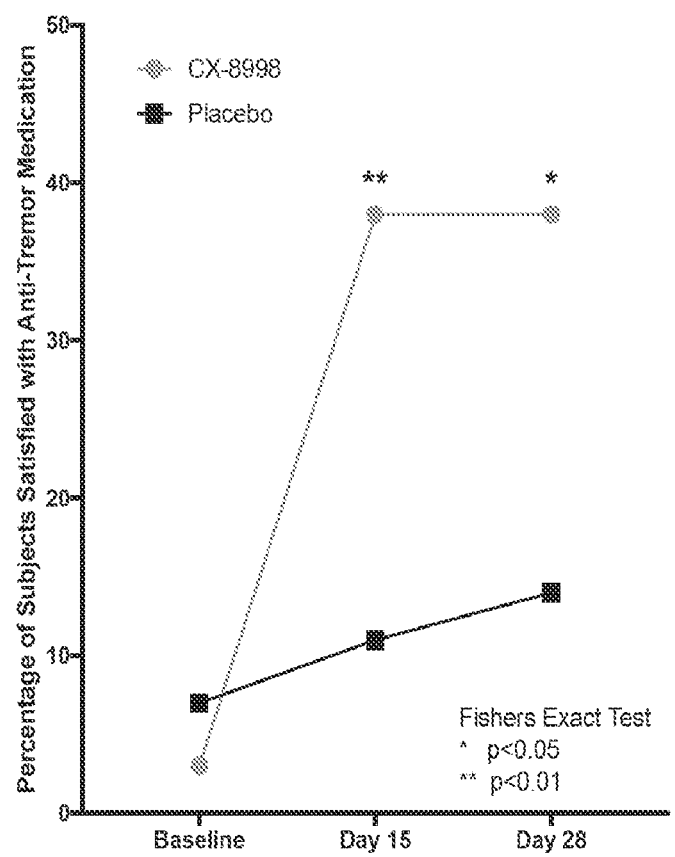
FIG. 9 is a graph showing the increase vs placebo in a percentage of subjects satisfied with anti-tremor medication at day 15 and day 28 (QUEST sub-item).

Percentage of subjects responding affirmatively to the following question were summarized at baseline, Day 15 and Day 28: "In the past month are you satisfied with tremor control by your anti-tremor medications?(Y/N)". Statistical significance compared to placebo was calculated using Fisher's exact test (FIG. 9 and Table 9).

TABLE 9

Patient satisfaction when asked: In the past month are you satisfied with tremor control by your anti-tremor medications? (Y/N).

| | CX-8998 | | Placebo | | p-value Fishers Exact Test |
|---|---|---|---|---|---|
| | % Yes | N | % Yes | N | |
| Baseline | 3 | 39 | 7 | 44 | 0.619 |
| Day 15 | 38 | 39 | 11 | 44 | 0.005 |
| Day 28 | 38 | 37 | 14 | 42 | 0.011 |

Example 10. CX-8998 Plasma Concentrations Resulting in Clinical Efficacy at Day 15 and Day 28

CX-8998 efficacy in rat models of CNS disease have demonstrated CX-8998 efficacy at human equivalent concentrations of 300-700 nM. Dose response analyses of human pharmaco-EEG data confirmed that reductions of alpha power of about 25% or greater (and indirect marker of CNS target engagement) occurred in a dose- and concentration—dependent manner at plasma CX 8998 concentrations greater than 200 to 300 nM (4 mg BID). Modeling suggested a single dose of 8 mg would result in reduction of 25% or greater in alpha power for approximately 12 hours post-dose. Dose response analysis of adverse event data suggested that incidence of CNS and psychiatric adverse events is increased at concentrations greater than 800 nM. Based on human PK profiles from healthy volunteers, final steady state concentrations of CX-8998 between 200 and 800 nM were targeted in T-CALM with a 10 mg BID dose under fed conditions.

All T-CALM subjects had blood sample drawn prior to administration of CX-8998 at Visits 2 (trough concentration at 4 mg BID dose), 3 (trough concentration at 8 mg BID), and 4 (trough concentration at 10 mg BID). Additionally, at Visit 4, a post-dose sample will be collected as close to 4 hours post-dose as possible, but within the window of 4-6 hours post-dose (i.e., a total of two PK samples are collected at Visit 4.)

Figure 10:
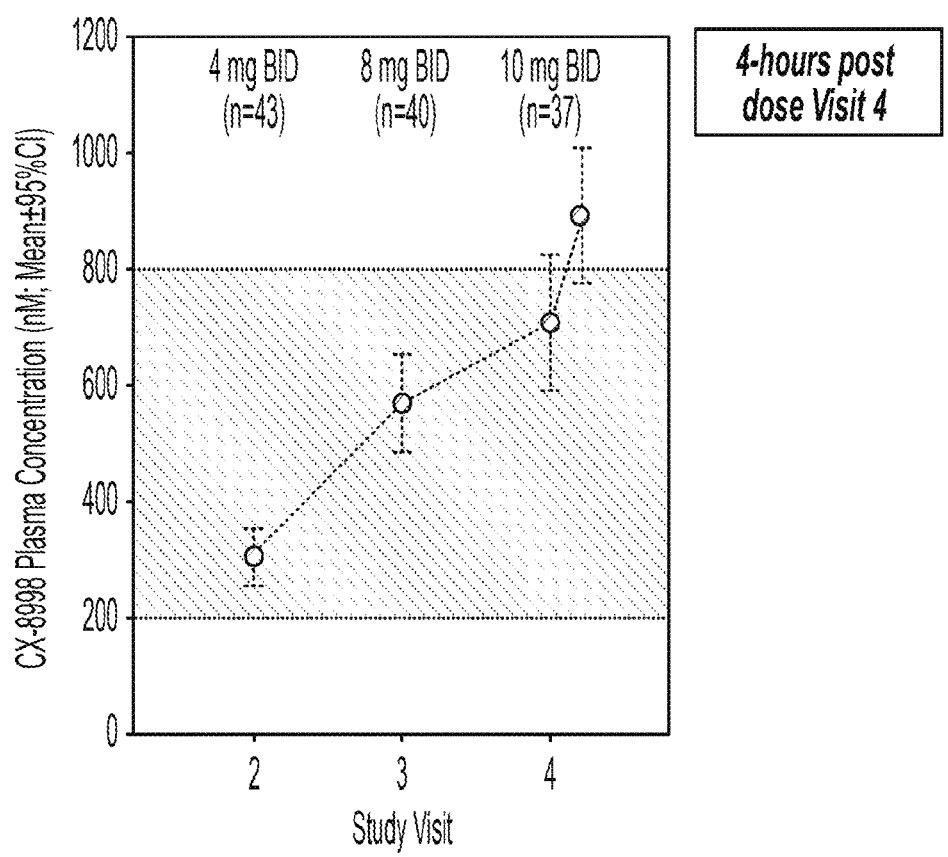
FIG. 10 is a graph showing CX-8998 plasma concentrations resulting in clinical efficacy at day 15 and day 28.
Figure 11A:
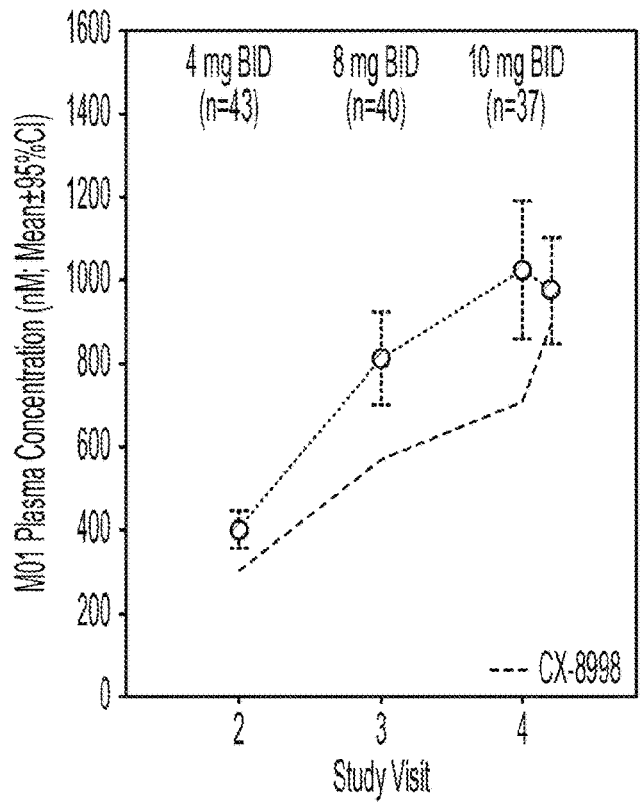
FIGS. 11A-11D contain graphs showing CX-8998 metabolite exposure following twice daily (BID) dosing of CX-8998.
Figure 11B:
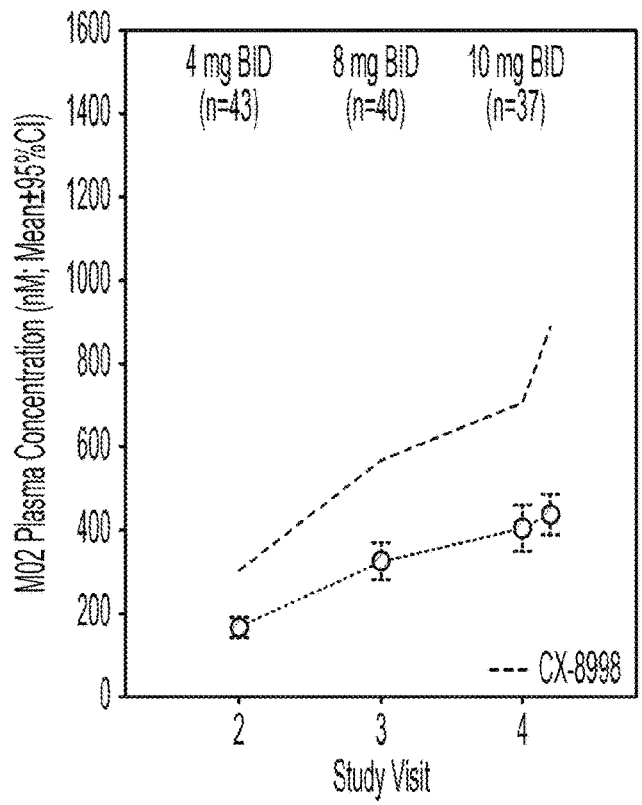
Figure 11C:
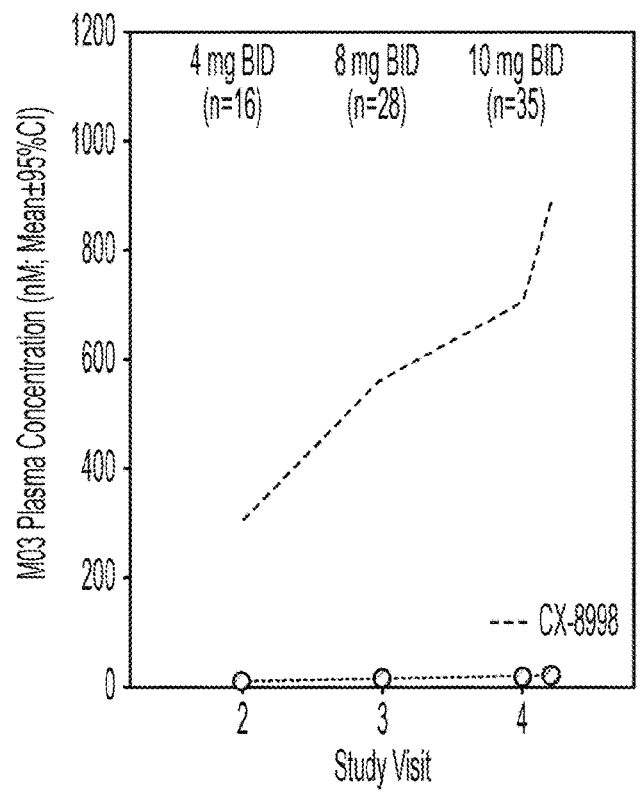
Figure 11D:
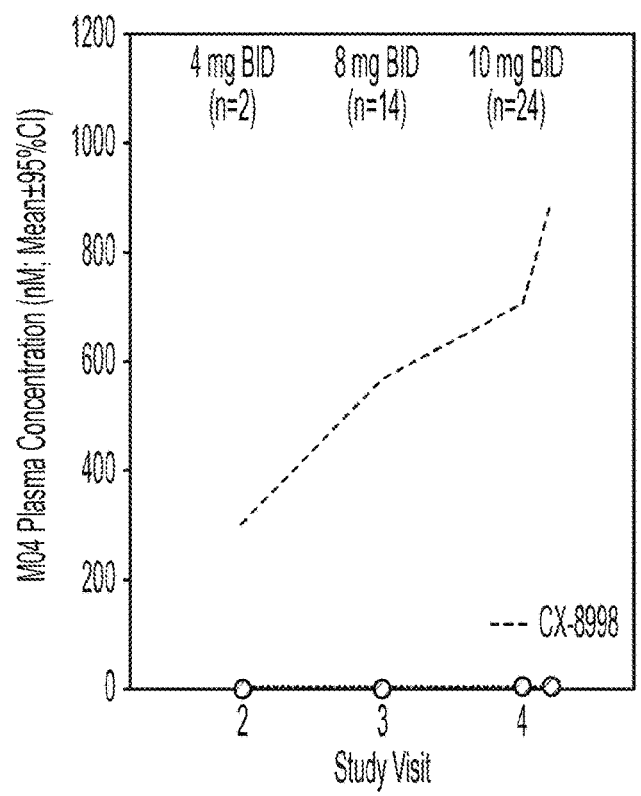

Cavion has developed and validated liquid chromatography-tandem mass spectrometry (LC/MS/MS) bioanalytical methods for the simultaneous quantitation of CX-8998 and metabolites (M01, M02, M03, and M04) in rat, dog, and human plasma as per recent FDA guidance (FDA, Guidance for Industry: Bioanalytical Method Validation, May 2018, available at: fda.gov/downloads/drugs/guidances/ucm070107.pdf). Assay performances were satisfactory and met acceptance criteria for system performance suitability, quantitation range, calibration linearity, assay accuracy and precision, and assay recovery. These "5-in-1" bioanalytical methods were used to quantitate CX-8998 and its 4 metabolites in samples that were collected in T-CALM (FIG. 10 and Table 10).

TABLE 10

CX-8998 Plasma Concentration (nM).

| | Dose Level | Sample Time | Mean | STD | 95% CI | Min, Max | N |
|---|---|---|---|---|---|---|---|
| Visit 2 (Day 8) | 4 mg BID | trough | 304 | 161 | (254, 354) | (23, 883) | 43 |
| Visit 3 (Day 15) | 8 mg BID | trough | 568 | 262 | (484, 651) | (85, 1280) | 40 |
| Visit 4 (Day 28) | 10 mg BID | trough | 707 | 355 | (589, 826) | (18, 1806) | 37 |
| | | 4 hours post-dose | 866 | 371 | (773, 1007) | (18, 1793) | 36 |

Example 11. CX-8998 Metabolite Exposure Following BID Dosing of CX-8998

CX-8998 metabolites M01-M04 are active Cav3 antagonists. The "5-in-1" bioanalytical methods were used to quantitate CX-8998 metabolites M86, M02, M03 and M04 in samples that were collected in T-CALM (FIG. 11 and Table 11).

TABLE 11

CX-8998 Plasma Concentrations (nM).

| | Dose Level | Sample Time | Mean | STD | 95% CI | Min, Max | N |
|---|---|---|---|---|---|---|---|
| M01 Plasma Concentration (nM) | | | | | | | |
| Visit 2 (Day 8) | 4 mg BID | trough | 398 | 152 | (351, 444) | (122, 732) | 43 |
| Visit 3 (Day 15) | 8 mg BID | trough | 812 | 352 | (700, 925) | (73, 1966) | 40 |
| Visit 4 (Day 28) | 10 mg BID | trough | 1023 | 501 | (856, 1191) | (84, 2933) | 37 |
| | | 4 hours Post-dose | 976 | 383 | (847, 1106) | (84, 2286) | 36 |
| M02 Plasma Concentration (nM) | | | | | | | |
| Visit 2 (Day 8) | 4 mg BID | trough | 168 | 75 | (145, 192) | (15, 353) | 43 |
| Visit 3 (Day 15) | 8 mg BID | trough | 325 | 134 | (282, 368) | (38, 658) | 40 |
| Visit 4 (Day 28) | 10 mg BID | trough | 406 | 168 | (350, 462) | (31, 888) | 37 |
| | | 4 hours Post-dose | 438 | 141 | (390, 486) | (31, 769) | 36 |
| M03 Plasma Concentration (nM) | | | | | | | |
| Visit 2 (Day 8) | 4 mg BID | trough | 11 | 5.9 | (7.9, 14) | (7, 29) | 16 |
| Visit 3 (Day 15) | 8 mg BID | trough | 16 | 6.6 | (13, 18) | (8, 34) | 28 |
| Visit 4 (Day 28) | 10 mg BID | trough | 20 | 13 | (16, 25) | (8, 65) | 35 |
| | | 4 hours Post-dose | 22 | 13 | (18, 27) | (8, 68) | 34 |
| M04 Plasma Concentration (nM) | | | | | | | |
| Visit 2 (Day 8) | 4 mg BID | trough | 4.5 | 0.38 | (1.1, 7.8) | (4.2, 4.7) | 2 |
| Visit 3 (Day 15) | 8 mg BID | trough | 4.9 | 1.9 | (3.8, 6.0) | (3.0, 9.0) | 14 |
| Visit 4 (Day 28) | 10 mg BID | trough | 5.6 | 5.3 | (3.3, 7.8) | (2.6, 28) | 24 |
| | | 4 hours Post-dose | 6.4 | 3.8 | (4.9, 7.9) | (2.7, 16) | 27 |

These data demonstrate that a composition including a combination of more than one Cav3 antagonist (e.g. CX-8998 plus its active metabolites) is relevant to the treatment of movement disorders.

Example 12. Responder Analysis for Tetras and CGI-I

Responder analysis was utilized to describe the proportion of subjects demonstrating a certain threshold of response to treatment based on a cut-off value for a particular scale. Table 12 summarizes the proportion of subjects who achieved an improvement from baseline of at least 5 points in the three TETRAS scales (performance subscale, activities of daily living and total score) and the proportion of subjects scored as improved (minimally improved, much improved and very much improved) using the CGI-I. Statistical analysis was conducted by Fisher's exact test.

TABLE 12

CX-8998 Plasma Concentrations (nM).
Summary of CX-8998 Responder Analysis

| | CX-8998 | | Placebo | | |
|---|---|---|---|---|---|
| Question | N | Number (%) | N | Number (%) | P-value |
| What proportion of subjects had improvement of at least 5 points by TETRAS Total score at Day 28? | 37 | 21 (56.8%) | 42 | 13 (31%) | 0.025 |
| What proportion of subject had improvement of at least 5 points by TETRAS Total score at Day 15? | 39 | 22 (56.4%) | 43 | 13 (30.2%) | 0.025 |
| What proportion of subjects had improvement of at least 5 points by TETRAS-PS score at Day 28? | 37 | 16 (43.2%) | 42 | 8 (19.1%) | 0.027 |
| What proportion of subjects had improvement of at least 5 points by TETRAS-PS score at Day 15? | 39 | 12 (30.8%) | 44 | 10 (22.7%) | ns |
| What proportion of subjects had improvement of at least 5 points by TETRAS-ADL score at Day 28? | 37 | 11 (29.7%) | 42 | 10 (23.81%) | ns |

TABLE 12-continued

CX-8998 Plasma Concentrations (nM).
Summary of CX-8998 Responder Analysis

| Question | CX-8998 N | Number (%) | Placebo N | Number (%) | P-value |
|---|---|---|---|---|---|
| What proportion of subjects had improvement of at least 5 points by TETRAS-ADL score at Day 15? | 39 | 18 (46.2%) | 43 | 8 (18.6%) | 0.009 |
| What proportion of subjects showed improvement by CGI-I at Day 28? | 37 | 24 (64.9%) | 41 | 9 (22.0%) | <0.001 |
| What proportion of subjects showed improvement by CGI-I at Day 15? | 39 | 25 (64.1%) | 44 | 20 (45.5%) | ns |

Proportion of subjects achieving a response as defined by at least 5 points of improvement on a TETRAS endpoint or any level of improvement by Clinical Global Impression. Statistical analysis by Fishers Exact Test. Following tables show granular data for each endpoint.

TETRAS Total Score at Day 15

| Change from Baseline | Placebo N = 43 | CX-8998 N = 39 |
|---|---|---|
| >20 point improvement | 2 (4.7%) | 2 (5.1%) |
| >10 to 20 point improvement | 6 (14.0%) | 12 (30.8%) |
| >5 to 10 point improvement | 4 (9.3%) | 6 (15.4%) |
| >2.5 to 5 point improvement | 9 (20.9%) | 7 (17.9%) |
| >1 to 2.5 point improvement | 5 (11.6%) | 2 (5.1%) |
| >0 to 1 point improvement | 3 (7.0%) | 2 (5.1%) |
| 0 change | 2 (4.7%) | 1 (2.6%) |
| >0 to 1 point worsening | 0 | 2 (5.1%) |
| >1 to 2.5 point worsening | 0 | 1 (2.6%) |
| >2.5 to 5 point worsening | 8 (18.6) | 4 (10.3%) |
| >5 to 10 point worsening | 2 (4.7%) | 0 |
| >point worsening | 1 (2.3%) | 0 |

TETRAS Total Score at Day 28

| Change from Baseline | Placebo N = 42 | CX-8998 N = 37 |
|---|---|---|
| >20 point improvement | 2 (4.8%) | 5 (13.5%) |
| >10 to 20 point improvement | 6 (14.3%) | 8 (21.6%) |
| >5 to 10 point improvement | 3 (7.1%) | 7 (18.9%) |
| >2.5 to 5 point improvement | 6 (14.3%) | 5 (13.5%) |
| >1 to 2.5 point improvement | 4 (9.5%) | 2 (5.4%) |
| >0 to 1 point improvement | 6 (14.3%) | 2 (5.4%) |
| 0 change | 1 (2.4%) | 0 |
| >0 to 1 point worsening | 2 (4.8%) | 4 (10.8%) |
| >1 to 2.5 point worsening | 6 (14.3%) | 2 (5.4%) |
| >2.5 to 5 point worsening | 2 (4.6%) | 1 (2.7%) |
| >5 to 10 point worsening | 2 (4.6%) | 0 |
| >10 point worsening | 2 (4.6%) | 0 |

TETRAS-PS Score at Day 15

| Change from Baseline | Placebo N = 44 | CX-8998 N = 39 |
|---|---|---|
| >10 point improvement | 3 (6.8%) | 3 (7.7%) |
| >5 to 10 point improvement | 7 (15.9%) | 8 (20.5%) |
| >2.5 to 5 point improvement | 6 (13.6%) | 10 (25.6%) |
| >1 to 2.5 point improvement | 7 (15.9%) | 4 (10.3%) |
| >0 to 1 point improvement | 6 (13.6%) | 3 (7.7%) |
| 0 change | 5 (11.4%) | 2 (5.1%) |
| >0 to 1 point worsening | 5 (11.4%) | 2 (5.1%) |
| >1 to 2.5 point worsening | 4 (9.1%) | 5 (12.8%) |
| >2.5 to 5 point worsening | 1 (2.3%) | 2 (5.1%) |
| >5 to 10 point worsening | 0 | 0 |
| >10 point worsening | 0 | 0 |

TETRAS-PS Score at Day 28

| Change from Baseline | Placebo N = 42 | CX-8998 N = 37 |
|---|---|---|
| >10 point improvement | 2 (4.5%) | 4 (10.3%) |
| >5 to 10 point improvement | 5 (11.4%) | 8 (20.5%) |
| >2.5 to 5 point improvement | 15 (34%) | 11 (28.2%) |
| >1 to 2.5 point improvement | 5 (11.4%) | 5 (12.8%) |
| >0 to 1 point improvement | 6 (13.6%) | 6 (15.4%) |
| 0 change | 0 | 1 (2.6%) |
| >0 to 1 point worsening | 3 (6.8%) | 2 (5.1%) |
| >1 to 2.5 point worsening | 5 (11.4%) | 1 (2.6%) |
| >2.5 to 5 point worsening | 3 (6.8%) | 1 (2.6%) |
| >5 to 10 point worsening | 0 | 0 |
| >10 point worsening | 0 | 0 |

TETRAS-ADL Score at Day 15

| Change from Baseline | Placebo N = 43 | CX-8998 N = 39 |
|---|---|---|
| >10 point improvement | 2 (4.7%) | 5 (12.8%) |
| >5 to 10 point improvement | 4 (9.3%) | 11 (28.2%) |
| >2.5 to 5 point improvement | 8 (18.6%) | 7 (17.9%) |
| >1 to 2.5 point improvement | 9 (20.9%) | 2 (5.1%) |
| >0 to 1 point improvement | 6 (14.0%) | 5 (12.8%) |
| 0 change | 6 (14.0%) | 2 (5.1%) |
| >0 to 1 point worsening | 4 (9.3%) | 1 (2.6%) |
| >1 to 2.5 point worsening | 2 (4.7%) | 3 (7.7%) |
| >2.5 to 5 point worsening | 6 (14.0%) | 3 (7.7%) |
| >5 to 10 point worsening | 1 (2.3%) | 0 |
| >10 point worsening | 1 (2.3%) | 0 |

| TETRAS-ADL Score at Day 28 | | |
|---|---|---|
| Change from Baseline | Placebo N = 42 | CX-8998 N = 37 |
| >10 point improvement | 4 (9.5%) | 5 (13.5%) |
| >5 to 10 point improvement | 2 (4.8%) | 6 (16.2) |
| >2.5 to 5 point improvement | 7 (16.7%) | 7 (18.9%) |
| >1 to 2.5 point improvement | 3 (7.1%) | 3 (8.1%) |
| >0 to 1 point improvement | 4 (9.5%) | 2 (5.4%) |
| 0 change | 5 (11.9%) | 5 (13.5%) |
| >0 to 1 point worsening | 6 (14.3%) | 3 (8.1%) |
| >1 to 2.5 point worsening | 2 (4.8%) | 3 (8.1%) |
| >2.5 to 5 point worsening | 5 (11.9%) | 3 (8.1%) |
| >5 to 10 point worsening | 3 (7.1%) | 0 |
| >10 point worsening | 1 (2.4%) | 0 |

| Change from Baseline | Placebo N = 44 | CX-8998 N = 39 |
|---|---|---|
| CGI-I Score at Day 15 | | |
| 3-very much improved | 1 (2%) | 0 |
| 2-much improved | 5 (11%) | 6 (15%) |
| 1-minimally improved | 14 (32%) | 19 (49%) |
| 0-no change | 21 (48%) | 14 (36%) |
| −1-minimally worse | 2 (5%) | 0 |
| −2-much worse | 1 (2%) | 0 |
| −3-very much worse | 0 | 0 |
| CGI-I Score at Day 28 | | |
| 3-very much improved | 1 (2%) | 0 |
| 2-much improved | 2 (5%) | 9 (23%) |
| 1-minimally improved | 7 (16%) | 15 (38%) |
| 0-no change | 30 (68%) | 13 (33%) |
| −1-minimally worse | 2 (5%) | 0 |
| −2-much worse | 0 | 0 |
| −3-very much worse | 0 | 0 |

| Change from Baseline | Placebo N = 44 | CX-8998 N = 39 |
|---|---|---|
| PGIC Score at Day 15 | | |
| 3-very much improved | 1 (2%) | 1 (3%) |
| 2-much improved | 3 (7%) | 8 (21%) |
| 1-minimally improved | 8 (18%) | 17 (44%) |
| 0-no change | 27 (61%) | 11 (28%) |
| −1-minimally worse | 1 (2%) | 1 (3%) |
| −2-much worse | 4 (9%) | 1 (3%) |
| −3-very much worse | 0 | 0 |
| PGIC Score at Day 28 | | |
| 3-very much improved | 2 (5%) | 3 (8%) |
| 2-much improved | 2 (5%) | 7 (18%) |
| 1-minimally improved | 6 (14%) | 10 (26%) |
| 0-no change | 29 (66%) | 14 (36%) |
| −1-minimally worse | 2 (5%) | 1 (3%) |
| −2-much worse | 1 (2%) | 1 (3%) |
| −3-very much worse | 0 | 1 (3%) |

Example 13. Relationship Between Cx-8998 Plasma Concentration and Response

Evaluation of the relationship between the $C_{min}$ exposure level of CX-8998 and response (E) as measured by change from baseline in TETRAS-PS using the Hill Equation:

Response=$E_{max}*C_{min}^b/(C_{min}^b EC_{50}^b)$

The $E_{max}$ and $EC_{50}$ values were estimated to be approximately −4.1 and 250 nM; however, the value for "b" was not statistically significant.

Summary of PK/PD Findings: The evaluation was done under steady state conditions, using concentration values ($C_{min}$) for CX-8998, combinations of analytes or total active moiety (TAM; the sum of the exposures to all measured Cav3 antagonists, e.g. total exposure of CX-8998 and all of its metabolites) and using either trough (T=0 hours) or post dose (T=4 hours; day 28 only) concentration samples for each study visit. Pharmacodynamic variables (Response) evaluated included change from baseline in TETRAS performance subscale, TETRAS activities of daily living, TETRAS total score.

The analysis found that concentration ranges were not low enough to fully define the PK/PD relationship, which suggests that the full pharmacological effect has been reached within the anticipated therapeutic range of 200 to 800 nM.

Figure 12:
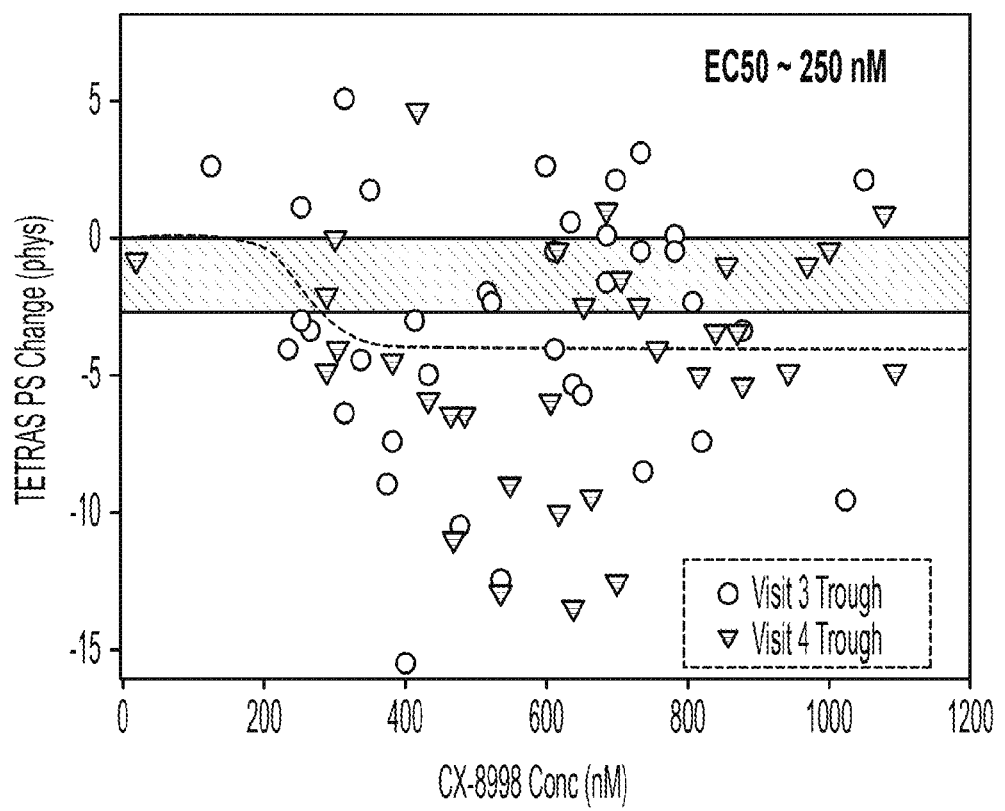
FIG. 12 is a graph showing the relationship between CX-8998 plasma concentration and response. Baseline and placebo response is represented by the shaded region.

Change in TETRAS PS is shown in FIG. 12 and is representative of similar results obtained with other PD markers (e.g., change in total TETRAS score).

Example 14. Patient Population

The patient population enrolled in T-CALM had a mean baseline TETRAS-PS score of 28.4 points, mean baseline TETRAS-ADL score of 26 points and mean time from ET diagnosis of 23 years. In addition, the majority of patients (64%) were also taking concomitant anti-tremor medications and those who were not taking ET medications were refractory to or intolerant of first and second line ET therapies. Thus efficacy was observed on top of standard of care in a moderate to severe ET population refractory to existing therapies.

TABLE 13

Patient Demographics.

| | | CX-8998 n = 48 | Placebo n = 47 | Total n = 95 |
|---|---|---|---|---|
| Demographics well matched | Age, years (SD) | 64 (9.6) | 63 (10.8) | 63 (10.2) |
| | Age Group (% > 65 yrs) | 26 (54%) | 25 (53%) | 51 (54%) |
| | Male, n (%) | 25 (52%) | 25 (53%) | 50 (53%) |
| | White, n (%) | 45 (94%) | 46 (98%) | 91 (96%) |
| | Weight, kg* (SD) | 88.8 (19.25) | 84.8 (20.72) | 86.8 (19.98) |
| Baseline characteristics | Years Since Tremor Onset (SD) | 24 (16.3) | 21 (15.7) | 23 (16.0) |

TABLE 13-continued

| Patient Demographics. | | CX-8998 n = 48 | Placebo n = 47 | Total n = 95 |
|---|---|---|---|---|
| moderate to severe on tremor meds | Alcohol Response (% Yes) | 23 (48%) | 16 (34%) | 39 (41%) |
| | On Anti-Tremor Meds (%) | 28 (58%) | 33 (70%) | 61 (64%) |
| | TETRAS-PS-Central (SD) | 23.1 (6.27) | 22.8 (5.67) | 22.9 (5.95) |
| | TETRAS-PS-Investigator (SD) | 28.3 (5.95) | 28.5 (6.35) | 28.4 (6.13) |
| | TETRAS-ADL | 26 (6.0) | 26 (7.0) | 26 (6.5) |

Example 15. Adverse Event Profile

This is a summary of the most common (>2%) treatment-emergent adverse events related to study drug by system organ class and preferred term that confirms the benign nature of CX-8998 safety and tolerability profile.

TABLE 14

Summary of adverse events.

| MedDRA System Organ Class/ Preferred Term[1,] | CX-8998 (n = 48) | Placebo (n = 47) |
|---|---|---|
| Subjects with at least 1 treatment-emergent adverse event[2] | 28 (58%) | 23 (49%) |
| Nervous System Disorders | 20 (42%) | 10 (21%) |
| Dizziness | 10 (21%) | 3 (6%) |
| Headache | 4 (8%) | 2 (4%) |
| Disturbance in attention | 2 (4%) | 1 (2%) |
| Dysgeusia | 2 (4%) | 0 |
| Paraesthesia | 2 (4%) | 1 (2%) |
| Somnolence | 1 (2%) | 2 (4%) |
| Hypesthesia | 0 | 2 (4%) |
| Psychiatric Disorders | 12 (52%) | 1 (2%) |
| Euphoric mood | 3 (6%) | 0 |
| Insomnia | 3 (6%) | 0 |
| Abnormal dreams | 2 (4%) | 1 (2%) |
| Hallucination | 2 (4%) | 0 |
| Gastrointestinal Disorders | 9 (19%) | 7 (15%) |
| Dry mouth | 2 (4%) | 1 (2%) |
| Nausea | 1 (2%) | 3 (6%) |
| Vomiting | 0 | 2 (4%) |
| Infections and Infestations | 4 (8%) | 3 (6%) |
| Urinary Tract Infection | 2 (4%) | 1 (2%) |
| Ear and Labyrinth Disorders | 2 (4%) | 0 |
| Tinnitus | 2 (4%) | 0 |

Example 16. Toleration to Adverse Events with Dose Titration

Figure 13:
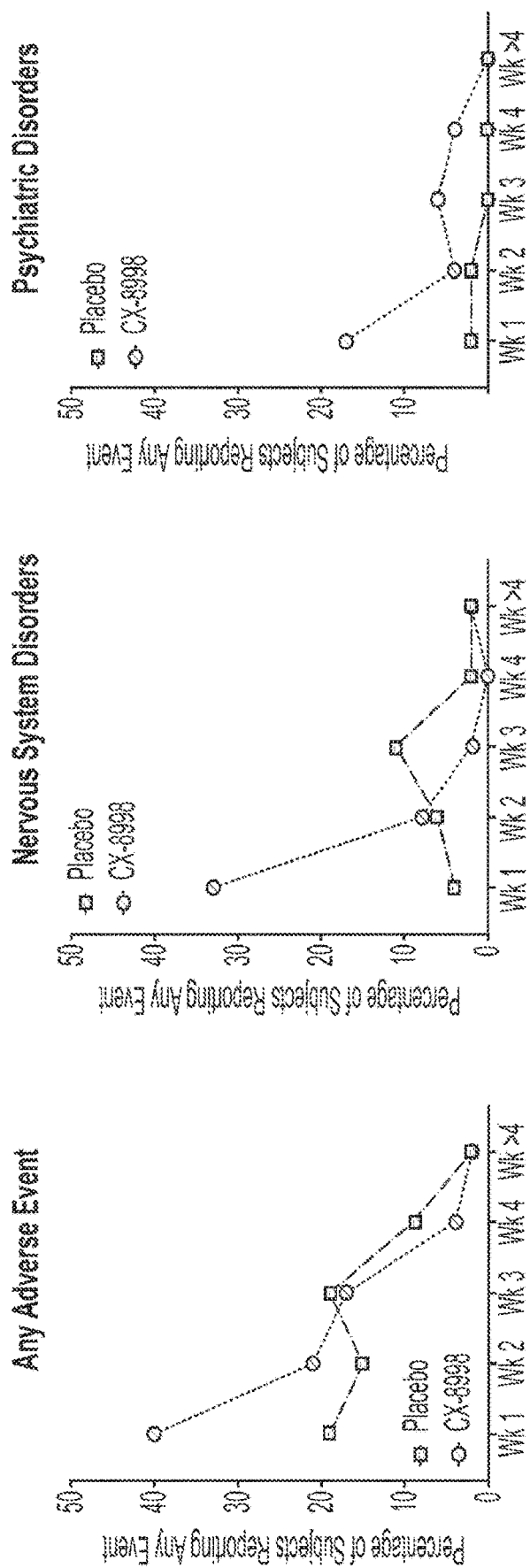
FIG. 13 contains graphs showing toleration to adverse events with dose titration.

T-CALM employed the following dose titration scheme: Week 1 at 4 mg BID (8 mg/day), Week 2 at 8 mg BID (16 mg/day) and Weeks 3 & 4 at 10 mg BID (20 mg/day). Adverse event reports decrease after the first week of dosing despite the fact that dose was being increased at the beginning of Weeks 2 and 3. This shows that patients tolerate quickly to CX-8998 related CNS and psychiatric adverse events (FIG. 13). Adverse Events were coded using MedDRA V20.0. Only treatment emergent adverse events with an onset date and time after the initiation of study drug until 30 days after discontinuation of drug were reported. For subjects who experience the same coded event more than once, a single event was presented. Adverse events were attributed to a study week based on the onset date, i.e. events that started on or after Visit 1 and prior to Visit 2 were classified as Study Week 1.

TABLE 15

Adverse events in other system organ classes.

| System Organ Class | CX-8998 | | | | | Placebo | | | | |
|---|---|---|---|---|---|---|---|---|---|---|
| | 1 | 2 | 3 | 4 | >4 | 1 | 2 | 3 | 4 | >4 |
| Any Event | 19 (40%) | 10 (21%) | 8 (17%) | 2 (4%) | 1 (2%) | 9 (19%) | 7 (15%) | 9 (19%) | 4 (9%) | 1 (2%) |
| Central Nervous System Disorders | 16 (33%) | 4 (8%) | 1 (2%) | 0 | 1 (2%) | 2 (4%) | 3 (6%) | 5 (11%) | 1 (2%) | 1 (2%) |
| Psychiatric Disorders | 8 (17%) | 2 (4%) | 3 (6%) | 2 (4%) | 0 | 1 (2%) | 1 (2%) | 0 | 0 | 0 |
| Gastrointestinal Disorders | 7 (15%) | 1 (2%) | 1 (2%) | 0 | 0 | 4 (9%) | 3 (6%) | 0 | 0 | 0 |
| Infections and Infestations | 0 | 2 (4%) | 2 (4%) | 0 | 0 | 2 (4%) | 0 | 0 | 1 (2%) | 0 |
| Investigations | 1 (2%) | 1 (2%) | 1 (2%) | 1 (2%) | 0 | 1 (2%) | 0 | 1 (2%) | 0 | 0 |
| General Disorders and Administration Site Conditions | 3 (6%) | 0 | 0 | 0 | 0 | 0 | 0 | 0 | 0 | 0 |

TABLE 15-continued

Adverse events in other system organ classes.

| System Organ Class | CX-8998 | | | | | Placebo | | | | |
|---|---|---|---|---|---|---|---|---|---|---|
| | 1 | 2 | 3 | 4 | >4 | 1 | 2 | 3 | 4 | >4 |
| Metabolism and Nutrition Disorders | 1 (2%) | 0 | 1 (2%) | 1 (2%) | 0 | 0 | 0 | 1 (2%) | 0 | 0 |
| Musculoskeletal and Connective Tissue Disorders | 1 (2%) | 1 (2%) | 1 (2%) | 0 | 0 | 0 | 0 | 0 | 0 | 0 |
| Ear and Labyrinth Disorders | 2 (4%) | 0 | 0 | 0 | 0 | 0 | 0 | 0 | 0 | 0 |
| Injury, Poisoning and Procedural Complications | 1 (2%) | 0 | 1 (2%) | 0 | 0 | 1 | 0 (2%) | 0 | 0 | 0 |
| Respiratory, Thoracic and Mediastinal Disorders | 1 (2%) | 0 | 1 (2%) | 0 | 0 | 0 | 1 (2%) | 0 | 0 | 0 |
| Eye Disorders | 1 (2%) | 0 | 0 | 0 | 0 | 0 | 0 | 0 | 0 | 0 |
| Neoplasms | 1 (2%) | 0 | 0 | 0 | 0 | 0 | 0 | 0 | 0 | 0 |
| Skin and Subcutaneous Tissue Disorders | 1 (2%) | 0 | 0 | 0 | 0 | 1 (2%) | 1 (2%) | 0 | 2 (4%) | 0 |
| Vascular Disorders | 0 (2%) | 1 | 0 | 0 | 0 | 0 | 0 | 0 | 0 | 0 |

Example 17. No Cardiovascular Safety Findings at Efficacious Doses

Figure 14:
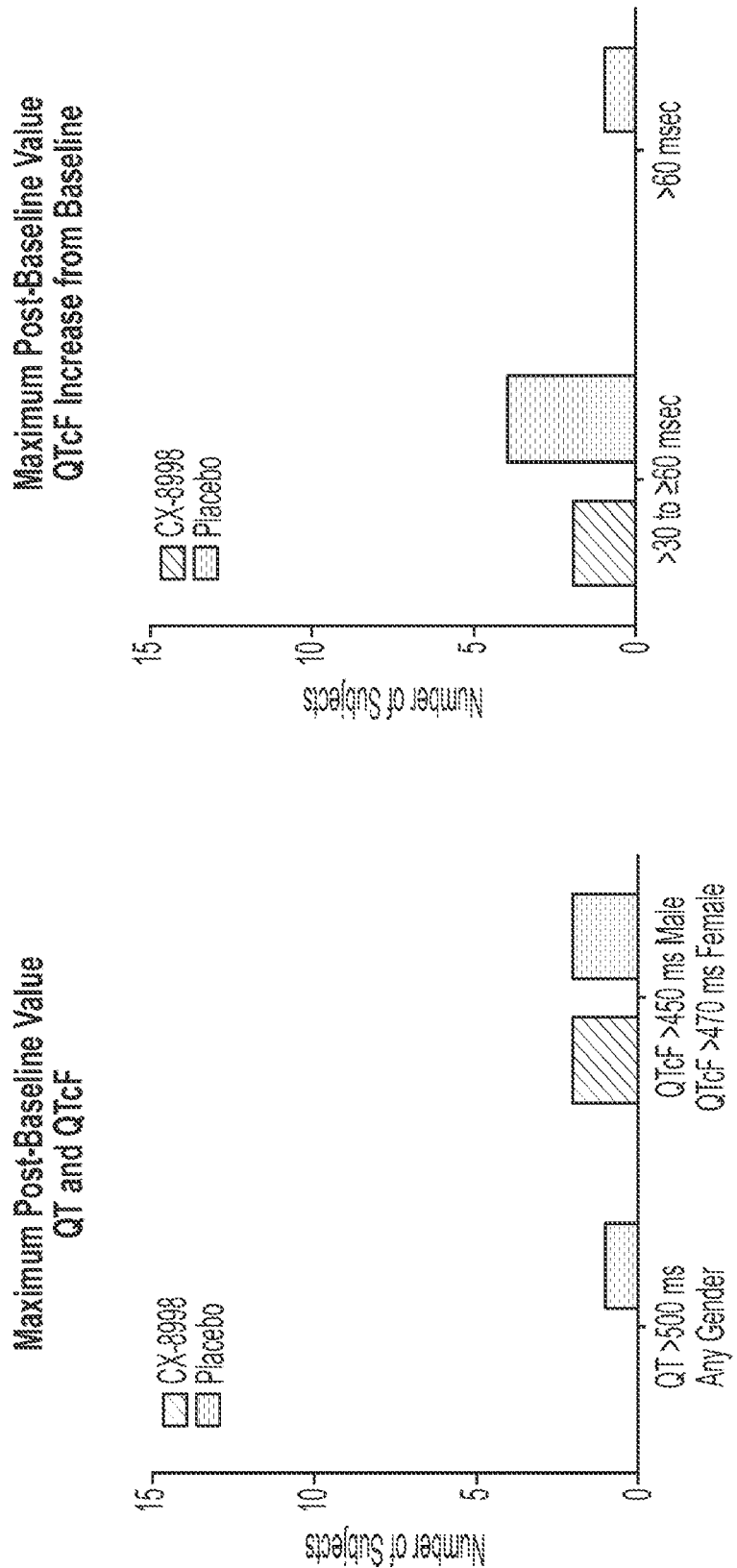
FIG. 14 contains graphs showing a summary of electrocardiogram outliers in a safety analysis set.
Figure 15:
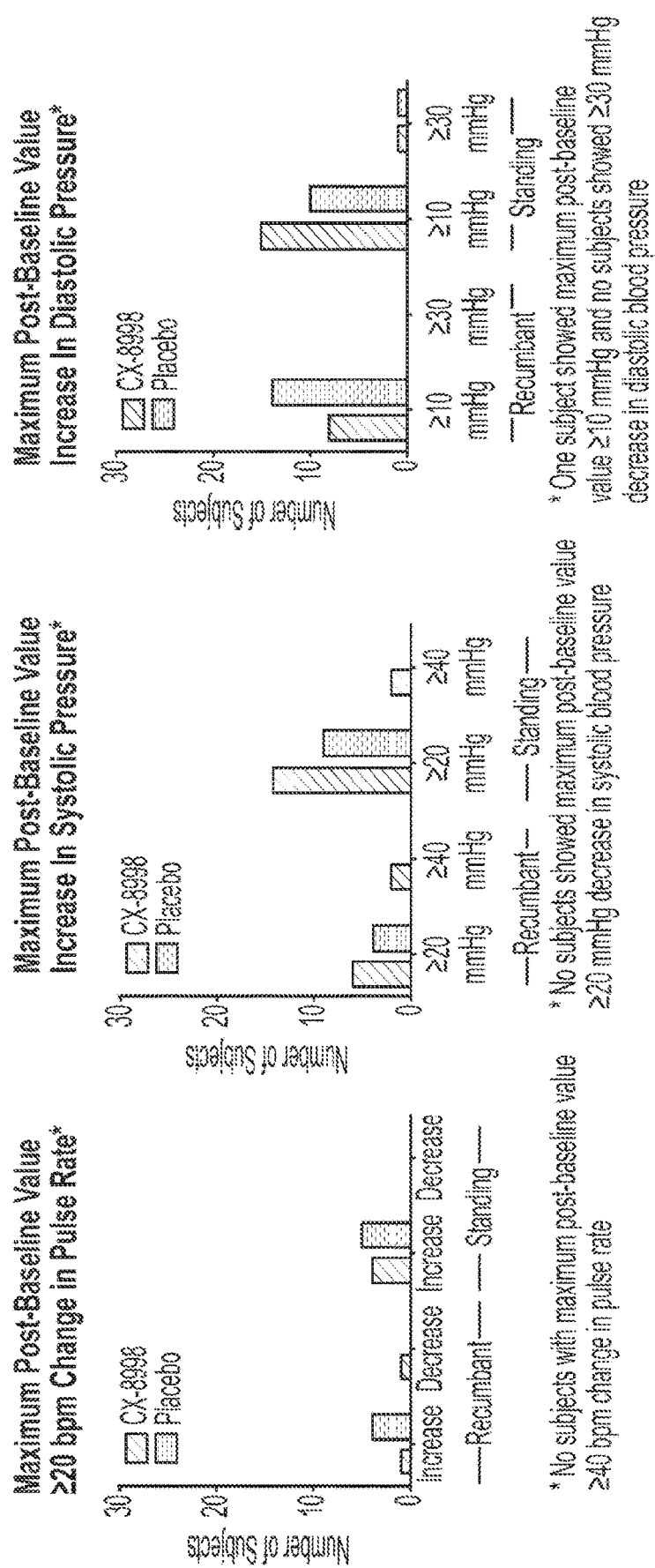
FIG. 15 contains graphs showing no difference between CX-8998 and Placebo in a safety analysis set.

An integrated analysis of electrocardiogram outliers revealed no CVS safety signals. Electrocardiogram results were calculated as the average of the triplicate records at each time point. Baseline was defined as the mean of the triplicate values obtained pre-dose at Day 1. If this value was not available, the mean of the triplicate records obtained at screening were used. A summary of electro cardiogram outliers is shown in FIG. 14. No difference was seen between CX-8998 and Placebo (FIG. 15).

Example 18. Subgroup Analysis

Figure 16:
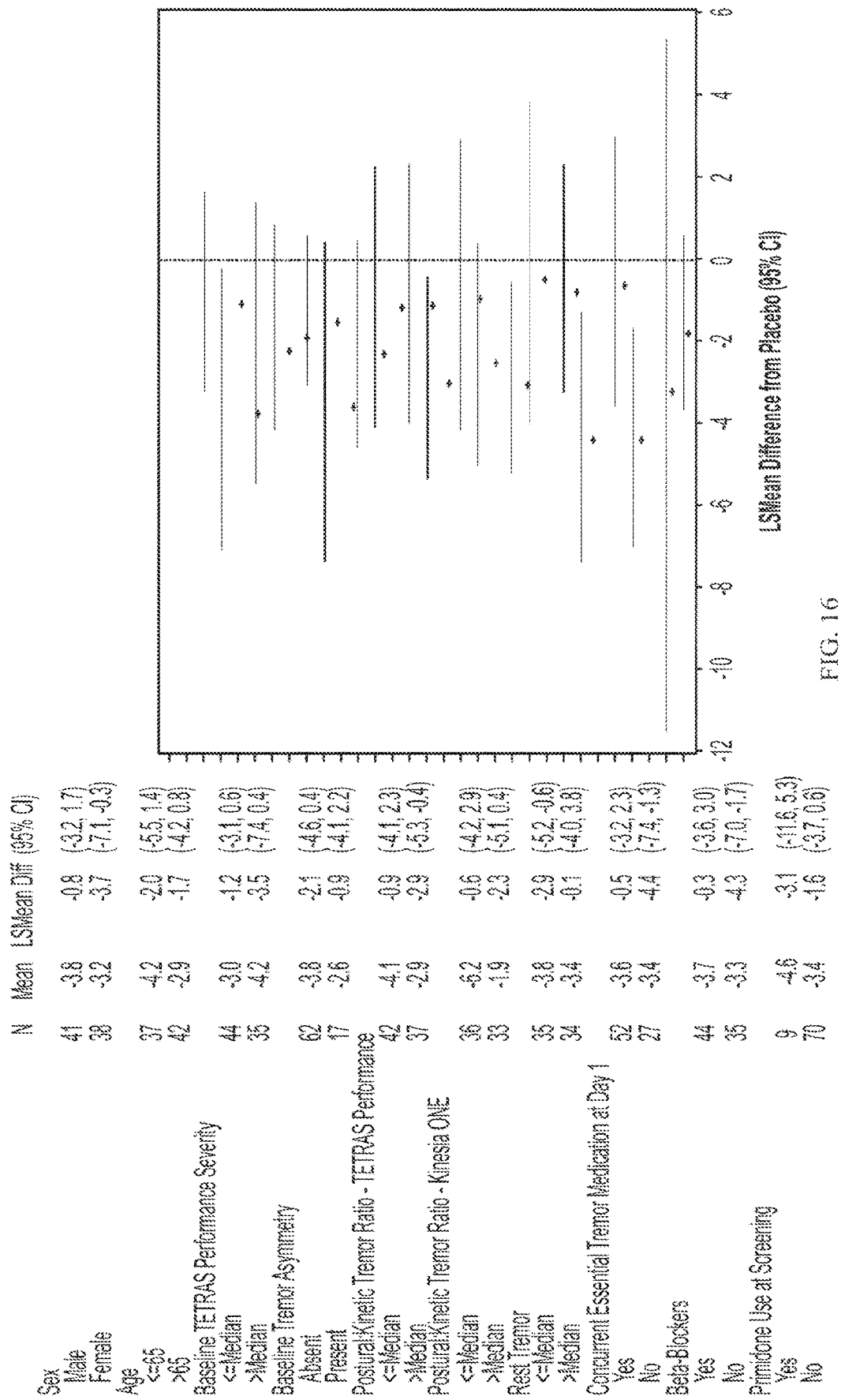
FIG. 16 is a dataset and forest plot for a subgroup analysis of TETRAS performance subscale total score in a physician rated full analysis set.
Figure 17:
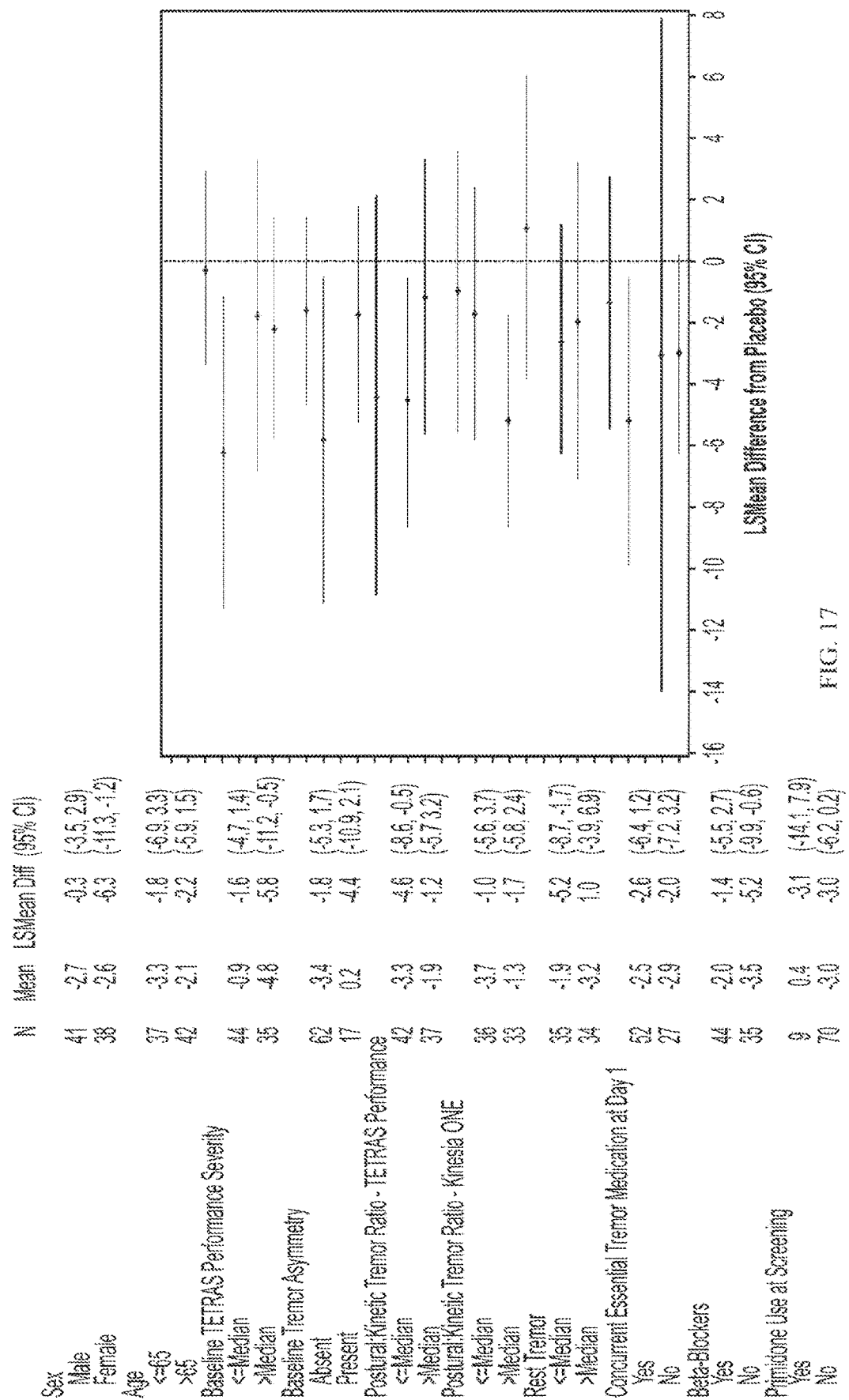
FIG. 17 is a dataset and forest plot for a subgroup analysis of TETRAS activities of daily living subscale in a full analysis set.

Exploratory subgroup analyses of the primary and secondary efficacy endpoints includes the following subgroups formed from baseline parameters:
1. Sex: male and female
2. Age at the time of informed consent as defined by: subjects up to 65 years of age and subjects >65 years of age
3. Baseline severity as assessed by centrally rated TETRAS performance score baseline values: greater than and less than the median value.
4. Baseline tremor asymmetry defined as a >1 point difference between the right and left side on any one of the TETRAS performance subscale items 4A (postural tremor), 4B (wingbeating tremor) or 4C (kinetic tremor): asymmetry present and asymmetry absent
5. Baseline ratio of TETRAS performance postural tremor (subscale item 4A) versus kinetic tremor (subscale item 4C) as defined by the ratio of total postural tremor (sum of left and right hand) divided by total kinetic tremor (sum of left and right hand): greater than and less than the median ratio
6. Baseline ratio of Kinesia ONE postural tremor versus kinetic tremor defined and grouped similarly to the ratio above
7. Baseline rest tremor as defined as total rest score (sum of rest for left and right hand) measured by Kinesia ONE at baseline of greater than (presence) or less than (absence) the median total rest tremor score: presence of rest tremor and absence of rest tremor
8. Concurrent essential tremor medication at Day 1: yes and no, also a subgroup on subjects taking beta-blockers will be examined
9. Primidone use at study start as defined as subjects who discontinued primidone use within two weeks prior to or during the screening period: taking primidone and not taking primidone Individual endpoints including TETRAS-PS (FIG. 16) and TETRAS-ADL (FIG. 17) representative of the results are shown. Subsets that may show increase improvement with Cav3 antagonist treatment include females, patients with higher severity of tremor, and subjects not concurrently taking antitremor medications. Subjects with lower levels of rest tremor and a lower ration of postural to kinetic tremor may also achieve greater level of improvement.

Example 19. Analytical Methods for Measuring CX-8998 and Metabolites in Human Plasma with a Single Bioanalytical Assay Separating M02 & M04

A liquid chromatography tandem mass spectrometry (LC/MS/MS) method was developed, qualified and validated for the simultaneous quantitation of CX-8998 and M01, M02, M03, and M04 concentrations in human plasma K2EDTA. To develop a 5-in-1 assay for the simultaneous quantitation of analytes CX-8998, M01, M02, M03 and M04 in human plasma, an HPLC method which is capable to retain and separate all compounds within a reasonable run time was necessary. Furthermore, due to the isobaric nature of M02 and M04, baseline separation was required for accurate quantitation of these metabolites.

With MW around 400 g/mol and calculated log P values between 3 and 5, all 5 compounds were prime candidates to be analyzed by reverse phase chromatography. Based on the structural differences between the analytes, separation between CX-8998, M01, M03 and either M02 or M04 was not difficult. The challenge was to develop a condition which can achieve baseline resolution between M02 and its isobaric positional isomer, M04. Various early screenings using Agilent Zorbax extended C18, Agilent Eclipse XDB C18, and Phenomenex Synergi MaxRP columns were tested (data not shown); however, none were able to satisfactorily separate M02 and M04. Eventually, the Phenomenex Luna C18 column showed the highest resolving power between M02 and M04 and was selected for further HPLC method optimization.

Figure 18:
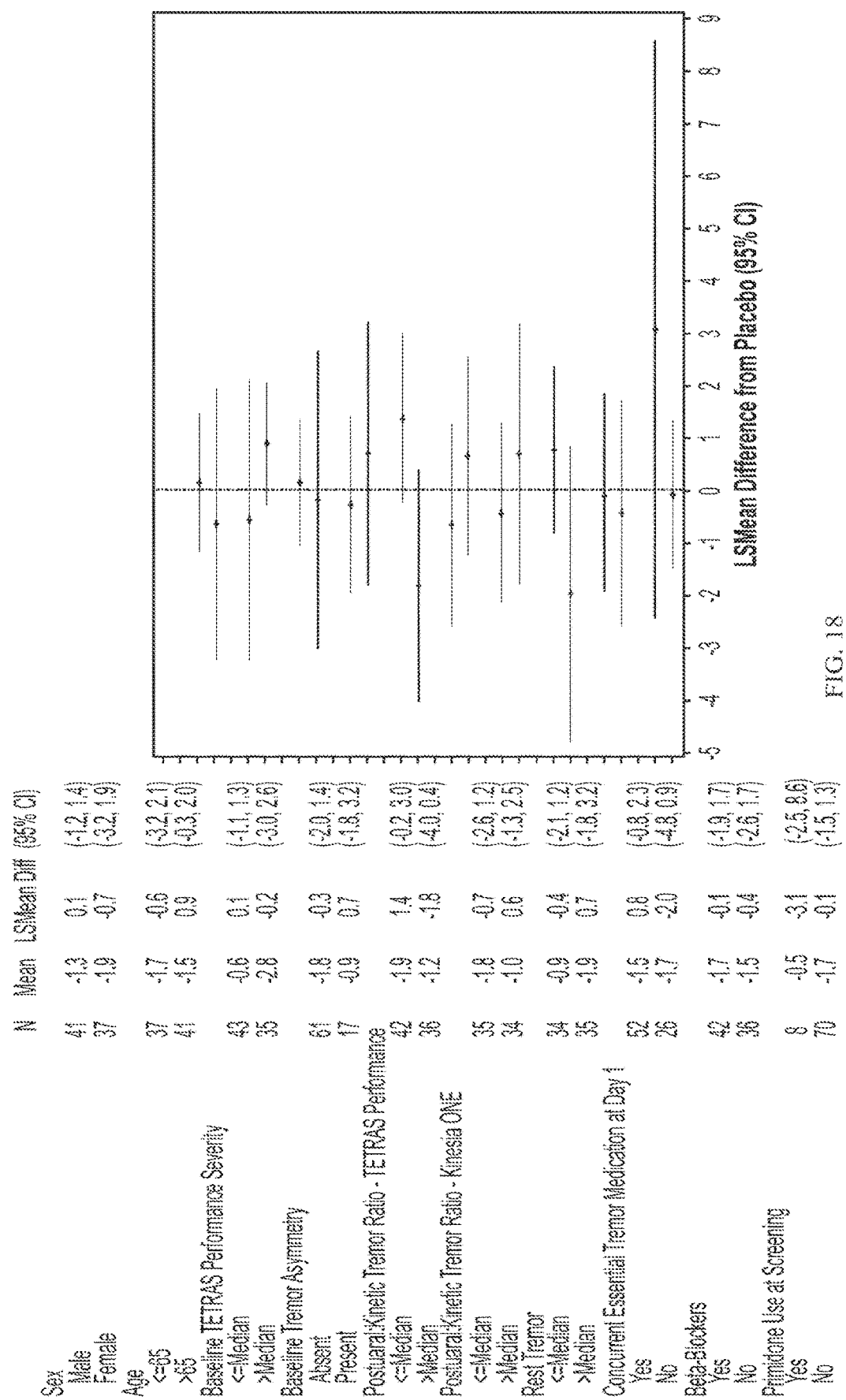
FIG. 18 contains chromatograms of CX-8998 showing partial separation and suboptimal peak widths for metabolites M01, M02, M03, and M04.

Phenomenex Luna C18 Chromatography was initially investigated. During initial trials using the Luna C18 (30× 2.0 mm, 3 μm) column, only partial separation was achieved between M02 and M04 and peak widths for M01 and M03 were suboptimal (FIG. 18).

Optimizations to reduce peak width and increase peak resolution involved adjustments in:
  sample solvent compositions (lower organic content for enhanced retention)
  mobile phase modifiers (reduce secondary interactions)
  ion-pairing (alter retention behaviour to improve peak shape)
  solvent strength of organic mobile phases (lowering strength to enhance retention and change in selectivity)

However, none resulted in satisfactory separation between M02.and M04. Furthermore, peak widths were still suboptimal.

Figure 19:
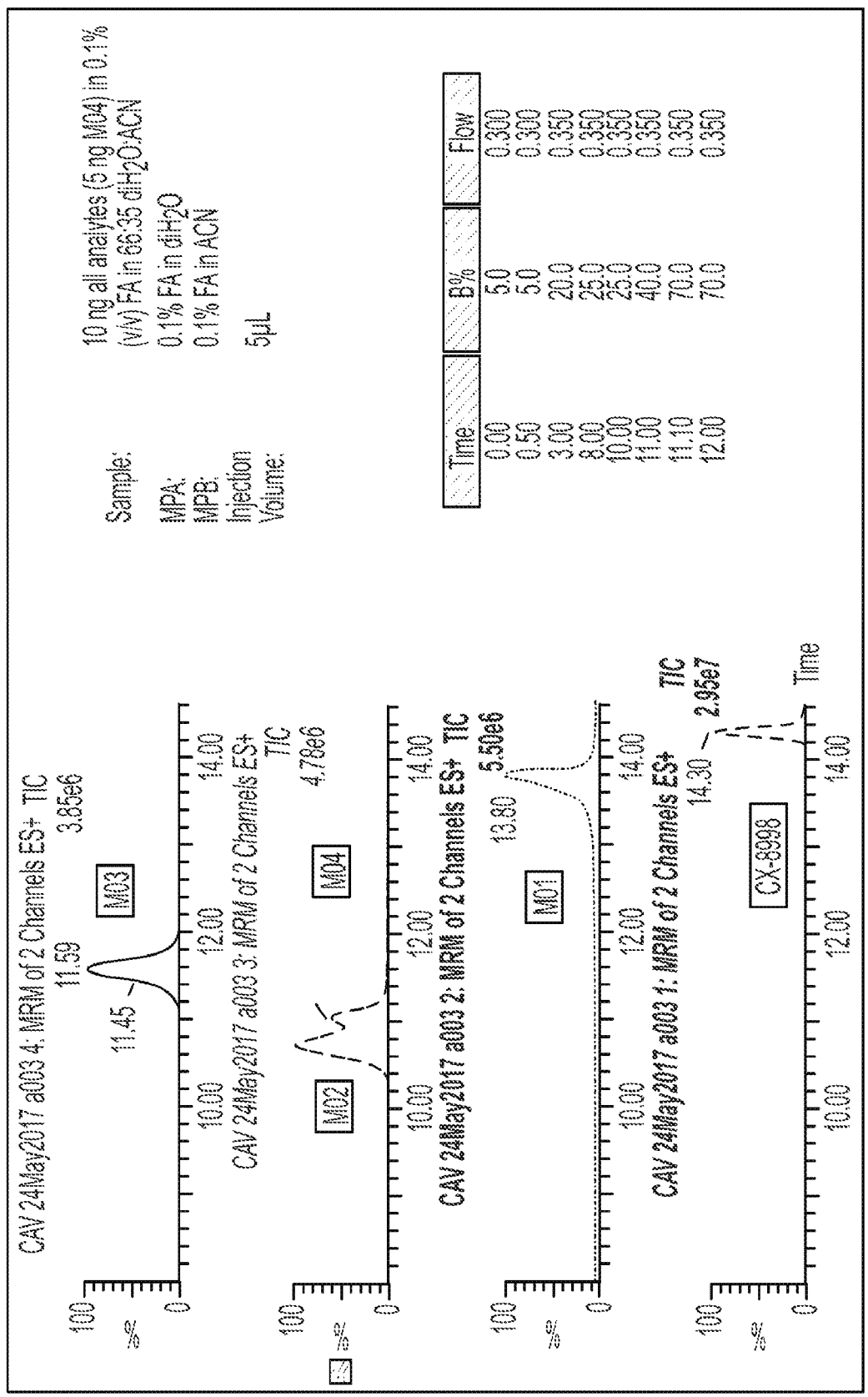
FIG. 19 contains chromatograms of CX-8998 showing unwanted secondary interactions resulting in poor peak shapes.

Phenomenex Luna Phenyl-Hexyl Chromatography: A chromatography based mainly on hydrophobic interactions (e.g., C18) was concluded not strong enough to achieve the required separation. The introduction of additional interaction types can enhance selectivity. A phenyl-hexyl column provides unique electrostatic, hydrogen bonding, and dipole-dipole interactions based on its electron rich aromatic phenyl-hexyl phase. It was hypothesized these unique chemistries can generate sufficient specificity to separate M02 and M04. Slightly better peak resolution between the analytes compared to a C18-based system was observed, however, this column type (30×2 mm, 3 μm) exhibited unwanted secondary interactions resulting in poor peak shapes (FIG. 19).

Figure 20:
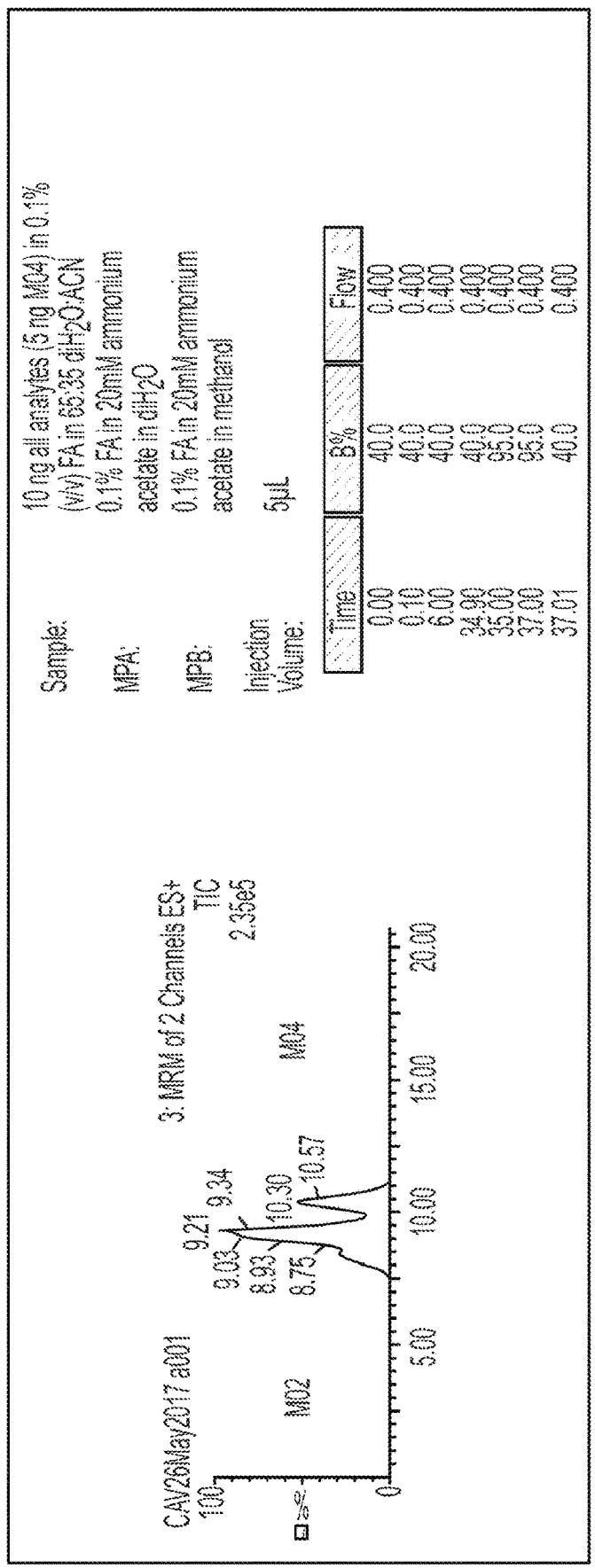
FIG. 20 contains chromatograms of CX-8998 showing near baseline separation of CX-8998 and its metabolites M01, M02, M03, and M04.

Phenomenex Kinetex PFP Chromatography: The highly electronegative pentafluorophenyl (PFP) bonded phase offers alternative selectivity (hydrophobic, pi-pi interactions, dipole-dipole, hydrogen-bonding, and shape selectivity) compared to traditional C18-based or phenyl-hexyl reverse-phase columns in part due to the electron deficient phenyl ring and high retention for halogen related compounds. Near baseline separation of all five analytes from a plasma sample was achieved using this column chemistry type (100×2.1 mm, 2.6 μm, and FIG. 20).

An excessively long run time was necessary to provide sufficient separation of all analytes, thus this method was prohibitively long and would be logistically challenging for the analysis of prospective clinical plasma test samples. The ideal run time should be 15 minutes or less. Several chromatographic optimizations were investigated to further reduce runtime:
  increasing column temperatures to enable the use of higher flow rates without hampering column efficiency
  shorter column length Unfortunately, these changes resulted in deteriorated resolution between M02 and M04. Shortening of the method run time was not possible.

Sample Derivatization Development: Analyte derivatization was investigated as an alternative to chromatographically separate M02 and M04 while maintaining a reasonable method run time. Since the structural difference between M02 and M04 was only by the position of one hydroxyl group (3°-OH in M02; 1°-OH in M04), it should be possible to selectively react with the 1°-OH group while the sterically hindered 3°-OH group remain non-reacted. This should provide stronger structural difference to allow separation during chromatography. Various OH-group derivatization methods from the literature were reviewed and 4, involving selective acylation and dansylation of the primary alcohol moiety, were selected and tested.

TABLE 16

Chromatographic optimization parameters.

| Condition | 1 | 2 | 3 | 4 |
|---|---|---|---|---|
| Reagent | Acetic anhydride | Acetic anhydride | TFA | Dansyl Chloride |
| Donating Group | Acetate, MW 42 | Acetate, MW 42 | Acetate, MW 42 | Dansyl, MW 176 |
| Temperature | 50° C. | 50° C. | RT | 60° C. |
| pH | Acidic (in acetic acid) | Basic (in pyridine) | Acidic (TFA) | Basic (sodium bicarbonate) |
| Time (h) | 1.5 | 0.5 | 0.25 | 0.42 |
| Reaction with M02 | No | No | No | no |
| Reaction with M04 | various forms detected | No | various forms detected | Yes |

Figure 21:
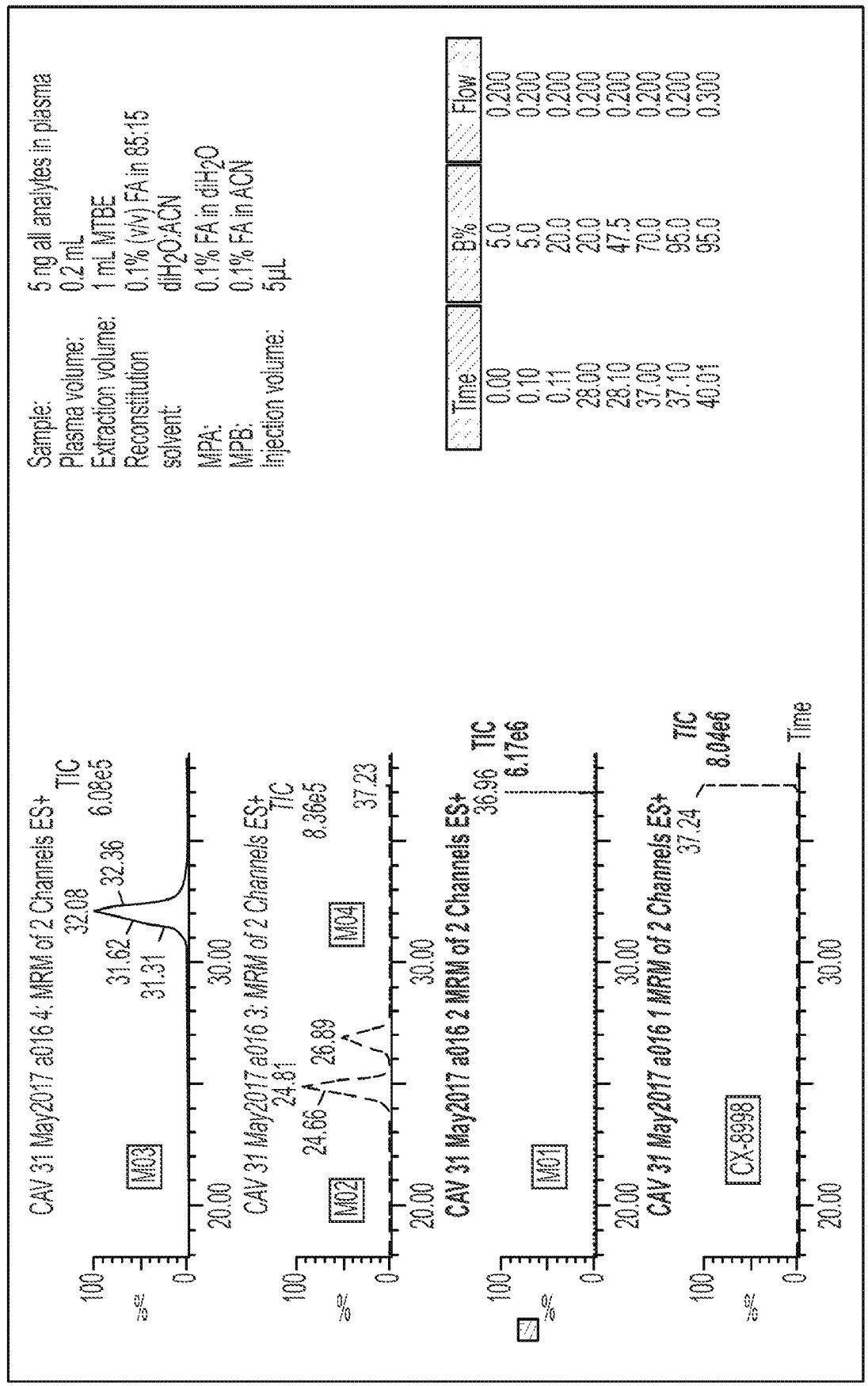
FIG. 21 contains chromatograms showing that acetylation with acetic anhydride under basic conditions appeared to be selective for M04 and showed high reaction yield.

Acetylation under acidic conditions was selective but appeared to form a complex mixture of M04 reaction products with low reaction yield. Minimal derivatization was observed with dansylation and reaction with TFA resulted in complex mixture of M04 reaction products (data not shown). Acetylation with acetic anhydride under basic conditions appeared to be selective for M04 and showed high reaction yield (FIG. 21).

Signal intensity for M04 appeared to be 100-fold lower than that of other analytes due to its reaction with the reagent. Formation of a M04 product peak at 8.48 minute (compared to the unreacted M04 peak at 7 minutes) was detected with a m/z of 439.4, which corresponded to the mass of singly acetylated M04 (M04-Ac) entity. This was confirmed by the observation of a daughter fragment at 204 m/z, in line with the daughter fragment observed for all other analytes.

Figure 22:
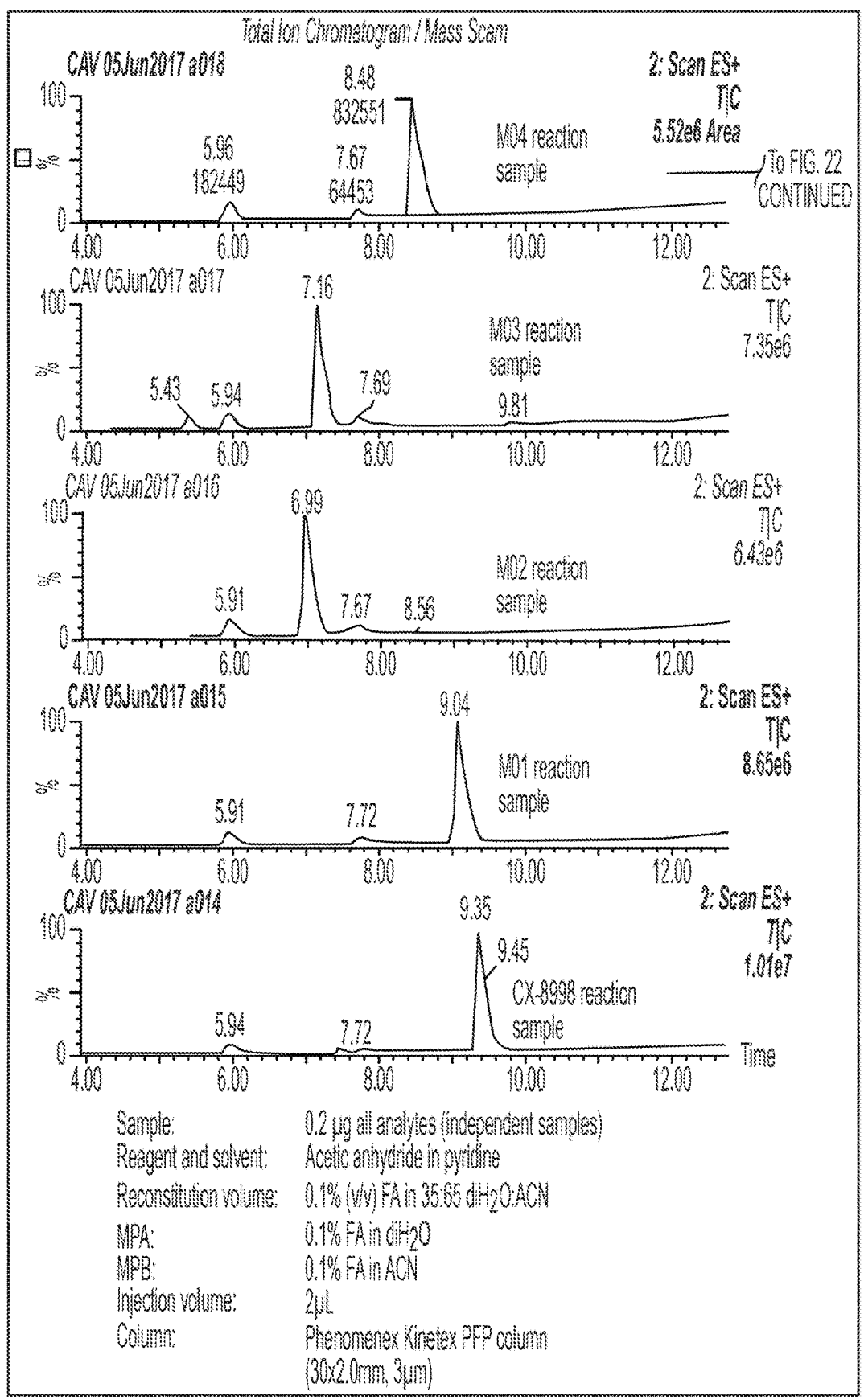
FIG. 22 is a graph showing a reaction time course at 50° C. for M04-Ac formed in individuals analyte reaction vs mixed analyte reaction.
Figure 22:
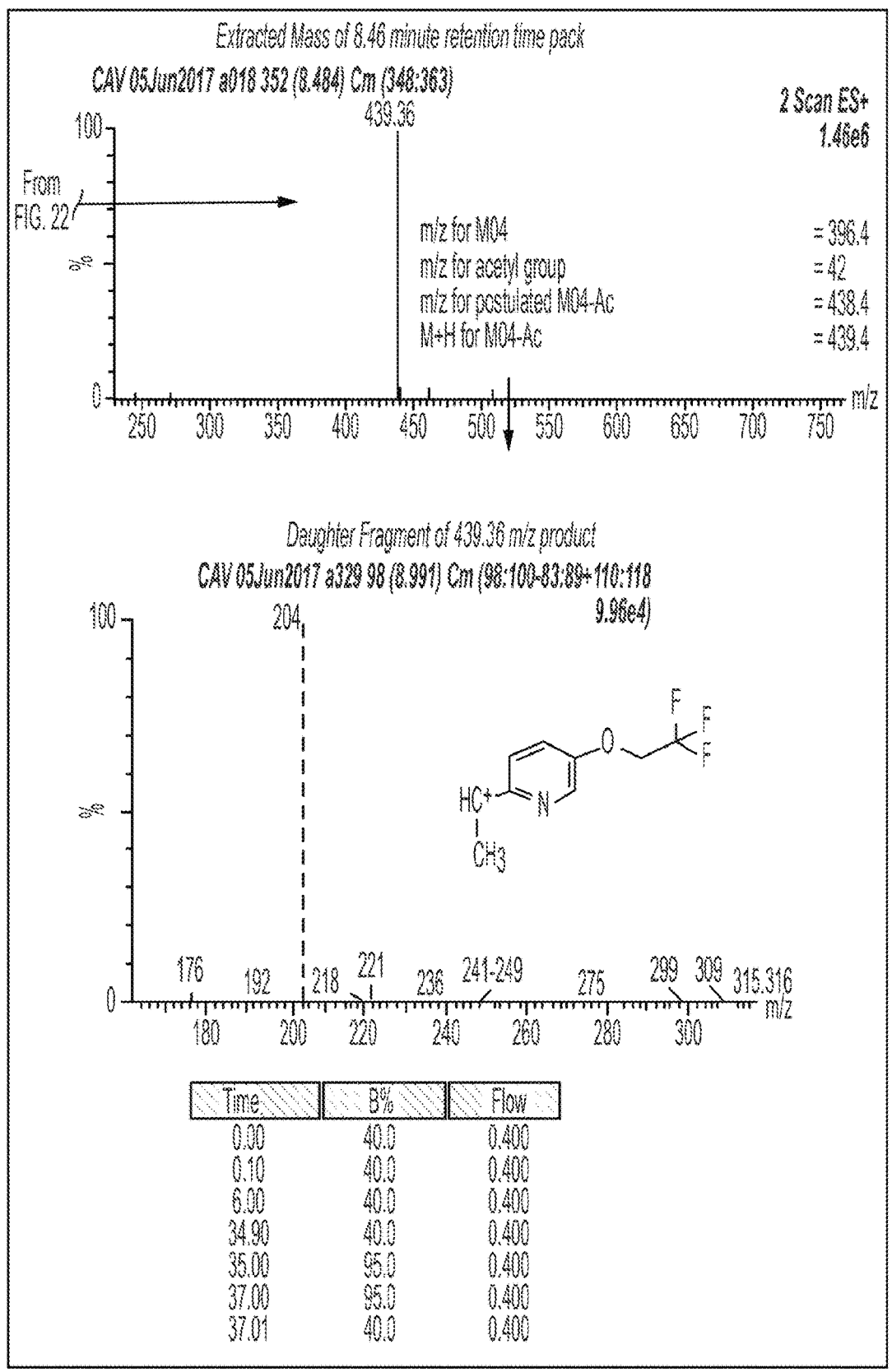

Kinetics of the M04 Acetylation Reaction: A plasma reaction and stability time course experiment was subsequently performed to determine reaction kinetics up to 2 hours at 50° C. Reaction kinetics was evaluated for M04 at 2.5 μg/mL independently and as a mixture containing the other analytes, in equal volumes with acetic anhydride and pyridine, to verify efficiency of the reaction. The derivatization reaction reached a plateau in the formation of M04-Ac between ~30 to 60 minutes of reaction at 50° C. with or without the presence of other analytes. Approximately 6% of M04 remained unreacted after ~30 minutes of reaction (FIG. 22).

TABLE 17

M04 Acetylation Reaction.

| Reaction Time (min) | % M04 Peak Area Remaining |
|---|---|
| 0 | 100.0 |
| 25 | 5.9 |

TABLE 17-continued

M04 Acetylation Reaction.

| Reaction Time (min) | % M04 Peak Area Remaining |
|---|---|
| 38 | 4.6 |
| 70 | 2.8 |
| 130 | 2.3 |

Figure 23:
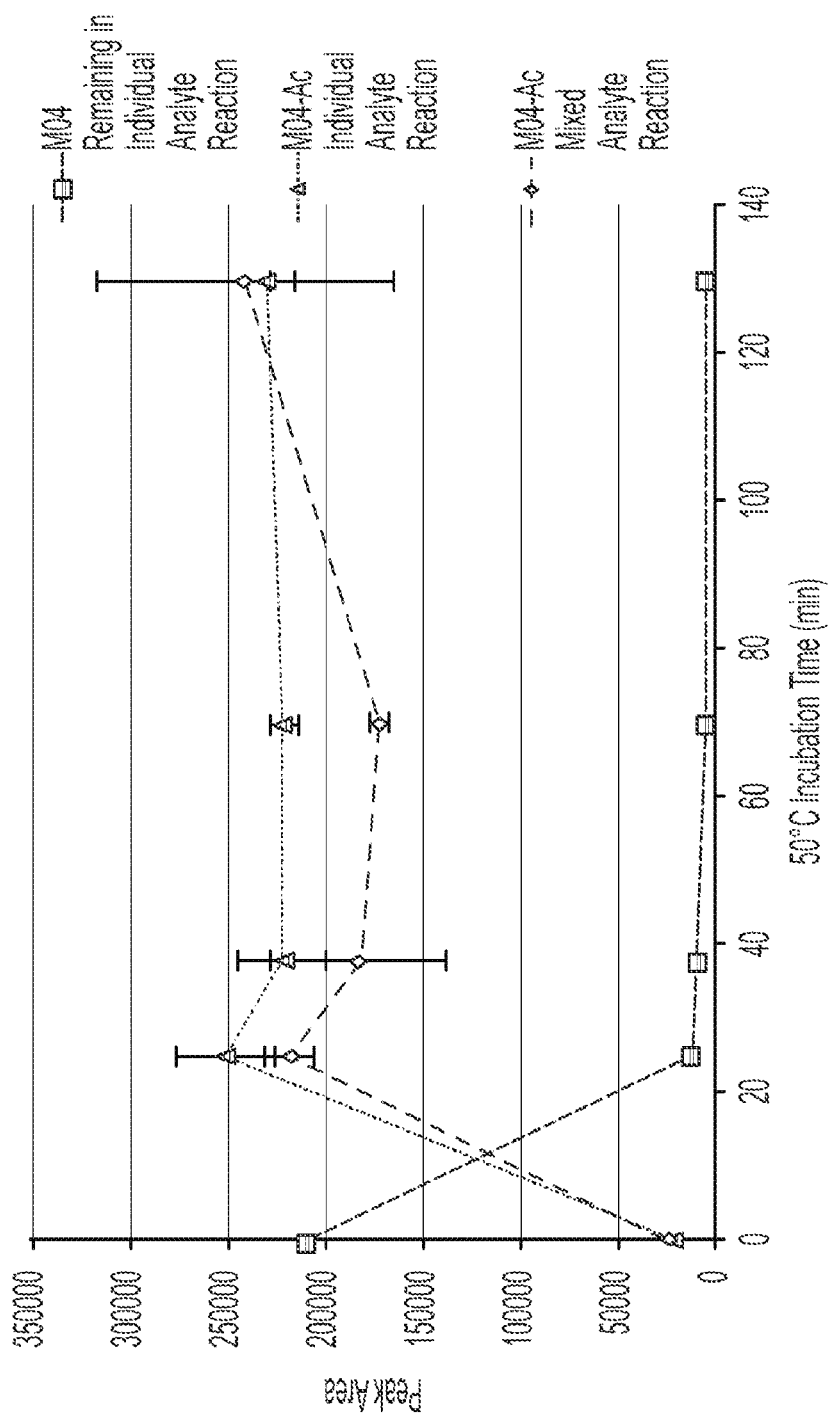
FIG. 23 is a graph showing the percent of M04 remaining following an increase of either acetic anhydride or pyridine during the derivatization reaction at 50° C. for 30 minutes in human plasma extracts.

To reduce the amounts of unreacted M04 remaining, pyridine and acetic anhydride volumes were increased by up to 2.5-fold and 5-fold, respectively (FIG. 23).

Figure 24:
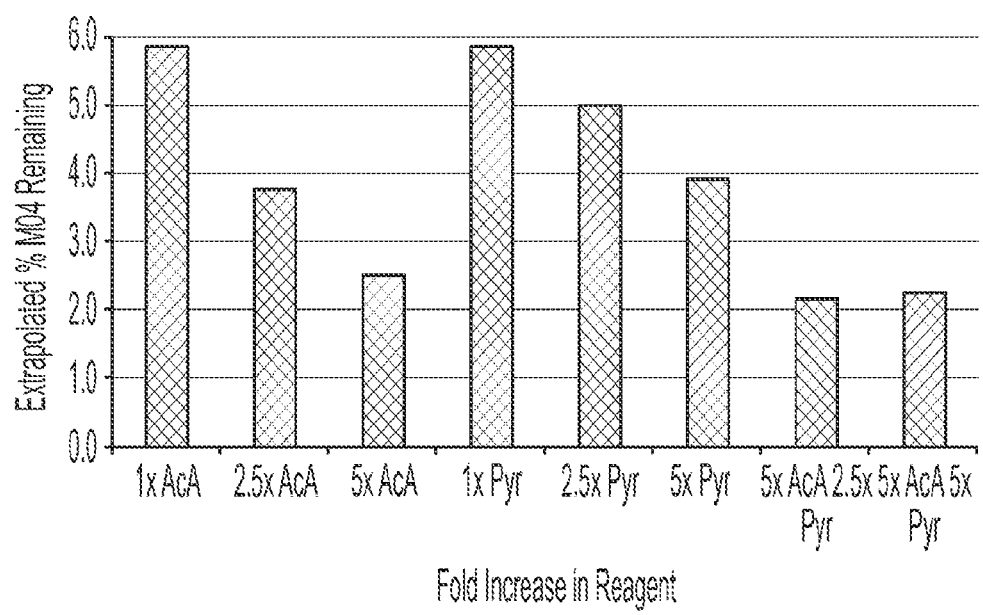
FIG. 24 is a graph showing a reaction time course at 50° C. in samples containing individual analytes based on peak areas.

The best yield was achieved when the plasma:pyridine:acetic anhydride volume ratio was at 1:2.5:5 (% M04 unreacted ~2.2%). This condition was selected for method validation. Increase in reaction temperature as a means to improve reaction yield was not investigated due to potential concerns of analyte instability. Stability was also evaluated for CX-8998, M01, M02, and M03 at 2.5 µg/mL in the presence of equal volumes of acetic anhydride and pyridine at 50° C. Overall, CX-8998, M01, M02, and M03 appeared to be stable up to 130 minutes of reaction at 50° C. (FIG. 24).

Following optimization of the chromatography, the following 5-in-1 LC/MS/MS assay for the quantitation of CX-8998, M01, M02, M03, and M04 concentrations from 1 to 2000 ng/mL in human plasma K2EDTA was performed.

Sample preparation procedures: With reference to a previously validated method for CX-8998, M01, and M02 involving protein precipitation (Merck, West Point, SBP 261), the following procedure was adopted and qualified:

1. Prepare serial dilutions of reference and internal standard solutions in 1:1 diH2O:ACN
2. Add 10 µL each of the reference standard and internal standard solutions to 0.2 mL of human plasma K2EDTA
3. Precipitate plasma proteins with 0.6 mL of ACN
4. Centrifuge and obtain supernatant
5. Evaporate dry supernatant at 50° C.
6. Reconstitute samples in 0.1 mL of dichloromethane with sonication for 5 minutes
7. Derivatization with 20 µL* each of acetic anhydride and pyridine at 50° C. for 30 minutes

*Volumes were optimized subsequent to method qualification to use 100 µL of acetic anhydride and 50 µL of pyridine. This was a minor modification with no anticipated impact to assay performance aside from higher reaction yields for M04-Ac. Therefore, these volume ratios were not re-qualified.

8. Evaporate dry at 50° C.
9. Reconstitute samples in 0.1% formic acid in 1:1 diH2O:ACN with sonication for 10 minutes Chromatographic Parameters

| MPA | 0.1% (v/v) FA in diH2O |
|---|---|
| MPB | 0.1% (v/v) FA in ACN |
| Column | Phenomenex Kinetex PFP (50 × 2.1 mm, 100 Å, 5 µm) |
| Injection volume | 10 µL |
| Run time | 14 min |
| Autosampler temp | 2° C. to 8° C. |
| Column temp | 30° C. |
| Needle wash | 0.1% (v/v) FA in CAN |

TABLE 18

HPLC Gradient Time Table.

| Time | % B | Flow (mL/min) |
|---|---|---|
| 0.00 | 20 | 0.5 |
| 0.10 | 20 | 0.5 |
| 0.11 | 25 | 0.5 |
| 4.50 | 29 | 0.5 |
| 4.51 | 36 | 0.5 |
| 8.50 | 40 | 0.5 |
| 8.51 | 98 | 0.5 |
| 10.00 | 98 | 0.5 |
| 10.01 | 98 | 0.8 |
| 11.50 | 98 | 0.8 |
| 11.51 | 20 | 0.8 |
| 13.90 | 20 | 0.8 |
| 13.91 | 20 | 0.8 |
| 14.00 | 20 | 0.8 |

Mass Spectrometry Parameters: The analytes were monitored using Micromass Quattro@-LC tandem triple quadruple mass spectrometer, controlled by Micromass MassLynx® software Version 4.0. Representative MS parameters (ESI positive, MRM mode) were as follows:

TABLE 19

Mass Spectrometry Parameters.

| Analyte | MRM | Cone (V) | Collision Energy (eV) |
|---|---|---|---|
| CX-8998 | 381 > 204 | 40 | 24 |
| M01 | 379 > 204 | 40 | 23 |
| M02 | 397 > 204 | 38 | 23 |
| M03 | 411 > 204 | 40 | 22 |
| M04-Ac | 439 > 204 | 45 | 21 |
| $d_3$-CX-8998 (ITS) | 384 > 207 | 40 | 25 |
| $d_3$-M01 (ITS) | 382 > 207 | 40 | 24 |
| $d_3$-M02 (ITS) | 400 > 207 | 38 | 24 |
| $d_3$-M03 (ITS) | 414 > 207 | 40 | 22 |
| $d_3$-M04-Ac (ITS) | 442 > 207 | 40 | 23 |

Figure 25:
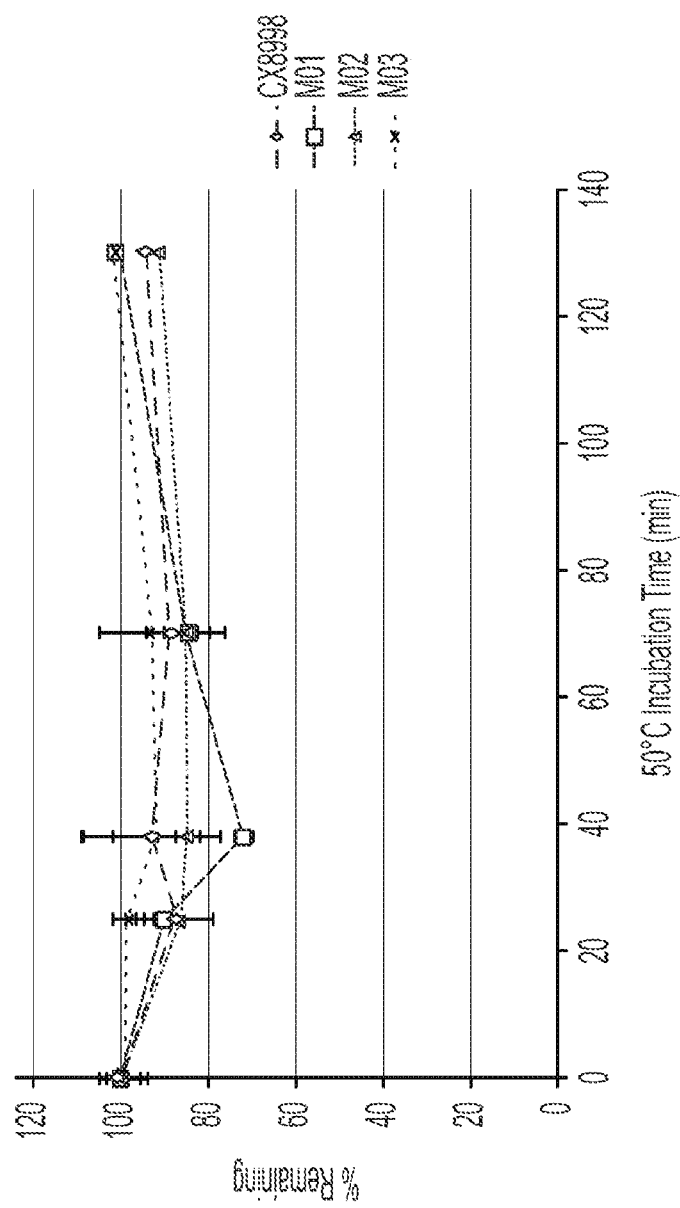
FIG. 25 is a representative chromatogram of CX-8998, M01, M02, M03, and M04 in human plasma sample.

Chromatography. A representative chromatographic performance following an injection of a 10 ng/mL of CX-8998, M01, M02, M03, and M04 in human plasma sample is shown in FIG. 25.

In this study, a 5-in-1 LC/MS/MS assay was developed for the simultaneous quantitation of CX-8998 and its metabolites M01, M02, M03 and M04 in human plasma K2EDTA. Due to the isobaric nature of M02 and M04, full separation could not be achievable via hydrophobic interactions by traditional C18-based reverse-phase systems. A variety of other alternative reverse-phase columns were evaluated and near complete separation was achieved utilizing a pentafluorophenyl (PFP) bonded column, albeit with prohibitively long run times. Consequently, an acetylation derivatization approach specific for M04 was successfully developed which enabled satisfactory chromatographic separation for all five analytes in reasonable assay runtimes.

The LC/MS/MS assay for the simultaneous quantitation of all five analytes was subsequently qualified with a calibration range of 1 to 2000 ng/mL for all analytes in human plasma. Assay performances were satisfactory and met acceptance criteria for system performance suitability, quantitation range, calibration linearity, assay accuracy and precision, and assay recovery. Slight chromatographic carry-over was observed for CX-8998. Some reference standard impurities were observed; however, levels were negligible and have minimal impact on calibration. Low residual levels of unreacted M04 was observed resulting in interference in M02 detection. Overall, this is expected to have minimal impact as only a total bias of ~7.1% to M02 quantitation resulting from the sum of all interferences. The accuracy limit of the assay for quantitation of M02 at varying ratios of M04 in samples was ascertained during method validation.

Example 20. Wide Safety Margins Between Human Therapeutic Exposures and Toxicology Findings in Nonclinical Studies Safety margins for CX-8998 and its metabolites M01 and M02 were calculated from exposures in the 90-day repeat-dose toxicology studies in rats and dogs at the NOAEL doses (300 mg/kg/day and 30 mg/kg/day, respectively) for total (bound and unbound) CX-8998, M01, and M02, based on estimated human plasma concentration ($C_{ss}$) and area under the curve ($AUC_{24}$) values at steady state for 10 mg BID dosing. In addition, safety margins for the sum of the exposures of the active components (CX-8998, M01 and M02) or so called "total active moiety" (TAM) was also calculated.

Calculated safety margins for total CX-8998 $AUC_{24}$ in males and females were 19-fold and 41-fold respectively in rats and 24-fold and 26-fold in dogs. Calculated total margins for CX-8998 $C_{ss}$ in males and females were 39- and 91-fold respectively in rats and 68- and 74-fold in dogs. In rat, margins were approximately 2-fold lower in males than in females while in dog margins were similar across the 2 sexes.

The calculated safety margins for total $AUC_{24}$ (female/male) are 41-/19-, 13-/6.8-, and 62-/31-fold for CX-8998, M01, and M02, respectively, in rat and 26-/24-, 5.6-/6.5, and 25-/26-fold, respectively, in dog (Table 20). The calculated safety margins for total $C_{ss}$ (female/male) are 91-/39-, 21-/13-, and 104-/56-fold for CX-8998, M01, and M02 respectively, in rats, and 74-/68-, 8-/10-, and 46-fold, respectively, in dogs.

The calculated safety margins for total $AUC_{24}$ TAM are 32- and 16-fold in female and male rats respectively and 17- and 16-fold in both female and male dogs. The calculated safety margins for total $C_{ss}$ TAM are 62- and 31-fold in female and male rats respectively and 39- and 37-fold in female and male dogs respectively.

Example 21. CX-8998 Formulation Development

CX-8998 was formulated into 1 mg, 2 mg, 3 mg, 4 mg, 8 mg, 12 mg, and 18 mg capsules and used as single morning doses. Capsules with varied doses provide highly flexible titration schedules, and allow ideal dosing regimens.

The performance of CX-8998 immediate release capsules was evaluated in human subjects and in a simulated gastrointestinal tract where 900 mL of acidic medium was used to mimic the stomach.

Figure 26:
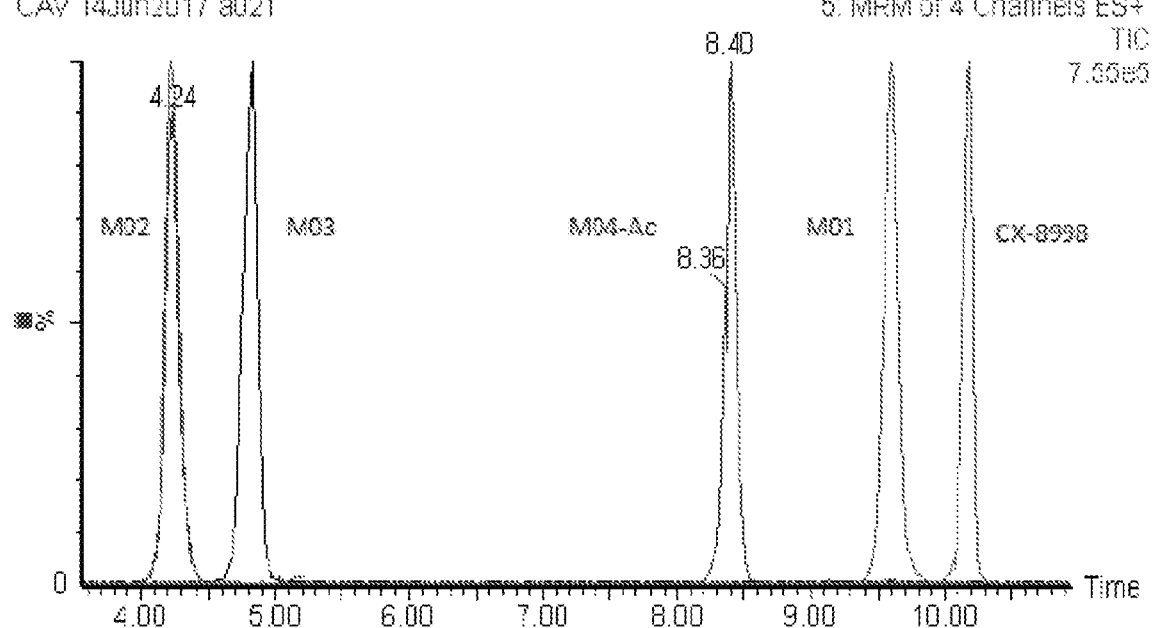
FIG. 26 is a graph showing a release CX-8998 from an immediate release (IR) bead.
Figure 27:
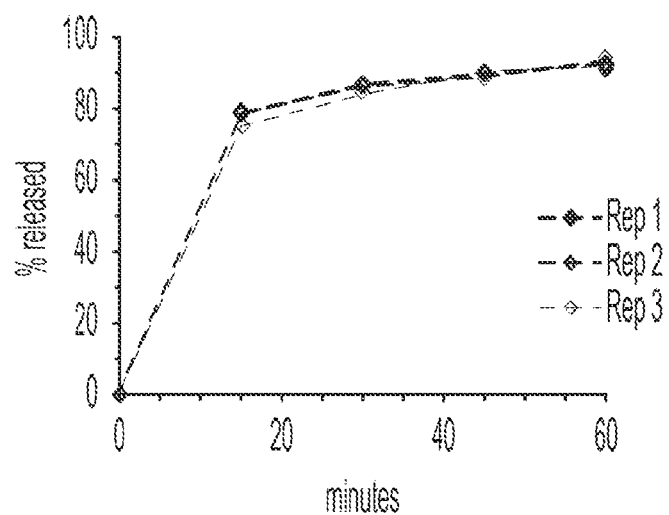
FIG. 27 contains graphs showing a profile of immediate release of CX-8998 of a single daily dose and the steady state of the daily dose.
Figure 29:
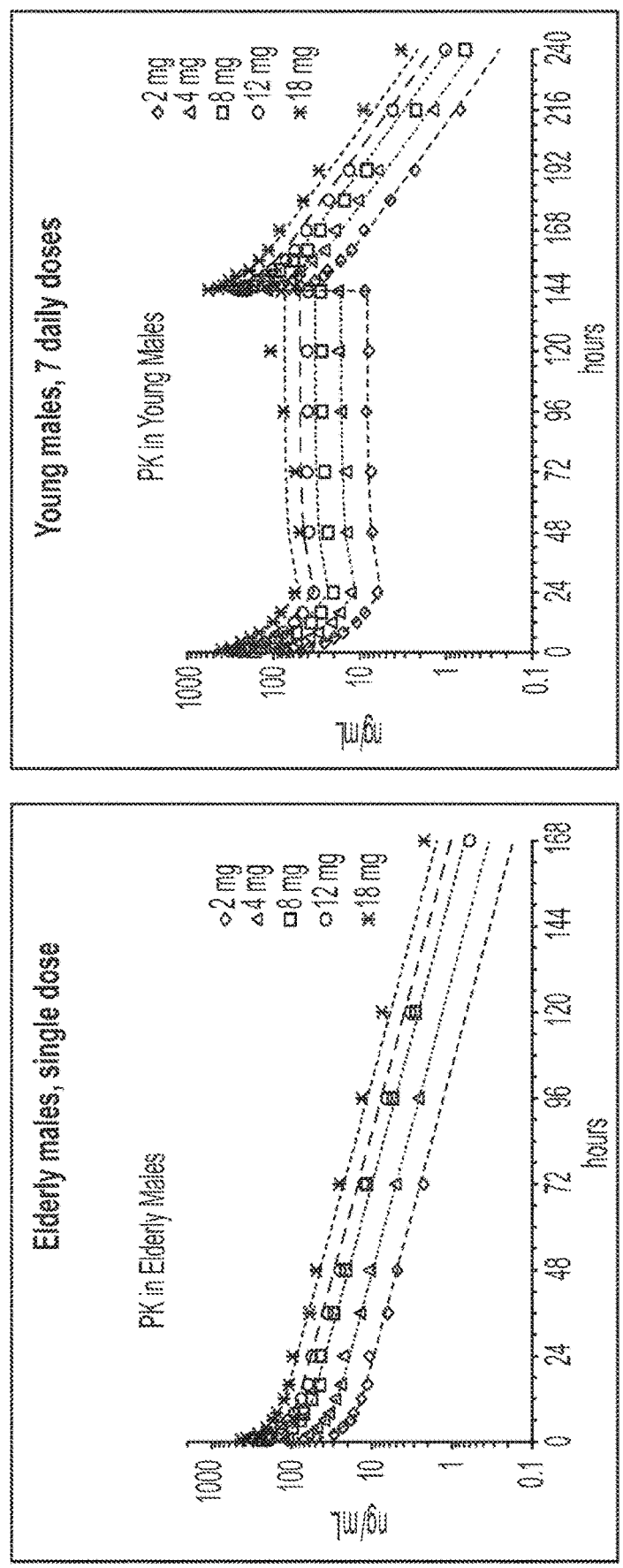
FIG. 29 is a graph showing an age effect on the release of CX-8998.
Figure 30:
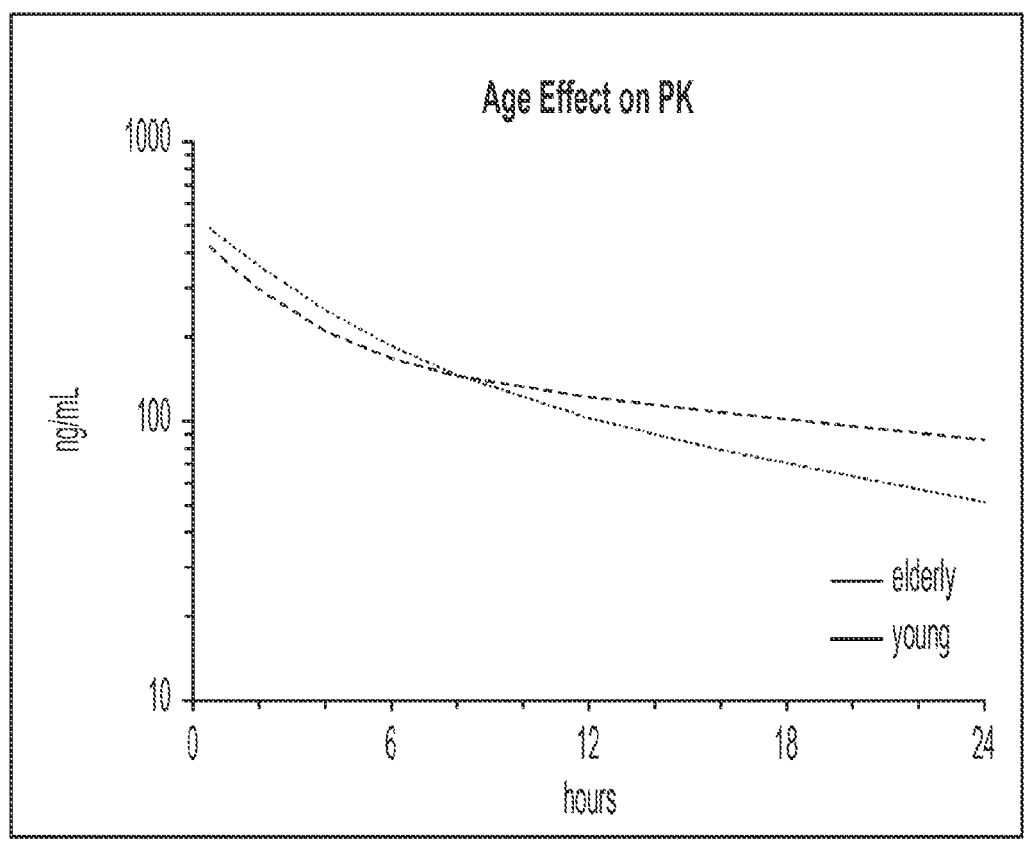
FIG. 30 is a graph showing an age effect on pharmacokinetics (PK).

Rapid release of CX-8998 from the immediate release formulation in the acid medium is shown in FIG. 26. Overall, the plasma profiles followed a 2 compartment PK model that was dose proportional in the 2-18 mg dose range. Slight shifts in both terminal elimination rate and redistribution were seen in elderly patients (FIG. 29).

In silico models were developed to generate theoretical release profiles that would yield desired plasma concentration values at steady-state between minimum effective concentration and maximum tolerated concentration. Models were validated against independent data sets to predict CX-8998 behavior in GI tract and systemically in young and elderly males.

Optimizations were carried out with 2 mg, 4 mg, 8 mg, 12 mg and 18 mg single morning doses in elderly males. PK parameters in elderly males are as shown below.

| Parameter | 2-compartments |
|---|---|
| CL (L/h) | 2.6576 |
| Vc (L/kg) | 0.18219 |
| K12 (1/h) | 1.495 |
| K21 (1/h) | 0.28064 |

Figure 31:
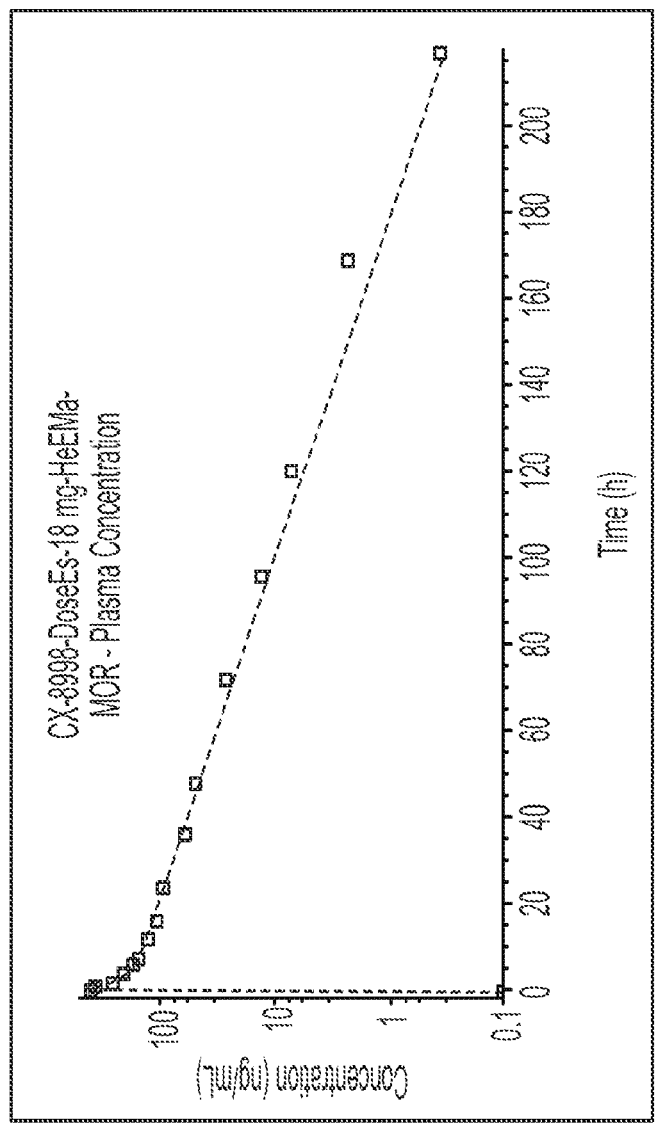
FIG. 31 contains graphs of plasma concentrations of CX-8998 in elderly patients following a single morning dose.
Figure 32:
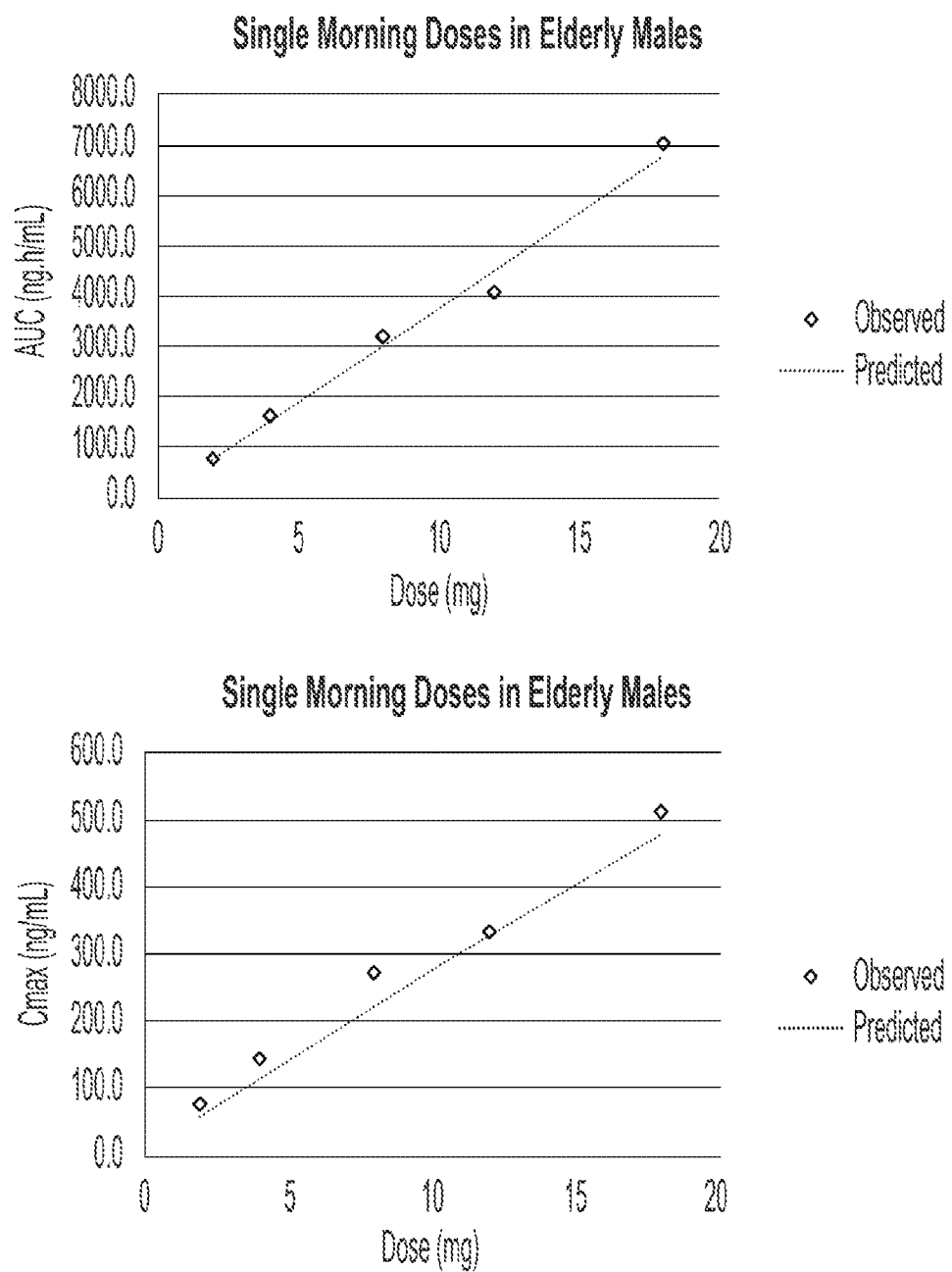
FIG. 32 contains graphs showing output correlations.

Plasma concentrations of CX-8998 in elderly patients following a single morning dose of 2 mg, 4 mg, 8 mg, 12 mg, or 18 mg capsules are shown in FIG. 31. Predicted and observed output correlations for elderly patients are shown in FIG. 32.

Optimizations were carried out simultaneously with 1 mg, 3 mg, 8 mg, and 12 mg single morning doses in healthy males. PK parameters in young males are as shown below.

TABLE 20

Total Margins (in Fold) Based on Rat and Dog Day 90 TK Assessments and Human Estimated Exposures at Steady State

| | | Total Margins for Human 10 mg BID at Steady State | | | | | |
|---|---|---|---|---|---|---|---|
| | | CX-8998 | | M01 | | M02 | |
| NOAEL Dose | Parameter | Female | Male | Female | Male | Female | Male |
| Rat 300 mg/kg | $C_{ss}$[a] | 91 | 39 | 21 | 13 | 104 | 56 |
| | $AUC_{24hr}$[b] | 41 | 19 | 13 | 6.8 | 62 | 31 |
| | TAM $C_{ss}$[c] | 62 | 31 | — | — | — | — |
| | TAM AUC[d] | 32 | 16 | — | — | — | — |
| Dog 30 mg/kg | $C_{ss}$[a] | 74 | 68 | 8.0 | 10 | 46 | 46 |
| | $AUC_{24hr}$[b] | 26 | 24 | 5.6 | 6.5 | 25 | 26 |
| | TAM $C_{ss}$[c] | 39 | 37 | — | — | — | — |
| | TAM AUC[d] | 17 | 16 | — | — | — | — |

[a] $C_{ss}$ margin calculated from rat and dog $C_{max}$ and human estimated $C_{ss}$ at steady state for each analyte.
[b] AUC margin calculated from rat and dog AUC and human estimated AUC at steady state for each analyte.
[c] $C_{ss}$ total active moiety (TAM) margin calculated from rat and dog $C_{max}$ TAM and human estimated $C_{ss}$ TAM at steady state (1,967 nM).
[d] AUC TAM margin calculated from rat and dog AUC TAM and human estimated AUC TAM at steady state (40,728 nM * hr).

| Parameter | 2-compartments |
|---|---|
| CL (L/h) | 3.9515 |
| Vc (L/kg) | 0.32511 |
| K12 (1/h) | 0.21431 |
| K21 (1/h) | 0.13625 |

Maximum CX-8998 exposures associated with different doses in healthy volunteers are as follows:

| Study | PN001 Part 1 | PN001 Part 2 | PN002 Part 1 | PN002 Part 2 | Average | PN002 Part 2 |
|---|---|---|---|---|---|---|
| Dose | 16 mg | 18 mg | 18 mg | 12 mg | 16 | 12 mg |
| # of Doses | 1 | 1 | 1 | 1 | 1 | 7 |
| $C_{max}$ (nM) | 940 (259) | 1180 (352) | 1330 (325) | 798 (167) | 1062 (271) | 895 |
| t1/2 (h) | 14.3 | 14.8 | 26.1 | 18.4 | 18.4 | 14.2 |
| $AUC_{0-24}$ (h*nM) | 8520 (2380) | 9930 (1340) | 9440 (1720) | 4990 (1100) | 8220 | 6100 (604) |
| $AUC_{inf}$ (h*nM) | 12500 (5000) | 14600 (3120) | 18500 (6620) | 7310 (1110) | 13200 | NC |

Figure 33:
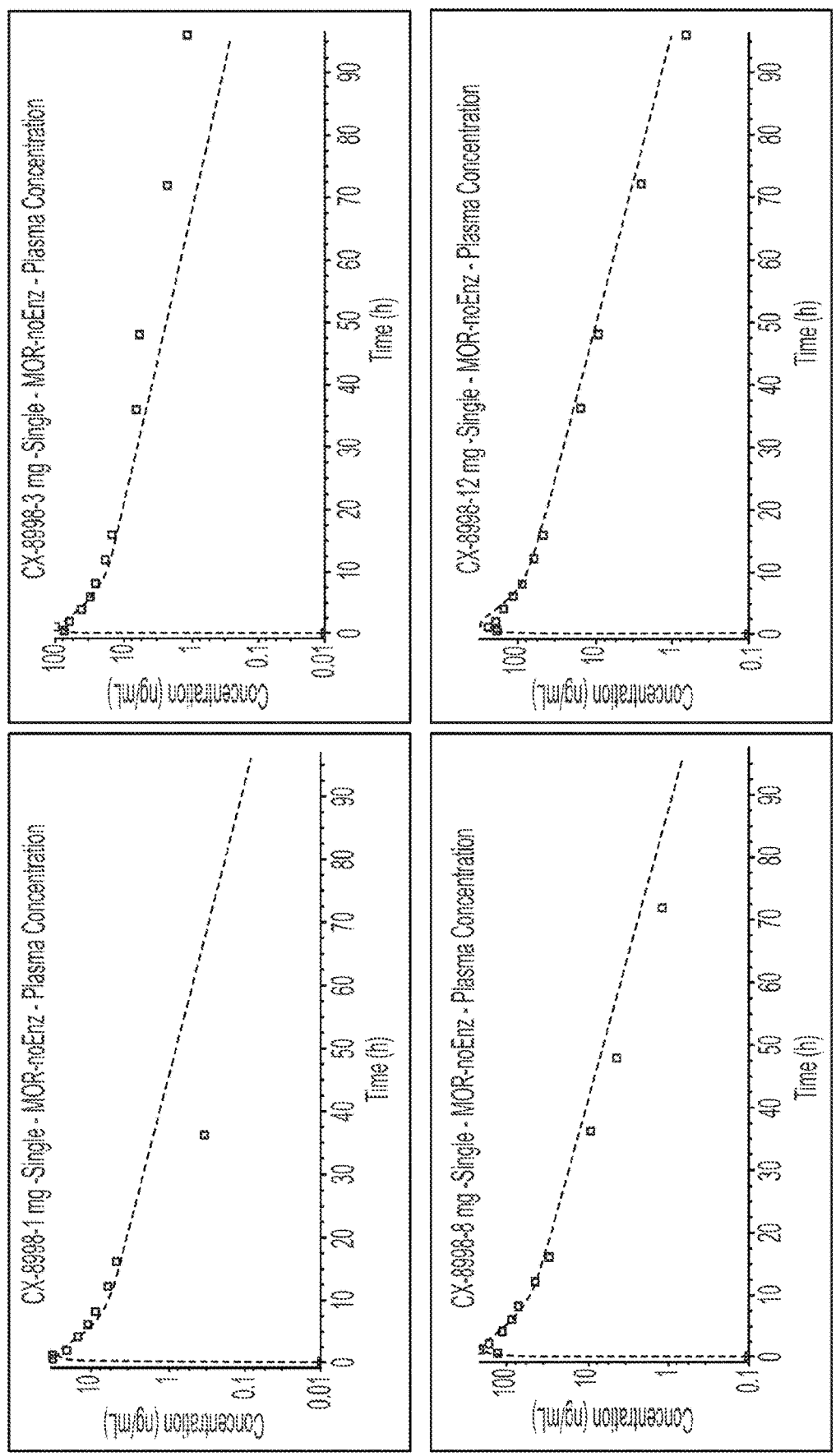
FIG. 33 contains graphs of plasma concentrations of CX-8998 in young patients following a single morning dose.
Figure 34:
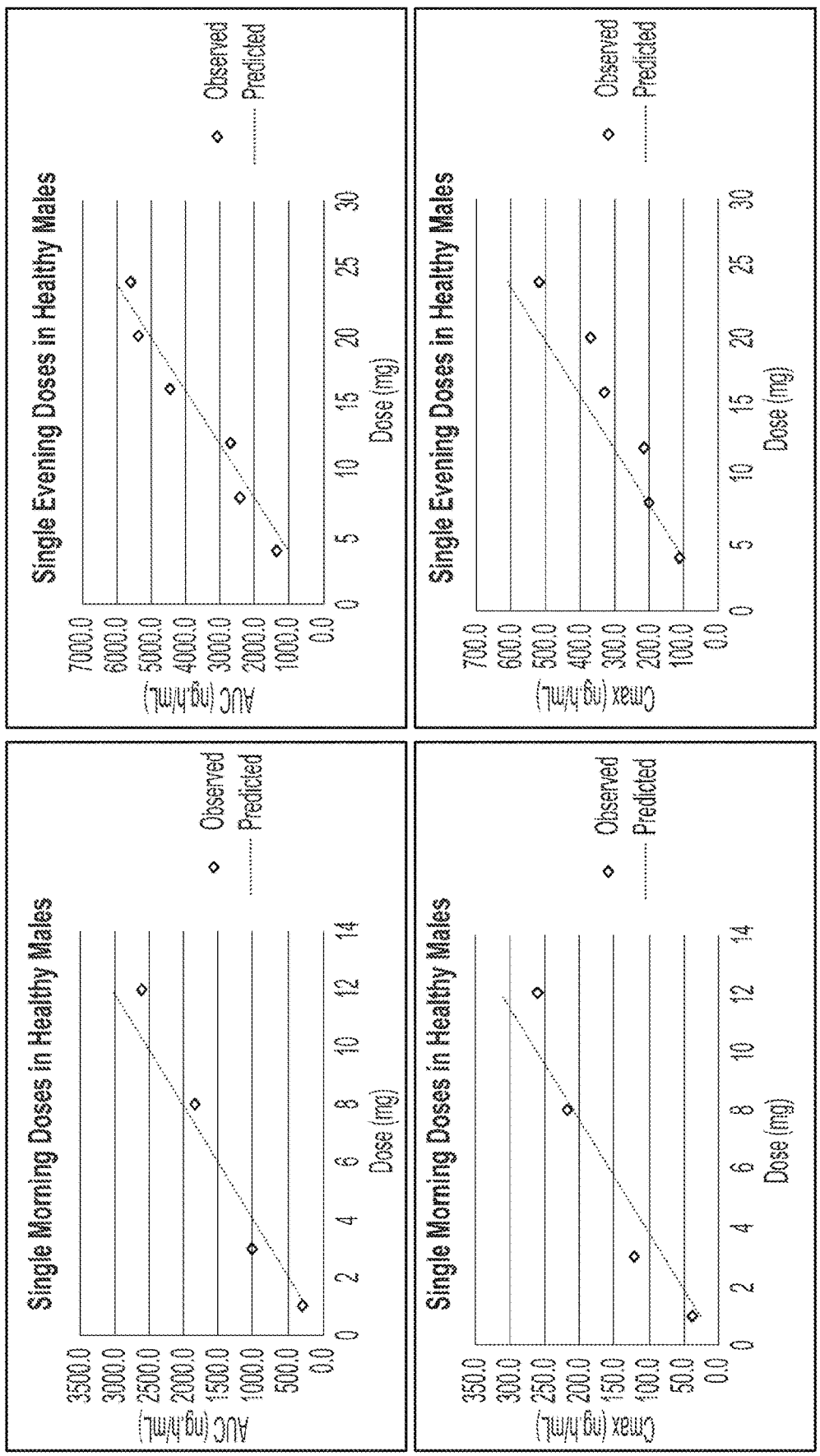
FIG. 34 contains graphs showing output correlations.
Figure 35:
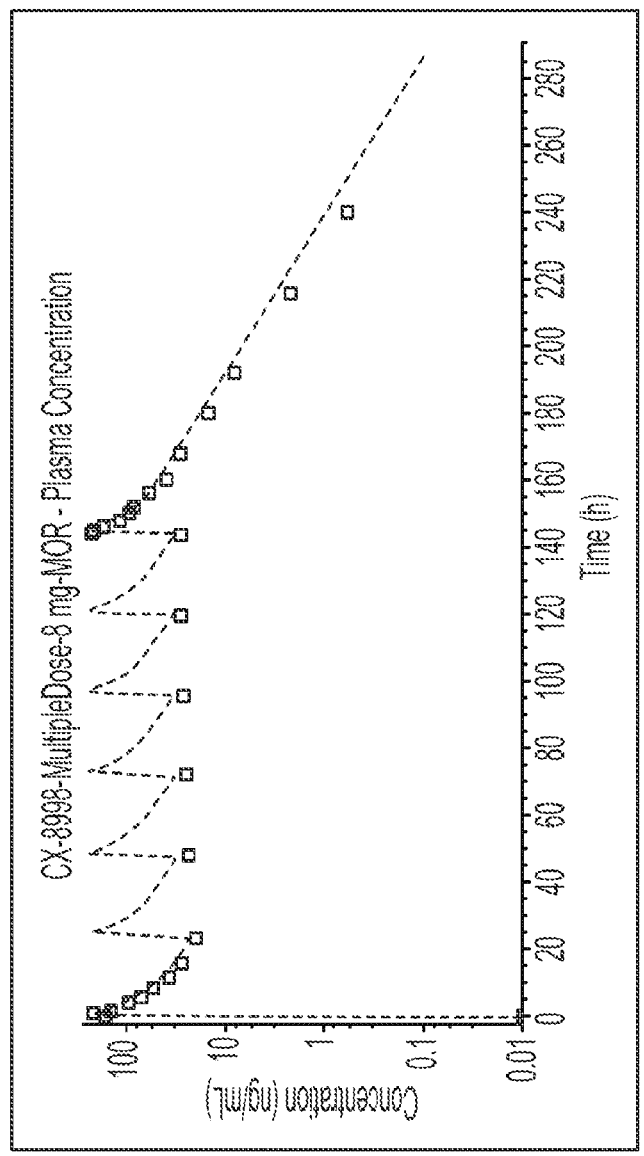
FIG. 35 contains graphs of plasma concentrations of CX-8998 in young patients following multiple doses.
Figure 35:
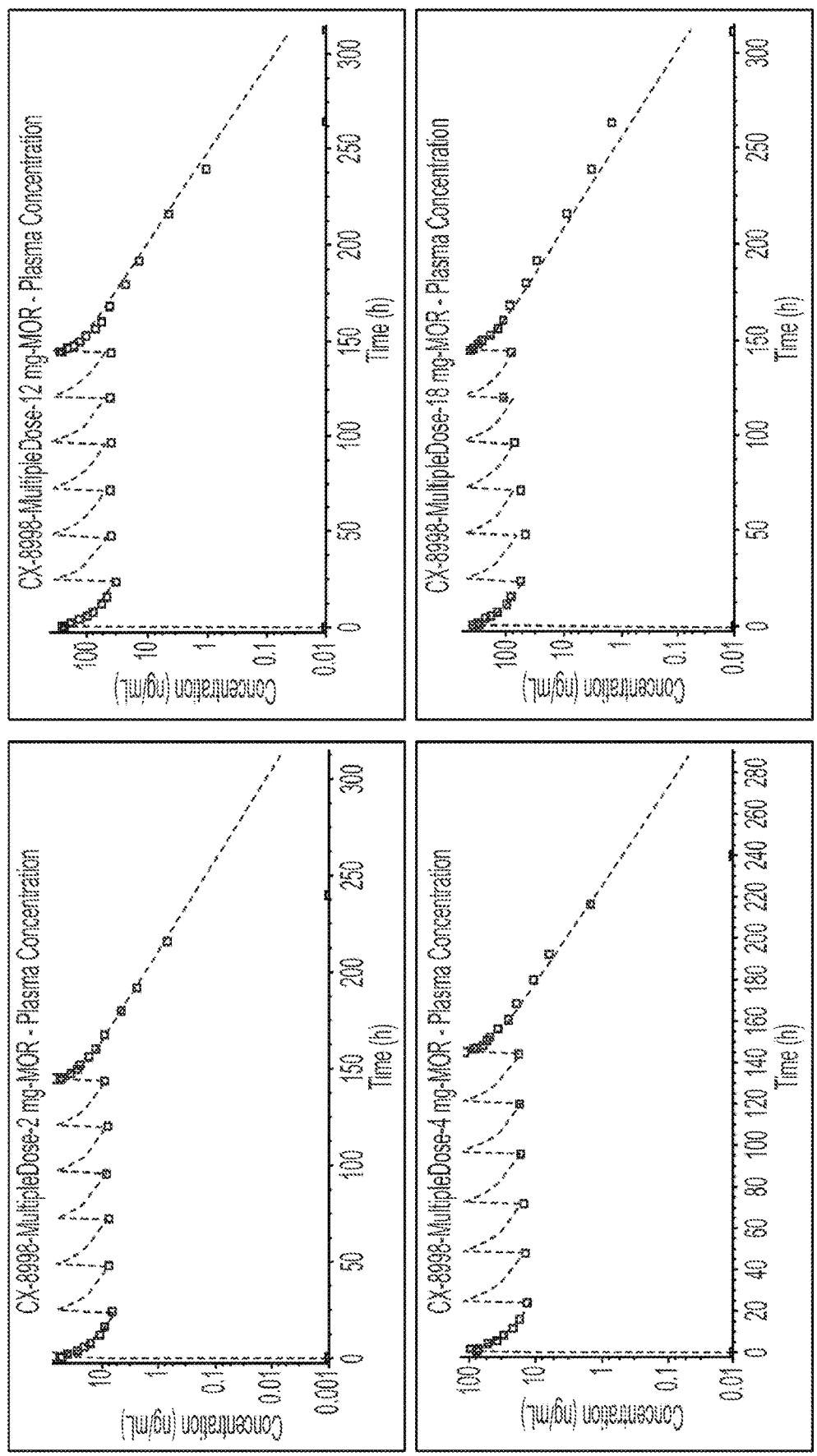

Plasma concentrations of CX-8998 in young patients following a single morning dose of 1 mg, 3 mg, 8 mg, and 12 mg capsules are shown in FIG. 33. Predicted and observed output correlations for young patients are shown in FIG. 34. Plasma concentrations of CX-8998 in young patients following multiple single morning doses of 1 mg, 3 mg, 8 mg, and 12 mg capsules are shown in FIG. 35.

A comparison of Simulated release profiles for a single daily dose and for multiple daily doses of 12 mg/day in young and elderly subjects is shown in FIG. 28.

Figure 36:
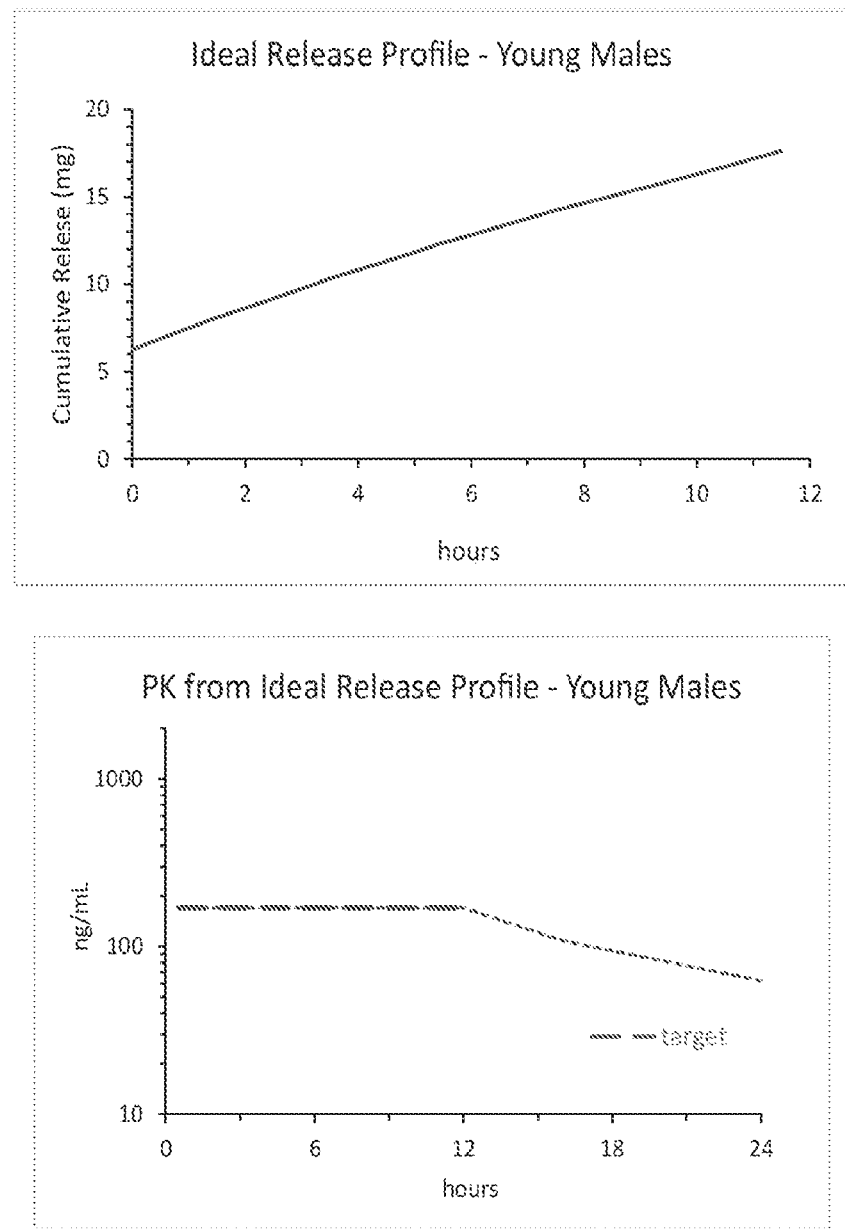
FIG. 36 contains graphs showing a release profile for young adult males having about a 6 mg burst followed by ~12 mg at an almost constant rate over 12 hours.
Figure 37:
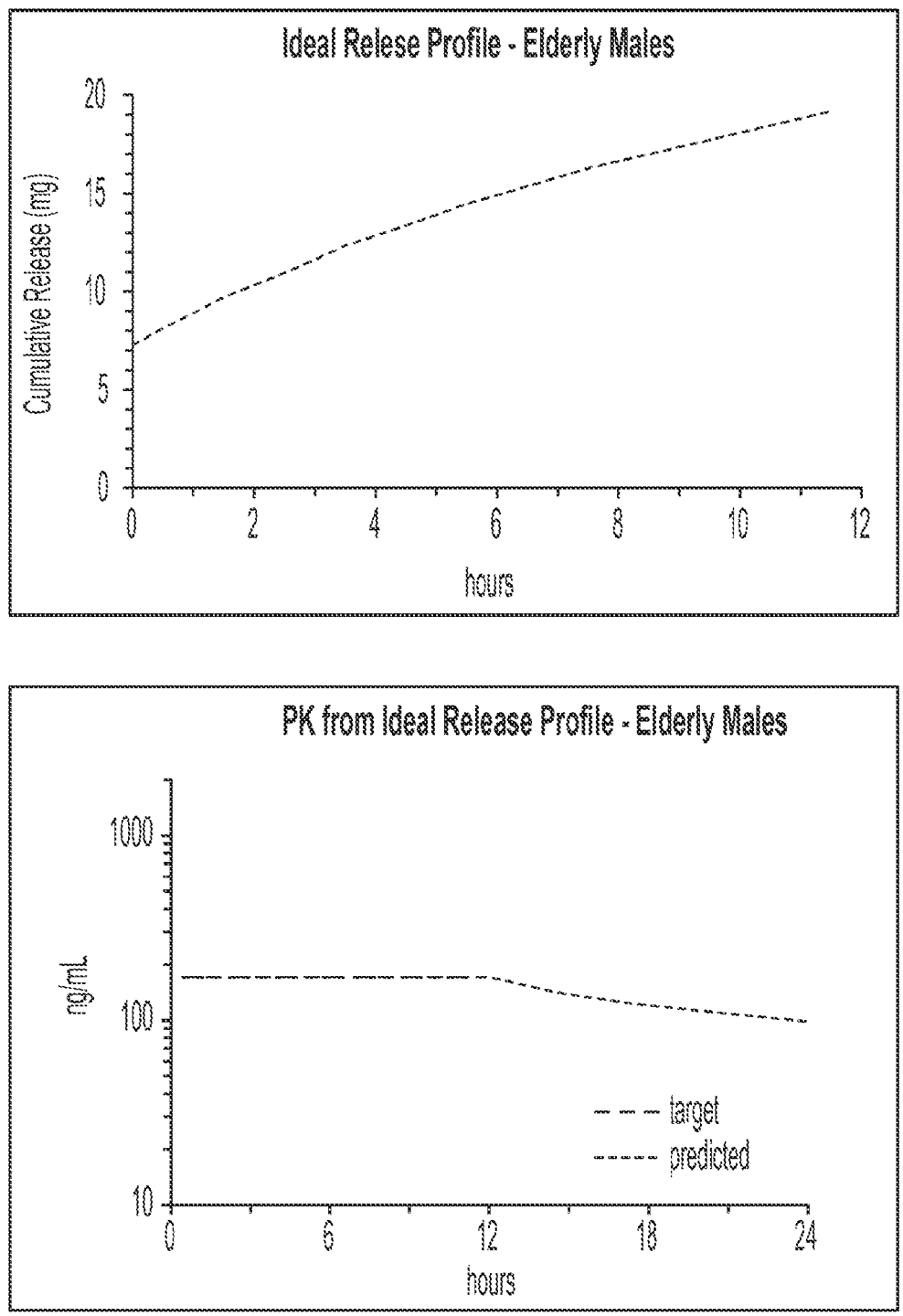
FIG. 37 contains graphs showing a release profile for elderly adult males having about a 7 mg burst followed by ~12 mg at a slightly diminishing rate over 12 hours.

Release profiles from different matrices were evaluated using the in silico model to determine target release profiles by optimization of matrix or by combining beads of different release profiles (e.g. immediate release (IR)+sustained release (SR) or IR+ delayed release (DR)). Zero order release from an osmotic pump tablet is shown in FIG. 38. First order release from a matrix tablet having coated beads in a capsule is shown in FIG. 39. Burst and zero order release from an osmotic pump tablet with an IR release coating is shown in FIG. 40. Burst and first order release from a mixture of IR and slow release beads in a matric tablet with an IR coating is shown in FIG. 41. A double burst with a 3 hour delay from a mixture of IR beads and pH 6 enteric-coated beads from an IR tablet with enteric coating and an IR coating is shown in FIG. 42. A double burst with a 6 hour delay from a mixture of IR beads and pH 7 enteric-coated beads from an IR tablet with enteric coating and an IR coating is shown in FIG. 10. Based on model an ideal release profile for young adult males is about a 6 mg burst followed by ~12 mg at an almost constant rate over 12 hours (FIG. 36), and an ideal release profile for elderly males is about a 7 mg burst followed by ~12 mg at a slightly diminishing rate over 12 hours (FIG. 37).

Sustained release (SR) beads were developed with multiple types of sustained release and enteric coatings. Some SR matrix beads were developed using typical polymers (e.g, hydroxypropyl methylcellulose or carbopol) to achieve sustained release. Some SR matrix beads were developed using pH independent sustained release osmotic pumps to achieve zero order release from the tablet. Some SR matrix beads were developed using a delayed release (DR) coating of IR beads to obtain release at pH 6 or 7, and to take advantage of poor solubility of CX-8998 at higher pH values to provide sustained release. Some SR matrix beads were developed using Eudragit RS/RL30D coating of IR beads to achieve an approach that depends on slow erosion of coating thereby sustaining the release of the drug from an IR matrix.

Example 22. Twice Daily (BID) CX-8998

A randomized, double-blind, placebo-controlled, parallel-group study (NCT03101241) of 95 patients with ET that have an inadequate response to anti-tremor medication (e.g., propranolol) was performed. Following consent and screening, subjects were randomized to receive oral doses of either CX-8998 (titrated up to 10 mg BID) or placebo for 28 days. Clinical rating scales, patient-reported outcomes and accelerometer recordings of tremor and digital spirography were collected at baseline (visit 1), day 15 (visit 3) and day 28 (visit 4).

Plasma concentrations of CX-8998 showed predictable steady state exposure that achieved target levels from multiple different dosages delivered twice daily (FIG. 10).

Figure 44:
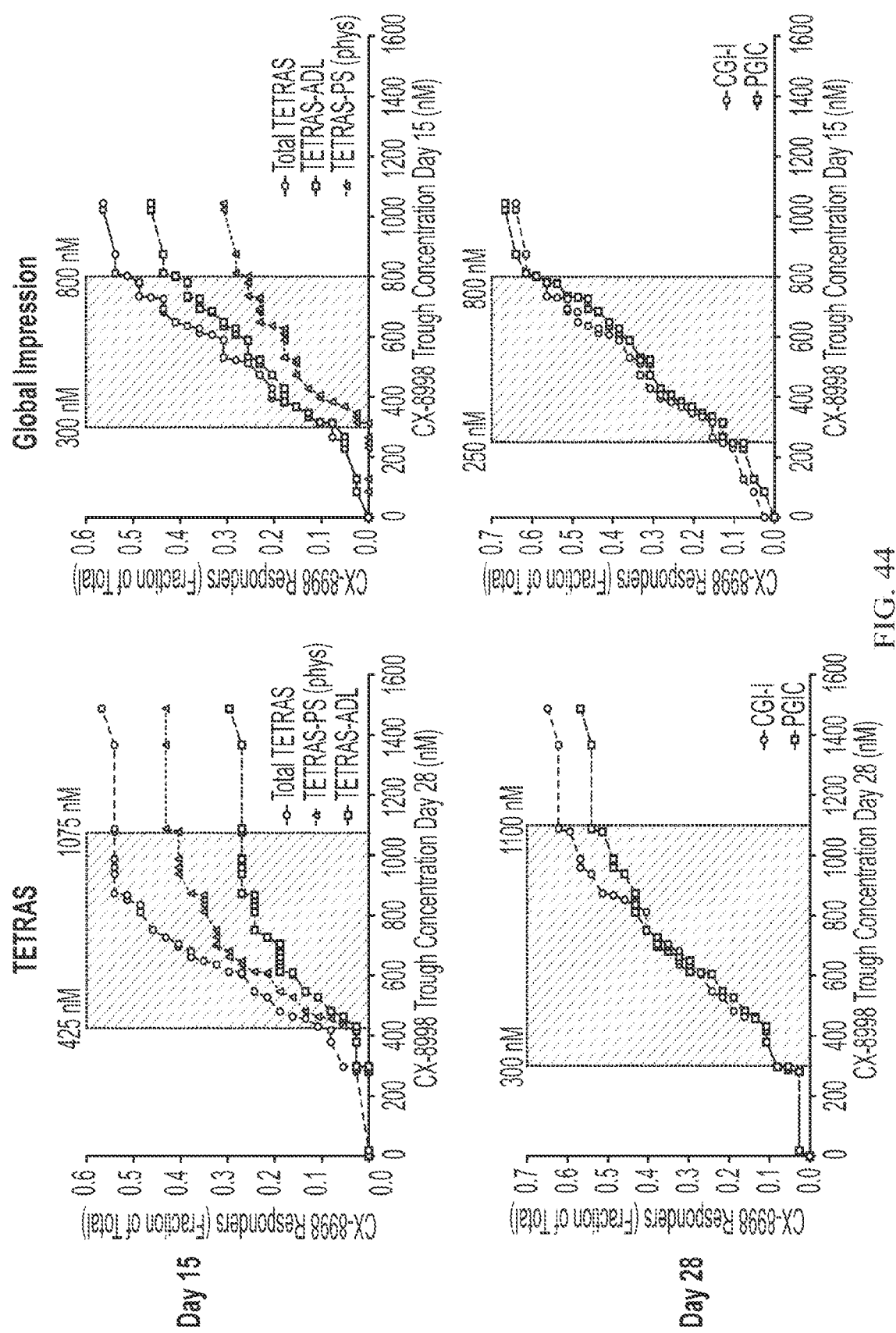
FIG. 44 contains graphs showing target range exposure of CX-8998 in TETRAS and Global responders.

Investigator-rated TETRAS (The Essential Tremor Rating Assessment Scale) Performance Subscale (p=0.027), TETRAS ADL (p=0.049), TETRAS total score (p=0.007) and Clinician Global Impression of Improvement (p=0.001) significantly improved (FIG. 44). There were no major safety and tolerability concerns.

Figure 45:
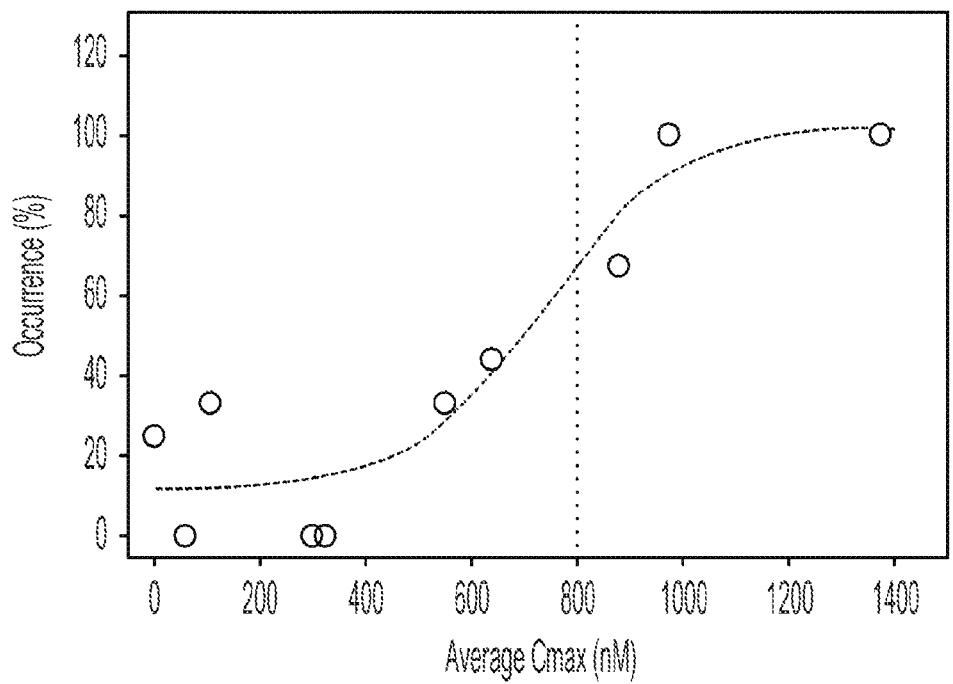
FIG. 45 contains a graph showing upper dose limits.

Upper Dose Limits Based on Tolerability Profile: up to 10 mg BID Yields Concentrations Associated with Lower Occurrence of CNS AEs. The sigmoidal relationship suggests that the frequency of CNS AEs may begin to increase substantially at CX-8998 plasma concentrations of approximately 700-800 nM (FIG. 45).

The study achieved proof-of-concept in ET and identified key pivotal study design parameters including primary and secondary efficacy endpoints, patient population and titration scheme. CX-8998 was safe and well tolerated in ET patients. These results are expected to enable late-stage development of CX-8998 in ET.

CX-8998 formulations were developed that include a total active moiety (TAM) of CX-8998 and CX-8998 metabolites. For example a TAM can be the sum of CX-8998, M01, and M02 concentrations adjusted for plasma protein binding (fu) and potency relative to CX-8998 (Cu,ss_TAM) as shown in Table 21.

TABLE 21

Css of CX-8998, M01, M02, and Total Active Moiety (TAM) Simulated from CX-8998 10 mg BID.

| PK Parameter | CX-8998 | M01 | M02 | Total Active Moiety (CX-8998 + M01 + M02) |
|---|---|---|---|---|
| Cp,ss (nM) | 583 | 771 | 343 | — |
| fu (%) | 0.4 | <0.1 | 14 | — |
| Potency | 1.0 | 1.57 | 0.21 | — |
| Cu,ss (nM) | 2.3 | <0.8 | 48 | — |
| Cu,ss_adj (nM) | 2.3 | <1.2 | 10.1 | 14.4 |

Figure 46:
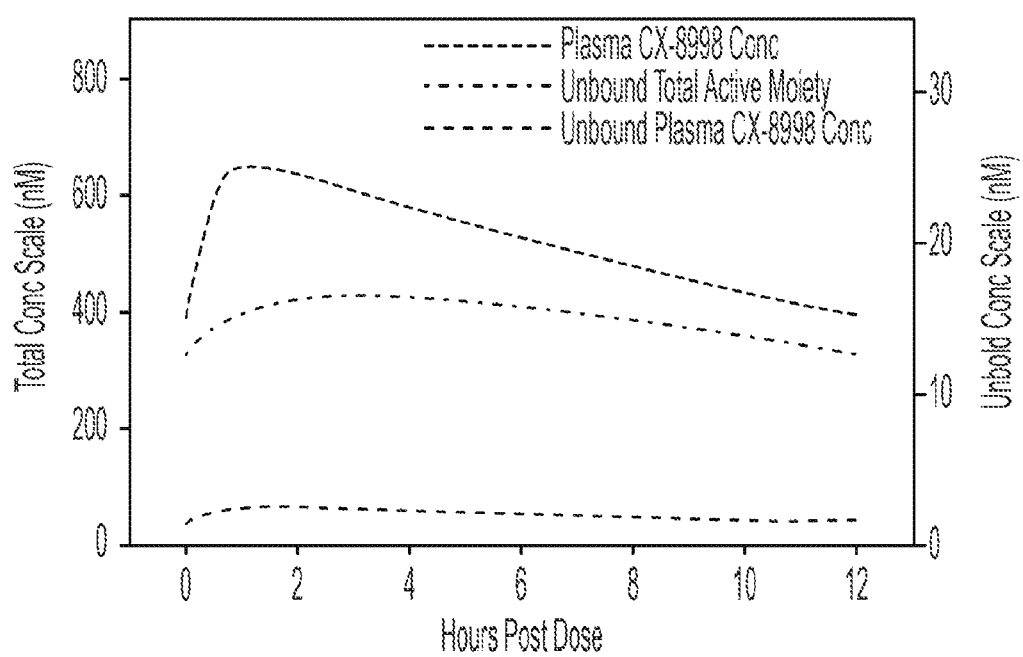
FIG. 46 is a graph showing target exposure levels and PK profiles of total and unbound CX-8998 in plasma and TAM following administration of CX-8998 10 mg BID.

Target exposure levels and PK profiles of total and unbound CX-8998 in plasma and TAM following administration of CX-8998 10 mg BID are shown in FIG. 46.

Example 23. Target CX-8998 Concentrations

Exemplary target concentrations for CX-8998 were established as shown in Appendix A.

Example 24. Study Design and Methodology for Efficacy Endpoint and Digital Biomarker Selection The T-CALM study assesses the efficacy of CX-8998, at doses up to 10 mg BID, for reduction of severity (amplitude) of ET. An optional/additional component of the main T-CALM study is the T-CALM digital substudy that evaluates the feasibility of 3 different digital monitoring platforms for accurate quantification of changes in motor function in ET patients. An exemplary T-CALM design is shown in FIG. 47.

The T-CALM study is a proof of concept, multicenter, double-blind, randomized, placebo-controlled, parallel-group trial. The screening period is up to 4 weeks. Before any study procedures are conducted, patients read and sign informed consents. Primidone (a strong CYP3A4 inducer) use is excluded due to the potential of CX-8998 to be subject to CYP3A metabolism. Thus, patients taking primidone are given 6 weeks of screening to allow for safe discontinuation of the drug. Stable doses of a single anti-tremor medication other than primidone as a standard of care are allowed during the study. Patients that meet screening criteria are randomized to treatment group A or B. Group A receives titrated doses of CX-8998 up to 10 mg BID. Group B receives matching placebo. Randomized study participants enter a 4-week, double-blind, dose titration period followed by a 1-week safety follow up after the last dose of study medication. At baseline (day 1), patients have safety and tremor evaluations prior to administration of study treatments. During the first week, patients receive 4 mg of study drug or matching placebo twice daily. On day 8 (week 2), patients are assessed at the clinic for safety and dose titration to 8 mg (or matching placebo) twice daily. On day 15 (week 3), patients report to clinic for safety and efficacy evaluations and final dose titration to 10 mg (or matching placebo) twice daily. The final efficacy visit is day 28 (week 4). The final safety visit takes place on day 35 (week 5). Blood samples are collected pre-dose on days 8, 15 and 28 and at approximately 4 hours post-dose on day 28 for plasma concentration measurements of CX-8998. If intolerable adverse events (AEs) are evident at any of the doses, the dose may be decreased to the next lowest dose at day 8 or 15 or at any time prior to those scheduled visits. If the lowest scheduled dose (4 mg BID) is intolerable, it can be decreased to 2 mg BID. After dose reduction, an increase in dose is not be allowed. If patients do not tolerate dose reduction, they are withdrawn from treatment.

Patients that have been screened and met the eligibility criteria for the main T-CALM study have the option to additionally participate in the T-CALM digital substudy. Enrollment of patients in the substudy is randomized to CX-8998 or placebo in the same proportion (1:1) as the main study. After informed consent is signed, patients are given the option to use one or both of two digital tools, iMotor or Kinesia 360, or to conduct additional testing with Kinesia One for objective measurement of motor function. The dosing regimen and schedule of safety assessments for the substudy are identical to that of the main study. At the screening visit, patients in the iMotor arm of the substudy have evaluations completed in the presence of a study staff member. Patients in the Kinesia 360 arm of the substudy wear the device to collect data for 2 days after screening and then return the device to the study site. Data collected for these 2 days serve as baseline motor assessments for Kinesia 360. At baseline (day 1), baseline iMotor evaluations are taken prior to dosing and after completion of the main T-CALM safety and tremor assessments. At the end of weeks 1 and 2, safety and Kinesia 360 and iMotor evaluations arecollected. The final efficacy measurements for both devices are collected at the end of week 4 visit. The final safety visit is at the end of week 5.

The study enrolls a population of moderate to severe ET patients inadequately treated with standard of care approaches. Key eligibility criteria for the main T-CALM study are as follows:
1. Signed, informed consent are obtained for all study participants
2. Males and females 18-75 years of age are enrolled
3. Patients with moderate to severe ET and initial diagnosis prior to age 65 are included
4. Tremor severity score of at least 2 in at least one upper limb of the 3 maneuvers on TETRAS-PS
5. TETRAS-PS score of at least 15 at screen
6. On stable doses of up to one concurrent anti-tremor medication permitted; use of strong CYP inducer primidone is excluded
7. Surgical intervention excluded A complete list of inclusion/exclusion criteria for the main T-CALM study is available online at ClinicalTrials.gov under registration number NCT03101241.

Eligibility criteria for the optional T-CALM digital substudy are as follows:
1. Patients must meet all eligibility criteria of the main T-CALM study protocol
2. Patients must be able to comply with user requirements as assessed by site personnel
3. Patients are not issued digital devices/downloads until they have consented to participate in the optional T-CALM digital substudy The primary, secondary and exploratory efficacy endpoints for the main T-CALM study are listed below:

The primary endpoint is the change from baseline to day 28 of the TETRAS performance subscale. The secondary endpoints are the change from baseline to day 28 for the TETRAS Activity of Daily Living Schedule and for the Kinesia One score. There are several exploratory endpoints. The change from baseline to days 15 and 28 for Total TETRAS score (independent video rater) and for Kinesia One is measured. The change from baseline to day 15 for the TETRAS performance subscale (independent video rater) and Kinesia One Score is evaluated. Treatment success at the end of therapy will be measured by Patient Global Impression of Change (PGIC), Clinical Global Impression of Improvement (CGI-I), Goal Attainment Scaling (GAS) and Quality of Life in Essential Tremor Questionnaire (QUEST).

There are 2 exploratory endpoints for the T-CALM digital substudy. Kinesia 360 measures the change in tremor amplitude from baseline to days 15 and 28. The iMotor test evaluates 5 simple motor functions including digital spirography from baseline to days 15 and 28.

Several performance scales and an objective biometric monitoring are utilized in the main T-CALM study. These tools generate relevant and convergent efficacy data that may more accurately define the response of patients to ET therapies.

The Essential Tremor Rating Assessment Scale (TETRAS; see, e.g., Elble et al., 2012 Mov Disord. 27:1567-1569) and is composed of a 9-item performance subscale and a 12-item activities of daily living (ADL) subscale. These subscales provide a rapid clinical evaluation (<10 minutes) of ET using pen and paper methodology. The performance subscale measures tremor amplitude (severity) in the head, face, voice, limbs and trunk as well as functional tests including handwriting, drawing a spiral and holding a pen over a dot on a 5-point rating scale where 0 represents no tremor and 4 indicates severe tremor. The sum of the individual scores generates an overall performance subscale score from 0 to 64. The TETRAS performance subscale is scored by both investigators at the clinical site and independent video raters. The scores of the independent video rater are statistically analyzed as the change from baseline to day 28 and serve as the primary efficacy endpoint. The most optimal rating methodology (investigator vs independent video rated TETRAS performance subscale) is selected for late-stage development. The performance subscale data is also used for exploratory analysis of efficacy on day 15. The ADL subscale evaluates activities of daily living such as speaking, eating, drinking, dressing, personal hygiene, writing and carrying items. The patient scores each item from 0 (normal activity) to 4 (severe abnormality). The overall score ranges from 0 to 48 and are analyzed as the change from baseline to day 28 as a secondary efficacy endpoint.

The total TETRAS score (sum of the performance subscale and ADL) on the change from baseline to days 15 and 28 is evaluated as an exploratory endpoint.

Kinesia One platform is deployed in T-CALM as a digital marker of tremor severity. Kinesia One is FDA cleared for monitoring Parkinson's motor symptom severity with only limited data on assessment of tremor in ET patients. The algorithmically derived score was developed primarily in Parkinson's disease algorithms and has limited validation in ET (see, e.g., Hoffman et al., 2011 *Conf Proc IEEE Eng Med Biol Soc.* 2011:4378-81). The Kinesia One device is placed on the index finger of each ET patient and worn in the clinic after completion of the TETRAS Performance subscale. Four tasks are performed by the patient on the left and right sides to assess resting, postural, kinetic and lateral wing beating tremor. The Kinesia One score change in score from baseline to day 28 is evaluated as a secondary efficacy endpoint. The Kinesia One data is also utilized for exploratory analysis of efficacy on the change from baseline to day 15 for accelerometry score and for change from baseline on amplitude measures for days 15 and 28. Consistent finger sensor placement and consistent task execution are critical factors for valid Kinesia One scores.

Due to the deleterious effects of ET on daily activities and well-being, several quality of life assessments are conducted to more accurately assess the patient's perception of the disorder and the effects of pharmacotherapy from baseline to the conclusion of treatment (day 28). Each of these questionnaires and scales requires substantial input from the ET patient and the data is used to address exploratory efficacy endpoints.

The Quality of Life in Essential Tremor Questionnaire (QUEST) (see, e.g., Tröster et al., 2005 *Parkinsonism Relat Disord.* 11:367-373) is used to evaluate the consequences of ET on daily life of ET patients from baseline to day 28. The questionnaire contains 30 items that involve 5 subscales (physical, psychosocial, communication, hobbies/leisure and work/finance) and a total score. There are also 3 additional items that pertain to sexual capability, satisfaction with tremor control and side effects of pharmacotherapy. If the treatment program for ET is beneficial, whether symptomatic or curative, patients are likely respond in a positive manner to QUEST. The QUEST includes questions that are not expected to change within a 28-days timeframe.

However, some items such as the satisfaction with tremor control may generate insightful data.

The Clinical Global Impressions Scale (CGI) generates a clinician's perception of a patient's functioning prior to and after study medication (see, e.g., Guy, *Assessment Manual for Psychopharmacology.* Rockville, MD: Department of Health, Education, and Welfare Public Health Service Alcohol, Drug Abuse, and Mental Health Administration, 1976). The CGI overall score considers patient history, psychosocial situations, symptoms and behavior with respect to the ability to function. The CGI-Improvement (CGI-I) will involve a single 7-point rating of total improvement or change from baseline CGI-Severity (CGI-S). The clinician rater will select one response (from 1=very much improved to 7=very much worse) based upon the question, "Compared to your patient's condition at the onset of treatment, how much has your patient changed?"

The Patient Global Impression of Change (PGIC) will quantify a patient's impression of improvement or decline over time with respect to ET treatment (see, e.g., Guy, *Assessment Manual for Psychopharmacology.* Rockville, MD: Department of Health, Education, and Welfare Public Health Service Alcohol, Drug Abuse, and Mental Health Administration, 1976). The patient will use the PGIC scale to assess current health status versus initiation of treatment and calculate the difference. The 7-point scale will ask the question, "With respect to your ET, how would you describe yourself now compared to when you started taking the study drug?" The patient replies with one of 7 answers from very much worse to very much improved.

The Goal Attainment Scaling (GAS) (see, e.g., Kiresuk et al., 1968 *Community Ment Health J.* 4:443-453) requires interaction between the physician and ET patient for development of a written set of individual patient-desired goals to track progress of treatment. At baseline, each patient establishes 3 individual health goals and rates each goal as fairly important=1, very important=2 or extremely important=3. The clinician rates the degree of difficulty for each goal as probable=1, possible=2 or doubtful=3. During the study, progress is scored on a 5-point scale from worse than baseline=−2 to best anticipated outcome=+2.

Two additional biometric monitoring tools are employed in the T-CALM digital substudy to explore their ability to measure changes in motor function of ET patients. The data is used for exploratory efficacy endpoints.

The Kinesia 360 (Great Lakes NeuroTechnologies, Cleveland, OH, USA) (see, e.g., Pullam et al., 2014 *Parkinsonism Relat Disord.* 20:37-40) is a home monitoring system that utilizes wrist and ankle sensors to objectively and continuously tabulate motion data. The Kinesia 360 kit contains a smartphone with the installed Kinesia 360 application, two wearable sensors and charging equipment. The sensors capture 3-dimensional linear acceleration and angular velocity from the wrist and ankle of each ET patient throughout each day. At the end of each day, the motion data are uploaded from the smartphone to a central server. The data are processed to detail the occurrence and severity of tremor as well as the patient's level of daily activity.

The iMotor (Apptomics, Inc., Wellesley Hills, MA, USA) (see, e.g., Mitsi et al., 2017 *Front. Neurol.* 13:273) is a tablet-based application that objectively measures motor function in patients with abnormal movement. The iMotor test is only conducted during scheduled visits. Each ET patient is required to conduct 5 simple tasks (finger tapping, hand tapping, hand pronation and supination, reaction to a mild stimulus, and a spiral drawing with a digital stylus) on a tablet. Each task has a time limit of 30 seconds and will be done twice (once with each hand).

All treatment-emergent adverse events are coded into the Medical Dictionary for Regulatory Activities (MedDRA) version 20 with system organ classes and preferred terms and displayed in frequency tables by treatment group. Adverse events are characterized by maximum severity, drug-related adverse events, serious adverse events and adverse events leading to discontinuation of study.

Other safety assessments include physical examination, neurological examination, vital signs, clinical laboratory tests (hematology, chemistry and urinalysis), urine drug screen, pregnancy tests, electrocardiogram (ECG), Columbia Suicide Severity Rating Scale (C-SSRS), Epworth Sleepiness Scale (ESS) and University of Miami Parkinson's Disease Hallucinations Questionnaire (UM-PDHQ) (see, e.g., Papapetropoulos et al., 2008 *BMC Neurol.* 8:21).

All statistical analyses are performed with the SAS system, version 9.4 or higher based on a prespecified statistical analysis plan. Based upon phase 2 studies of comparable design, a sample size of approximately 92 patients are appropriately powered to provide proof-of-concept safety and efficacy data on CX-8998 in the main T-CALM study.

There is not a formal sample size determination. It is proposed that at least 30 patients are randomized to CX-8998 or placebo.

Example 25. Safety and Efficacy of CX-8998, a Selective Modulator of the T-Type Calcium Channel, in Patients with Essential Tremor Essential tremor (ET) is a debilitating disorder that significantly impairs quality of life (QOL). Current pharmacotherapies are not optimal. T-CALM evaluated safety and efficacy of a selective T-type calcium channel modulator, CX-8998, in ET patients.

This Example describes a phase 2, randomized, double-blind, proof-of-concept trial (T-CALM) that evaluated CX-8998, titrated to 10 mg twice daily, in ET patients, age 18-75. Patients had moderate to severe ET and were allowed stable dosages of up to 1 concurrent anti-tremor medication (excluding primidone). Study participants were randomized (1:1) to receive CX-8998 or placebo for 28 days. Primary and secondary endpoints were change from baseline to Day 28 on TETRAS-performance scale (PS) and TETRAS-activities of daily living (ADL) scores, respectively. Exploratory endpoints included global impression of change (CGI), global goal attainment (GAS), and QOL scores. Safety and tolerability were monitored. T-CALM is registered with ClinicalTrials.gov, NCT03101241.

T-CALM was designed to be adequately powered to enable decision making for further development of CX-8998 in inadequately treated ET. Eligibility criteria were carefully defined to ensure selection of a well-defined cohort of ET patients. Clinically meaningful and convergent clinician-measured and patient-reported outcomes with validated performance scales, objective biometric tools, and quality of life questionnaires were utilized as key endpoints to assess drug efficacy. The results of the T-CALM trial demonstrated that CX-8998 reduced tremor severity on the basis of several clinically relevant and confluent efficacy endpoints, and CX-8998 had a favorable safety and tolerability profile.

Methods

Study Design and Participants

T-CALM was designed as a phase 2, proof-of-concept, multicenter (22 U.S. sites), double-blind, randomized, placebo-controlled trial to evaluate efficacy, safety, and tolerability of CX-8998, after titration to a target dosage of 10 mg BID for 28 days, in patients with moderate to severe ET.

Key eligibility criteria for the T-CALM study were signed, informed consent, males and females 18-75 years of age, initial diagnosis of ET prior to age 65, tremor severity score of at least 2 in at least one upper limb during any of the three maneuvers of TETRAS-PS item 4 (upper limbs held forward and horizontally, upper limbs extended laterally and horizontally with elbows flexed and hands positioned close to each other near chin and finger-nose or chin-nose movements), TETRAS-PS total score of at least 15 at screening, either no anti-tremor medications, or a stable dosage of only one concurrent anti-tremor medication. Primidone was excluded because it is a strong CYP inducer that could impact the metabolism of CX-8998. Patients with surgical interventions for ET were also excluded. A complete list of inclusion/exclusion criteria is available online at ClinicalTrials.gov under registration number NCT03101241.

Randomization and Masking

Patients were randomized in a 1:1 ratio to receive CX-8998 or placebo. Randomization was stratified by concomitant use of anti-tremor medication and study site (sub study participation or non-participation). The randomization code was prepared by an unblinded statistician who was not involved in conduct of the study.

The sponsor, patients, investigators, and any others involved in conduct of the study or analysis of data were unaware of treatment assignments until after study completion and unblinding. CX-8998 was formulated in capsules of the active drug mixed with a blend of excipients. Matched placebo was formulated in identical capsules with a blend of comparable excipients.

Procedures

Figure 47A:
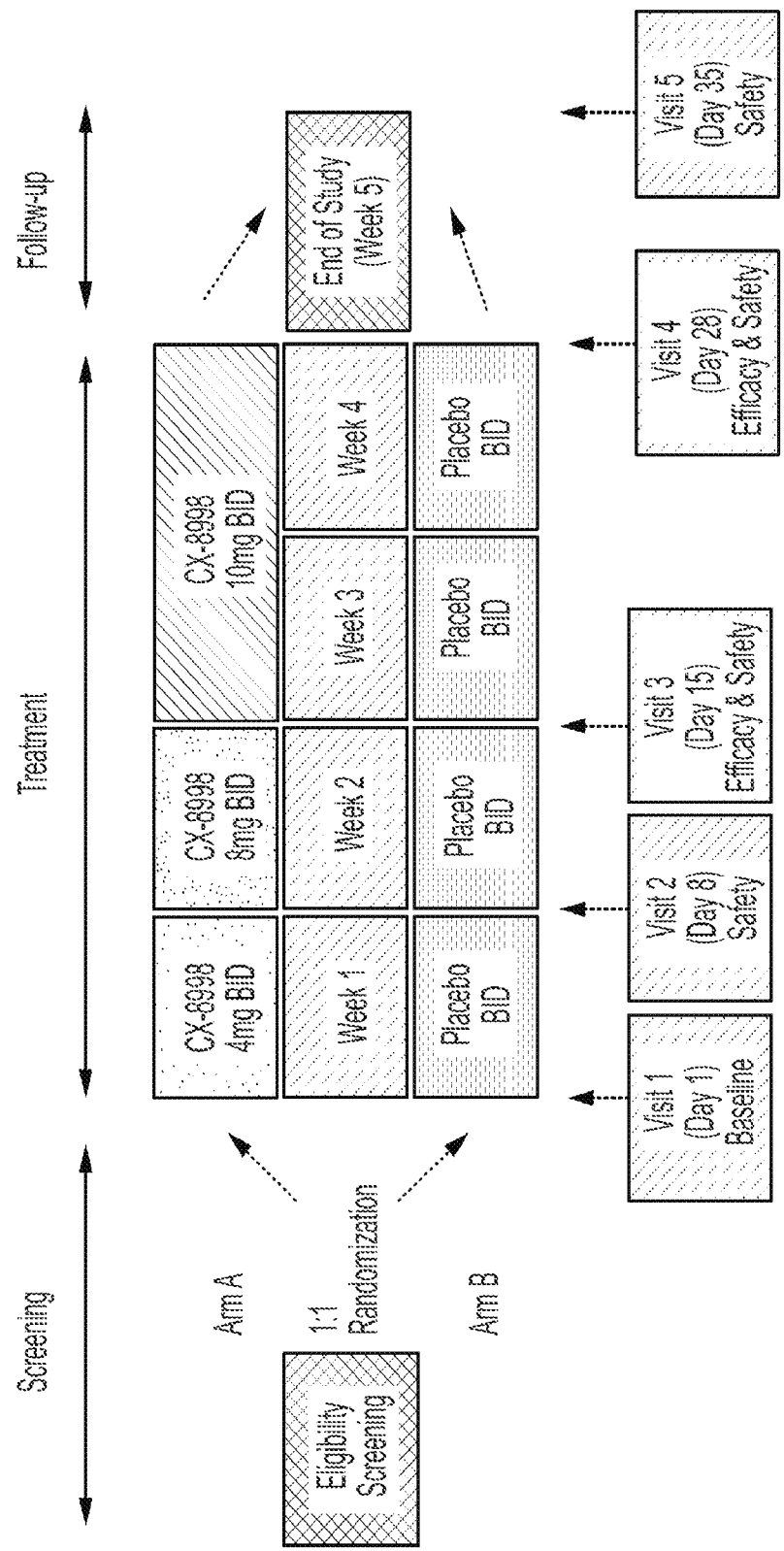
FIGS. 47A-47B show exemplary T-CALM designs.
Figure 47B:
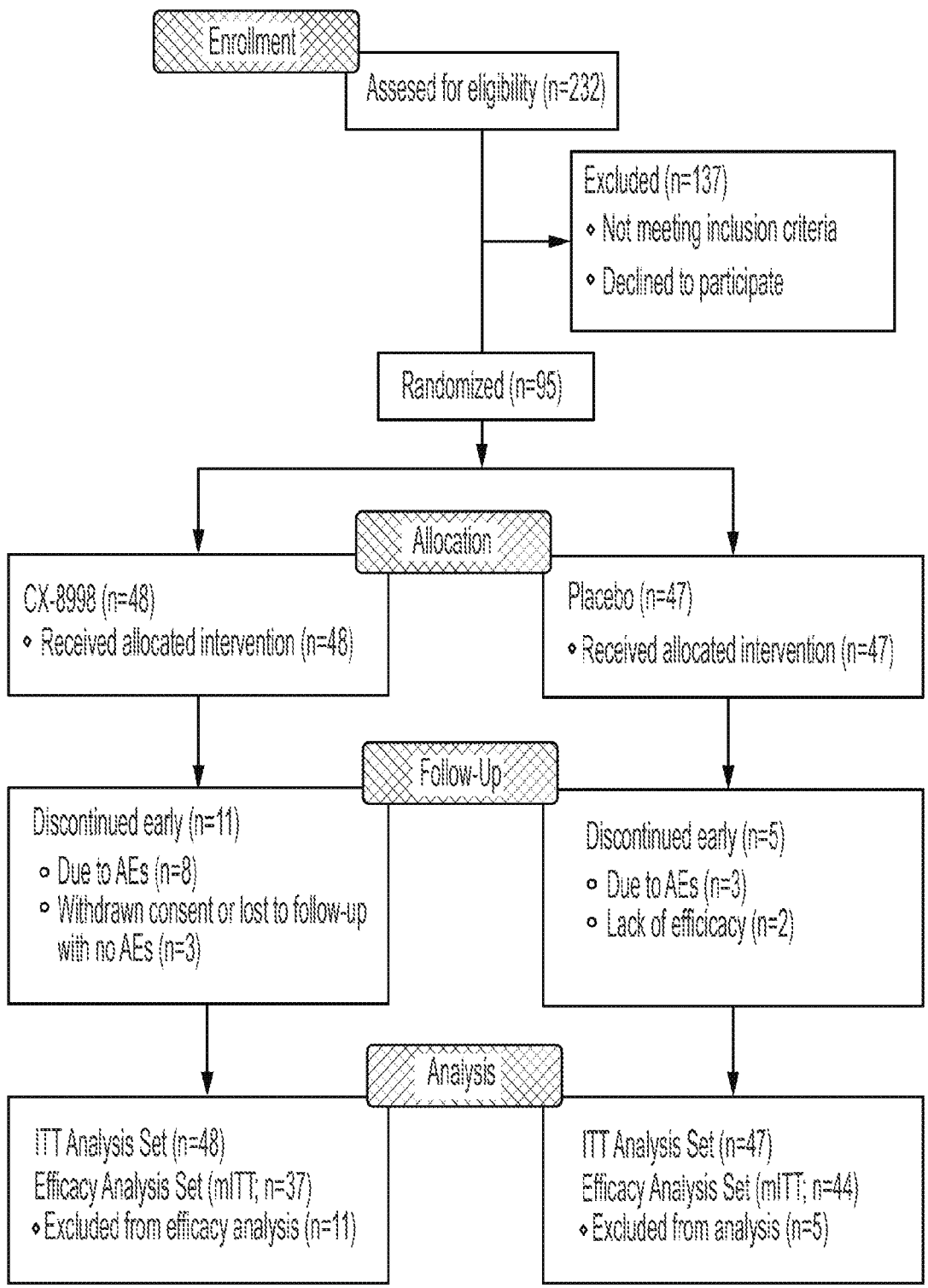

A study schematic is shown in FIG. 47A. After informed consent, eligible subjects were randomized to receive titrated dosages of CX-8998 up to 10 mg BID or matching placebo during a 4-week double-blind dosing period followed by a 1-week safety follow-up. Subjects received CX-8998 4 mg BID (or matching-placebo BID) during week 1 followed by an assessment in clinic for safety and dosage increase to 8 mg BID or matching placebo BID on day 8. On day 15 (week 3), patients were evaluated at the clinic for safety and efficacy and for final dose titration to 10 mg BID or matching placebo BID. The final efficacy visit occurred on day 28 (week 4). Reduction to the next lowest dosage was allowed, if needed, during weeks 1 and 2, and only 1 reduction was permitted. Patients who could not tolerate dosage reduction were withdrawn from the study. Reescalation of dose was not allowed.

Safety procedures involved collection of all TEAEs (treatment-emergent adverse events) coded into the Medical Dictionary for Regulatory Activities (MedDRA) version 20. Adverse events were classified by maximum severity, drug-related adverse events, serious adverse events, and adverse events leading to patient discontinuation. Other safety assessments were physical examination, neurological examination, vital signs, clinical laboratory tests (hematology, chemistry and urinalysis), urine drug test at screen, pregnancy tests, electrocardiogram (ECG), Columbia Suicide Severity Rating Scale (C-SSRS), Epworth Sleepiness Scale (ESS), and University of Miami Parkinson's Disease Hallucinations Questionnaire (UM-PDHQ).

Outcomes

An overview of the methods for T-CALM efficacy and safety endpoints is presented in Table 22. The Essential Tremor Rating Assessment Scale (TETRAS) consists of a 9-item performance subscale (PS) and a 12-item activities of daily living (ADL) subscale. The primary endpoint was the change from baseline to Day 28 on the TETRAS-PS score. The TETRAS-PS was scored by investigators of each patient (in real time) at the clinical site and by five independent video raters who reviewed and scored videotapes of each patient. Both sets of scores were statistically analyzed. In the absence of precedent, the objective of this dual approach was to select the optimal rating methodology (investigator versus independent video rater TETRAS-PS) for late-stage clinical development. The secondary endpoints were change from baseline to Day 28 on the TETRAS-ADL subscale score, change from baseline to Day 28 on accelerometry score measured by Kinesia ONE, and safety and tolerability: change from baseline in electrocardiogram (ECG) parameters, clinical safety laboratory assessments, Columbia Suicide Severity Rating Scale (C-SSRS), Epworth Sleepiness Scale (ESS), University of Miami Parkinson's Disease Hallucinations Questionnaire (UM-PDHQ), vital signs, number (%) of study dropouts, and number (%) of study dropouts due to AEs. The following exploratory endpoints were also included: change from baseline to Day 15 and 28 on TETRAS total score; change from baseline to Day 15 on TETRAS-PS score, TETRAS-ADL subscale score and Kinesia ONE; score and treatment success at Day 15 and Day 28 measured by Patient Global Impression of Change {PGIC), Clinical Global Impressions {CGI) scale, Goal Attainment Scale (GAS), and Quality of Life in Essential Tremor (QUEST) questionnaire.

TABLE 22

Methods for Evaluation of T-CALM Efficacy and Safety Endpoints

| Methods | Endpoints (Primary, Secondary, Exploratory) | Data Collection (Clinician-Rated, Patient-Rated, Digital Biomarker) | Overview of Scoring Systems |
|---|---|---|---|
| The Essential Tremor Rating Assessment Scale-Performance Scale (TETRAS-PS)[1,2] | Primary-baseline to day 28 (investigator and central video-rated) Exploratory-baseline to day 15 (investigator and central video-rated) | Clinician-Rated | 9 performance items rated for tremor severity in head, face, voice limbs, and trunk and 3 functional tests (writing, drawing, and holding pen over dot); each item scored 0 (no tremor) to 4 (severe tremor) with total score of 0 to 64. |
| The Essential Tremor Rating Assessment Scale-Activities of Daily Living (TETRAS-ADL)[1,2] | Secondary-baseline to day 28 Exploratory-baseline to day 15 | Clinician-Rated | 12 daily activities scored from 0 (normal) to 4 (severe abnormality) with total score of 0 to 48 |
| The Essential Tremor Rating Assessment Scale-Total Score = Performance Scale Plus Activities of Daily Living (TETRAS-TS = PS + ADL)[1,2] | Exploratory-baseline to day 15 and day 28 PS (investigator and central video-rated) plus ADL | PS-Clinician-Rated ADL-Clinician-Rated | Sum of PS and ADL scores |
| Kinesia ONE[3] | Secondary-baseline to day 28 Exploratory-baseline to day 15 | Digital Biomarker | Algorithmic score of four 15 second tasks to measure amplitude of resting, postural, kinetic and lateral wing tremor |
| Quality of Life in Essential Tremor (QUEST)[4] | Exploratory-day 15 and day 28 | Patient-Rated | 30 QOL items scored as never, rarely, sometimes, frequently, always, NA |
| Clinical Global Impressions (CGI)[5] | Exploratory-baseline to day 15 and day 28 | Clinician-Rated | 7-point rating scale of total improvement or change in tremor severity scored as 1 (very much improved) to 7 (very much worse) |
| Patient Global Impression of Change (PGIC)[5] | Exploratory-baseline to day 15 and day 28 | Patient-Rated | 7-point rating scale of total improvement or change in tremor severity scored as 1 (very much improved) to 7 (very much worse) |
| Goal Attainment Scale (GAS)[6] | Exploratory-day 15 and day 28 | Clinician-Rated and Patient-Rated | 3 health goals developed and rated by patient (3-point importance scale of fairly to extremely important) and clinician (3-point goal attainment scale of probable to doubtful); patient progress toward goals rated by 5-point scale from −2 (unfavorable outcome) to +2 (best anticipated outcome) |
| Columbia Suicide Severity Rating Scale (C-SSRS)[7] | Secondary-baseline and all subsequent clinic visits | Patient-Rated | 6 questions on suicidal ideation and behavior rated by yes or no answers |
| Epiworth Sleepiness Scale (EPS)[8] | Secondary-baseline and all subsequent clinic visits | Patient-Rated | 8 daytime sleepiness situations rated from 0 (no chance of dozing) to 3 (high chance of dozing); total score ranged from 0 (lower normal sleepiness) to 24 (severe excessive sleepiness) |
| University of Miami Parkinson's Disease Hallucinations Questionnaire (UM-1PDHQ)[9] | As needed | Patient-Rated | 6 quantitative hallucination items (modality, frequency, duration, insight, sensation, and emotional burden) with total score from 0 (minimum) to 14 (maximum) and 14 qualitative hallucination items with most scored as yes or no |

1Elble et al., Mov. Disord. 2008; 23 (Suppl 1): S1-6.
2Elble et al., Mov Disord. 2012; 27 (12): 1567-1569.
3Mostile et al., Mov Disord. 2010; 25 (12): 1938-1943.
4Troster et al., Parkinsonism Relat Disord. 2005; 11 (6): 367-373.
5Guy, Assessment Manual for Psychopharmacology. Rockville, MD: Department of Health, Education, and Welfare Public Health Service Alcohol, Drug Abuse, and Mental Health Administration, 1976.
6Kiresuk et al., Community Ment Health J. 1968; 4 (6): 443-453.
7Posner et al., Am J Pschiatry 2011; 168 (12): 1266-1277.
8Kenderska et al., Sleep Med Rev. 2014; 18 (4): 321-331.
9Papapetropoulos et al., BMC Neurol. 2008; 8: 21.

Statistical Analysis

All statistical analyses were performed with the SAS system, version 9.4 or higher. A sample size of 43 patients per treatment group had at least 90% power to detect at least a 5.5-point difference between CX-8998 and placebo for the primary endpoint of the change from baseline to Day 28 on the TETRAS-PS score assuming a standard deviation of 7.5 and alpha=0.05. This calculation was based on the Wilcoxon-Mann-Whitney test for two independent means and assumed normal distributions for each treatment group with a common, but unconfirmed, standard deviation. Approximately 92 patients were planned for enrollment to ensure 86 patients were available for inclusion in the efficacy analyses. The Intent to Treat (ITT) analysis set contained all randomized patients and was used for patient disposition and demographics. The Safety Analysis Set (SAS) had all randomized patients who received at least 1 dose of study drug. The Full Analysis Set (FAS) included all patients who received at least 1 dose of study drug and had both baseline and at least 1 post-baseline efficacy assessment. FAS was utilized for all efficacy assessments.

The primary efficacy endpoint was analyzed with FAS and analysis of covariance (ANCOVA) model, with fixed effects for treatment, anti-tremor medication use, study site, and baseline TETRAS-PS score. Testing was performed with least square (LS) means from the ANCOVA model and a two-sided test at the alpha=0.05 level of significance. Multiple imputation was used to estimate missing data for patients who were missing a TETRAS-PS score on Day 28. Secondary and exploratory efficacy endpoints were similarly analyzed. P-values for secondary and exploratory analysis were considered nominal.

Results

The T-CALM study period was 2017-2018 with Aug. 29, 2017 as the date of the first patient visit and Jul. 16, 2018 as the date of the last patient visit. Disposition of patients is presented in FIG. 47B. The ITT analysis set included 95 patients randomized to receive CX-8998 (N=48) or placebo (N=47). The study was completed by 37 (77%) patients in the CX-8998 group and 42 (89%) patients on placebo. Discontinuation due to adverse events took place in 8 (17%) of CX-8998-treated patients and 3 (6%) of placebo-treated patients. The primary efficacy analysis set (prespecified mITT) comprised 37 subjects in the CX-8998 group and 44 subjects in the placebo group who received at least one dose of study drug and completed a baseline and at least one post-baseline efficacy assessment.

Demographic characteristics at baseline are shown in Table 23. Male and female patients were almost equally distributed among CX-8998 and placebo groups. Age, race, and ethnicity were similar between CX-8998 and placebo groups. ET characteristics at baseline are shown in Table 24. CX-8998 and placebo groups were matched for most ET baseline characteristics. The only exception was the use of beta-blocker medication by 62% of the placebo-group compared to 44% of CX-8998 group.

TABLE 23

Demographic Characteristics at Baseline (ITT Analysis Set)

| Parameter | CX-8998 (N = 48) | Placebo (N = 47) | Total (N = 95) |
|---|---|---|---|
| Sex | | | |
| Male | 25 (52%) | 25 (53%) | 50 (53%) |
| Female | 23 (48%) | 22 (47%) | 45 (47%) |
| Age at informed consent, years | | | |
| Mean (SD) | 64 (9.6) | 63 (10.8) | 63 (10.2) |
| Median | 66 | 66 | 66 |
| Minimum, maximum | 28, 75 | 21, 75 | 21, 75 |
| Age group | | | |
| ≤65 years | 22 (46%) | 22 (47%) | 44 (46%) |
| >65 years | 26 (54%) | 25 (53%) | 51 (54%) |
| Race | | | |
| White | 45 (94%) | 46 (98%) | 91 (96%) |
| Black or African American | 3 (6%) | 1 (2%) | 4 (4%) |
| Ethnicity | | | |
| Not Hispanic or Latino | 48 (100%) | 45 (96%) | 93 (98%) |
| Hispanic or Latino | 0 (0%) | 1 (2%) | 1 (1%) |
| Not reported | 0 (0%) | 1 (2%) | 1 (1%) |

ITT = intent to treat.

TABLE 24

Essential Tremor Characteristics at Baseline (ITT Analysis Set)

| Parameter | CX-8998 (N = 48) | Placebo (N = 47) | Total (N = 95) |
|---|---|---|---|
| Time since onset of essential tremor, years[1] | | | |
| Mean (SD) | 24 (16.3) | 21 (15.7) | 23 (16.0) |
| Median | 20 | 18 | 19 |
| Minimum, maximum | 3, 63 | 1, 62 | 1, 63 |
| Essential tremor improves with alcohol | | | |
| Yes | 23 (48%) | 16 (34%) | 39 (41%) |
| No | 11 (23%) | 13 (28%) | 24 (25%) |
| Unknown | 14 (29%) | 18 (38%) | 32 (34%) |
| Baseline TETRAS-PS total score[2] | | | |
| Mean (SD) | 23.1 (6.27) | 22.8 (5.67) | 22.9 (5.95) |
| Median | 22.3 | 22.5 | 22.5 |
| Minimum, maximum | 11.5, 46.5 | 12.5, 43.5 | 11.5, 46.5 |
| Baseline TETRAS-ADL subscale score[2] | | | |
| Mean (SD) | 26 (6.0) | 26 (7.0) | 26 (6.5) |
| Median | 26 | 26 | 26 |
| Minimum, maximum | 13, 38 | 9, 42 | 9, 42 |
| Baseline TETRAS-ADL total score[2] | | | |
| Mean (SD) | 49.2 (10.59) | 48.9 (10.46) | 49.1 (10.47) |
| Median | 47.0 | 48.5 | 47.5 |
| Minimum, maximum | 28.0, 81.5 | 28.5, 85.5 | 28.0, 85.5 |
| Anti-tremor medication at study entry | | | |
| Yes | 22 (46%) | 21 (45%) | 43 (45%) |
| No | 26 (54%) | 26 (55%) | 52 (55%) |
| Baseline TETRAS-PS severity group[2,3] | | | |
| ≤Median at baseline | 25 (52%) | 24 (51%) | 49 (52%) |
| >Median at baseline | 23 (48%) | 23 (49%) | 46 (48%) |
| Tremor asymmetry group[3,4] | | | |
| Asymmetry absent | 42 (88%) | 35 (74%) | 77 (81%) |
| Asymmetry present | 6 (13%) | 12 (26%) | 18 (19%) |
| Postural-to-kinetic tremor ratio group: | | | |

TABLE 24-continued

Essential Tremor Characteristics at Baseline (ITT Analysis Set)

| Parameter | CX-8998 (N = 48) | Placebo (N = 47) | Total (N = 95) |
|---|---|---|---|
| TETRAS-PS[3,5] | | | |
| ≤Median at baseline | 23 (48%) | 26 (55%) | 49 (52%) |
| >Median at baseline | 25 (52%) | 21 (45%) | 46 (48%) |
| Concurrent essential tremor medication on Day 1 (baseline) | | | |
| No | 20 (42%) | 14 (30%) | 34 (36%) |
| Yes | 28 (58%) | 33 (70%) | 61 (64%) |
| Using beta-blocker at Day 1 (baseline) | 21 (44%) | 29 (62%) | 50 (53%) |
| Primidone use at screening | | | |
| Yes | 5 (10%) | 6 (13%) | 11 (12%) |
| No | 43 (90%) | 41 (87%) | 84 (88%) |

ADL = activities of daily living;
ITT = intent to treat;
TETRAS = The Essential Tremor Rating Assessment Scale;
TETRAS-PS = TETRAS performance subscale.
[1]Time since onset of essential tremor was estimated by subtracting age at onset of essential tremor from age at informed consent.
[2]Baseline was defined as the last non-missing value that was obtained before or ≤15 minutes after initiation of study drug.
[3]This subgroup was used in the exploratory analyses.
[4]Tremor asymmetry was defined as a >1-point difference between the right and left side on any of the following TETRAS-PS items: 4A (postural tremor), 4B (wing-beating tremor), or 4C (kinetic tremor).
[5]The ratio of postural tremor (subscale item 4A) to kinetic tremor (subscale item 4C) was defined as the ratio of the total postural tremor (sum of left and right hand) score divided by the total kinetic tremor (sum of left and right hand) score as provided by TETRAS-PS.

Except for primidone, patients were allowed use of up to a single concomitant anti-tremor drug during the study. These medications were used by 28 patients (58%) in the CX-8998 group and 33 patients (70%) in placebo group. Some patients in the CX-8998 (10%) and placebo (17%) groups were taking more than 1 concomitant anti-tremor medication (e.g. benzodiazepines, beta-blockers) to treat comorbid conditions such as anxiety, insomnia, and hypertension. Non-selective beta-blockers, such as propranolol, were the most frequently used anti-tremor medications in both CX-8998 (29%) and placebo (36%) groups. Concomitant anti-tremor medications were not used by 20 CX-8998 and 14 placebo patients, and 11 of these patients (12%) were reported by investigational sites as having tried and discontinued standard-of-care medications (propranolol, primidone, or both) for either efficacy or tolerability reasons. The remaining 23 patients had either no history of anti-tremor medication use, or information was not attainable. Compliance with study drug administration was comparable for CX-8998 (99.3%) and placebo (97.7%).

Figure 48A:
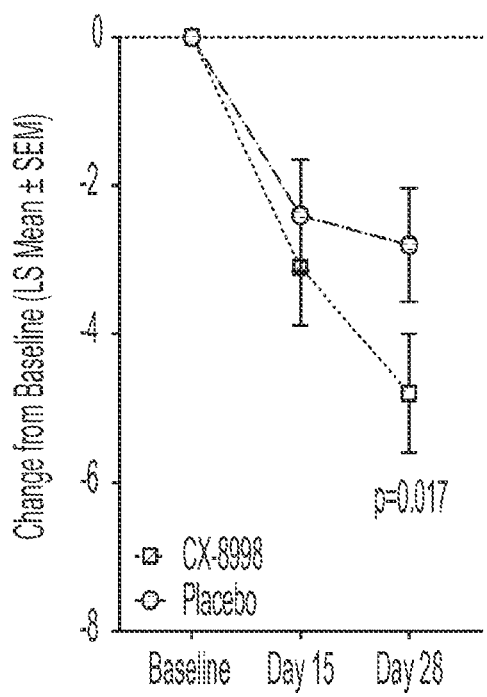
FIGS. 48A-48D contain graphs showing changes from baseline in investigator rated TETRAS-PS.
Figure 48B:
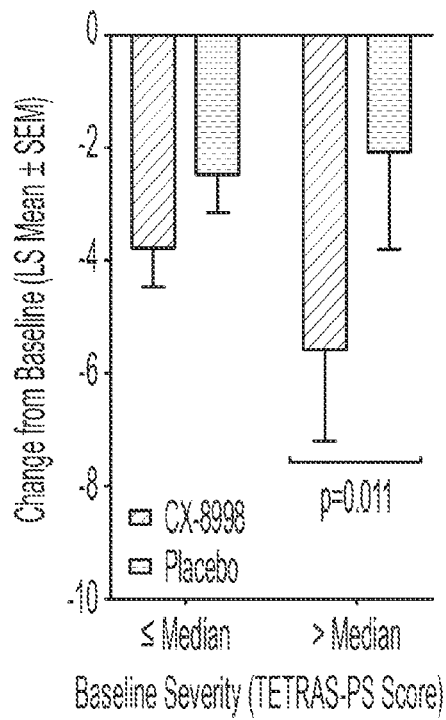
Figure 48C:
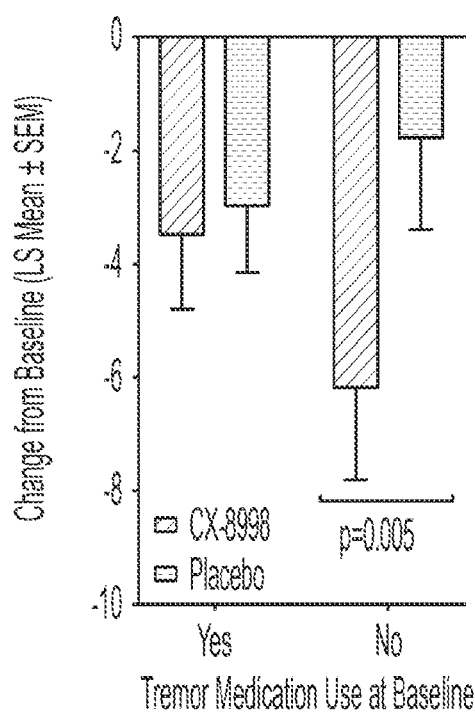
Figure 48D:
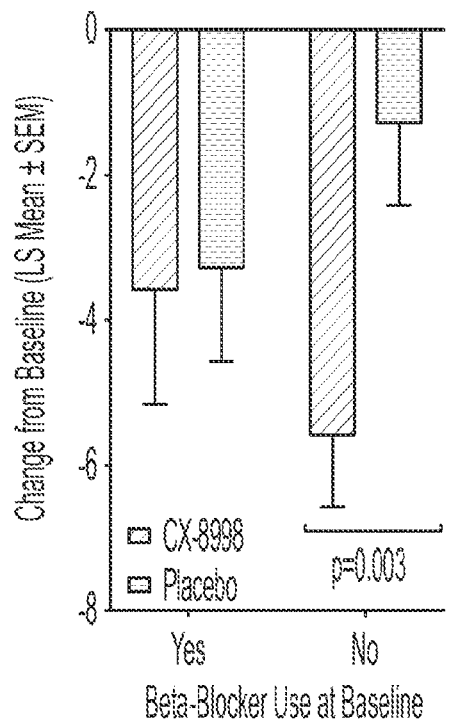

The LS mean (±SE) change from baseline to Day 28 in TETRAS-PS as the primary endpoint, scored by independent video raters, was −1.8±0.81 for CX-8998 and −2.3±0.78 for placebo and the difference was not significant (p=0.696) (Table 25). When the same endpoint was scored by investigators (in person), the mean score was significantly improved (p=0.017) by CX-8998 (−4.8±0.80) compared to placebo (−2.8±0.77), as shown in FIG. 48A and Table 25). Sensitivity analyses confirmed the findings for the primary endpoint (measured by both independent video raters and investigators). A prespecified subgroup analysis of the primary endpoint scored by the investigators showed a more robust response in patients with more severe ET (FIG. 48B and Table 26). Prespecified subgroup analysis based on concurrent anti-tremor medication use showed significantly greater improvement compared to placebo in subgroups not taking concurrent anti-tremor medications at baseline. (FIGS. 48C and 48D and Table 26).

TABLE 25

TETRAS-PS Subscale Primary Endpoint

| TETRAS-PS Total Score[1] | Independent Video Raters[2] | | Investigator Rated[2] | |
|---|---|---|---|---|
| | CX-8998 (N = 39) | Placebo (N = 44) | CX-8998 (N = 39) | Placebo (N = 44) |
| Baseline, N | 39 | 44 | 39 | 44 |
| Mean (SD) | 22.7 (6.44) | 22.8 (5.84) | 28.3 (5.95) | 28.5 (6.35) |
| Median (minimum, maximum) | 22.0 (11.5, 46.5) | 22.8 (12.5, 43.5) | 27.5 (20.5, 42.5) | 27.8 (19.5, 45.0) |
| Day 28, N | 38 | 43 | 37 | 42 |
| Mean (SD) | 21.1 (6.71) | 20.7 (7.96) | 23.6 (5.50) | 25.8 (7.65) |
| Median (minimum, maximum) | 20.0 (10.5, 49.0) | 20.5 (0.0, 44.5) | 22.5 (14.0, 37.0) | 25.8 (0.0, 45.5) |
| Change from baseline to Day 28, N | 38 | 43 | 37 | 42 |
| Mean (SD) | −1.6 (4.36) | −2.0 (4.98) | −4.4 (4.16) | −2.8 (5.13) |
| Median (minimum, maximum) | −1.5 (−11.0, 7.0) | −1.5 (−23.0, 7.5) | −4.0 (−13.5, 4.5) | −2.5 (−26.0, 4.5) |
| Analysis Results[3,4] | | | | |
| LS mean (SE) | −1.8 (0.81) | −2.3 (0.78) | −4.8 (0.80) | −2.8 (0.77) |
| LS mean difference from placebo (95% CI) | 0.5 (−1.5, 2.5) | | −2.0 (−4.0, 0.0) | |
| p-value[5] | 0.696 | | 0.017 | |

ANCOVA = analysis of covariance;
CI = confidence interval;
LS = least squares;
TETRAS = The Essential Tremor Rating Assessment Scale;
TETRAS-PS = TETRAS performance subscale.
[1]TETRAS-PS quantifies tremor in the head, face, voice, limbs, and trunk. The overall subscale score ranges from 0 to 64. A decrease in score is indicative of improvement.
[2]The change from baseline to Day 28 on the TETRAS-PS total score, as scored by the independent video raters, was the protocol-specified primary efficacy endpoint. TETRAS-PS was also scored in real time by the investigators and was analyzed post hoc (using the same methodology that was used for the independent video rater assessments) as if it were the primary endpoint.
[3]Missing values were replaced by multiple imputation. LS means, standard errors, difference from placebo, 95% CIs, and p-values were estimated using an ANCOVA model, with effects for treatment, anti-tremor medication use, site type, and baseline value of TETRAS-PS total score.
[4]Missing items on the subscale at Day 28 were imputed using PROC MI, and 10 datasets were produced for analysis. The results of the ANCOVA model of the 10 datasets were combined using PROC MIANALYZE to produce the LS means, difference from placebo, 95% CI, and p-value.
[5]The analysis was performed on ranked data; LS means, standard errors the difference from placebo, and 95% CIs were estimated using unranked data, and the p-value was calculated using ranked data.

TABLE 26

TETRAS-PS Prespecified Subset Analysis

| | Independent Video Raters[2] | | Investigator Rated[2] | |
|---|---|---|---|---|
| TETRAS-PS Total Score[1] | CX-8998 (N = 39) | Placebo (N = 44) | CX-8998 (N = 39) | Placebo (N = 44) |
| Baseline TETRAS-PS Severity <=Median, N | 22 | 22 | 22 | 22 |
| Mean (SD) | −0.1 (3.98) | −1.6 (3.34) | −3.4 (3.74) | −2.5 (3.95) |
| Median (minimum, maximum) | 0 (−9.5, 7.0) | −1.0 (−10, 4.5) | −3.0 (−13.5, 1.0) | −1.8 (−11.5, 4.5) |
| LS mean (SE) | −0.6 (0.82) | −1.8 (0.79) | −3.8 (0.67) | −2.5 (0.65) |
| LS mean difference from placebo (95% CI) | 1.2 (−1.1, 3.4) | | −1.2 (−3.1, 0.6) | |
| p-value | 0.296 | | 0.166 | |
| Baseline TETRAS-PS Severity > Median, N | 16 | 21 | 15 | 20 |
| Mean (SD) | −3.6 (4.14) | −2.5 (6.31) | −5.8 (4.48) | −3.1 (6.27) |
| Median (minimum, maximum) | −3.0 (−11, 2.5) | −1.5 (−23.0, 7.5) | −6.0 (−13, 4.5) | −3.3 (−26, 4.5) |
| LS mean (SE) | −3.5 (1.47) | −2.2 (1.57) | −5.6 (1.60) | −2.1 (1.70) |
| LS mean difference from placebo (95% CI) | −1.3 (−4.8, 2.3) | | −3.5 (−7.4, 0.4) | |
| p-value | 0.266 | | 0.011 | |
| Using Concurrent Tremor Medication at Day 1, N | 24 | 30 | 23 | 29 |
| Mean (SD) | −1.1 (3.71) | −2.6 (5.06) | −3.9 (4.31) | −3.3 (5.55) |
| Median (minimum, maximum) | −1.3 (−9.5, 5.5) | −1.5 (−23, 4.5) | −3.5 (−13.5, 4.5) | −3.0 (−26, 4.5) |
| LS mean (SE) | −1.6 (1.14) | −3.4 (1.05) | −3.5 (1.29) | −3.0 (1.15) |
| LS mean difference from placebo (95% CI) | 1.8 (−0.7, 4.3) | | −0.5 (−3.2, 2.3) | |
| p-value | 0.202 | | 0.570 | |
| No Concurrent Tremor Medication at Day 1, N | 14 | 13 | 14 | 13 |
| Mean (SD) | −2.5 (5.33) | −0.7 (4.69) | −5.0 (3.97) | −1.7 (3.99) |
| Median (minimum, maximum) | −3.3 (−11, 7.0) | −0.5 (−10, 7.5) | −4.5 (−12.5, 1.0) | −1.5 (−11.5, 4.5) |
| LS mean (SE) | −4.3 (2.05) | −2.3 (2.08) | −6.2 (1.60) | −1.8 (1.59) |
| LS mean difference from placebo (95% CI) | −2.0 (−5.8, 1.8) | | −4.4 (−7.4, −1.3) | |
| p-value | 0.312 | | 0.005 | |
| Using Beta-blocker at Day 1, N | 18 | 26 | 18 | 26 |
| Mean (SD) | −1.5 (3.68) | −3.0 (5.34) | −4.2 (4.55) | −3.4 (5.85) |
| Median (minimum, maximum) | −1.3 (−9.5, 4.0) | −2.3 (−23, 4.5) | −4.0 (−13.5, 4.5) | −3.3 (−26, 4.5) |
| LS mean (SE) | −2.5 (1.36) | −3.9 (1.14) | −3.6 (1.56) | −3.3 (1.27) |
| LS mean difference from placebo (95% CI) | 1.4 (−1.4, 4.3) | | −0.3 (−3.6, 3.0) | |
| p-value | 0.333 | | 0.527 | |
| No Beta-blocker Use at Day 1, N | 20 | 17 | 19 | 16 |
| Mean (SD) | −1.6 (4.99) | −0.6 (4.09) | −4.5 (3.89) | −1.8 (3.65) |
| Median (minimum, maximum) | −2.0 (−11, 7.0) | −0.5 (−10, 7.5) | −4.0 (−12.4, 1.0) | −1.8 (−11.5, 4.5) |
| LS mean (SE) | −1.3 (1.10) | −0.1 (1.31) | −5.6 (0.97) | −1.3 (1.11) |
| LS mean difference from placebo (95% CI) | −1.2 (−4.3, 1.8) | | −4.3 (−7.0, −1.7) | |
| p-value | 0.425 | | 0.003 | |

ANCOVA = analysis of covariance;
CI = confidence interval;
LS = least squares;
TETRAS = The Essential Tremor Rating Assessment Scale;
TETRAS-PS = TETRAS performance subscale.

[1] TETRAS-PS quantifies tremor in the head, face, voice, limbs, and trunk. The overall subscale score ranges from 0 to 64. A decrease in score is indicative of improvement.
[2] The change from baseline to Day 28 on the TETRAS-PS total score, as scored by the independent video raters, was the protocol-specified primary efficacy endpoint. TETRAS-PS was also scored in real time by the investigators and was analyzed post hoc (using the same methodology that was used for the independent video rater assessments) as if it were the primary endpoint.
[3] The analysis was performed on ranked data; LS means, standard errors, the difference from placebo, and 95% CIs were estimated using unranked data, and the p-value was calculated using ranked data.

Figure 49A:
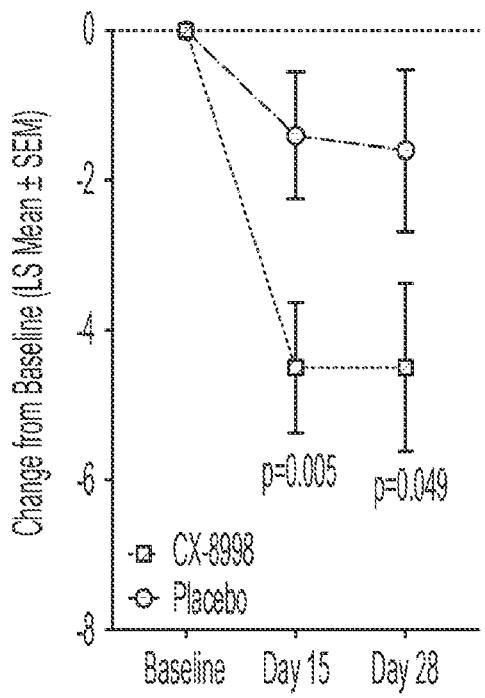
FIGS. 49A-49D contain graphs showing change from baseline for TETRAS-ADL and total TETRAS FIGS. 50A-50B contain graphs showing clinical global impression of improvement at day 28.
Figure 49B:
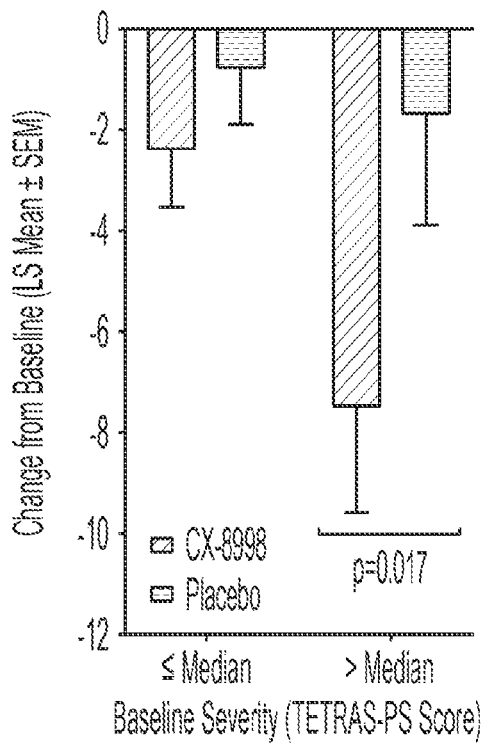
Figure 49C:
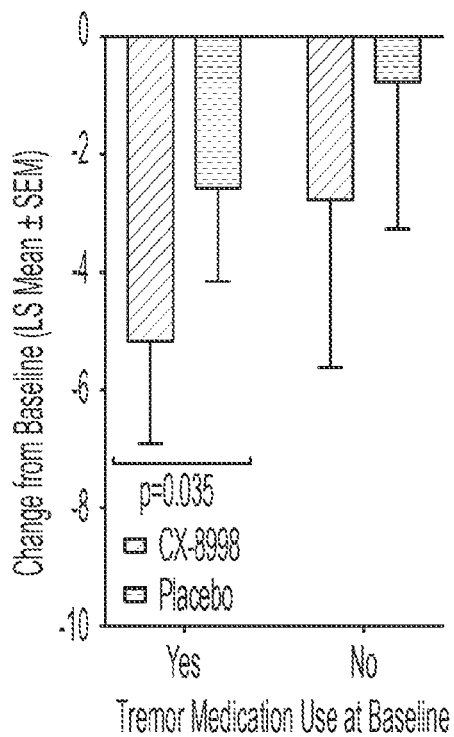

The TETRAS-ADL subscale score was evaluated at Day 15 (exploratory endpoint) and at Day 28 (secondary endpoint), and the difference between treatment groups for the change from baseline showed a significant decrease (improvement) for the CX-8998 group compared to placebo at both time points. As presented in FIG. 49A, the LS mean (±SE) was −4.5±0.87 and −1.4±0.85 (p=0.005) at Day 15 and −4.5±1.12 and −1.6±1.08 (p=0.049) at Day 28 for CX-8998 and placebo, respectively. Prespecified subgroup analysis of the secondary endpoint at Day 28 showed greater responses in CX-8998 patients with more severe ET (FIG. 49B). In contrast to the TETRAS-PS, prespecified subgroup analysis of TETRAS-ADL scores based on concurrent anti-tremor medication use showed significantly greater improvement compared to placebo in the subgroup taking concurrent anti-tremor medications at baseline (FIG. 49C).

To estimate the clinical detectable change of the TETRAS-ADL improvement, a post-hoc analysis of TETRAS-ADL scores was conducted on the subset of patients who achieved a score of minimally improved as measured by CGI-I or PGIC as anchors. This analysis revealed that a 3- to 4-point reduction from baseline in the TETRAS-ADL score represented a detectable change to clinicians, whereas a 2- to 4-point reduction in score from baseline represented a noticeable change to patients (Table 27).

TABLE 27

Post-hoc Analysis of TETRAS-ADL Meaningful Difference Based on CGI-I and PGIC

| TETRAS-ADL Score[1] | Day 15 | | Day 28 | |
|---|---|---|---|---|
| | CX-8998 (N = 39) | Placebo (N = 44) | CX-8998 (N = 39) | Placebo (N = 44) |
| Minimally Improved by CGI-I, N | 19 | 14 | 15 | 7 |
| Mean (SD) | −3.7 (4.21) | −3.1 (3.77) | −4.4 (8.10) | −3.3 (4.61) |
| Median (minimum, maximum) | −2.0 (−11, 3) | −3.0 (−9, 3) | −1.0 (−24, 3) | −2.0 (−11, 2) |
| Minimally Improved by PGIC, N | 17 | 8 | 10 | 6 |
| Mean (SD) | −3.3 (4.27) | −1.5 (6.16) | −1.6 (3.84) | −3.2 (5.19) |
| Median (minimum, maximum) | −4.0 (−13, 4) | −2.5 (−9, 12) | −1.0 (−7, 3) | −1.5 (−11, 2) |

ADL = activities of daily living;
SD = standard deviation;
TETRAS = The Essential Tremor Rating Assessment Scale;
CGI-I = clinical global impression of improvement;
PGIC = patient global impression of improvement.
[1]TETRAS-ADL subscale assesses items such as eating and drinking, dressing and personal hygiene, carrying items, and finer motor skills. Each item is rated on a scale for 0 to 4 on which 0 = normal activity and 4 = severe abnormality. The sum of the individual scores provides an overall score, which ranges from 0 to 48.

Figure 49D:
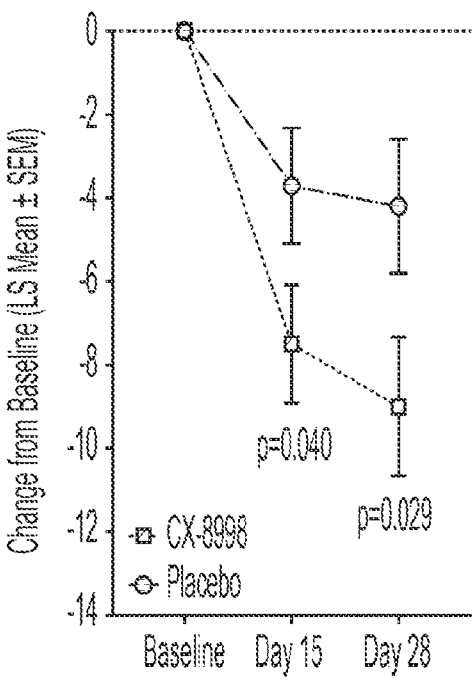
Figure 52:
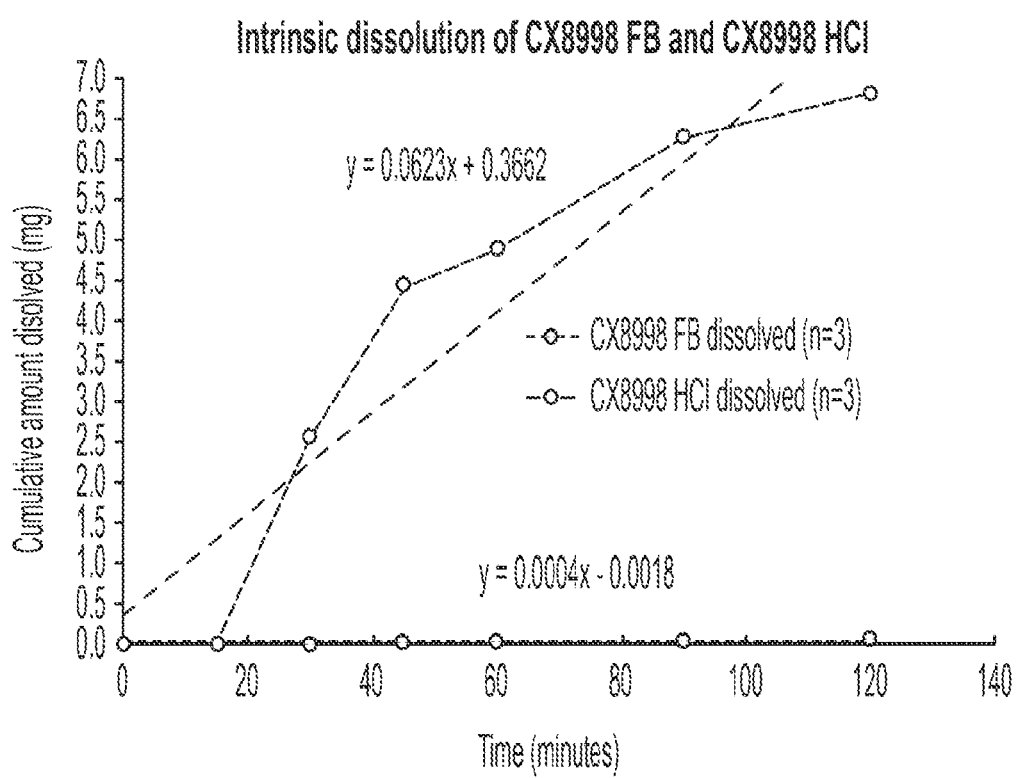
FIG. 52 contains a graph showing intrinsic dissolution of CX-8998 free base (FB) and CX-8998 HCl formulations.
Figure 53:
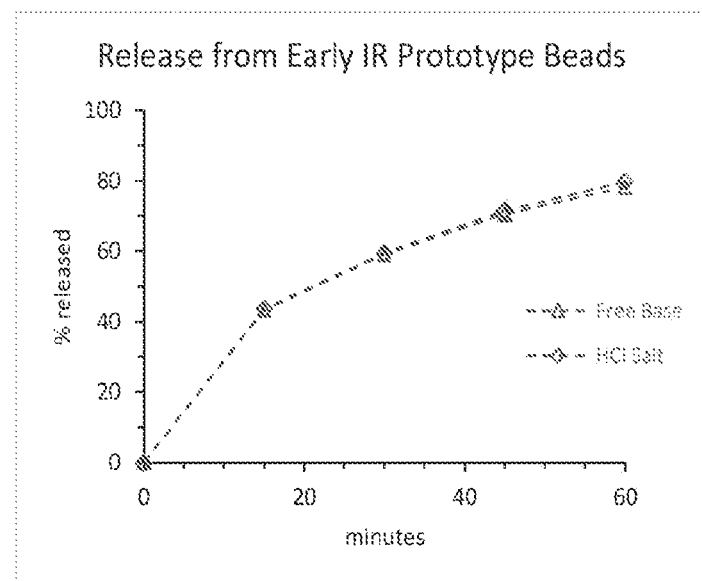
FIG. 53 contains a graph showing release from IR beads.

The LS mean (±SE) total TETRAS score (TETRAS-PS score rated by investigators plus TETRAS-ADL subscale score rated by patients) significantly improved at Day 15 (−7.5±1.42 and −3.7±1.38, p=0.040) and at Day 28 (−9.0±1.66 and −4.2±1.60, p=0.029) for CX-8998 compared to placebo, respectively (FIG. 49D). When the TETRAS-PS score was rated by independent video raters, the total TETRAS score trended toward improvement for the CX-8998 group but was not statistically significant at either Day 15 or 28.

Kinesia ONE score (triaxiale accelerometry and gyroscopy) at Day 15 (exploratory endpoint) and Day 28 (secondary endpoint) did not show a significant difference between CX-8998 and placebo at either time point. (Table 28)

TABLE 28

| Kinesia ONE Total Score[1] | Kinesia ONE Score | | | |
|---|---|---|---|---|
| | Day 15 | | Day 28 | |
| | CX-8998 (N = 39) | Placebo (N = 44) | CX-8998 (N = 39) | Placebo (N = 44) |
| Baseline, N | 39 | 44 | 39 | 44 |
| Mean (SD) | 10.6 (4.33) | 12.0 (5.35) | 10.6 (4.33) | 12.0 (5.35) |
| Median (minimum, maximum) | 10.0 (4.3, 25.9) | 11.0 (3.7, 25.0) | 10.0 (4.3, 25.9) | 11.0 (3.7, 25.0) |
| Day 15 or Day 28, N | 38 | 42 | 37 | 41 |
| Mean (SD) | 9.1 (4.46) | 10.8 (5.21) | 9.3 (4.28) | 10.4 (4.84) |
| Median (minimum, maximum) | 7.9 (2.6, 27.3) | 10.1 (2.8, 25.9) | 7.8 (3.8, 26.0) | 10.3 (3.3, 24.2) |

TABLE 28-continued

| Kinesia ONE Total Score[1] | Kinesia ONE Score | | | |
|---|---|---|---|---|
| | Day 15 | | Day 28 | |
| | CX-8998 (N = 39) | Placebo (N = 44) | CX-8998 (N = 39) | Placebo (N = 44) |
| Change from baseline to Day 15 or Day 28, N | 38 | 42 | 37 | 41 |
| Mean (SD) | −1.5 (3.06) | −1.4 (2.97) | −1.4 (3.35) | −1.8 (3.00) |
| Median (minimum, maximum) | −1.1 (−12.2, 4.9) | −0.8 (−13.9, 2.3) | −0.7 (−11.7, 5.4) | −1.3 (−13.7, 3.6) |
| Analysis Results[2,3] | | | | |
| LS mean (SE) | −2.0 (0.52) | −1.6 (0.51) | −1.7 (0.52) | −1.6 (0.50) |
| LS mean difference from placebo (95% CI) | −0.4 (−1.7, 0.9) | | 0.0 (−1.4, 1.3) | |
| p-value[5] | 0.350 | | 0.421 | |

ANCOVA = analysis of covariance;
CI = confidence interval;
LS = least squares.
[1]Kinesia ONE scores are presented as the sum of the scores of the left and right hands. Values for each test range from 0 (no tremor) to 4 (severe tremor). The total overall score is the sum of all individual items.
[2]LS means, standard errors, difference from placebo, 95% CIs, and p-values were estimated using an ANCOVA model, with effects for treatment, anti-tremor medication use, site type, and baseline value of the accelerometry total score.
[3]The analysis was performed on ranked data; LS means, standard errors, the difference from placebo, and 95% CIs were estimated using unranked data, and the p-value was calculated using ranked data.

The LS mean (±SE) CGI-I score was significantly greater (improved) at Day 28 (exploratory endpoint) by CX-8998 (1.0±0.13) compared to placebo (0.4±0.13), p=0.001 (FIG. 50A and Table 29). At Day 28, 23% of patients treated with CX-8998 were rated as much/very much improved compared to 7% on placebo (FIG. 50B). The mean PGIC score was significantly greater (improved) at Day 15 (exploratory endpoint) (p=0.003) and trended toward significant improvement at Day 28 (exploratory endpoint) (p=0.089). (Table 30) The mean GAS score was significantly greater (improved) at Day 28 (exploratory endpoint) for CX-8998 patients (44.8±1.72) compared to placebo (40.0±1.67), p=0.034. Detailed results on the GAS including a post-hoc analysis of the proportion of patients who achieved 1 or more or 2 or more goals is presented in Table 31.

TABLE 29

| | | CGI-I | | | |
|---|---|---|---|---|---|
| | | Day 15 (Exploratory Endpoint) | | Day 28 (Exploratory Endpoint) | |
| CGI-I Category1 | | CX-8998 (N = 39) | Placebo (N = 44) | CX-8998 (N = 39) | Placebo (N = 44) |
| −3 | Very much worse | 0 | 0 | 0 | 0 |
| −2 | Much worse | 0 | 1 (2%) | 0 | 0 |
| −1 | Minimally worse | 0 | 2 (5%) | 0 | 2 (5%) |
| 0 | No change | 14 (36%) | 21 (48%) | 13 (33%) | 30 (68%) |
| 1 | Minimally improved | 19 (49%) | 14 (32%) | 15 (38%) | 7 (16%) |
| 2 | Much improved | 6 (15%) | 5 (11%) | 9 (23%) | 2 (5%) |
| 3 | Very much improved | 0 | 1 (2%) | 0 | 1 (2%) |

TABLE 29-continued

CGI-I

|  | Day 15 (Exploratory Endpoint) | | Day 28 (Exploratory Endpoint) | |
| --- | --- | --- | --- | --- |
| CGI-I Category1 | CX-8998 (N = 39) | Placebo (N = 44) | CX-8998 (N = 39) | Placebo (N = 44) |
| N | 39 | 44 | 37 | 42 |
| Mean (SD) | 1 (0.7) | 1 (0.9) | 1 (0.8) | 0 (0.7) |
| Median (minimum, maximum) | 1 (0, 2) | 0 (−2, 3) | 1 (0, 2) | 0 (−1, 3) |
| Analysis Results2 | | | | |
| LS mean (SE) | 0.9 (0.14) | 0.6 (0.14) | 1.0 (0.13) | 0.4 (0.13) |
| LS mean difference from placebo (95% CI) | 0.3 (−1.0, 0.6) | | 0.6 (0.3, 0.9) | |
| p-value | 0.152 | | 0.001 | |

1The CGI-I was rescaled to allow a more intuitive interpretation of the results.
2Least squares (LS) means, standard errors, difference from placebo, 95% confidence intervals (CIs), and p-values were estimated using an analysis of covariance (ANCOVA) model, with effects for treatment, anti-tremor medication use, and site type.

TABLE 30

GIC

|  |  | Day 15 (Exploratory Endpoint) | | Day 28 (Exploratory Endpoint) | |
| --- | --- | --- | --- | --- | --- |
| PGIC Category[1] | | CX-8998 (N = 39) | Placebo (N = 44) | CX-8998 (N = 39) | Placebo (N = 44) |
| −3 | Very much worse | 0 | 0 | 1 (3%) | 0 |
| −2 | Much worse | 1 (3%) | 4 (9%) | 1 (3%) | 1 (2%) |
| −1 | Minimally worse | 1 (3%) | 1 (2%) | 1 (3%) | 2 (5%) |
| 0 | No change | 11 (28%) | 27 (61%) | 14 (36%) | 29 (66%) |
| 1 | Minimally improved | 17 (44%) | 8 (18%) | 10 (26%) | 6 (14%) |
| 2 | Much improved | 8 (21%) | 3 (7%) | 7 (18%) | 2 (5%) |
| 3 | Very much improved | 1 (3%) | 1 (2%) | 3 (8%) | 2 (5%) |
| N |  | 39 | 44 | 37 | 42 |
| Mean (SD) |  | 1 (1.0) | 1 (1.0) | 1 (1.3) | 0 (0.9) |
| Median (minimum, maximum) |  | 1 (−2, 3) | 0 (−2, 3) | 1 (−3, 3) | 0 (−2, 3) |
| Analysis Results2 | | | | | |
| LS mean (SE) |  | 0.9 (0.17) | 0.3 (0.16) | 0.8 (0.19) | 0.4 (0.18) |
| LS mean difference from placebo (95% CI) |  | 0.7 (0.2, 1.1) | | 0.4 (−0.1, 0.9) | |
| p-value |  | 0.003 | | 0.089 | |

[1]The PGIC was rescaled to allow a more intuitive interpretation of the results.
2Least squares (LS) means, standard errors, difference from placebo, 95% confidence intervals (CIs), and p-values were estimated using an analysis of covariance (ANCOVA) model, with effects for treatment, anti-tremor medication use, and site type.

TABLE 31

GAS

| Statistic for | Day 15 (Exploratory Endpoint) | | Day 28 (Exploratory Endpoint) | |
| --- | --- | --- | --- | --- |
| Overall GAS Score1 | CX-8998 (N = 39) | Placebo (N = 44) | CX-8998 (N = 39) | Placebo (N = 44) |
| N | 39 | 43 | 37 | 41 |
| Mean (SD) | 42.1 (8.55) | 39.1 (7.65) | 44.4 (11.08) | 39.5 (8.41) |
| Median (minimum, maximum) | 36.9 (26.2, 63.7) | 36.8 (22.6, 63.7) | 41.2 (26.7, 69.7) | 36.8 (27.2, 77.4) |
| Analysis Results[2] | | | | |
| LS mean (SE) | 43.2 (1.36) | 40.3 (1.33) | 44.8 (1.72) | 40.0 (1.67) |
| LS mean difference from placebo (95% CI) | 2.9 (−0.6, 6.4) | | 4.8 (0.4, 9.3) | |
| p-value | 0.103 | | 0.034 | |

1The overall GAS score = 50 + (10 * sum of weights)/square root (0.7 * sum of weights**2) + [0.3 * (sum of weights)**2]. Weights were specified at baseline and were assigned as 1 = fairly important, 2 = very important, 3= extremely important.
[2]Least squares (LS) means, standard errors, difference from placebo, 95% confidence intervals (CIs), and p-values were estimated using an analysis of covariance (ANCOVA) model, with effects for treatment, anti-tremor medication use, and site type.

The QUEST questionnaire revealed that a higher percentage of CX-8998 patients compared to placebo experienced side effects from their treatment at Day 15 (36% versus 9%) and Day 28 (18% versus 9%) and a higher percentage of CX-8998 patients expressed satisfaction with symptom control at Day 15 (38% versus 11%) and Day 28 (38% versus 14%) (Table 32). No significant differences between CX-8998 and placebo groups were reported in the dimension scores at Days 15 or 28 (data not shown).

TABLE 32

Quality of Life in Essential Tremor Questionnaire (QUEST)
General Questions Related to Anti-Tremor Medication

| Question | | | CX-8998 (N = 39) | Placebo (N = 44) |
| --- | --- | --- | --- | --- |
| Side effect from tremor medication in past month? | | | | |
| Baseline | No |  | 35 (90%) | 43 (98%) |
|  | Yes |  | 4 (10%) | 1 (2%) |
| Day 15 | No |  | 25 (64%) | 40 (91%) |
|  | Yes |  | 14 (36%) | 4 (9%) |
| Day 28 | No |  | 30 (77%) | 38 (86%) |
|  | Yes |  | 7 (18%) | 4 (9%) |
| Satisfied with control by medication in past month? | | | | |
| Baseline | No |  | 38 (97%) | 41 (93%) |
|  | Yes |  | 1 (3%) | 3 (7%) |
| Day 15 | No |  | 24 (62%) | 39 (89%) |
|  | Yes |  | 15 (38%) | 5 (11%) |
| Day 28 | No |  | 22 (56%) | 36 (82%) |
|  | Yes |  | 15 (38%) | 6 (14%) |

At least 1 TEAE was present in 58% of patients in the CX-8998 group compared to 49% of placebo. As expected, TEAEs in the CX-8998 group were primarily neurologic and psychiatric. TEAEs were predominantly mild or moderate in both groups. TEAEs in the CX-8998 group were mostly reported during the first week of study whereas TEAEs in the placebo group were reported throughout the study (Table 33). The most commonly reported drug-related TEAEs in the CX-8998 group were dizziness, headache, euphoria, disturbance in attention, paresthesia, hallucination (illusions, visual mostly when eyes were closed), insomnia, and dry mouth. Dizziness, nausea, somnolence, and vomiting were the most common drug-related TEAEs with placebo (Table 33).

TABLE 33

Summary of Treatment-Emergent Adverse Events Reported in Two or More Subjects in Either Treatment Group by (Safety Analysis Set)

| MedDRA System Organ Class/Preferred Term[1,] | CX-8998 (n = 48) | Placebo (n = 47) |
|---|---|---|
| Subjects with at least 1 treatment-emergent adverse event[2] | 28 (58%) | 23 (49%) |
| Nervous System Disorders | 20 (42%) | 10 (21%) |
| Dizziness | 10 (21%) | 3 (6%) |
| Headache | 4 (8%) | 2 (4%) |
| Disturbance in attention | 2 (4%) | 1 (2%) |
| Dysgeusia | 2 (4%) | 0 |
| Paraesthesia | 2 (4%) | 1 (2%) |
| Somnolence | 1 (2%) | 2 (4%) |
| Hypesthesia | 0 | 2 (4%) |
| Psychiatric Disorders | 12 (52% | 1 (2%) |
| Euphoric mood | 3 (6%) | 0 |
| Insomnia | 3 (6%) | 0 |
| Abnormal dreams | 2 (4%) | 1 (2%) |
| Hallucination | 2 (4%) | 0 |
| Gastrointestinal Disorders | 9 (19%) | 7 (15%) |
| Dry mouth | 2 (4%) | 1 (2%) |
| Nausea | 1 (2%) | 3 (6%) |
| Vomiting | 0 | 2 (4%) |
| Infections and Infestations | 4 (8%) | 3 (6%) |
| Urinary Tract Infection | 2 (4%) | 1 (2%) |
| Ear and Labyrinth Disorders | 2 (4%) | 0 |
| Tinnitus | 2 (4%) | 0 |

[1]Adverse event mapping was based on MedDRA (Medical Dictionary for Regulatory Activities), version 20.1 thesaurus. Subjects who experienced the same event more than once were counted once for the preferred term. Subjects who experienced more than 1 event within a system organ class were counted only once in the system organ class.
[2]The number and percentage of subjects in the system organ class represents all subjects who had at least 1 adverse event (preferred term) in the system organ class. Only adverse events that were reported in 2 or more subjects in either treatment group in the nervous system, psychiatric system, and gastrointestinal system are displayed.

Serious adverse events (SAEs) of alcohol withdrawal syndrome, major depression, and suicidal ideation were reported in one patient on CX-8998. This patient had a history of chronic alcohol dependence and depression with suicide attempt that he did not disclose during screening. These SAEs were deemed to be unrelated to study drug. No SAEs occurred with placebo. Discontinuation of study treatment due to TEAEs occurred in 8 (17%) of CX-8998 patients compared to 2 (4%) in the placebo group. Dosage reduction due to TEAEs was conducted in 6% of CX-8998 patients and 2% of placebo patients and generally occurred during the first 2 weeks of treatment (Table 34).

TABLE 34

Discontinuations and Dosage Reductions

| Discontinuation[1] | CX-8998 (N = 48) | Placebo (N = 47) |
|---|---|---|
| Subjects with at least 1 event leading to discontinuation | 8 (17%) | 2 (4%) |
| Nervous System Disorders | 4 (8%) | 1 (2%) |
| Psychiatric Disorders | 4 (8%) | 0 |

| Dosage Reduction[2] | CX-8998 (N =48) | Placebo (N = 47) |
|---|---|---|
| Dosage reduced during study | 4 (8%) | 1 (2%) |
| Due to adverse event | 3 (6%) | 1 (2%) |
| Due to other reasons | 1 (2%)3 | 0 |

Dosage Reductions Due to Adverse Events

| Treatment Group | Subject Number | Study Day | Dosage Reduction From | Dosage Reduction To | Adverse Event (MedDRA Preferred Term)[4] | Study Day of Last Dose | Study Disposition |
|---|---|---|---|---|---|---|---|
| CX-8998 | 26-001 | 25 | 10 mg BID | 8 mg BID | Anxiety | 33 | Completed study |
|  | 31-023 | 8 | 8 mg BID | 4 mg BID | Electrocardiogram T-wave abnormal | 8 | Withdrawn (Day 8) Investigator decision |
|  | 33-004 | 8 | 4 mg BID | 2 mg BID | Headache | 15 | Withdrawn (Day 45) Lost to follow-up |
| Placebo | 38-018 | 15 | 4 capsules BID | 2 capsules BID | Headache | 28 | Completed study |

BID = twice daily; MedDRA = Medical Dictionary for Regulatory Activities.
[1]Adverse event mapping was based on MedDRA (Medical Dictionary for Regulatory Activities), version 20.0 thesaurus. Subjects who experienced the same event more than once were counted once for the preferred term. Subjects who experienced more than 1 event within a system organ class were counted only once in the system organ class.
[2]Reescalation of the dosage after dosage reduction was not allowed.
[3]Subject had inadequate drug supply at Visit 4.
[4]Events in all subjects were considered related to the study drug.

An analysis examined whether the observed differences in TETRAS performance subscore were due to differential scoring by item, and the extent to which such items can shed light into the factors underlying the discordant ratings (FIG. 51). The upper panel of FIG. 51 shows the difference scores (independent video rated [CR] minus investigator rated [PR]) by item, where negative scores indicate lower scoring by the independent video rater (CR) than the investigator (PR). As FIG. 51 indicates, first, all the items were scored comparatively lower by the independent video rater than the investigator. Secondly and more importantly, some items showed particularly large difference scores. These items were related to leg tremor, standing, face and protrusion of the tongue (Tp2: face tremor; Tp3: voice tremor; Tp5Al: left lower limb extended; Tp5Ar: right lower limb extended; Tp9: standing). Consistent with these observations, ANOVAs comparing independent video rated and investigator rated groups on individual items showed statistically significant differences for 14 out of the 19 items (p-values <0.05). All items pertaining to leg tremor, standing and subtle tremor reached significance. Interestingly, the discrepancies appear to be systematic in that the magnitude of differential scoring of particular items remained consistent across visits. For example, item 5Al and 5Ar showed large difference scores consistently across all visits (FIG. 51, lower panel).

No clinically meaningful differences were detected in clinical laboratory parameters of CX-8998 and placebo groups. No clinically significant abnormalities occurred in vital signs, ECG, or neurological and physical examinations.

Example 26. CX-8998 HC Salt and Free Base Formulations

A CX-8998 IR formulation releases as much CX-8998 as quickly as possible. An exemplary CX-8998 IR formulation was made using extrusion/spheronization to generate beads containing either CX-8998-HCl salt or CX-8998 free base.

In one experiment, formulations containing either CX-8998-HCl salt or CX-8998 free base are as shown in Table 35.

TABLE 35

Bead formulations with HCl salt and free base CX-8998 (wt %)

| Component | CX-8998 - HCl salt formulation | CX-8998 free base formulation |
|---|---|---|
| CX-8998 HCl salt | 3.5% | |
| CX8998 free base | | 3.2% |
| Microcrystalline cellulose | 88.75% | 88.95% |
| Sodium starch glycolate | 3.5% | 3.5% |
| Croscarmellose sodium | 3.5% | 3.5% |
| Magnesium stearate | 0.5% | 0.5% |
| Stearic acid | 0.50% | 0.50% |
| Methionine | 0.05% | 0.05% |

Figure 54A:
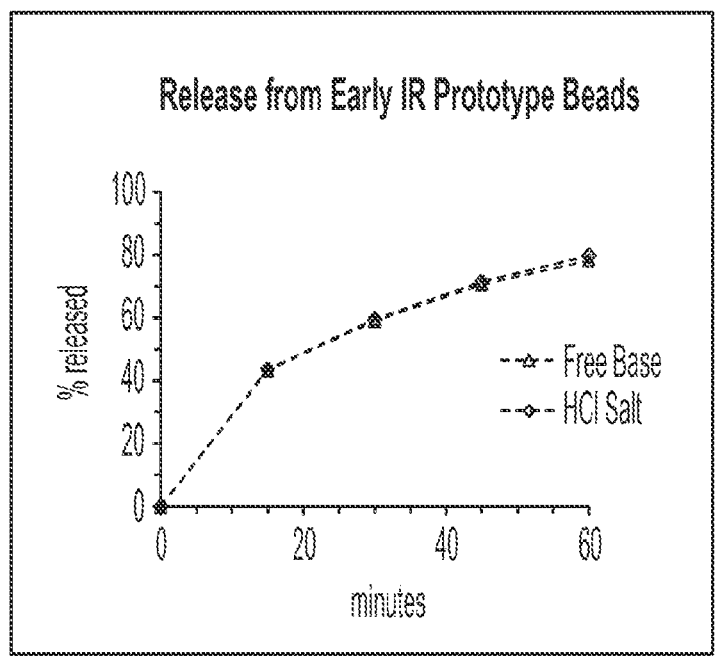
FIGS. 54A-54B contain graphs showing dissolution rates from IR beads having a first formulation (FIG. 54A) and second formulation (FIG. 54B).

Release profiles are shown in FIG. 54A.

Formulations containing microcrystalline cellulose, which is typically used in IR formulations of other active ingredients, released about 80% CX-8998, and took an hour to achieve this level of release.

In one experiment, formulations containing CX-8998 free base are as shown in Table 36.

TABLE 36

Bead formulations with HCl salt and free base CX-8998 (wt %)

| Component | CX-8998 formulation |
|---|---|
| CX8998 free base | 3.2 |
| Microcrystalline cellulose | 8.0 |
| Lactose monohydrate | 80.6 |
| Sodium starch glycolate | 3.5 |
| Croscarmellose sodium | 3.5 |
| Magnesium stearate | 0.50 |
| Steric acid | 0.50 |
| Polysorbate 80 | 0.2 |

Figure 54B:
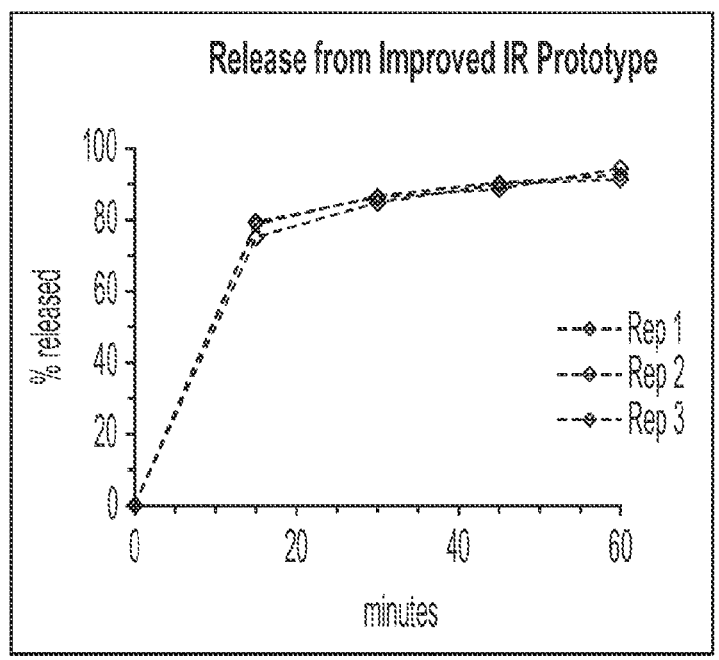

Release profiles are shown in FIG. 54B.

Formulations containing lactose monohydrate (e.g., and not containing microcrystalline cellulose released greater than 80% of CX-8998 within 20 minutes.

Example 27. CX-8998 Bead Formulation with No Microcrystalline Cellulose

Figure 55A:
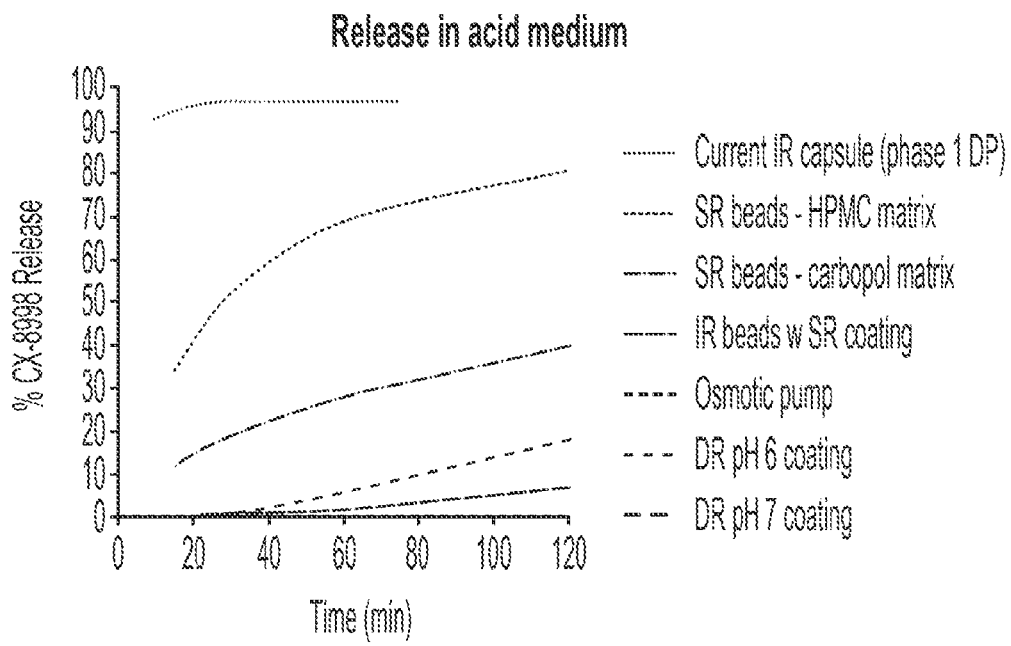
FIGS. 55A-55B contain graphs showing dissolution rates of CX-8998 formulations in acidic conditions (FIG. 55A) and pH neutral conditions (FIG. 55B).
Figure 55B:
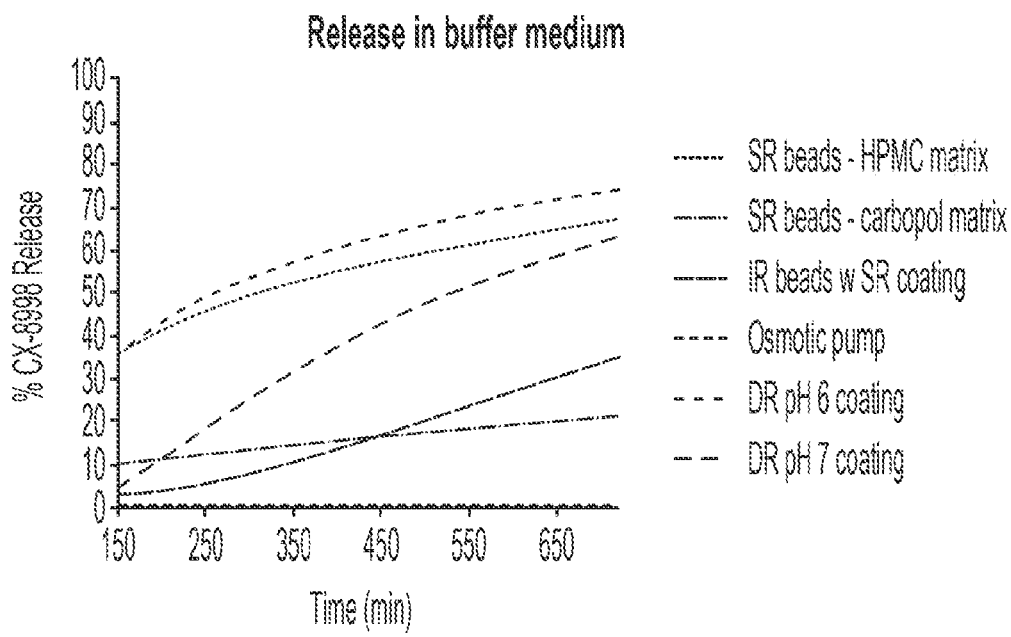

Microcrystalline cellulose is typically a key ingredient in drug beads formed by extrusion spheronization. A formulation containing no microcrystalline cellulose and providing fast release of CX-8998 is provided in Table 37. Dissolution results for this formulation are provided in FIG. 55.

TABLE 37

CX-8998 drug bead formulation containing no microcrystalline cellulose

| Component | Composition ((wt % of core bead wt)) |
|---|---|
| CX-8998 (HCl salt) | 5.0 |
| Lactose monohydrate | 57.7 |
| Crospovidone | 25.0 |
| Citric Acid Anhydrous | 8.0 |
| Sodium Lauryl Sulfate (SLS) | 2.0 |
| Hydroxypropyl Cellulose (HPC) | 2.0 |
| Butylated Hydroxyanisole (BHA) | 0.3 |
| Butylated Hydroxytoluene (BHT) | 0.1 |

BHA and BHT were dissolved in ethanol in one beaker while citric acid, SLS, and HPC were dissolved in water in a second beaker. The two solutions were combined and sprayed on the remaining ingredients, which were blended in a V-blender, to form a paste. The paste was then extruded through an extruder, and the extrudate was immediately transferred to a spheronizer. The resulting wet drug beads were dried in a fluid bed dryer.

Example 28. CX-8998 Delayed-Release (DR) Bead Formulation

A CX-8998 DR formulation can be any composition from which release of CX-8998 is largely delayed following administration. Release of CX-8998 from the composition of this example can be controlled by application of a pH-sensitive coating that is targeted to dissolve at a pH in the range of 6.0-6.5. The composition is provided in Table 38.

TABLE 38

CX-8998 drug bead formulation containing no microcrystalline cellulose

| Component | Composition (wt % of core bead wt) |
|---|---|
| Core Beads | |
| CX-8998 (HCl salt) | 5.0% |
| Lactose monohydrate | 57.7% |
| Crospovidone | 25.0% |
| Citric Acid Anhydrous | 8.0% |
| Sodium Lauryl Sulfate (SLS) | 2.0% |
| Hydroxypropyl Cellulose (HPC) | 2.0% |
| Butylated Hydroxyanisole (BHA) | 0.3% |
| Butylated Hydroxytoluene (BHT) | 0.1% |
| Coating | |
| Methacrylic Acid Copolymer L | 6.25% |
| Methacrylic Acid Copolymer S | 6.25% |
| Triethyl citrate | 1.25% |
| Talc, USP | 6.25% |

Core beads were prepared as described in Example 27. The dried beads were loaded into a fluid bed dryer with Wurster inserts and spray coated with the coating ingredients listed above suspended in 95% isopropanol. Spray coating was continued until the mass of the coating was about 20% of the mass of the uncoated beads. The beads were dried in the fluid bead until residual solvent content was negligible.

Example 29. CX-8998 Delayed Release Bead Formulation (Later Release)

Another delayed release bead formulation is targeted to release later in the intestinal tract. The composition of this formulation in provided in Table 39.

TABLE 39

CX-8998 drug bead formulation containing no microcrystalline cellulose

| Component | Composition (wt % of core bead wt) |
|---|---|
| Core Beads | |
| CX-8998 (HCl salt) | 5.0% |
| Lactose monohydrate | 57.7% |
| Crospovidone | 25.0% |
| Citric Acid Anhydrous | 8.0% |
| Sodium Lauryl Sulfate (SLS) | 2.0% |
| Hydroxypropyl Cellulose (HPC) | 2.0% |
| Butylated Hydroxyanisole (BHA) | 0.3% |
| Butylated Hydroxytoluene (BHT) | 0.1% |
| Coating | |
| Eudragit FS 30 D | 17.4%* |
| Plasacryl T20 | 2.6%* |

Core beads were prepared as described in Example 27. The dried beads were loaded into a fluid bed dryer with Würster inserts and spray coated with the coating ingredients listed above suspended in purified water. Spray coating was continued until the mass of the coating was about 20% of the mass of the uncoated beads. The beads were dried in the fluid bead.

Example 30. 8-mg CX-8998 Controlled Release Capsules for Twice Daily Dosing

A controlled release drug product was generated by combining the immediate release beads of Example 27 with the delayed release beads of Example 28. Size 0 hard gelatin capsules were manually filled with about 128 mg of the immediate release beads and about 104 mg of the delayed release beads per capsule. Each capsule thus filled contained the equivalent of 8 mg of CX-8998 free base.

Example 31. 8-mg CX-8998 Controlled Release Capsules for Once Daily Dosing

A controlled release drug product was generated by combining the immediate release beads of Example 27 with the delayed release beads of Example 29. Size 0 hard gelatin capsules were manually filled with about 85 mg of the immediate release beads and about 158 mg of the delayed release beads per capsule. Each capsule thus filled contained the equivalent of 8 mg of CX-8998 free base.

Example 32. 20-mg CX-8998 Controlled Release Capsules for Twice Daily Dosing

A controlled release drug product was generated by combining the immediate release beads of Example 27 with the delayed release beads of Example 28. Size 00 hard gelatin capsules were manually filled with about 320 mg of the immediate release beads and about 260 mg of the delayed release beads per capsule. Each capsule thus filled contained the equivalent of 20 mg of CX-8998 free base.

Example 33. 20-mg CX-8998 Controlled Release Capsules for Once Daily Dosing

A controlled release drug product was generated by combining the immediate release beads of Example 27 with the delayed release beads of Example 29. Size 0 hard gelatin capsules were manually filled with about 212 mg of the immediate release beads and about 395 mg of the delayed release beads per capsule. Each capsule thus filled contained the equivalent of 20 mg of CX-8998 free base.

Example 34. Dissolution of MR1 20 mg Capsules

The capsules described in Example 32 were tested in a USP type 2 dissolution apparatus for two hours in a medium containing 3% Tergitol in 0.1N hydrochloric acid and subsequently for 12 hours in a medium containing 3% Tergitol in pH 6.8 phosphate buffer. Mean data are provided in Table 40.

TABLE 40

Mean dissolution data for 20-mg "MR1" capsules

| hours | % of label claim dissolved |
|---|---|
| 1 | 50 |
| 2 | 60 |
| 2.5 | 68 |
| 3 | 86 |
| 4 | 97 |
| 6 | 102 |
| 10 | 102 |
| 14 | 102 |

Example 35. Dissolution of MR2 20 mg Capsules

The capsules described in Example 33 were tested in a USP type 2 dissolution apparatus for two hours in a medium containing 3% Tergitol in 0.1N hydrochloric acid and subsequently for 12 hours in a medium containing 3% Tergitol in pH 6.8 phosphate buffer. Mean data are provided in Table 41.

TABLE 41

Mean dissolution data for 20-mg "MR2" capsules

| hours | % of label claim dissolved |
|---|---|
| 1 | 48 |
| 2 | 49 |
| 2.5 | 51 |
| 3 | 54 |
| 4 | 61 |
| 6 | 72 |
| 10 | 84 |
| 14 | 91 |

Example 36. CX-8998 Formulation Pharmokokinetics

Figure 56:
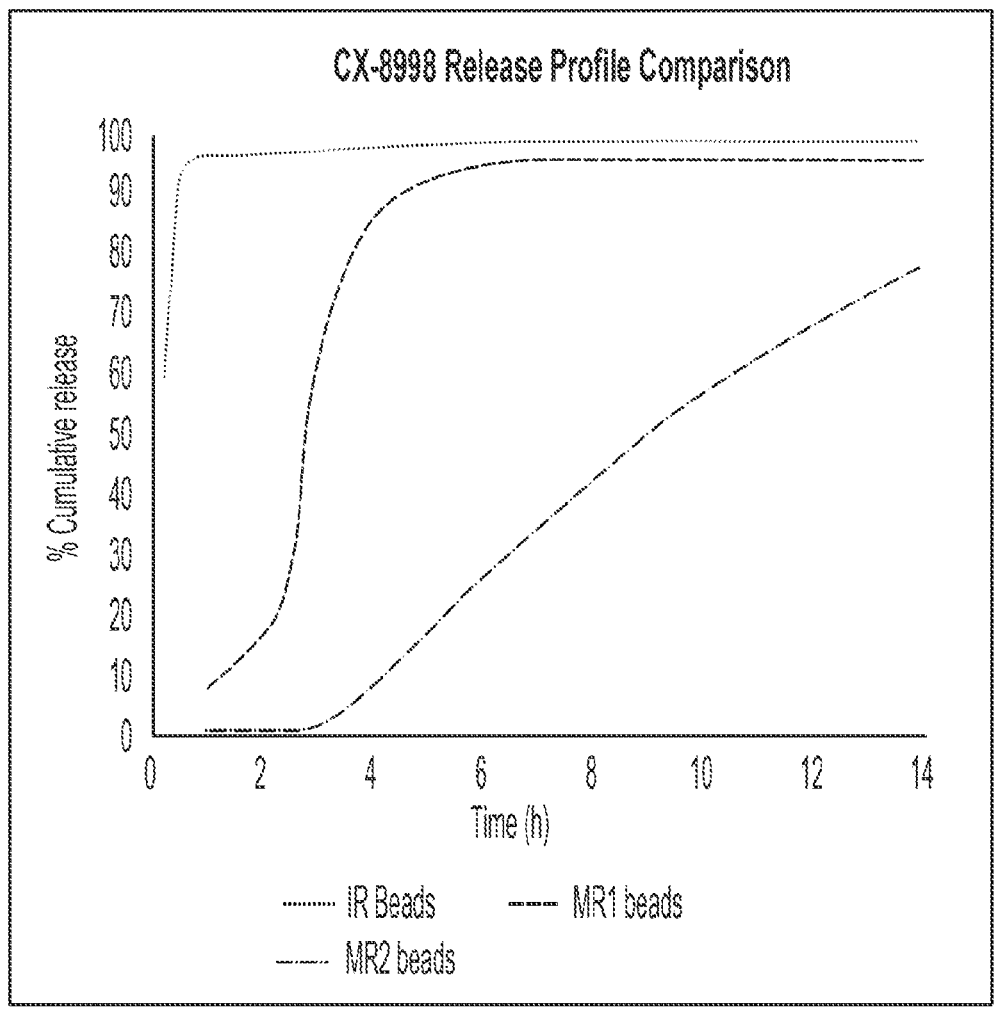
FIG. 56 contains a graph showing CX-8998 release profile of IR beads, MR1 beads, and MR2 beads.
Figure 57A:
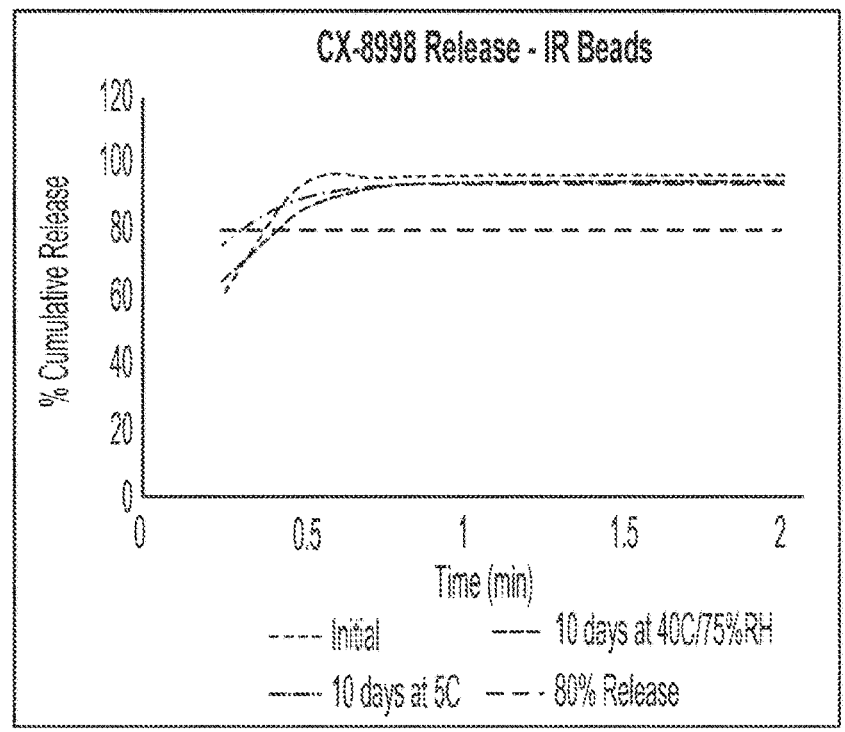
FIGS. 57A-57C contain graphs showing CX-8998 release profile of IR beads (FIG. 57A), MR1 beads (FIG. 57B), and MR2 beads (FIG. 57C) after storage.
Figure 57B:
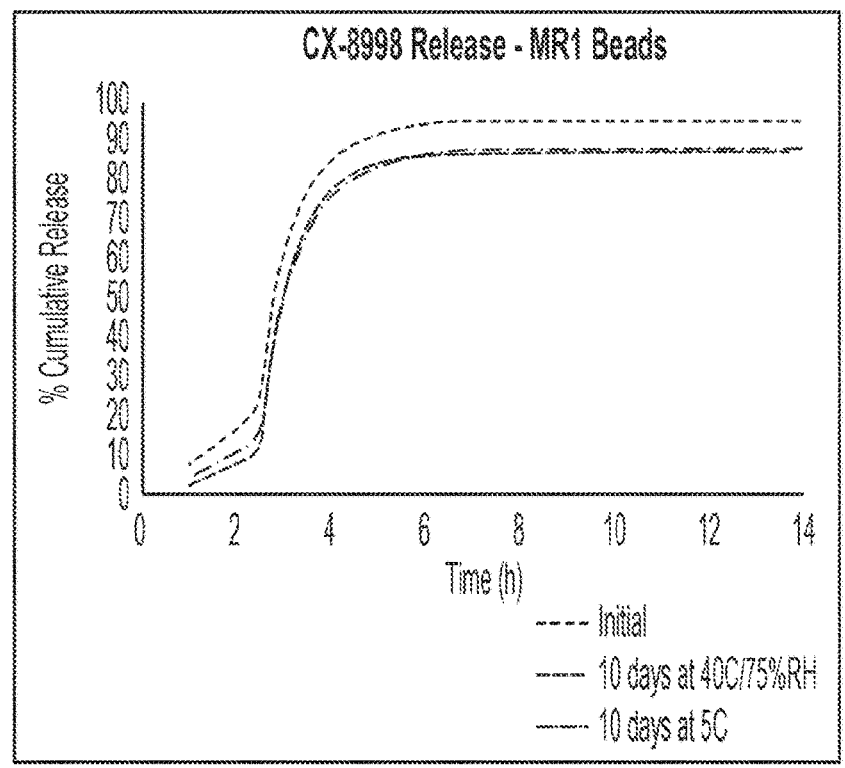
Figure 57C:
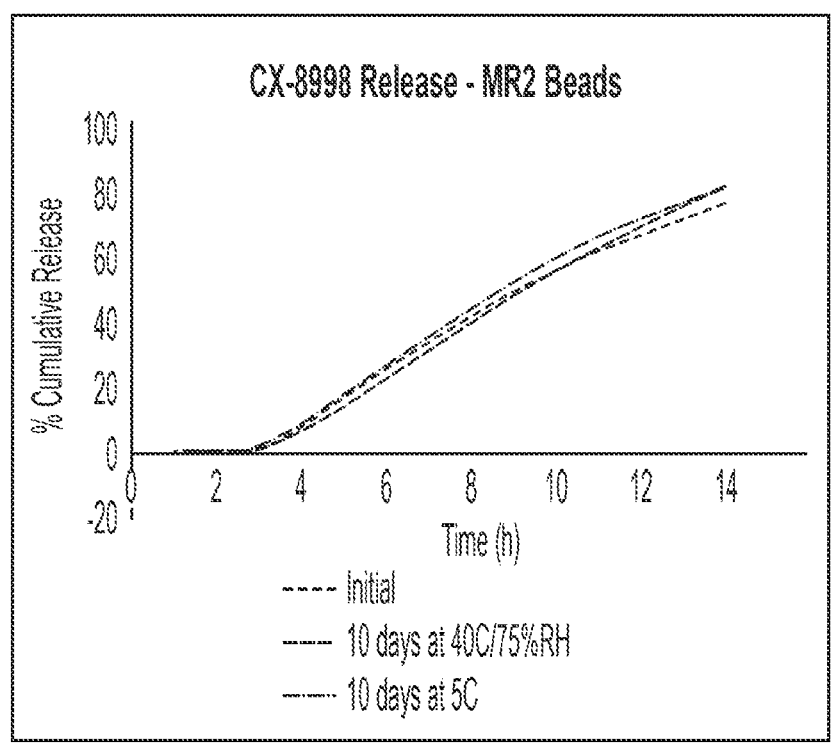

Bead formulations of Examples 27-29 were evaluated for dissolution. Dissolution rates of IR, MR1, and MR2 are shown in FIG. 56. Dissolution rates of IR, MR1, and MR2 after 10 days of storage at 40° C./75% RH or 10 days of storage at 5° C. are shown in FIG. 57.

Bead formulation dissolution rates were subjected to PK modeling. In vitro release profiles for IR, MR1, and MR2 beads were plugged into a PK model developed based on IR data. PK modeling for bead ratio and total dose was performed as separate 2-compartment models for elderly and non-elderly ("young") subjects. PK from different ratios of IR and MR1 and of IR and MR2 can be predicted. Total dose can be optimized based on a target for $C_{max}$, $C_{min}$, or $C_{ave}$.

Dissolution rates of IR and MR1 combinations in the elderly over a 7 day time course and at steady state are shown in FIG. 58. 60% IR/40% MR1 demonstrated quick uptake (low $t_{max}$) and blunted $C_{max}$.

Dissolution rates of IR and MR2/CR7 combinations in the elderly over a 7 day time course and at steady state are shown in FIG. 59. 60% IR/40% MR2/CR7 demonstrated quick uptake (low $t_{max}$), blunted $C_{max}$, and extended duration.

Dissolution rates of IR and MR1 combinations in the non-elderly over a 7 day time course and at steady state are shown in FIG. 60. 60% IR/40% MR1 demonstrated blunted $C_{max}$, but no improvement in duration of action over IR.

Dissolution rates of IR and MR2/CR7 combinations in the non-elderly over a 7 day time course and at steady state are shown in FIG. 61. 60% IR/40% MR2/CR7 demonstrated good ratios for non-elderly subjects.

Example 37. CX-8998 Combined Prototypes Formulation

A relative bioavailability study is used to confirm profiles between BID and QD (sustained release) are similar and achieve therapeutic minimums, and that BID and QD avoid maximum tolerated concentrations in target concentrations in ideal range for waking hours only.

Figure 62A:
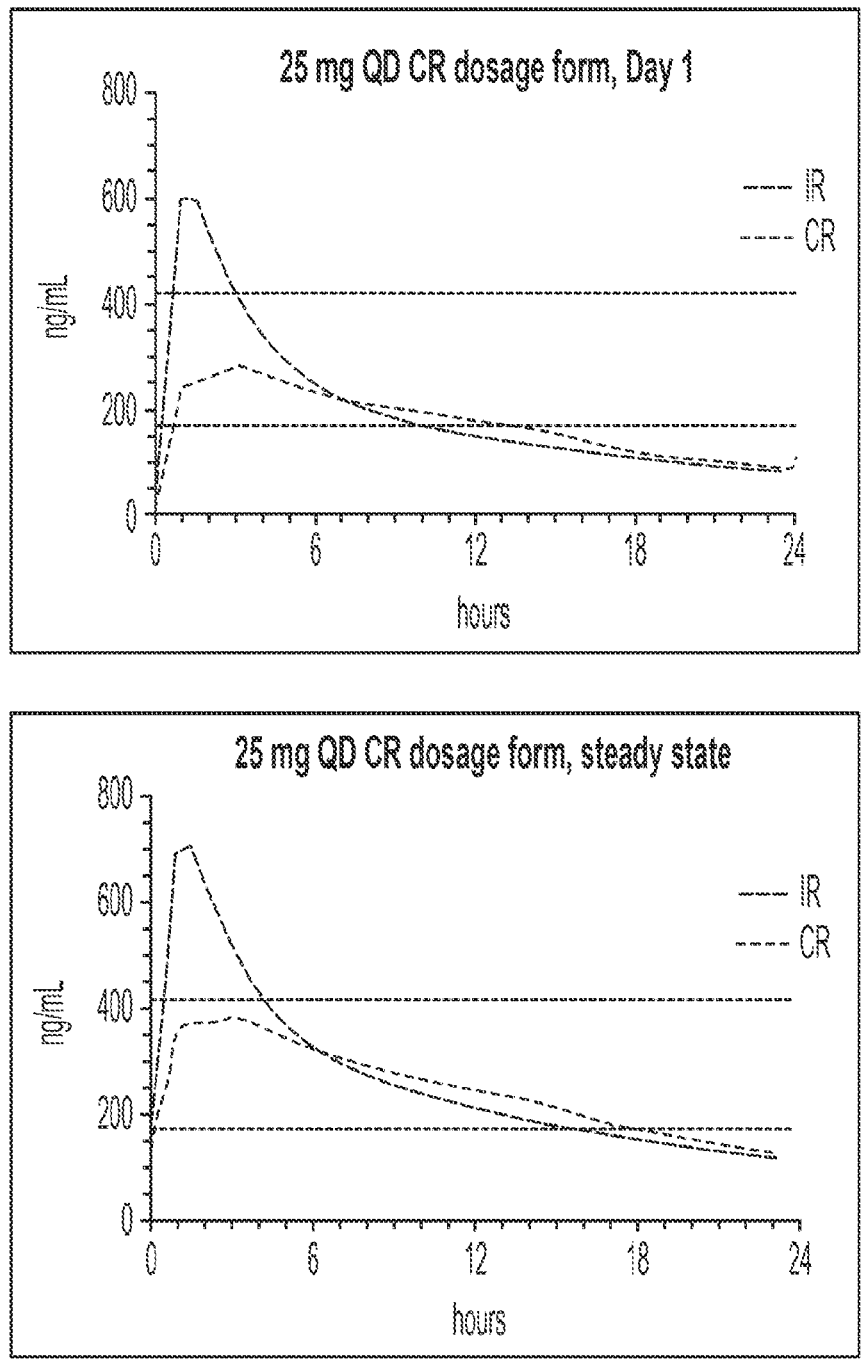
FIGS. 62A-62C contain graphs showing simulated dissolution rates of formulations having 40% IR, 25% MR1 (pH 6), and 35% MR2 (pH 7) at various dosage forms of 25 mg (FIG. 62A), 15 mg (FIG. 62B), and 8 mg (FIG. 62C).
Figure 62B:
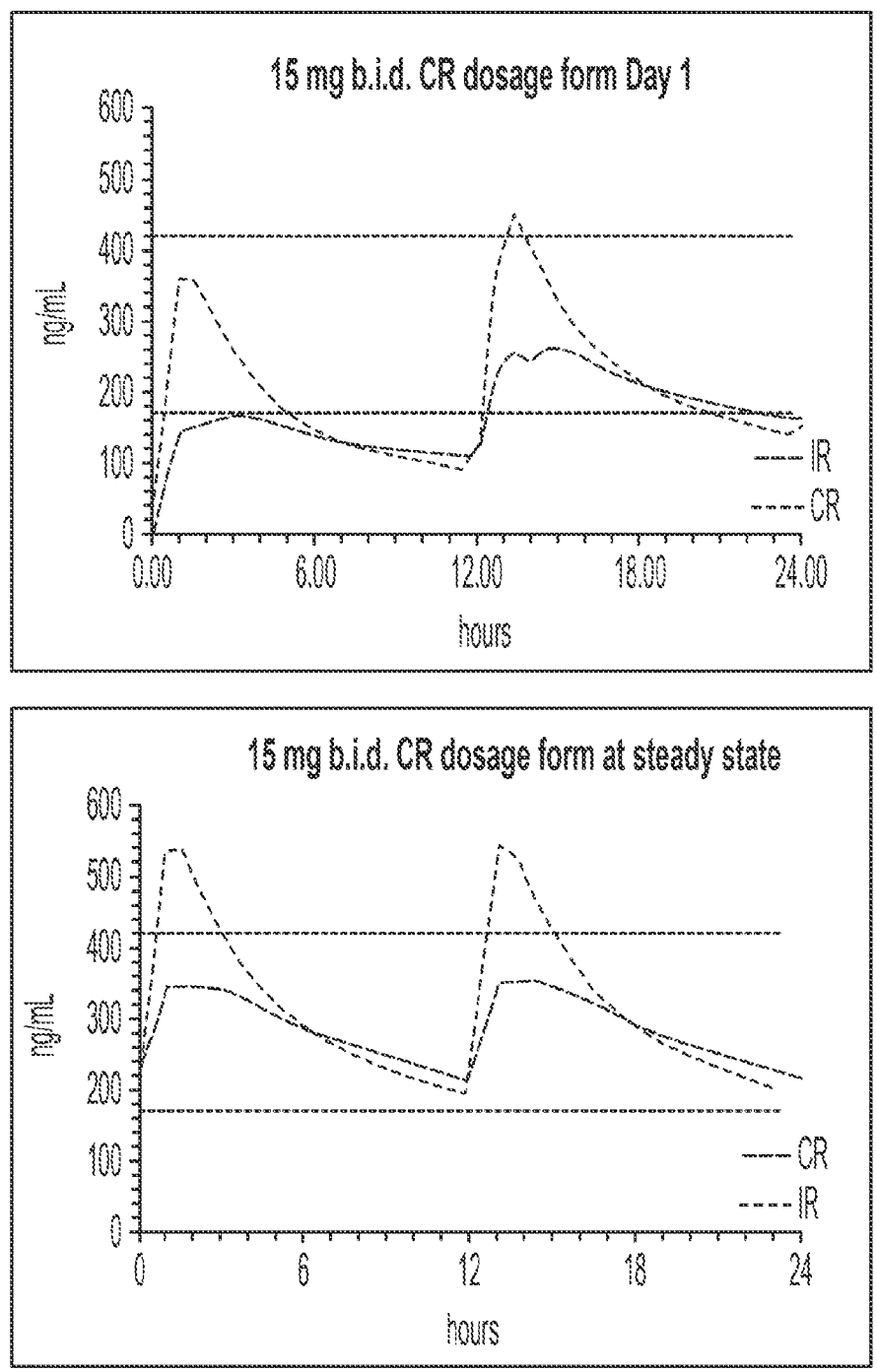
Figure 62C:
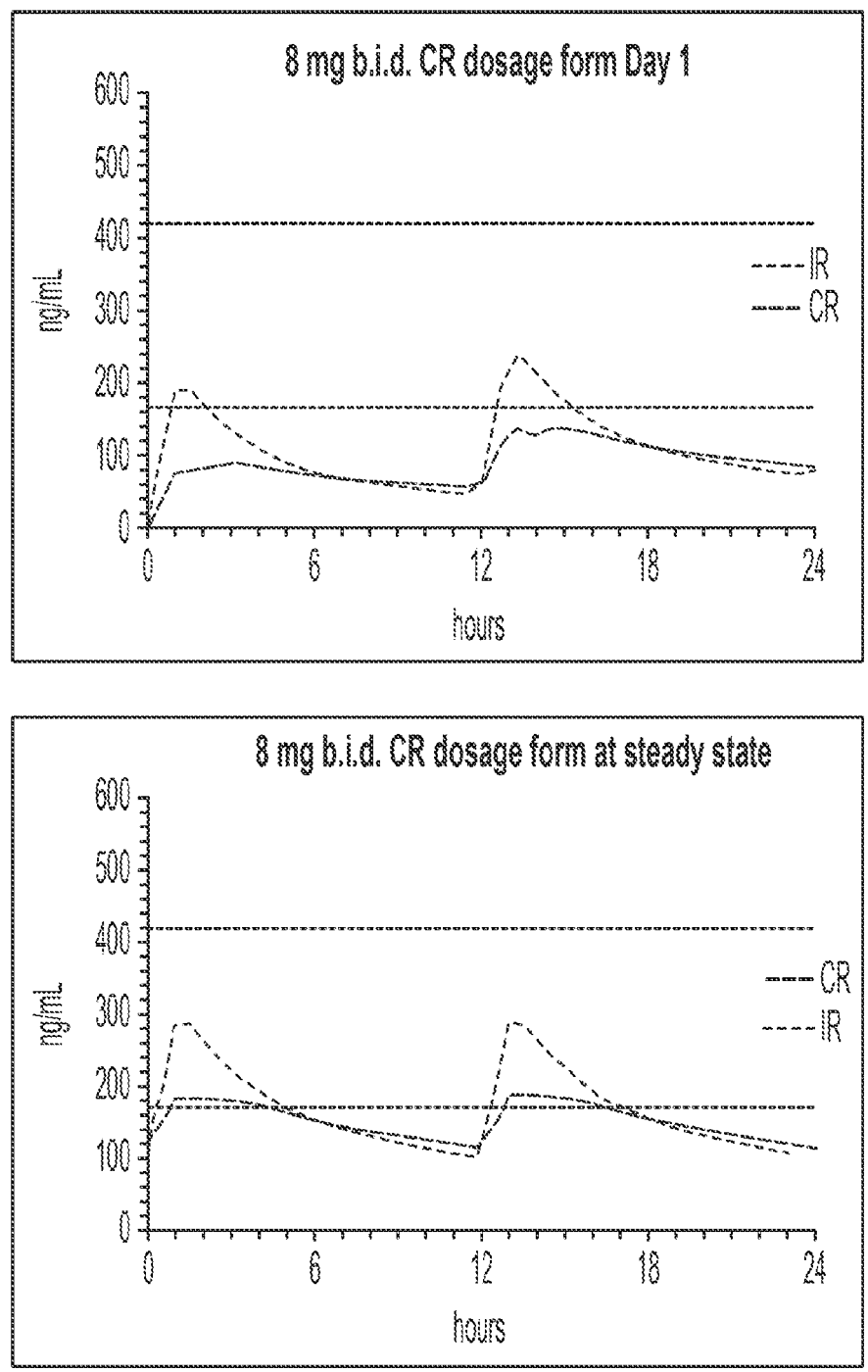

Simulations were performed using formulations having 40% IR, 25% MR1 (pH 6), and 35% MR2/CR7 (pH 7) at dosages of 25 mg, 15, mg, and 8 mg. Simulated dissolution rates of various dosage forms are shown in FIG. 62.

TABLE 42

$C_{max}$ of 25 mg QD Dosage Form

| | $C_{max}$ (ng/mL) | |
|---|---|---|
| dosage form | Day 1 | SS |
| IR | 614 | 719 |
| CR | 282 | 385 |

TABLE 43

$C_{max}$ of 15 mg QD Dosage Form

| | $C_{max}$ (ng/mL) | |
|---|---|---|
| dosage form | Day 1 | SS |
| IR | 453 | 550 |
| CR | 263 | 360 |

Example 38. Clinical Pharmacokinetics of CX-8998 Formulations

A bioavailability study was performed to evaluate the pharmacokinetics of various CX-8998 formulations in human subjects.

Methods

This is an open-label, single-dose, randomized, 3-way crossover, single-center study of the safety, tolerability, and PK of 2 CR test formulations, as compared with the original IR capsule formulation, in a maximum of 15 subjects. Subjects will be screened for study eligibility within 28 days before administration of the first dose of study drug. Subjects who meet the study eligibility criteria will be admitted to the clinical research unit in the afternoon of the day before administration of the first dose of study drug (Period 1/Day −1). Subjects who continue to meet the study eligibility criteria will be randomized to a treatment sequence and will receive single, 8 mg doses of each of the following CX-8998 treatments in randomized order, with each treatment separated from the previous one by a minimum 7-day washout period:

- Original IR capsule (4 capsules, each containing 2 mg CX-8998 under fasted conditions (Treatment A),
- CR test formulation #1 (multi-particulate capsule formulation containing 8 mg of CX-8998 in the form of IR and modified-release type 1 [MR1] beads) under fasted conditions (Treatment B), and
- CR test formulation #2 (multi-particulate capsule formulation containing 8 mg of CX-8998 in the form of IR and modified-release type 2 [MR2] beads) under fasted conditions (Treatment C).
- CR test formulation #2 (multi-particulate capsule formulation containing 8 mg of CX-8998 in the form of IR and modified-release type 2 [MR2] beads) under fed conditions (Treatment D).

Treatments A, B, and C will be separated by a minimum 7-day washout period. Subjects who receive Treatments A, B, and C may also receive an optional additional treatment consisting of CR test formulation #2 under fed conditions (Treatment D). Administration of Treatment D may be separated from administration of Treatments A, B, and C by approximately 4 weeks to allow for analysis of the bioanalytical samples from the first 3 treatments.

1 Treatments

The following is a list of the study treatment abbreviations and ordering that will be used in the TFLs.

| Study Treatment Name | Short name | Abbreviation | Treatment Order on TFLs |
|---|---|---|---|
| Original IR capsule, single 8 mg dose, fasted conditions | 8 mg CX-8998 IR (Fasted) | A | 1 |
| CR test formulation #1 (IR-MR1 beads), single 8 mg dose, fasted conditions | 8 mg CX-8998 IR-MR1 (Fasted) | B | 2 |
| CR test formulation #2 (IR-MR2 beads), single 8 mg dose, fasted conditions | 8 mg CX-8998 IR-MR2 (Fasted) | C | 3 |
| CR test formulation #2 (IR-MR2 beads), single 8 mg dose, fed conditions | 8 mg CX-8998 IR-MR2 (Fed) | D | 4 |

Abbreviations: CR = controlled release; IR = immediate release; MR1 = modified-release type 1; MR2 = modified-release type 2.

2 Sample Size Justification

In 2 previous single-dose PK studies, the average inter-subject coefficient of variation (CV %) following a 12 mg single dose of CX-8998 ranged from 21% to 35% for maximum observed plasma concentration ($C_{max}$) and from 22% to 26% for area under the curve (AUC) (Studies PN001/Part 1 and PN002/Part 2). Assuming that the intra-subject variability would be 18% (i.e., approximately 50% of the maximum CV % of 35%), a total of 13 subjects would be adequate to estimate the bioavailability of CX-8998 with >80% power, 5% probability, and p=1.0. A maximum of 15 subjects will be enrolled in the study.

Subjects who prematurely withdraw from the study for reasons other than treatment-related adverse events (TE-AEs) may be replaced, at the sponsor's discretion, to ensure that at least 13 subjects complete the study.

Results

A single dose, crossover clinical trial was conducted in 15 subjects ranging in age from 35-75 years. Demographic characteristics at baseline are shown in Table 44.

TABLE 44

Study Subject Demographics at Baseline

| Parameter | All Subjects N = 15 | Tremor POC N = 95 |
|---|---|---|
| Sex | | |
| Male | 6 (40%) | 50 (53%) |
| Female | 9 (60%) | 45 (47%) |
| Age | | |
| Mean (SD) | 53 (11.5) | 63 (10.2) |
| Median (min, max) | 51 (37, 70) | 66 (21, 75) |
| Race | | |
| Race 5 | 11 (73.3%) | 91 (96%) (white) |
| Race 3 | 3 (20%) | 4 (4%) (black) |
| Race 1 | 1 (6.7%) | |
| Ethnicity | | |
| Not Hispanic or Latino | 10 (66.7%) | 9 (98%) |
| Hispanic or Latino | 5 (33.3%) | 1 (1%) |
| Not Reported | 0 | 1 (1%) |
| Weight (kg) | | |
| Mean (SD) | 75.5 (11.1) | 86.8 (20.0) |
| Median (min, max) | 74.1 (55, 91.6) | 84.6 (49.3, 131.5) |
| Height (cm) | | |
| Mean (SD) | 166.7 (8.4) | 171.8 (10.4) |
| Median (min, max) | 167.5 (153.2, 180.8) | 172.7 (149.9, 193.0) |

Each subject received, in randomized order, an 8-mg dose of CX-8998, M01, or M02 immediate release capsules and each of the capsules of Example 30 (MR1 capsules) and Example 31 (MR2 capsules), with a 7 day washout period between doses.

Figure 63A:
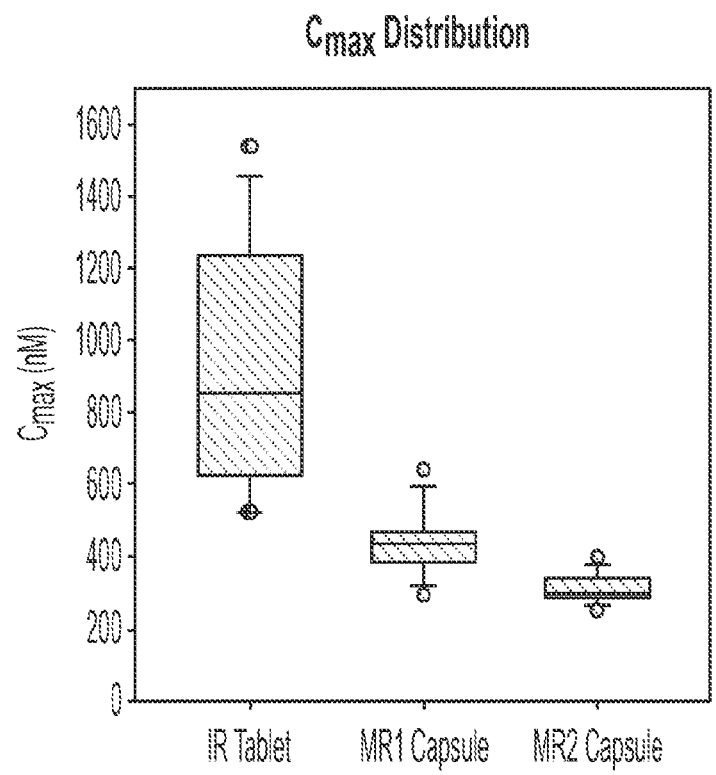
FIGS. 63A-63B contain graphs showing an exemplary distribution of $C_{max}$ (FIG. 63A) and $AUC_{0-72\,h}$ values (FIG. 63B) for CX-8998 following single-dose administration of CX-8998 (1×8 mg).
Figure 63B:
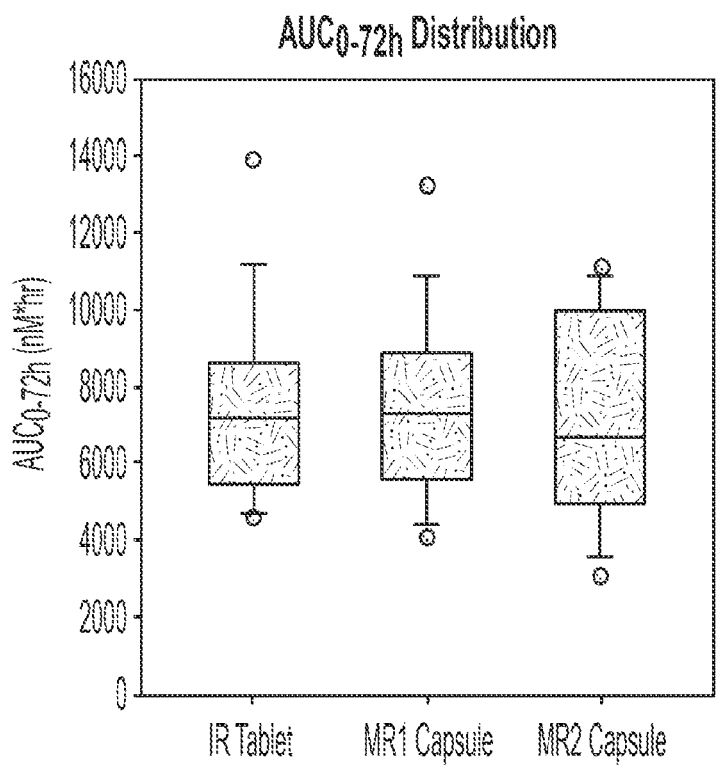
Figure 64A:
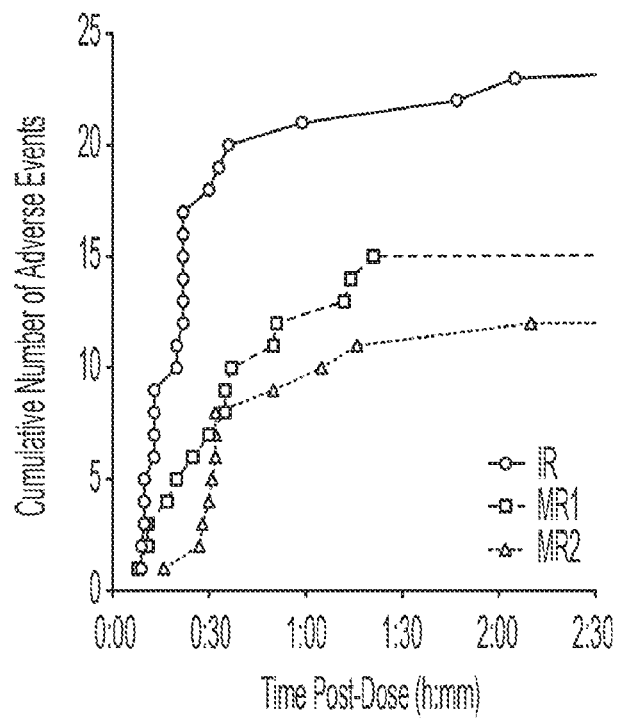
FIGS. 64A-64D contain graphs showing onset time (FIG. 64A), resolution time (FIG. 64B), duration time (FIG. 64C), and onset concentration (FIG. 64D) of adverse events following single-dose administration of CX-8998 (1×8 mg).
Figure 64B:
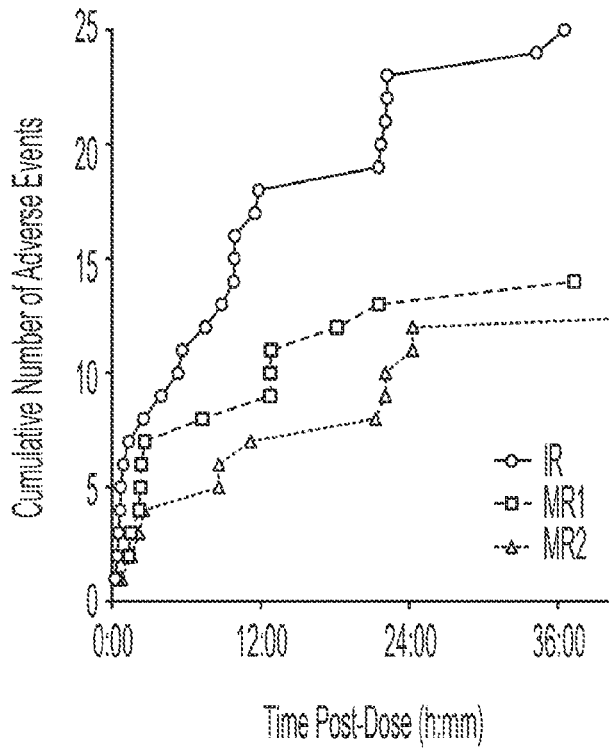
Figure 64C:
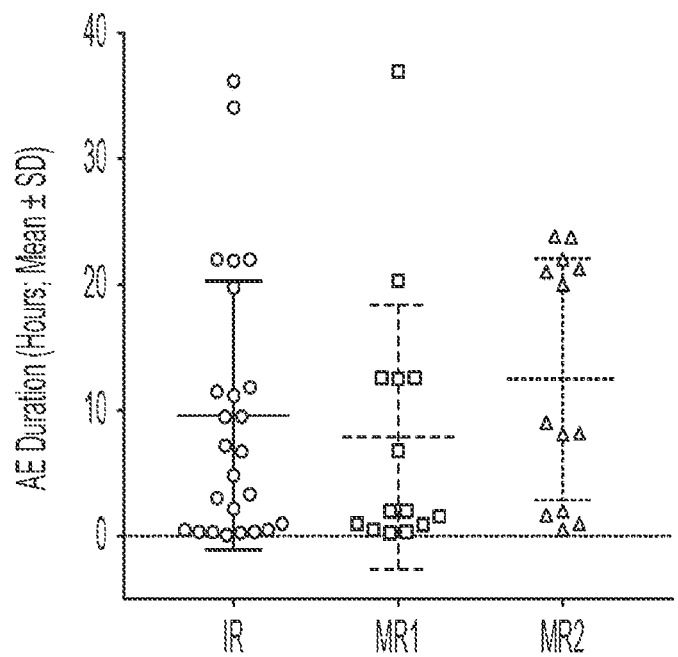
Figure 64D:
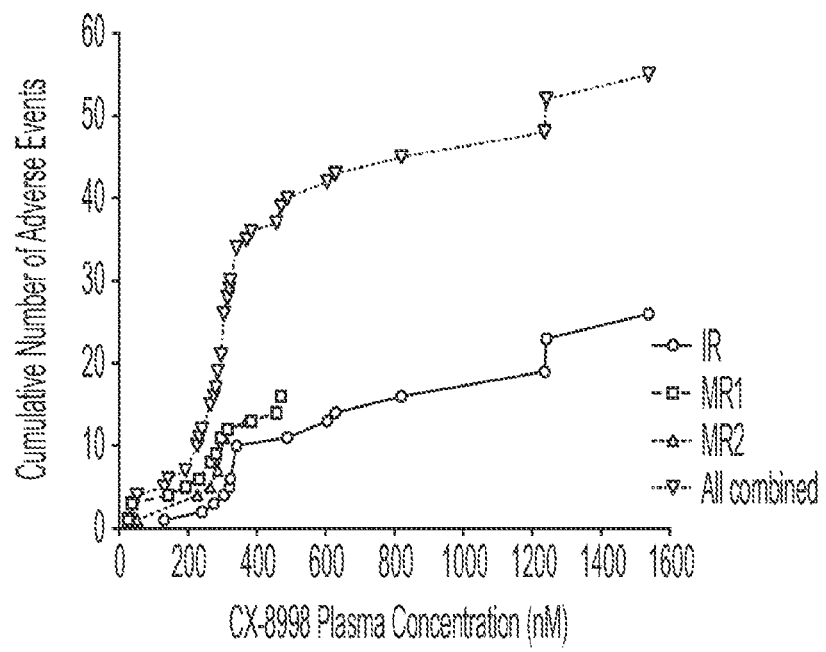

Compared to the immediate release dose, the CR capsules yielded lower $C_{max}$ values with similar AUC. Values for the pharmacokinetic parameters obtained from the study are provided in Tables 45-48 and in FIG. 63.

TABLE 45

PK parameters for CX-8998

| | IR Formulation | | | MR1 Formulation | | | MR2 Formulation | | |
|---|---|---|---|---|---|---|---|---|---|
| Subject No. | Cmax (nM) | Tmax (h) | $AUC_{728}$ (nMh) | Cmax (nM) | Tmax (h) | $AUC_{728}$ (nMh) | Cmax (nM) | Tmax (h) | $AUC_{728}$ (nMh) |
| 101 | 521 | 0.5 | 5185 | 423 | 1.0 | 5635 | 297 | 1.0 | 3085 |
| 102 | 875 | 1.0 | 8628 | 439 | 1.0 | 8950 | 316 | 1.5 | 10051 |
| 103 | 820 | 0.5 | 6910 | 471 | 1.0 | 7114 | 321 | 1.0 | 5947 |
| 104 | 528 | 1.5 | 9175 | 465 | 1.0 | 9494 | 397 | 4.0 | 11133 |
| 105 | 860 | 0.5 | 4786 | 350 | 1.0 | 4762 | 292 | 1.0 | 3862 |
| 106 | 1538 | 0.5 | 6911 | 565 | 1.0 | 7028 | 350 | 1.5 | 8064 |
| 107 | 1406 | 0.5 | 7288 | 468 | 0.5 | 7387 | 305 | 1.0 | 6813 |
| 108 | 626 | 1.0 | 4596 | 297 | 0.5 | 4102 | 305 | 0.5 | 4833 |
| 109 | 591 | 1.5 | 7940 | 355 | 1.5 | 8335 | 255 | 3.0 | 8180 |
| 110 | 712 | 1.5 | 13892 | 641 | 1.0 | 13265 | 342 | 1.5 | 10810 |
| 111 | 1236 | 0.5 | 7217 | 423 | 1.5 | 8177 | 287 | 1.0 | 6034 |
| 112 | 1241 | 0.5 | 7305 | 471 | 0.5 | 6271 | 371 | 1.0 | 6730 |
| 113 | 1138 | 1.0 | 9382 | 384 | 1.0 | 9351 | 371 | 1.0 | 10165 |
| 114 | 983 | 0.5 | 5463 | 460 | 0.5 | 5184 | 292 | 1.0 | 4975 |
| 115 | 668 | 1.5 | 6845 | 394 | 3.0 | 7996 | 281 | 1.5 | 6136 |
| N | 15 | 15 | 15 | 15 | 15 | 15 | 15 | 15 | 15 |
| Mean | 916 | 0.5 | 7435 | 440 | 1.0 | 7528 | 318 | 1.0 | 7119 |
| SD | 328 | | 2381 | 85 | | 2281 | 40 | | 2534 |
| CV % | 35.8 | | 31.2 | 19.3 | | 30.3 | 12.4 | | 35.6 |

Median value for Tmax

TABLE 46

PK parameters for M02

| Subject No. | IR Formulation | | | MR1 Formulation | | | MR2 Formulation | | |
|---|---|---|---|---|---|---|---|---|---|
| | Cmax (nM) | Tmax (h) | AUC$_{728}$ (nMh) | Cmax (nM) | Tmax (h) | AUC$_{728}$ (nMh) | Cmax (nM) | Tmax (h) | AUC$_{728}$ (nMh) |
| 101 | 129 | 12.8 | 5981 | 111 | 12.0 | 6045 | 94 | 12.0 | 3983 |
| 102 | 105 | 48.0 | 6690 | 121 | 24.0 | 7647 | 128 | 48.0 | 7566 |
| 103 | 97 | 48.0 | 5835 | 96 | 24.0 | 6019 | 79 | 48.0 | 4781 |
| 104 | 118 | 36.0 | 7642 | 101 | 36.0 | 6094 | 149 | 48.0 | 8555 |
| 105 | 131 | 1.0 | 6007 | 86 | 24.0 | 4807 | 70 | 24.0 | 4118 |
| 106 | 117 | 0.5 | 5438 | 124 | 24.0 | 7294 | 120 | 48.0 | 7276 |
| 107 | 156 | 24.0 | 8751 | 132 | 24.0 | 7802 | 110 | 48.0 | 6086 |
| 108 | 131 | 12.0 | 6138 | 109 | 16.0 | 5695 | 112 | 24.0 | 5822 |
| 109 | 86 | 48.0 | 5100 | 99 | 24.0 | 6098 | 98 | 48.0 | 5847 |
| 110 | 148 | 48.0 | 8547 | 220 | 48.0 | 13173 | 186 | 72.0 | 10232 |
| 111 | 122 | 48.0 | 7706 | 122 | 24.0 | 7221 | 90 | 24.0 | 5752 |
| 112 | 145 | 24.0 | 7677 | 135 | 24.0 | 7521 | 117 | 24.0 | 6720 |
| 113 | 116 | 24.0 | 6799 | 119 | 36.0 | 7063 | 131 | 24.0 | 7568 |
| 114 | 102 | 8.0 | 8093 | 99 | 24.0 | 5319 | 93 | 24.0 | 5124 |
| 115 | 127 | 24.0 | 7034 | 127 | 24.0 | 7161 | 95 | 48.0 | 5705 |
| N | 15 | 15 | 15 | 15 | 15 | 15 | 15 | 15 | 15 |
| Mean | 122 | 24 | 6829 | 120 | 24 | 6997 | 111 | 48 | 6342 |
| SD | 19 | | 1049 | 31 | | 1935 | 29 | | 3686 |
| CV % | 16.0 | | 15.4 | 26.0 | | 27.7 | | | 26.6 |

Median value for Tmax

TABLE 47

PK parameters for M01

| Subject No. | IR Formulation | | | MR1 Formulation | | | MR2 Formulation | | |
|---|---|---|---|---|---|---|---|---|---|
| | Cmax (nM) | Tmax (h) | AUC$_{728}$ (nMh) | Cmax (nM) | Tmax (h) | AUC$_{728}$ (nMh) | Cmax (nM) | Tmax (h) | AUC$_{728}$ (nMh) |
| 101 | 132 | 3.0 | 2281 | 85 | 8.0 | 1967 | 61 | 4.0 | 1102 |
| 102 | 133 | 4.0 | 4430 | 112 | 12.0 | 4769 | 69 | 12.0 | 3325 |
| 103 | 88 | 2.5 | 3890 | 90 | 6.0 | 3363 | 51 | 24.0 | 2684 |
| 104 | 87 | 8.0 | 4373 | 85 | 12.0 | 4278 | 104 | 16.0 | 5651 |
| 105 | 183 | 1.0 | 3920 | 82 | 4.0 | 3197 | 64 | 2.0 | 2343 |
| 106 | 159 | 2.0 | 3382 | 128 | 8.0 | 4048 | 77 | 12.0 | 3357 |
| 107 | 153 | 2.0 | 3778 | 57 | 1.0 | 2061 | 106 | 6.0 | 3173 |
| 108 | 129 | 3.0 | 2286 | 100 | 4.0 | 2661 | 70 | 12.0 | 2762 |
| 109 | 79 | 3.0 | 3831 | 71 | 24.0 | 3845 | 58 | 24.0 | 2897 |
| 110 | 104 | 24.0 | 6212 | 107 | 36.0 | 6557 | 81 | 48.0 | 4886 |
| 111 | 129 | 1.0 | 3674 | 89 | 12.0 | 3628 | 46 | 24.0 | 1901 |
| 112 | 87 | 8.0 | 2290 | 112 | 6.0 | 3347 | 92 | 8.0 | 3628 |
| 113 | 134 | 12.0 | 5553 | 104 | 12.0 | 5229 | 110 | 24.0 | 5126 |
| 114 | 127 | 2.0 | 3408 | 82 | 6.0 | 2362 | 77 | 12.0 | 2687 |
| 115 | 125 | 2.5 | 4126 | 98 | 24.0 | 4474 | 62 | 16.0 | 2996 |
| N | 15 | 15 | 15 | 15 | 15 | 15 | 15 | 15 | 15 |
| Mean | 123 | 3.0 | 3809 | 94 | 8.0 | 3719 | 75 | 32 | 3234 |
| SB | 30 | | 1102 | 18 | | 1247 | 20 | | 1208 |
| CV % | 23.9 | | 28.9 | 19.1 | | 33.5 | 26.7 | | 37.4 |

Median value for Tmax

TABLE 48

Bioavailability parameters for CX-8998 from MR1 and MR2 capsules

| Subject No. | MR1 | | MR2 | |
|---|---|---|---|---|
| | Cmax Ratio | AUC Ratio | Cmax Ratio | AUC Ratio |
| 101 | 0.813 | 1.09 | 0.57 | 0.60 |
| 102 | 0.502 | 1.04 | 0.35 | 1.16 |
| 103 | 0.574 | 1.03 | 0.39 | 0.86 |
| 104 | 0.881 | 1.02 | 0.75 | 1.21 |
| 105 | 0.407 | 0.99 | 0.34 | 0.81 |

TABLE 48-continued

Bioavailability parameters for CX-8998 from MR1 and MR2 capsules

| Subject No. | MR1 | | MR2 | |
|---|---|---|---|---|
| | Cmax Ratio | AUC Ratio | Cmax Ratio | AUC Ratio |
| 106 | 0.368 | 1.02 | 0.23 | 1.17 |
| 107 | 0.333 | 1.01 | 0.22 | 0.93 |
| 108 | 0.475 | 0.89 | 0.49 | 1.05 |
| 109 | 0.600 | 1.05 | 0.43 | 1.03 |
| 110 | 0.900 | 0.95 | 0.48 | 0.78 |
| 111 | 0.343 | 1.13 | 0.23 | 0.84 |
| 112 | 0.376 | 0.86 | 0.30 | 0.92 |
| 113 | 0.337 | 1.00 | 0.33 | 1.08 |
| 114 | 0.468 | 0.95 | 0.30 | 0.91 |
| 115 | 0.591 | 1.17 | 0.42 | 0.90 |
| N | 15 | 15 | 15 | 15 |
| Geometric Mean Ratio | 0.50 | 1.01 | 0.37 | 0.93 |
| Estimated 90% CI | [0.39, 0.61] | [0.97, 1.06] | [0.29, 0.45] | [0.84, 1.03] |

Adverse events following single-dose administration of CX-8998 were evaluated.

Treatment emergent adverse events, related to study drug, and observed in two or more subjects following a single 8 mg dose of CX-8998 are provided in Table 49 and in FIG. 64.

TABLE 49

Adverse Event observed in complete cohort (n =15).

| Adverse Event SOC PT | Any Treatment N = 15 | Original IR N = 15 | MR1* N = 15 | MR2** N = 15 |
|---|---|---|---|---|
| Any | 11 (73%) | 8 (53%) | 7 (47%) | 4 (27%) |
| Nervous System | 10 (67%) | 6 (40%) | 7 (47%) | 4 (27%) |
| Paresthesias | 7 (47%) | 6 (40%) | 4 (27%) | 3 (20%) |
| Dizziness | 5 (33%) | 3 (20%) | 5 (33%) | 3 (20%) |
| Headache | 5(33%) | 3 (20%) | 2 (13%) | 2 (13%) |
| Feeling abnormal | 4 (27%) | 3 (20%) | 0 | 1 (7%) |
| Psychiatric | 5 (33%) | 4 (27%) | 2 (13%) | 1 (7%) |
| Abnormal dreams | 3 (20%) | 2 (13%) | 1 (7%) | 0 |
| Euphoric mood | 2 (13%) | 2 (13%) | 1 (7%) | 1 (7%) |

Figure 65:
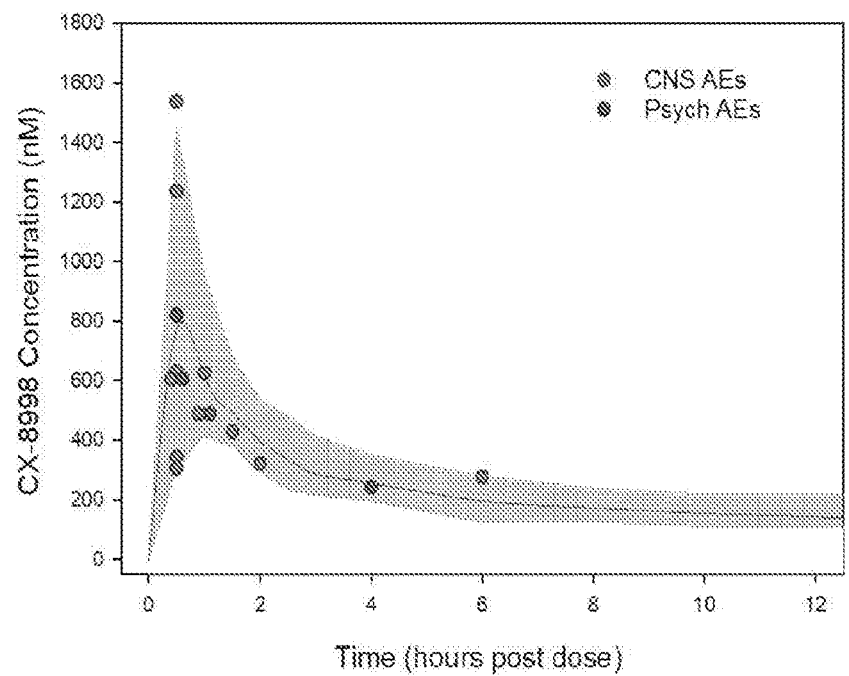
FIG. 65 contains a graph showing a PK profile of single-dose administration of IR CX-8998 (1×8 mg) in contrast with CNS and psychiatric adverse events concentrations. The shaded area represents the $5^{th}$-$95^{th}$ percentiles.
Figure 66:
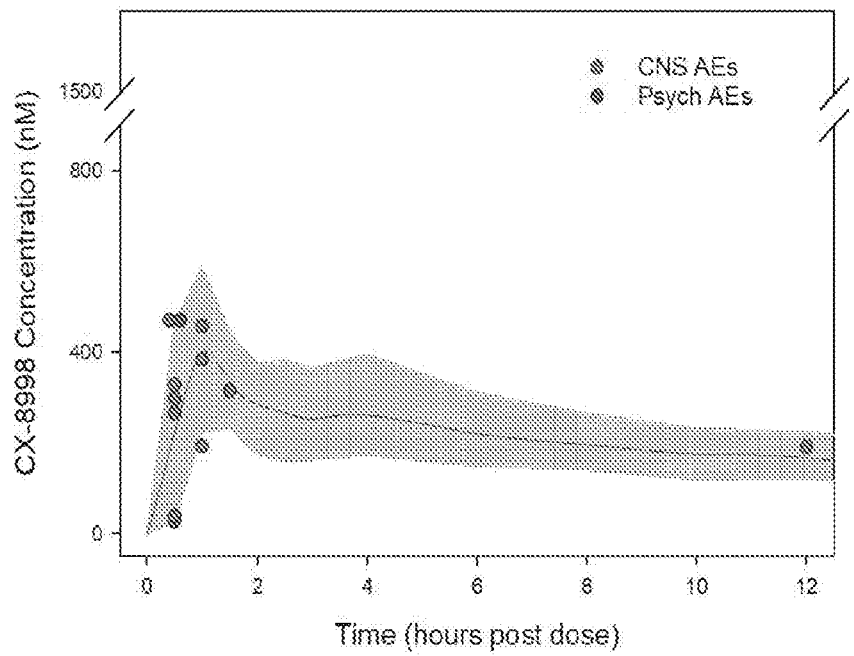
FIG. 66 contains a graph showing a PK profile of single-dose administration of MR1 CX-8998 (1×8 mg) in contrast with CNS and psychiatric adverse events concentrations. The shaded area represents the $5^{th}$-$95^{th}$ percentiles.
Figure 67:
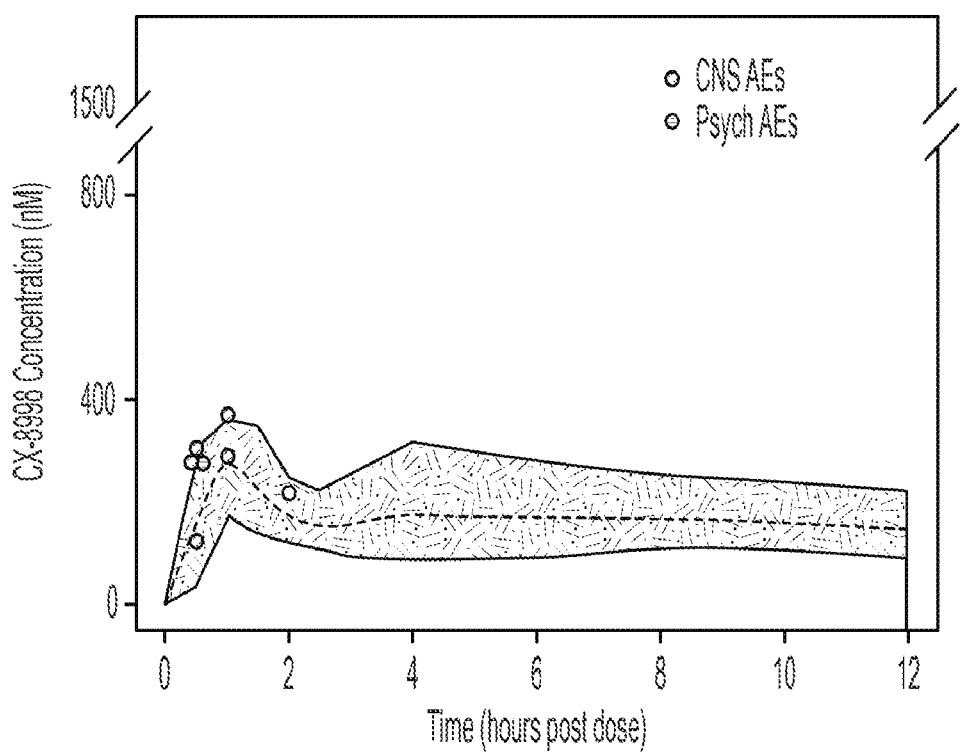
FIG. 67 contains a graph showing a PK profile of single-dose administration of MR2 CX-8998 (1×8 mg) in contrast with CNS and psychiatric adverse events concentrations. The shaded area represents the $5^{th}$-$95^{th}$ percentiles.
Figure 68:
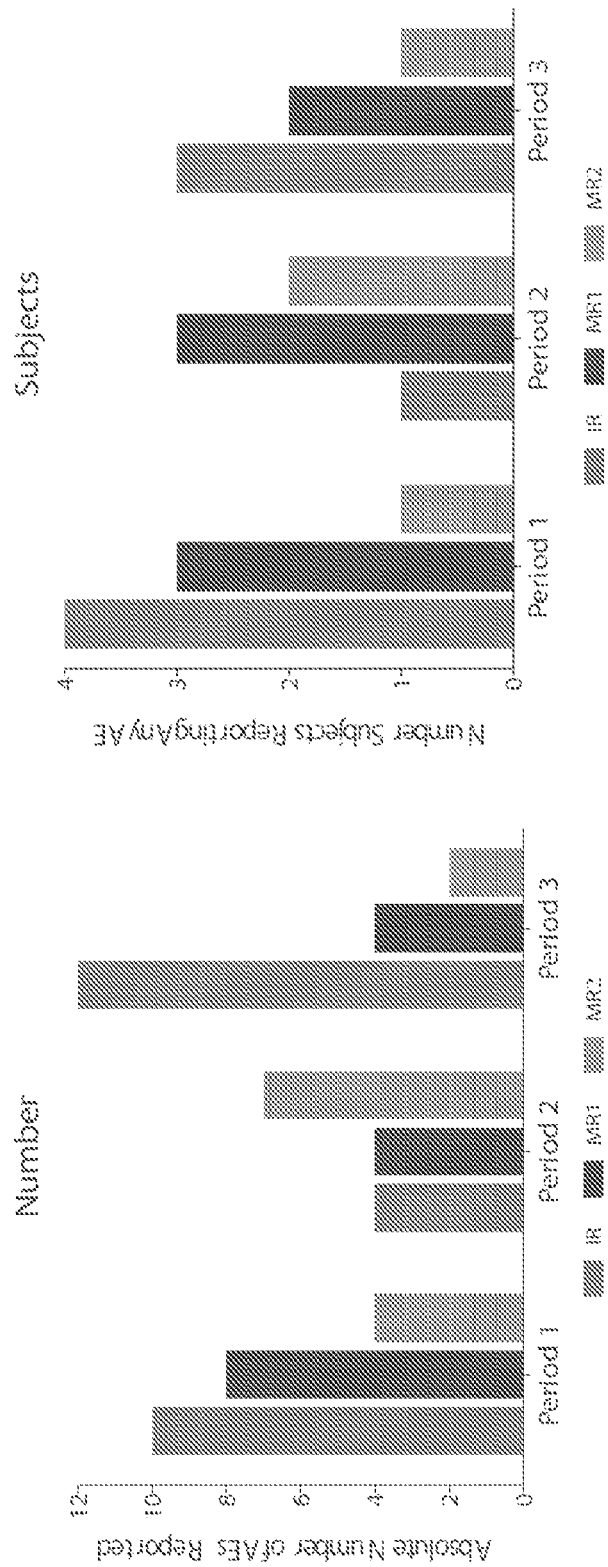
FIG. 68 contains graphs showing adverse events by treatment period.
Figure 69:
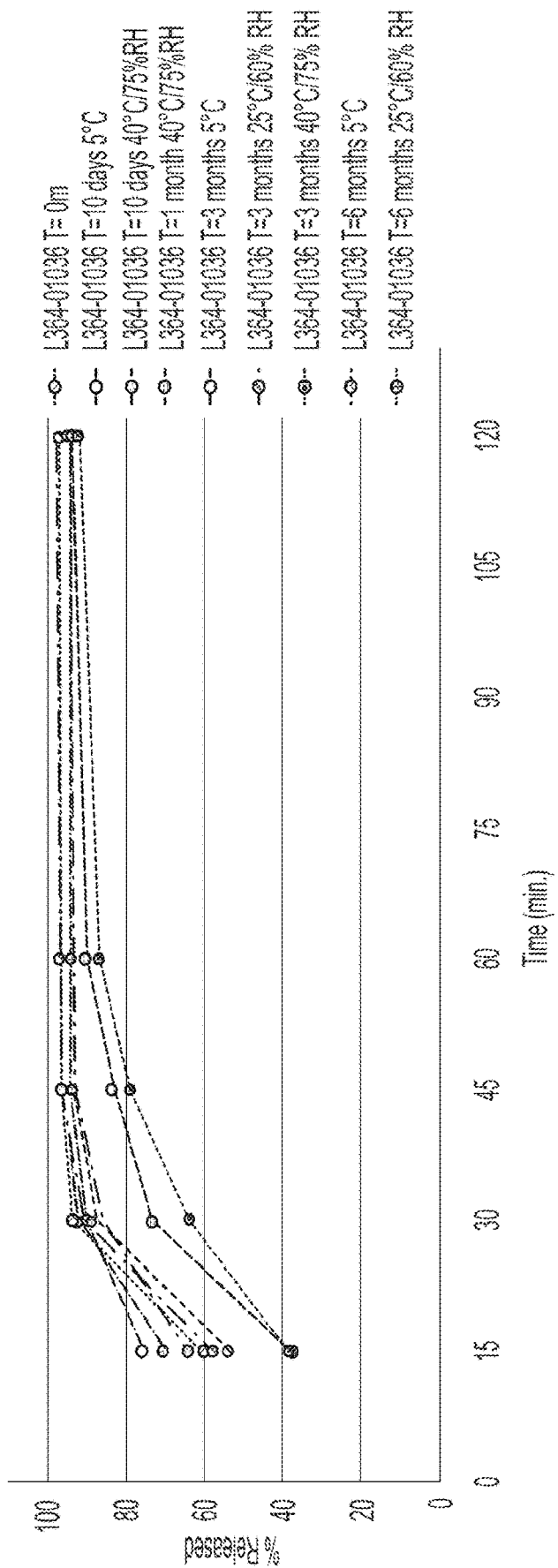
FIG. 69 contains a graphs showing an exemplary dissolution profile of IR CX-8998 beads from lot L364-01036.
Figure 70:
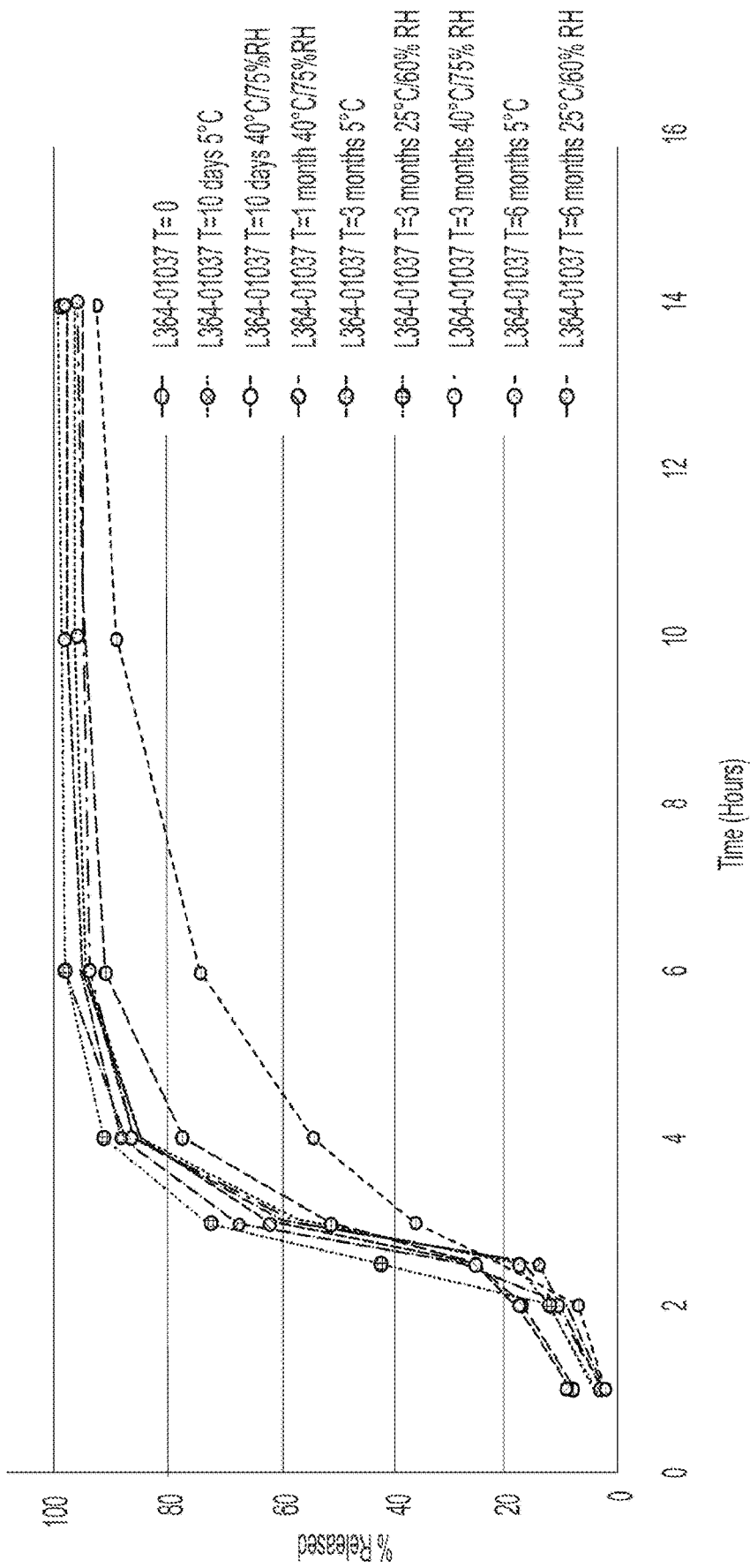
FIG. 70 contains a graphs showing an exemplary dissolution profile of CR (pH 6) CX-8998 beads from lot L364-01037.
Figure 71:
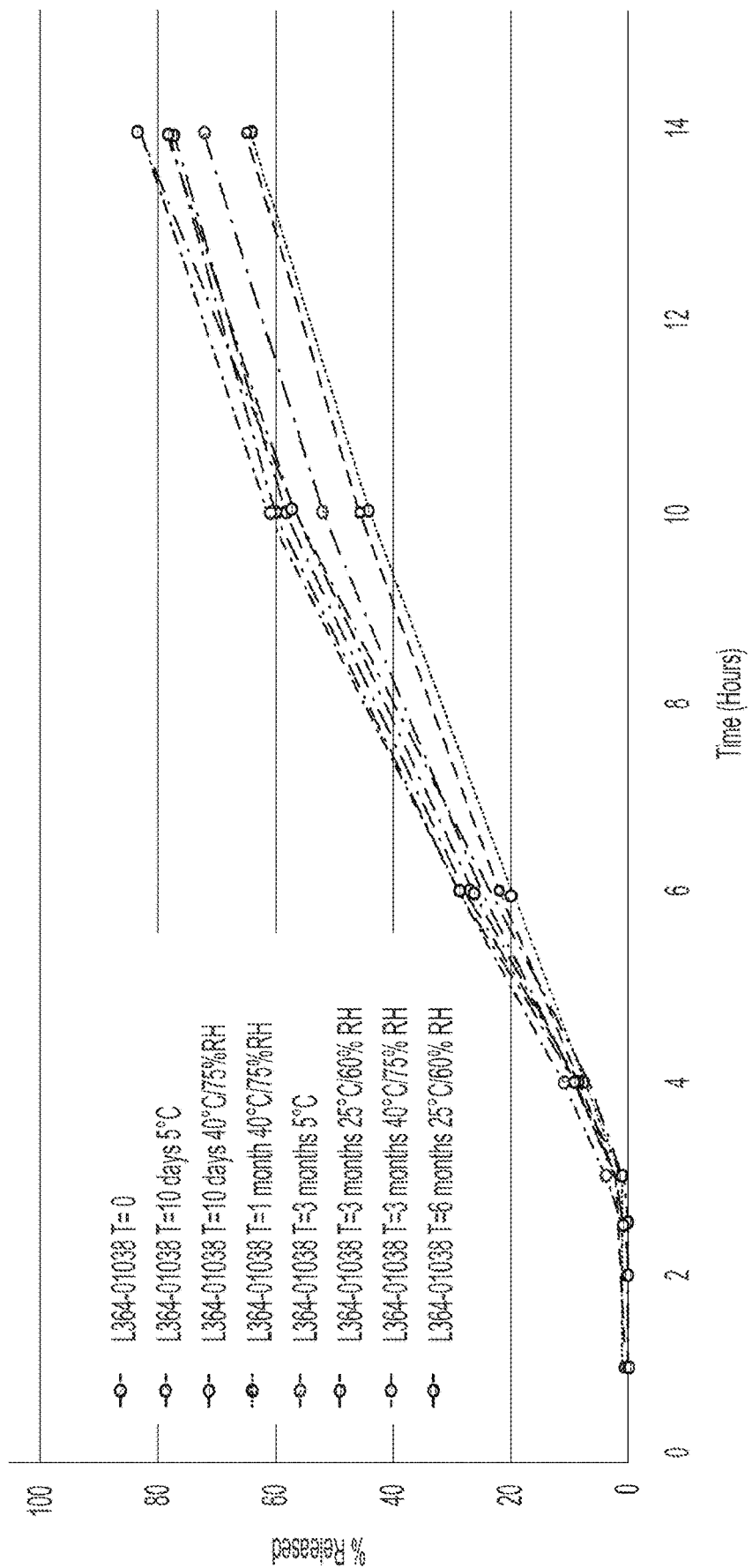
FIG. 71 contains a graphs showing an exemplary dissolution profile of CR (pH 7) CX-8998 beads from lot L364-01038.

*Modified release prototype formulation 1 (MRI for BID): 60% IR beads, 40% CR (pH 6) beads, single capsule, designed to achieve 25% reduction of $C_{max}$ relative to IR and 8 hours coverage above threshold
Modified release prototype formulation 2 (MR2 for QD): 40% IR beads, 60% CR (pH 7) beads, single capsule, designed to achieve 45% reduction in $C_{max}$ and 12-16 hours coverage above threshold Adverse events in view of the pharmacokinetics of CX-8998 are shown in FIGS. 66-68. For IR formulations, CNS adverse events and psychiatric adverse events generally occurred within 2-hours of dosing, and many CNS adverse events were associated with concentrations at or below the average concentration of CX-8998 (FIG. 65). For MR1 formulations, CNS adverse events and psychiatric adverse events generally occurred within 2-hours of dosing at CX-8998 concentrations generally lower than those observed with the IR formulation, suggesting that the threshold concentration for producing CNS adverse events and psychiatric adverse events is below 400 nM (FIG. 66). For MR2 formulations, CNS adverse events and psychiatric adverse events generally occurred within 2-hours of dosing at CX-8998 peak concentrations below 400 nM (FIG. 67**).

Adverse events in view of the treatment period of CX-8998 are shown in FIG. 68. There was no clear evidence of a period effect.

Figure 72A:
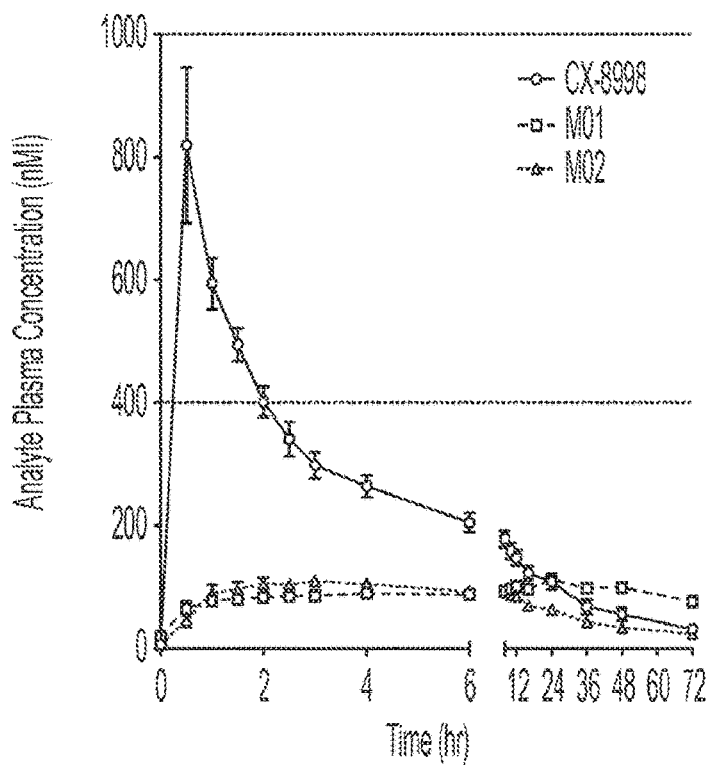
FIGS. 72A-72C contain graphs showing plasma concentrations of CX-8998, metabolite M01, and metabolite M02 following single-dose administration of IR CX-8998 (FIG. 72A), MR1 CX-8998 (FIG. 72B), or MR2 CX-8998 (FIG. 72C).
Figure 72B:
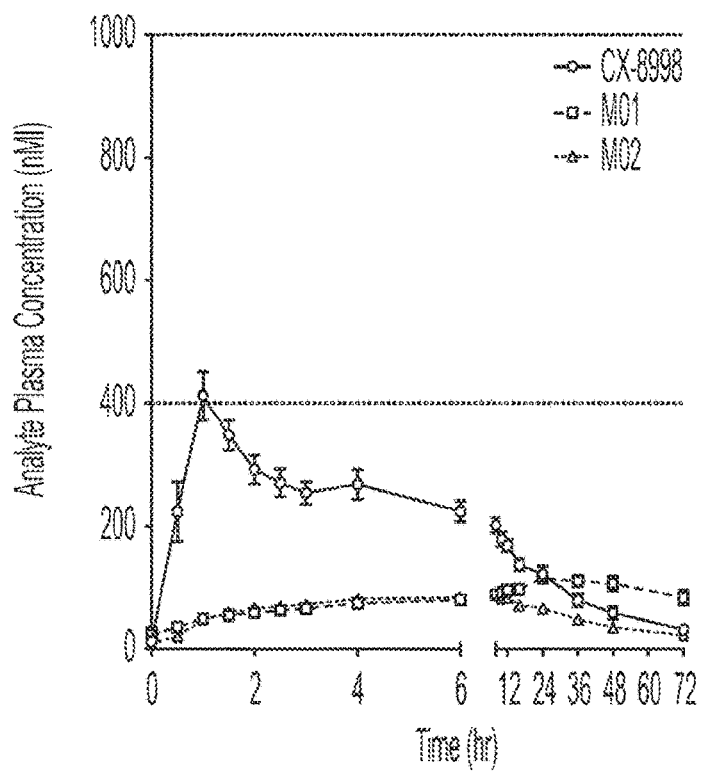
Figure 72C:
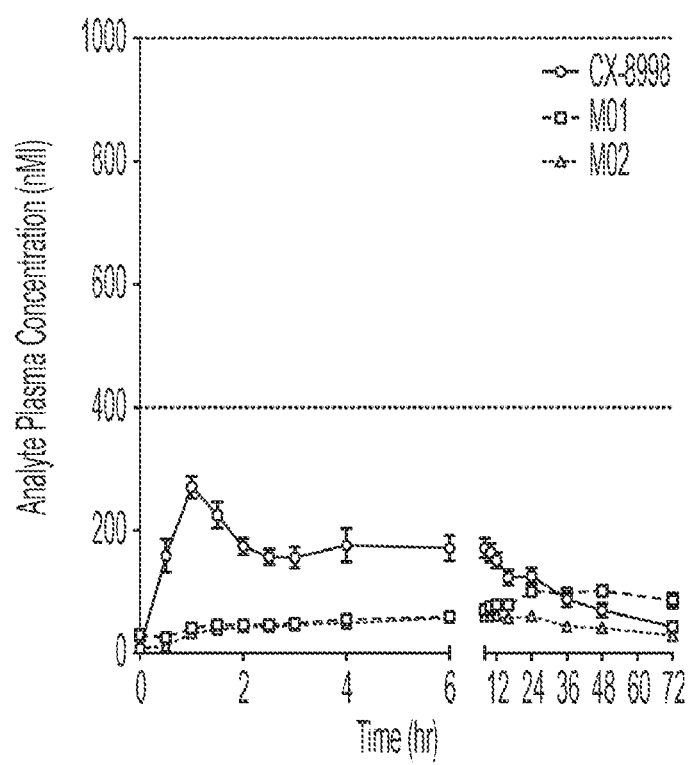
Figure 73A:
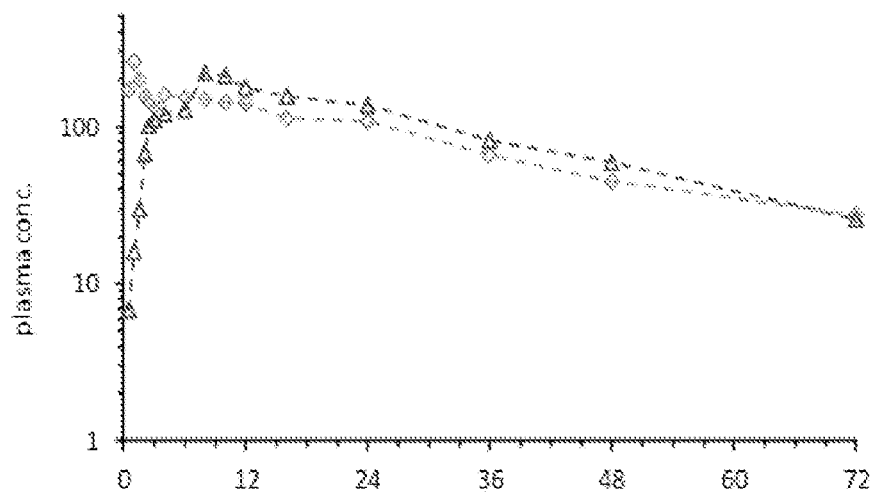
FIGS. 73A-73B contains a graph showing plasma concentrations of CX-8998 over time (in hours) in fasted versus fed patients on average (FIG. 73A) and for individual patients (FIG. 73B) where diamonds represent fasted state samples and triangles represent fed state samples.
Figure 73B:
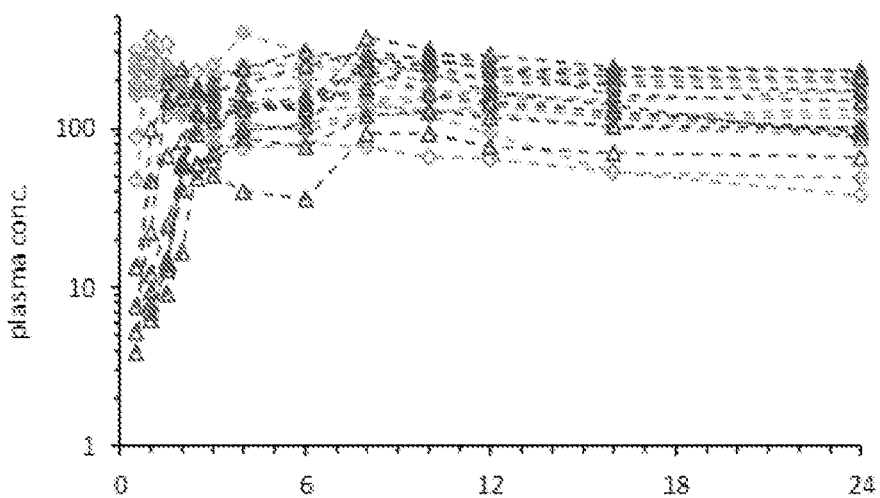

Plasma concentrations of CX-8998, metabolite M01, and metabolite M02 following administration of a single dose (1×8 mg) IR CX-8998, MR1 CX-8998, or MR2 CX-8998 were evaluated. Data are shown in Tables 50-52 and FIG. 72. No impact of formulation was seen on the AUC Ratio. $C_{max}$ effects were consistent with reduced parent.

TABLE 50

Metabolite M01 and M02 Concentrations Following a Single 8 mg Dose of IRCX-8998

| IR | CX-8998 | M01 | | M02 | |
|---|---|---|---|---|---|
| | | Value | Ratio | Value | Ratio |
| $T_{max}$ (hr) | 1.0 | 29 | — | 5 | — |
| $C_{max}$ (nM) | 913 | 124 | 0.14 | 122 | 0.13 |
| $AUC_{72hr}$ | 7486 | 6876 | 0.92 | 3671 | 0.49 |

TABLE 51

Metabolite M01 and M02 Concentrations Following a Single 8 mg Dose of MR1 CX-8998

| MR1 | CX-8998 | M01 | | M02 | |
|---|---|---|---|---|---|
| | | Value | Ratio | Value | Ratio |
| $T_{max}$ (hr) | 1.0 | 26 | — | 11 | — |
| $C_{max}$ (nM) | 447 | 121 | 0.27 | 94 | 0.21 |
| $AUC_{72hr}$ | 7530 | 7118 | 0.95 | 3343 | 0.44 |

TABLE 52

Metabolite M01 and M02 Concentrations Following a Single 8 mg Dose of MR2 CX-8998

| MR2 | CX-8998 | M01 | | M02 | |
|---|---|---|---|---|---|
| | | Value | Ratio | Value | Ratio |
| $T_{max}$ (hr) | 1.5 | 39 | — | 16 | — |
| $C_{max}$ (nM) | 319 | 113 | 0.35 | 73 | 0.23 |
| $AUC_{72hr}$ | 7125 | 6395 | 0.90 | 3142 | 0.44 |

Example 39. Clinical Pharmacokinetics of CX-8998 Formulations in Fed Versus Fasted Human Subjects A bioavailability study was performed to evaluate the pharmacokinetics of CX-8998 formulations in human subjects that were in a fed state compared to the pharmacokinetics of CX-8998 formulations in human subjects that were in a fasted state.

Methods

The methods were performed as described in Example 38, Treatment D.

Results

Plasma concentrations of CX-8998 following administration of a single dose (1×8 mg) of MR2 CX-8998 were evaluated. Data are shown in Table 53 and FIGS. 74 and 75. The p-values listed in Table 53 are for a 2-tailed t-test.

TABLE 53

Pharmacokinetics of CX-8998 formulations

| | AUC | $C_{max}$ | $t_{max}$ |
|---|---|---|---|
| fasted | 6786 | 315 | 1.3 |
| fed | 7570 | 254 | 8.9 |
| p-value | 0.61 | 0.12 | 0.00000005 |

Whether the patient is administered the CX-8998 in a fed state or a fasted state impacts early absorption of the CX-8998, but does not appear to significantly impact late absorption. The fed state of the patient when taking CX-8998 does not appear to significantly impact overall exposure of CX-8998 as measured by AUC.

Example 40. Exemplary Embodiments

Embodiment 1. An oral dosage form comprising:
an immediate release component comprising from about 2 mg to about 20 mg of a compound having the structure

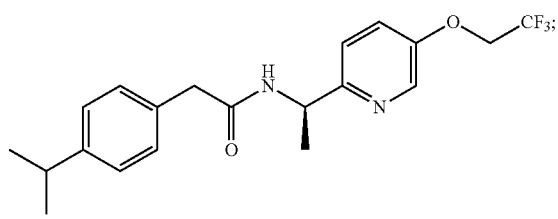 [SMILES: CC(C)c1ccc(CC(=O)N[C@H](C)c2ccc(OCC(F)(F)F)cn2)cc1]

a delayed release component comprising from about 2 mg to about 20 mg of said compound or a metabolite thereof.

Embodiment 2. The oral dosage form of claim 1, said oral dosage form further comprising one or more metabolites of said compound, wherein said metabolites are selected from the group consisting of

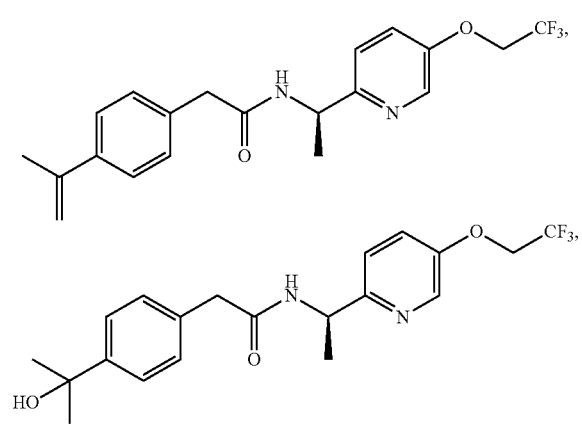

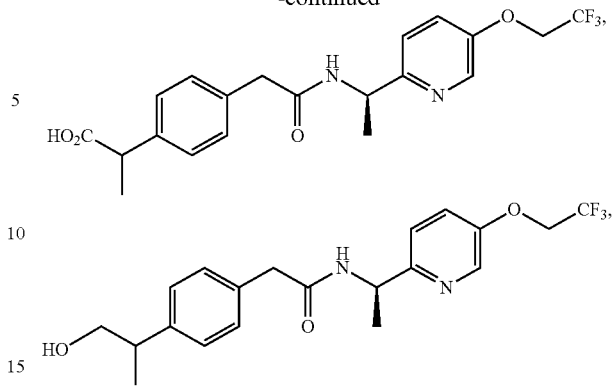

and combinations thereof.

Embodiment 3. The oral dosage form of Embodiment 1 of Embodiment 2, wherein said oral dosage form comprises a capsule, and wherein said immediate release component and said delayed release component are contained within said capsule.

Embodiment 4. The oral dosage form of Embodiment 3, wherein said capsule is a gelatin capsule.

Embodiment 5. The oral dosage form of Embodiment 4, wherein said gelatin capsule is a hard gelatin capsule.

Embodiment 6. The oral dosage form of any one of Embodiment 3 to Embodiment 5, wherein said capsule is a size 4 capsule.

Embodiment 7. The oral dosage form of any one of Embodiment 1 to Embodiment 6, wherein said immediate release component is in the form of a plurality of beads.

Embodiment 8. The oral dosage form of Embodiment 7, wherein said beads further comprise lactose monohydrate, crospovidone, citric acid, and sodium lauryl sulfate.

Embodiment 9. The oral dosage form of Embodiment 8, wherein said beads comprise, by weight, about 5% of said compound, about 60% lactose monohydrate, about 25% crospovidone, about 8% citric acid, and about 2% sodium lauryl sulfate.

Embodiment 10. The oral dosage form of any one of Embodiment 7 to Embodiment 9, wherein said beads are formed by extrusion and spheronization.

Embodiment 11. The oral dosage form of any one of Embodiment 1 to Embodiment 10, wherein said delayed release component is in the form of a plurality of beads coated with an enteric polymer having a pH of pH 5.5.

Embodiment 12. The oral dosage form of Embodiment 11, wherein said beads further comprise lactose monohydrate, crospovidone, citric acid, and sodium lauryl sulfate.

Embodiment 13. The oral dosage form of Embodiment 12, wherein said beads comprise, by weight, about 5% of said compound, about 60% lactose monohydrate, about 25% crospovidone, about 8% citric acid, and about 2% sodium lauryl sulfate.

Embodiment 14. The oral dosage form of any one of Embodiment 11 to Embodiment 13, wherein said beads are formed by extrusion and spheronization and film coated using a fluidized bed spray coating process.

Embodiment 15. The oral dosage form of any one of Embodiment 1 to Embodiment 14, wherein said immediate release component comprises about 10 mg of said compound, and wherein said delayed release component comprises about 10 mg of said compound.

Embodiment 16. The oral dosage form of any one of Embodiment 1 to Embodiment 14, wherein said immediate release component comprises about 7 mg of said compound, and wherein said delayed release component comprises about 13 mg of said compound.

Embodiment 17. The oral dosage form of any one of Embodiment 1 to Embodiment 16, wherein said immediate release component is formulated to release, when delivered to a human, at least 80% of said compound present in the immediate release component within 45 minutes.

Embodiment 18. The oral dosage form of any one of Embodiment 1 to Embodiment 17, wherein said delayed release component is formulated to provide, when delivered to a human, a minimum plasma level of from about 100 nM to about 300 nM of said compound.

Embodiment 19. The oral dosage form of Embodiment 18, wherein said minimum plasma level of said compound is maintained for about 12 hours.

Embodiment 20. The oral dosage form of Embodiment 18, wherein said minimum plasma level of said compound is maintained for about 24 hours.

Embodiment 21. The oral dosage form of any one of Embodiment 18 to Embodiment 20, wherein said minimum plasma level of said compound is about 200 nM.

Embodiment 22. The oral dosage form of any one of Embodiment 1 to Embodiment 21, wherein said delayed release component is formulated to provide, when delivered to a human, a maximum plasma level of from about 900 nM to about 1800 nM of said compound.

Embodiment 23. The oral dosage form of Embodiment 21, wherein said maximum plasma level of said compound is about 900 nM.

Embodiment 24. The oral dosage form of Embodiment 21, wherein said maximum plasma level of said compound is about 1000 nM.

Embodiment 25. A method of treating a human having a movement disorder, said method comprising:
administering to said human an oral dosage form, said oral dosage form comprising:
an immediate release component comprising from about 2 mg to about 16 mg of a compound having the structure

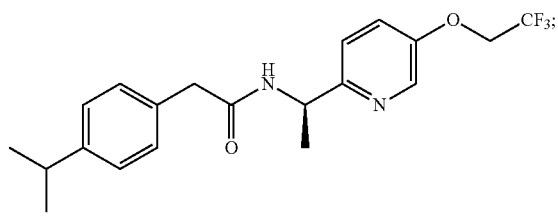 [SMILES: CC(C)c1ccc(CC(=O)N[C@H](C)c2ccc(OCC(F)(F)F)cn2)cc1]

a delayed release component comprising from about 2 mg to about 16 mg of said compound;
wherein said oral dosage form is administered once daily.

Embodiment 26. The method of Embodiment 25, said oral dosage form further comprising one or more metabolites of said compound, wherein said metabolites are selected from the group consisting of

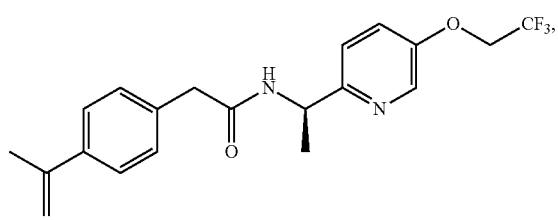

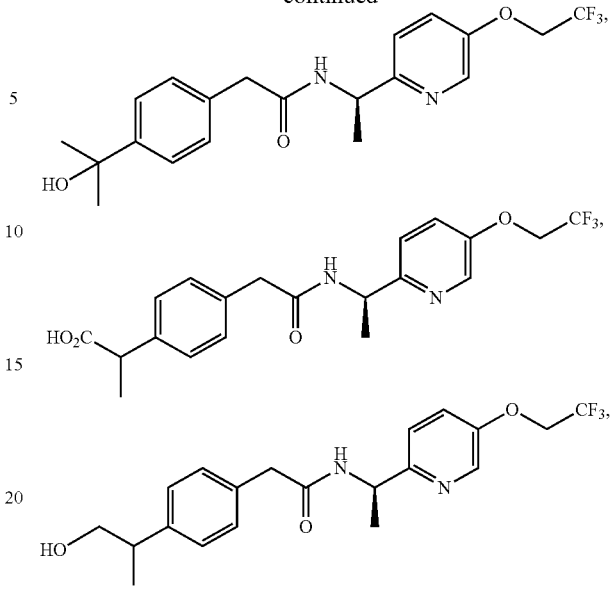

and combinations thereof.

Embodiment 27. The method of Embodiment 25 or Embodiment 26, wherein said human is an adult.

Embodiment 28. The method of Embodiment 27, wherein said adult is 60 years of age or older.

Embodiment 29. The method of any one of Embodiment 25 to Embodiment 28, wherein said movement disorder is essential tremor.

Embodiment 30. The method of any one of Embodiment 25 to Embodiment 28, wherein said movement disorder is Parkinson's disease.

Embodiment 31. The method of any one of Embodiment 25 to Embodiment 30, wherein said oral dosage form is administered in the morning.

Embodiment 32. The method of any one of Embodiment 25 to Embodiment 31, wherein said oral dosage form is administered within 4 hours of waking.

Embodiment 33. The method of any one of Embodiment 25 to Embodiment 32, wherein said delayed release component of said oral dosage form is formulated to release said compound within said delayed release component at an intestinal pH.

Embodiment 34. The method of any one of Embodiment 25 to Embodiment 33, wherein said human has fasted for at least 4 hours prior to administering said oral dosage form.

Embodiment 35. The method of any one of Embodiment 25 to Embodiment 34, wherein said compound is effective to reduce or eliminate one or more symptoms of the movement disorder.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. An oral dosage form comprising a Cav3 antagonist, wherein the Cav3 antagonist is CX-8998

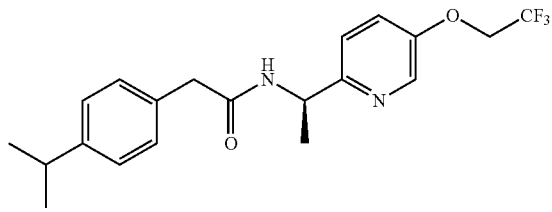 [SMILES: CC(C)c1ccc(CC(=O)N[C@H](C)c2ccc(OCC(F)(F)F)cn2)cc1]

or a pharmaceutically acceptable salt thereof,
wherein the oral dosage forms comprises a controlled release component comprising said Cav3 antagonist, and wherein the oral dosage form optionally contains an immediate release component comprising said Cav3 antagonist;
wherein said oral dosage form, when administered once daily to a human, is effective to maintain a maximum plasma concentration (Cmax) of said Cav3 antagonist divided by a mean plasma concentration of said Cav3 antagonist at 24 hours after administration $$\left(\frac{Cmax}{\text{plasma concentration at 24 hours}}\right)$$

from about 1.0 to about 4.0.

2. The oral dosage form of claim 1, wherein said human has been fasted for at least 4 hours prior to being administered said oral dosage form.

3. The oral dosage form of claim 1, wherein said oral dosage form, when administered once daily to said human, is effective to maintain a plasma concentration of said Cav3 antagonist of above a minimum effective concentration (MEC) of said Cav3 antagonist for at least about 15 hours, wherein said minimum effective concentration is about 200 nM.

4. The oral dosage form of claim 1, wherein said oral dosage form, when administered once daily to said human, is effective to maintain a plasma concentration of said Cav3 antagonist of above a minimum effective concentration (MEC) of said Cav3 antagonist for at least about 18 hours, wherein said minimum effective concentration is about 200 nM.

5. The oral dosage form of claim 1, wherein said oral dosage form, when administered once daily to said human, is effective to maintain a plasma concentration of said Cav3 antagonist of above a minimum effective concentration (MEC) of said Cav3 antagonist for at least about 24 hours, wherein said minimum effective concentration is about 200 nM.

6. The oral dosage form of claim 3, wherein said plasma concentration of said Cav3 antagonist is a plasma concentration at steady state.

7. The oral dosage form of claim 1, wherein said oral dosage form, when administered once daily to said human, is effective to maintain a mean plasma concentration of said Cav3 antagonist from about 400 nM to about 1000 nM for at least about 12 hours.

8. The oral dosage form of claim 1, wherein said oral dosage form, when administered once daily to said human, is effective to maintain a mean plasma concentration of said Cav3 antagonist from about 400 nM to about 1000 nM for at least about 15 hours.

9. The oral dosage form of claim 1, wherein said oral dosage form, when administered once daily to said human, is effective to maintain a mean plasma concentration of said Cav3 antagonist from about 400 nM to about 1000 nM for at least about 18 hours.

10. The oral dosage form of claim 7, wherein said oral dosage form, when administered once daily to said human, is effective to achieve said mean plasma concentration of said Cav3 antagonist in less than about 60 minutes.

11. The oral dosage form of claim 1, wherein said maximum plasma concentration (Cmax) of said Cav3 antagonist is less than about 1800 nM.

12. The oral dosage form of claim 1, wherein said maximum plasma concentration (Cmax) of said Cav3 antagonist is from about 900 nM to about 1800 nM.

13. The oral dosage form of claim 1, wherein said maximum plasma concentration (Cmax) of said Cav3 antagonist is from about 1200 nM to about 1800 nM.

14. The oral dosage form of claim 1, wherein said Cav3 antagonist is a hydrochloride salt.

15. The oral dosage form of claim 1, wherein the oral dosage form comprises a controlled release component comprising said Cav3 antagonist, and wherein the oral dosage form contains an immediate release component comprising said Cav3 antagonist.

16. The oral dosage form of claim 1, wherein said oral dosage form, when administered once daily to a human, is effective to maintain said maximum plasma concentration (Cmax) of said Cav3 antagonist divided by said mean plasma concentration of said Cav3 antagonist at 24 hours after administration $$\left(\frac{Cmax}{\text{plasma concentration at 24 hours}}\right)$$

from about 1.0 to about 3.0.

17. An oral dosage form comprising CX-8998, or a pharmaceutically acceptable salt thereof, wherein the oral dosage form comprises a first component that is formulated for delayed and/or sustained release of CX-8998 and a second component that is formulated for immediate release of CX-8998.

18. The oral dosage form according to claim 17, wherein CX-8998 is in the form of a hydrochloride salt.

19. The oral dosage form according to claim 17, wherein the oral dosage form includes about 40% of the first component formulated for delayed and/or sustained release of CX-8998 and about 60% of the second component formulated for immediate release of CX-8998.

20. The oral dosage form according to claim 17, wherein the CX-8998 is present in an amount of from about 0.5% to about 10% by weight of the free base equivalent of CX-8998.

21. The oral dosage form according to claim 17, wherein the first component comprises particles coated with a pH-sensitive enteric polymer.

22. A controlled release pharmaceutical composition comprising:
CX-8998, or a pharmaceutically acceptable salt thereof; and
at least one pharmaceutically acceptable excipient, wherein the at least one pharmaceutically acceptable excipient is lactose monohydrate; crospovidone; citric acid; or sodium lauryl sulfate.

23. The pharmaceutical composition according to claim 22, wherein the at least one pharmaceutically excipient is lactose monohydrate.

24. The pharmaceutical composition according to claim 22, wherein the at least one pharmaceutically excipient is crospovidone.

25. The pharmaceutical composition according to claim 22, wherein the at least one pharmaceutically excipient is citric acid.

26. The pharmaceutical composition according to claim 22, wherein the at least one pharmaceutically excipient is sodium lauryl sulfate.

27. The pharmaceutical composition according to claim 22, wherein the pharmaceutical composition comprises:
CX-8998, or a pharmaceutically acceptable salt thereof;
lactose monohydrate;
crospovidone;
citric acid; and
sodium lauryl sulfate.

28. The pharmaceutical composition according to claim 22, wherein the controlled release composition comprises a first component that is formulated for delayed and/or sustained release of CX-8998 and, optionally, a second component that is formulated for immediate release of CX-8998.

29. The pharmaceutical composition according to claim 28, wherein the oral dosage form comprises about 40% of the first component that is formulated for delayed and/or sustained release of CX-8998 and about 60% of the second component that is formulated for immediate release of CX-8998.

30. The pharmaceutical composition according to claim 28, wherein the first component comprises particles coated with a pH-sensitive enteric polymer.

31. The pharmaceutical composition according to claim 22, wherein the CX-8998 is present in an amount of from about 0.5% to about 10% by weight of the free base equivalent of CX-8998.

32. The pharmaceutical composition according to claim 22, wherein CX-8998 is in the form of a hydrochloride salt.

* * * * *